(12) United States Patent
Powell, Jr.

(10) Patent No.: US 9,446,105 B2
(45) Date of Patent: Sep. 20, 2016

(54) CHIMERIC ANTIGEN RECEPTOR SPECIFIC FOR FOLATE RECEPTOR β

(71) Applicant: THE TRUSTEES OF THE UNIVERSITY OF PENNSYLVANIA, Philadelphia, PA (US)

(72) Inventor: Daniel J. Powell, Jr., Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 29 days.

(21) Appl. No.: 14/211,784

(22) Filed: Mar. 14, 2014

(65) Prior Publication Data

US 2014/0286973 A1 Sep. 25, 2014

Related U.S. Application Data

(60) Provisional application No. 61/793,279, filed on Mar. 15, 2013.

(51) Int. Cl.
| | | |
|---|---|---|
| A61K 39/00 | (2006.01) | |
| C07K 14/725 | (2006.01) | |
| C07K 16/28 | (2006.01) | |
| C07K 16/30 | (2006.01) | |
| C07K 14/705 | (2006.01) | |

(52) U.S. Cl.
CPC ......... *A61K 39/0011* (2013.01); *C07K 14/705* (2013.01); *C07K 14/7051* (2013.01); *C07K 16/28* (2013.01); *C07K 16/3061* (2013.01); *A61K 2039/5158* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,199,942 A | 4/1993 | Gillis | |
| 5,225,539 A | 7/1993 | Winter | |
| 5,350,674 A | 9/1994 | Boenisch et al. | |
| 5,530,101 A | 6/1996 | Queen et al. | |
| 5,565,332 A | 10/1996 | Hoogenboom et al. | |
| 5,585,089 A | 12/1996 | Queen et al. | |
| 5,585,362 A | 12/1996 | Wilson et al. | |
| 5,766,886 A | 6/1998 | Studnicka et al. | |
| 5,858,358 A | 1/1999 | June et al. | |
| 5,883,223 A | 3/1999 | Gray | |
| 6,120,766 A | 9/2000 | Hale et al. | |
| 6,326,193 B1 | 12/2001 | Liu et al. | |
| 6,331,415 B1 | 12/2001 | Cabilly et al. | |
| 6,352,694 B1 | 3/2002 | June et al. | |
| 6,407,213 B1 | 6/2002 | Carter et al. | |
| 6,534,055 B1 | 3/2003 | June et al. | |
| 6,548,640 B1 | 4/2003 | Winter | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 2004/0101519 A1 | 5/2004 | June et al. | |
| 2005/0042664 A1 | 2/2005 | Wu et al. | |
| 2005/0048617 A1 | 3/2005 | Wu et al. | |
| 2006/0034810 A1 | 2/2006 | Riley et al. | |
| 2006/0121005 A1 | 6/2006 | Berenson et al. | |

FOREIGN PATENT DOCUMENTS

| | | |
|---|---|---|
| EP | 239400 | 9/1987 |
| EP | 519596 | 12/1992 |
| EP | 592106 | 4/1994 |
| WO | WO9109967 | 7/1991 |
| WO | WO9317105 | 9/1993 |
| WO | WO0129058 | 4/2001 |
| WO | WO0196584 | 12/2001 |

OTHER PUBLICATIONS

Baca et al., "Antibody Humanization Using Monovalent Phage Display." J. Biol. Chem., 272(16):10678-84 (1997).
Berge et al., "Selective Expansion of a Peripheral Blood CD8+ Memory T Cell Subset Expressing Both Granzyme B and L-Selectin During Primary Viral Infection in Renal Allograft Recipients." Transplant Proc. 30(8):3975-3977, 1998.
Bierer et al., "Cyclosporin A and FK506: molecular mechanisms of immunosuppression and probes for transplantation biology." Curr. Opin. Immun. 5:763-773, 1993.
Bird et al., "Single-chain antigen-binding proteins." 1988, Science 242:423-426.
Caldas et al., "Design and synthesis of germline-based hemi-humanized single-chain Fv against the CD18 surface antigen." Protein Eng., 13(5):353-60 (2000).
Carter et al., "Humanization of an anti-p185HER2 antibody for human cancer therapy." Proc. Natl. Acad. Sci. USA, 89:4285-4289 (1992).
Chothia et al., "Canonical structures for the hypervariable regions of immunoglobulins." J. Mol. Biol., 196:901-17 (1987)—Abstract.
Couto et al., "Designing human consensus antibodies with minimal positional templates." Cancer Res., 55 (23 Supp):5973s-5977s (1995).
Couto et al., "Anti-BA46 monoclonal antibody Mc3: humanization using a novel positional consensus and in vivo and in vitro characterization." Cancer Res., 55(8):1717-22 (1995).

(Continued)

*Primary Examiner* — Ruixiang Li
(74) *Attorney, Agent, or Firm* — Saul Ewing LLP; Kathryn Doyle

(57) ABSTRACT

The invention provides compositions and methods for treating leukemia, for example, acute myeloid leukemia (AML). The invention also relates to at least one chimeric antigen receptor (CAR) specific to folate receptor beta (FRβ), vectors comprising the same, and recombinant T cells comprising the FRβ CAR. The invention also includes methods of administering a genetically modified T cell expressing a CAR that comprises a FRβ binding domain in combination with a RXR agonist, such as all-trans retinoic acid.

9 Claims, 123 Drawing Sheets

(56) References Cited

OTHER PUBLICATIONS

Garland et al., "The use of Teflon cell culture bags to expand functionally active CD8+ cytotoxic T lymphocytes." J. Immunol Meth. 227(1-2):53-63, 1999.
Haanen et al., "Selective expansion of cross-reactive CD8(+) memory T cells by viral variants." J. Exp. Med. 190(9):1319-1328, 1999.
Henderson et al., "Comparison of the effects of FK-506, cyclosporin A and rapamycin on IL-2 production." Immun. 73:316-321, 1991.
Huston et al., "Protein engineering of antibody binding sites: recovery of specific activity in an anti-digoxin single-chain Fv analogue produced in *Escherichia coli*." 1988, Proc. Natl. Acad. Sci. USA 85:5879-5883.
Jones et al., "Replacing the complementarity-determining regions in a human antibody with those from a mouse." Nature, 321: 522-525, 1986.
Lanzavecchia et al., "The use of hybrid hybridomas to target human cytotoxic T lymphocytes." Eur. J. Immunol. 17, 105-111 (1987)—Abstract.
Leek, "Association of tumour necrosis factor alpha and its receptors with thymidine phosphorylase expression in invasive breast carcinoma." British Journal of Cancer 1998, 77, 2246-2251.
Liu et al., "Calcineurin is a common target of cyclophilin-cyclosporin A and FKBP-FK506 complexes." Cell 66:807-815, 1991.
Lissbrant, "Tumor associated macrophages in human prostate cancer: relation to clinicopathological variables and survival." International Journal of Oncology 2000, 17, 445-496—Abstract.
Morea et al., "Antibody modeling: implications for engineering and design." Methods, 20(3):267-79 (2000).
Mumtaz et al., "Design of liposomes for circumventing the reticuloendothelial cells." 1991 Glycobiology 5: 505-10.
Nagayoshi et al., "Effectiveness of anti-folate receptor beta antibody conjugated with truncated Pseudomonas exotoxin in the targeting of rheumatoid arthritis synovial macropages." 2005 Arthritis Rheum, 52:2666-75.
Padlan, "A possible procedure for reducing the immunogenicity of antibody variable domains while preserving their ligand-binding properties." 1991, Molecular Immunology, 28(4/5):489-498.
Pedersen et al., "Comparison of surface accessible residues in human and murine immunoglobulin Fv domains. Implication for humanization of murine antibodies." J. Mol. Biol., 235(3):959-73 (1994).
Presta, "Antibody engineering." Curr. Op. Struct. Biol., 3: 394-398, 1992.
Presta et al., "Humanization of an antibody directed against IgE." J. Immunol., 151:2623-2632 (1993).
Reichmann et al., "Reshaping human antibodies for therapy." Nature, 332: 323-329, 1988.
Roguska et al., "Humanization of murine monoclonal antibodies through variable domain resurfacing." 1994, PNAS, 91:969-973.
Roguska et al., "A comparison of two murine monoclonal antibodies humanized by CDR-grafting and variable doman resurfacing." Protein Eng., 9(10):895-904 (1996).
Salvesen et al., "Significance of tumour-associated macrophages, vascular endothelial growth factor and thrombospondin-1 expression for tumour angiogensis and prognosis in endometrial carcinomas." International Journal of Cancer 1999, 84, 538-543.
Sandhu J S, "A rapid procedure for the humanization of monoclonal antibodies." Gene, 150(2):409-10 (1994).
Sims et al., "A humanized CD18 antibody can block function without cell destruction." J. Immunol., 151:2296-2308 (1993).
Studnicka et al., "Human-engineered monoclonal antibodies retain full specific binding activity by preserving non-CDR complementarity-modulating residues." 1994, Protein Engineering, 7(6):805-814.
Tan et al., "'Superhumanized' antibodies: reduction of immunogenic potential by complementarity-determining region grafting with human germline sequences: application to an anti-CD28." J. Immunol., 169:1119-25 (2002).
Ui-Tei et al., "Sensitive assay of RNA interference in *Drosophila* and Chinese hamster cultured cells using firefly luciferase gene as target." 2000 FEBS Letters 479: 79-82.
Verhoeyen et al., "Reshaping human antibodies: grafting an antilysozyme activity." Science, 239:1534-1536 (1988).
Wu et al., "Humanization of a murine monoclonal antibody by simultaneous optimization of framework and CDR residues." J. Mol. Biol., 294:151-162 (1999).
Young, "Increased recurrence and metastasis in patients whose primary head and neck squamous cell carcinomas secreted granulocyte-macrophage colony-stimulating factor and contained CD34+ natural suppressor cells." International Journal of Cancer 1997, 74, 69-74.

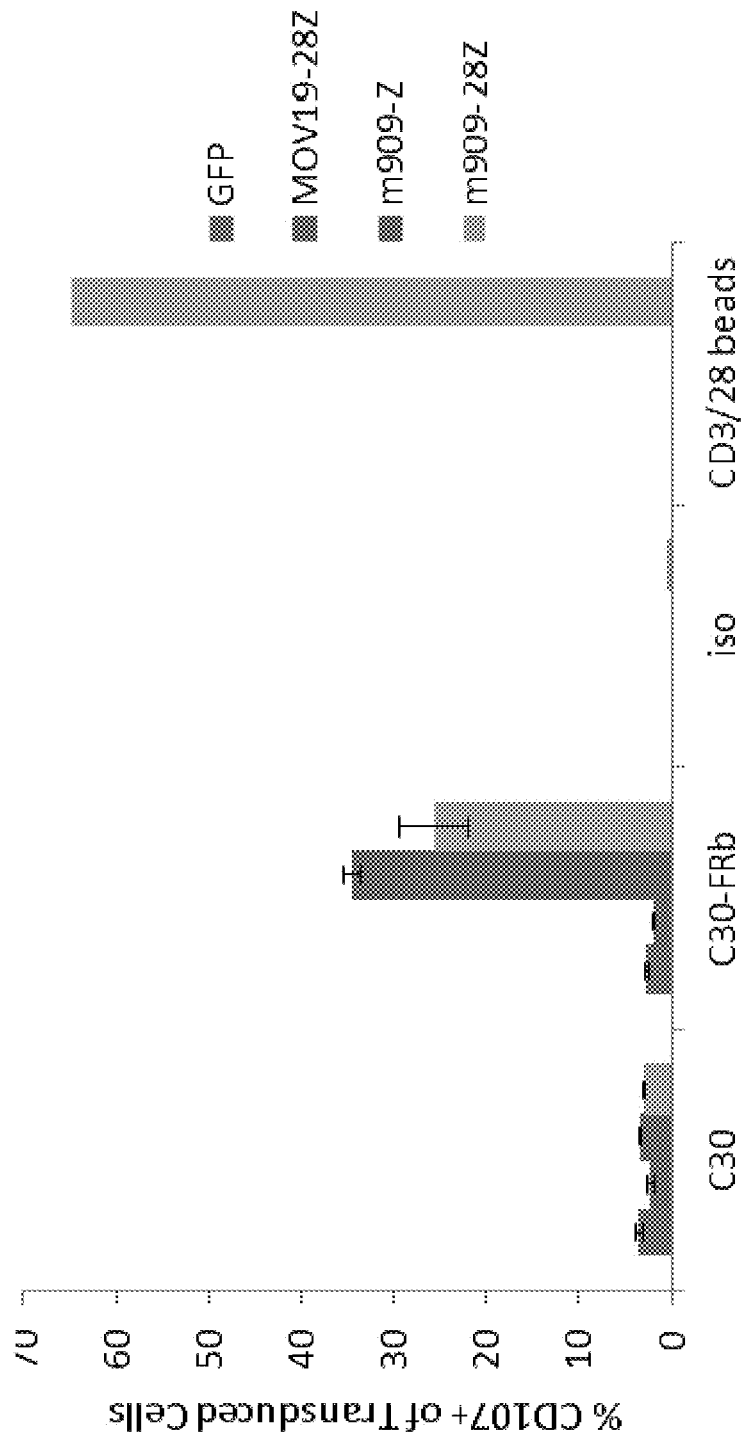

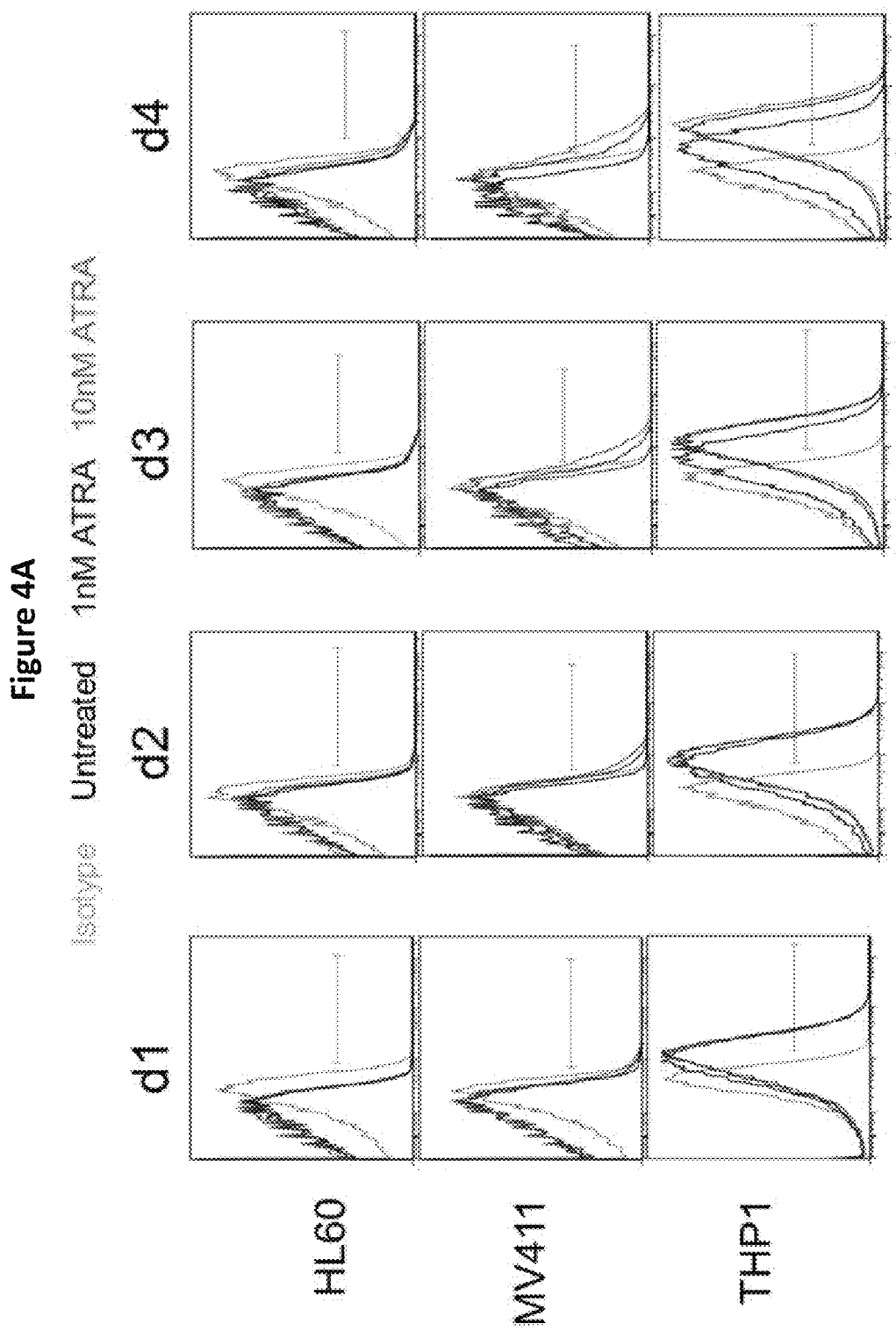

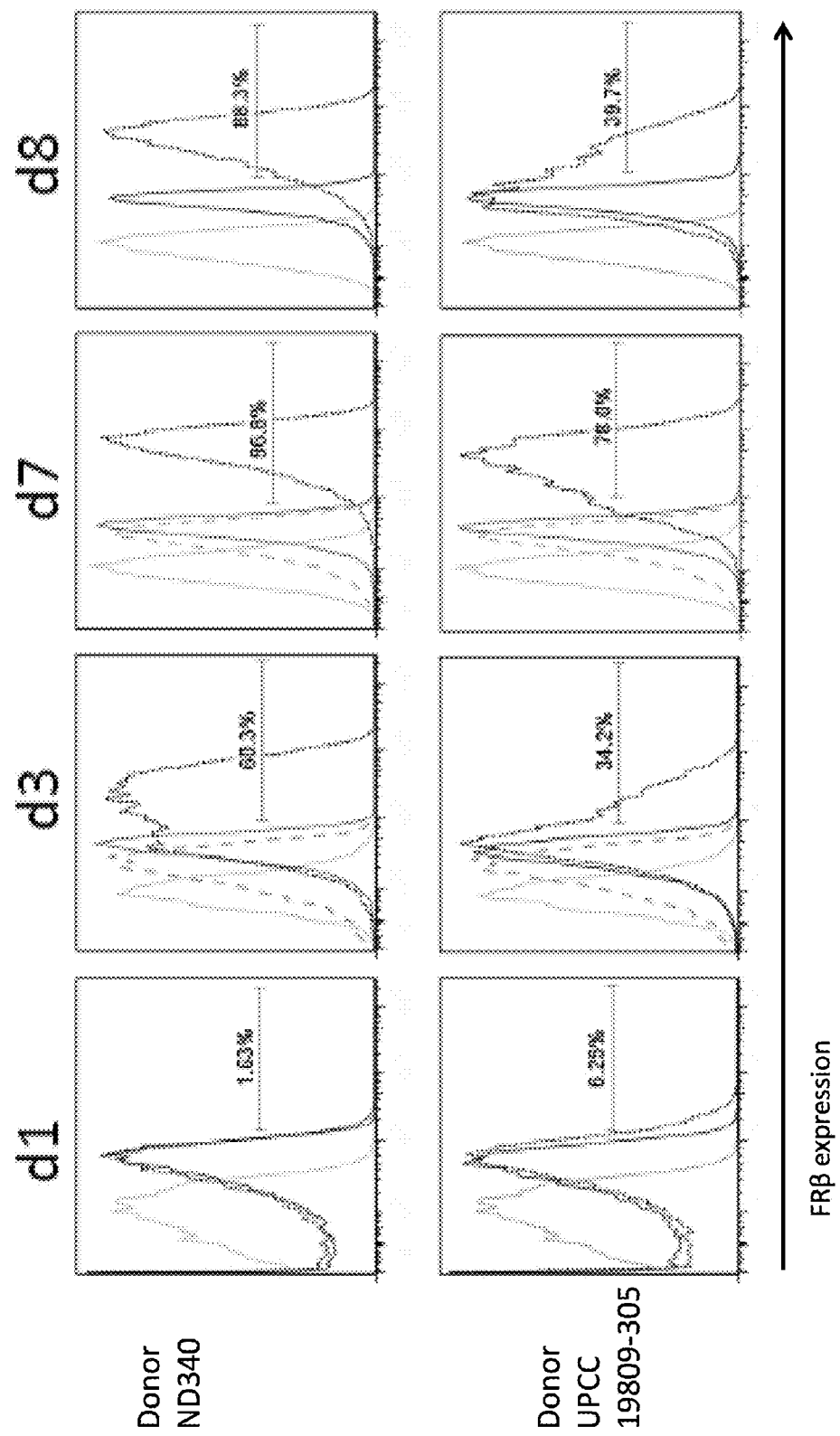

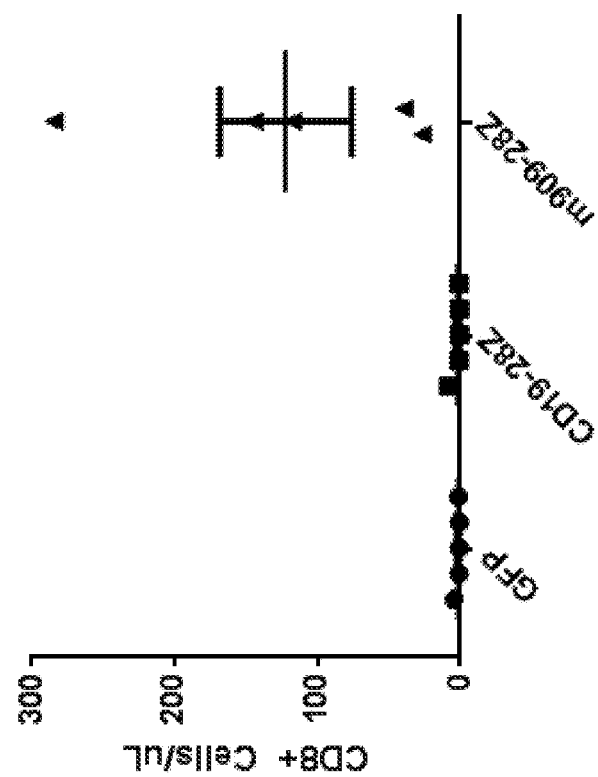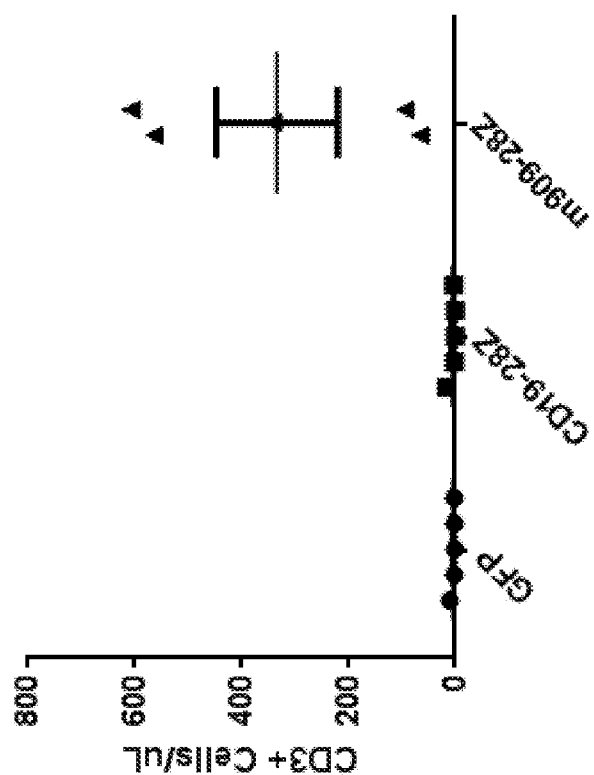
Figure 14D

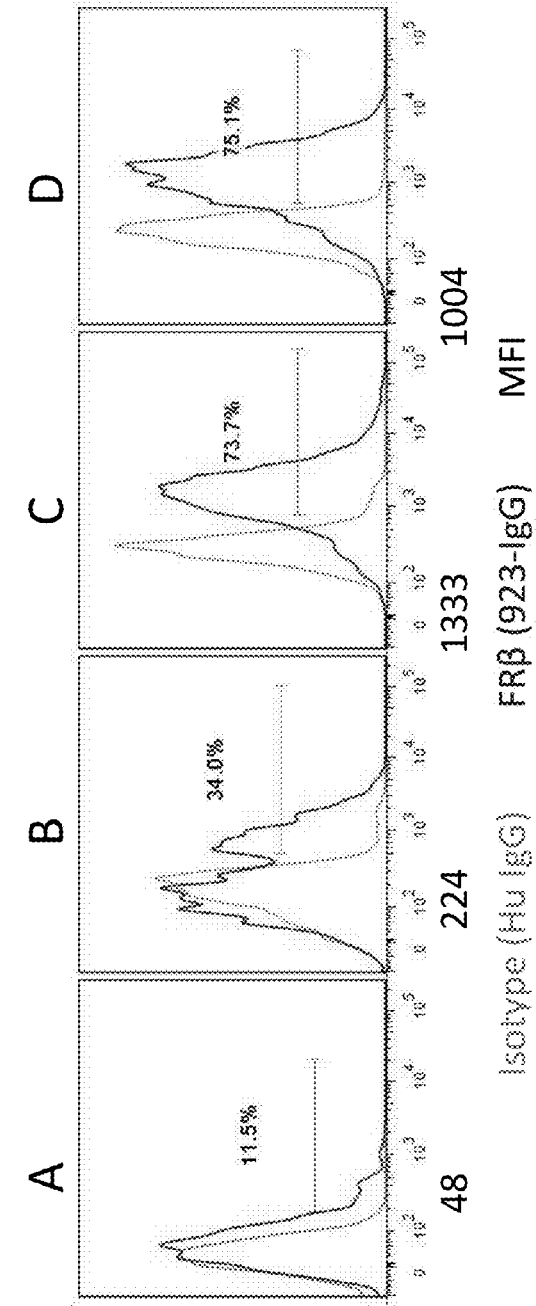
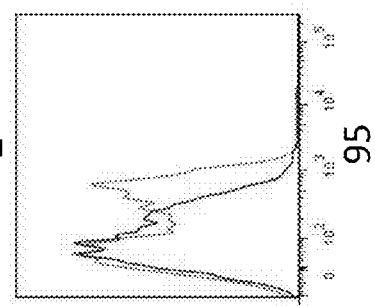

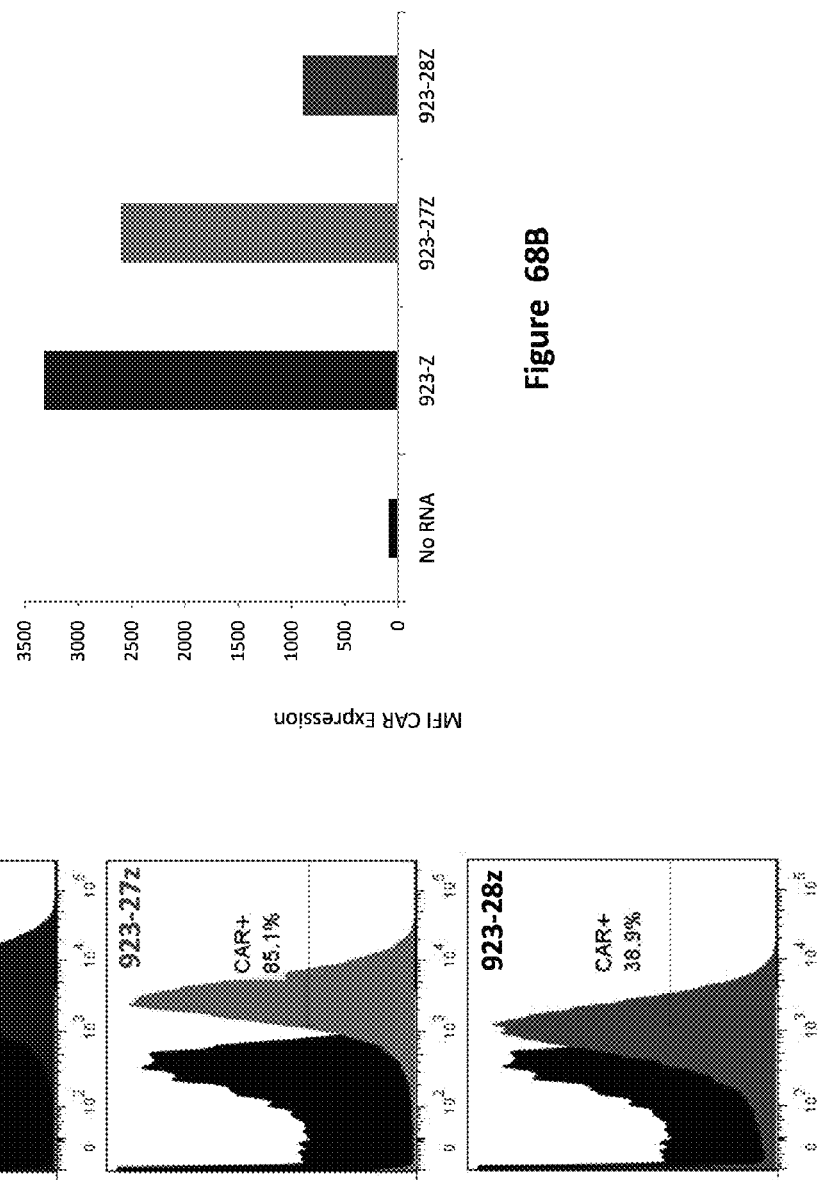

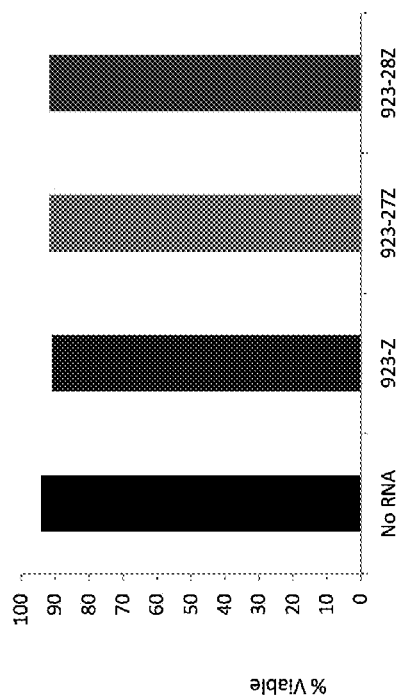
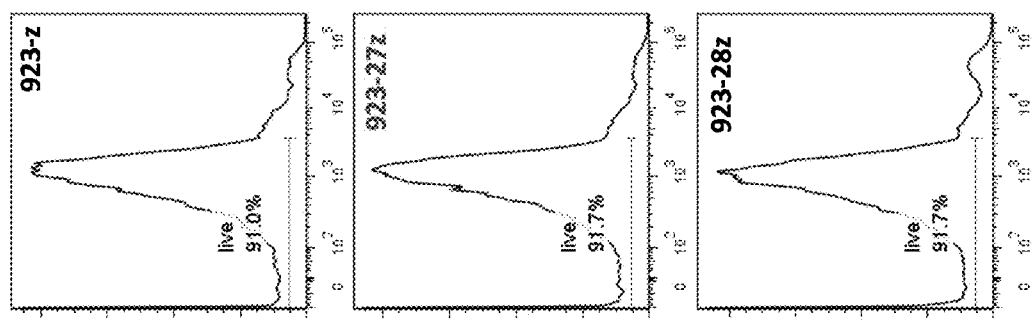
Figure 69A
Figure 69B

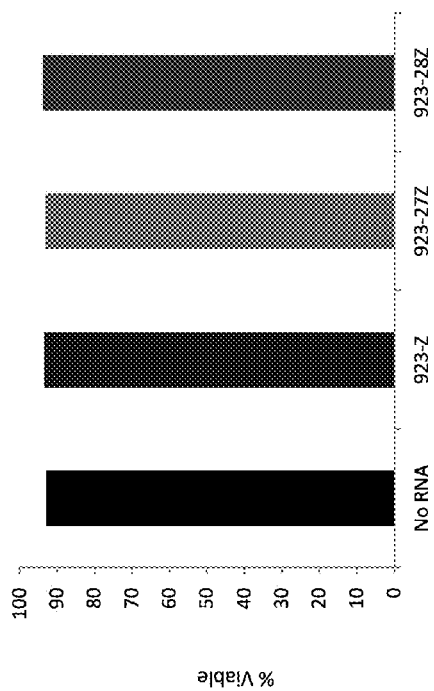
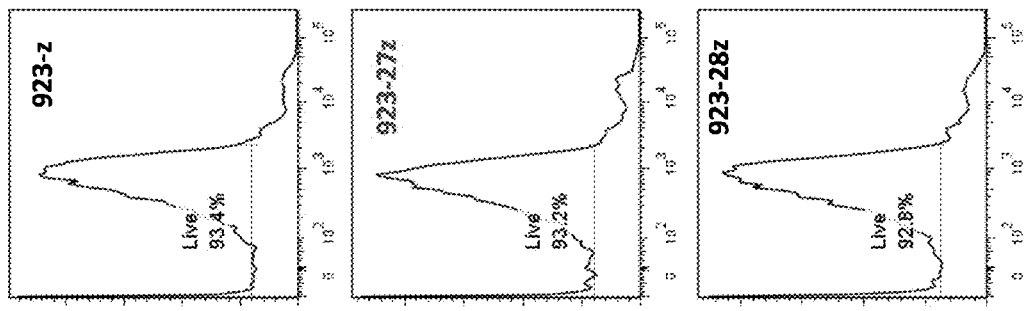
Figure 72A
Figure 72B

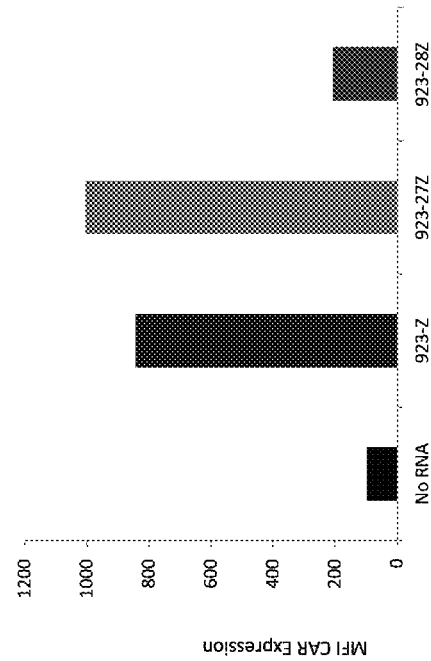
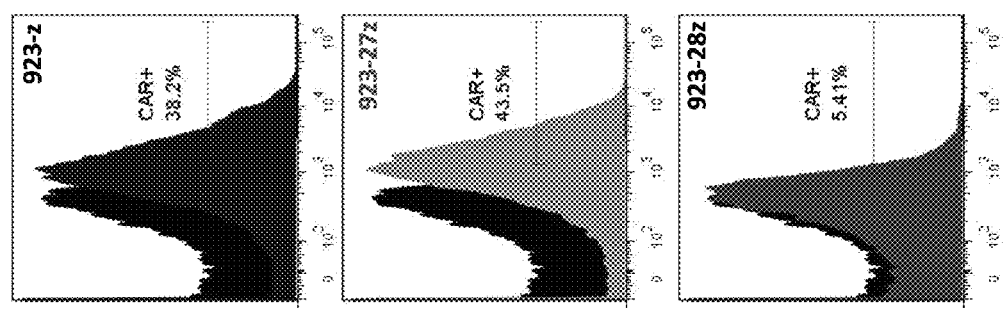
Figure 74A
Figure 74B

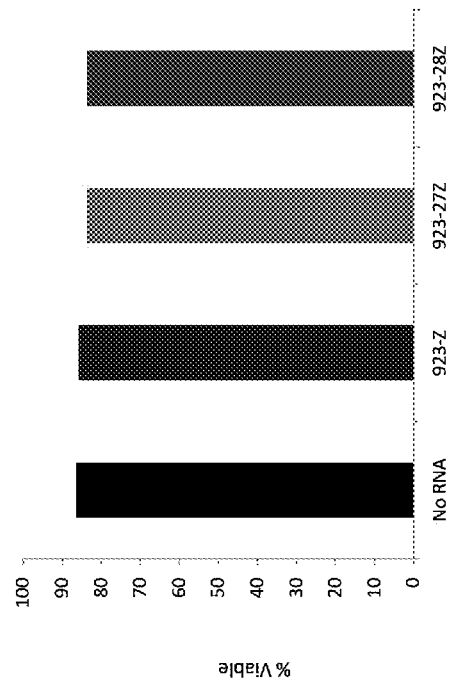
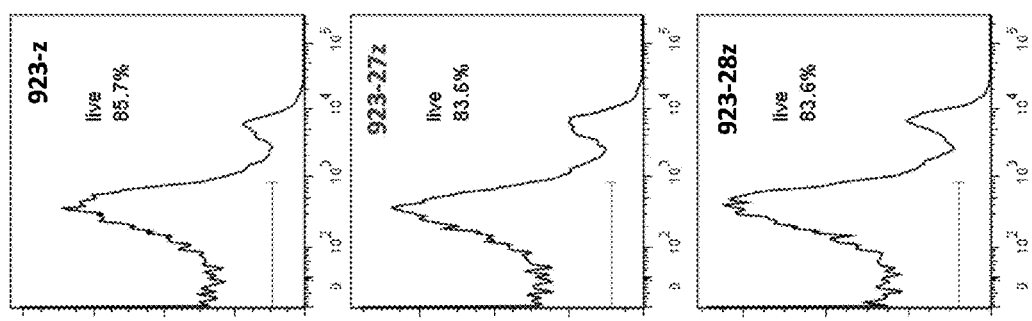
Figure 75A
Figure 75B

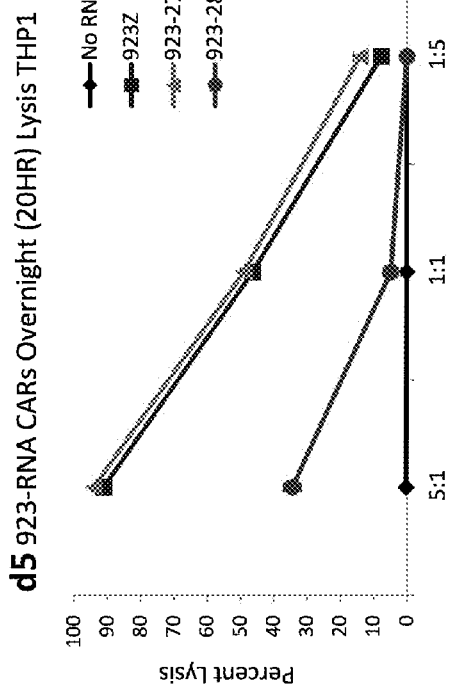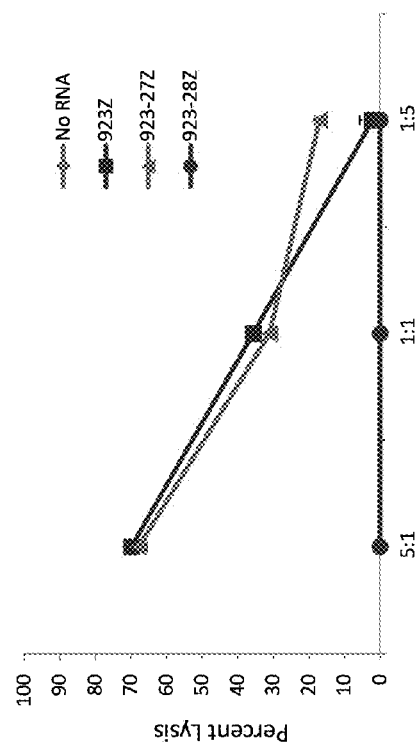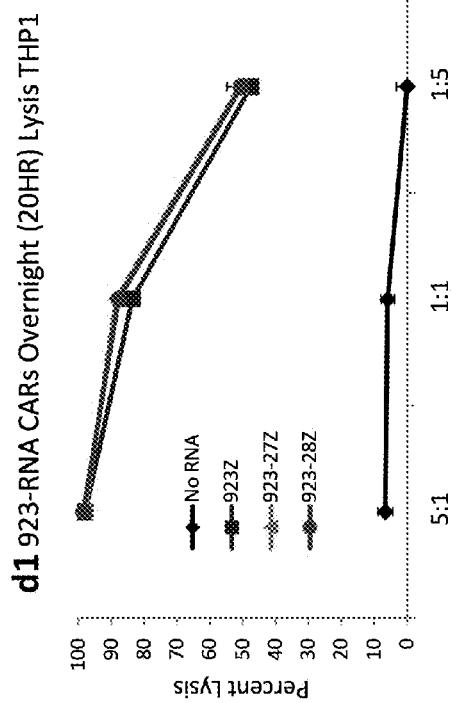
Figure 77

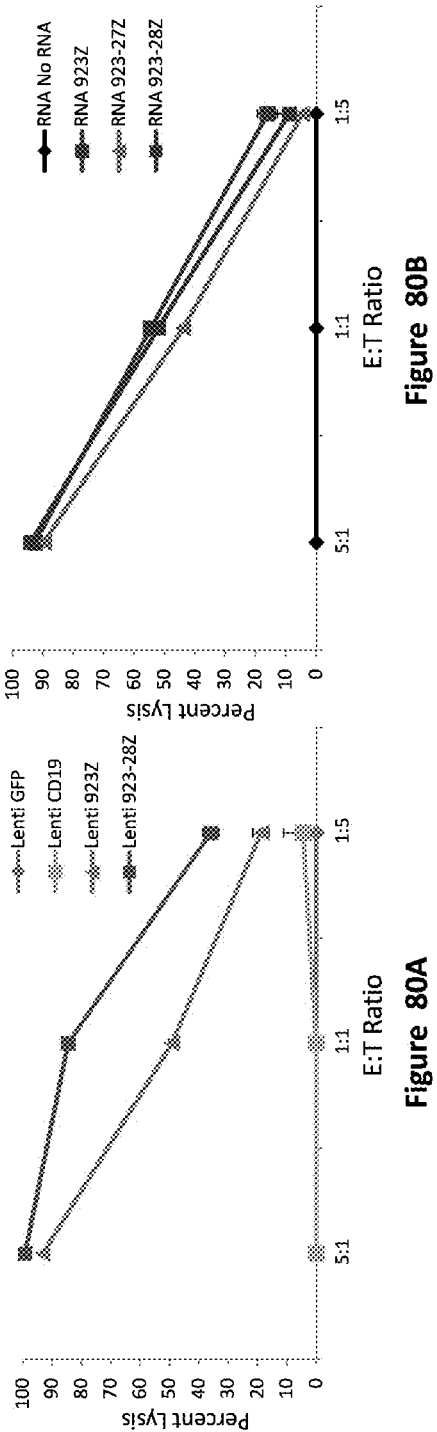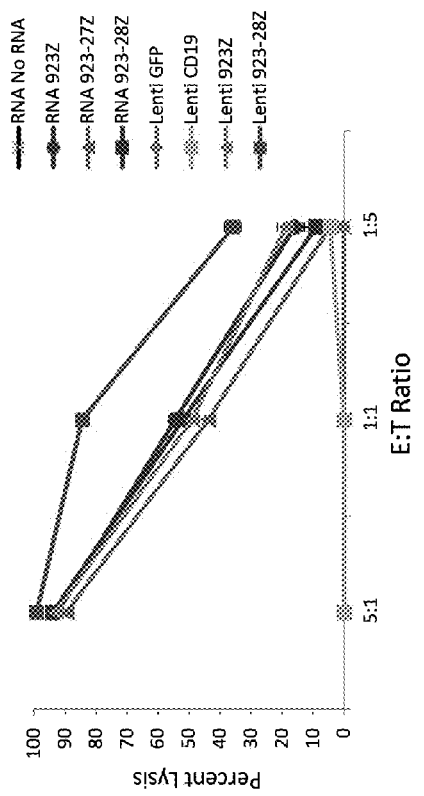

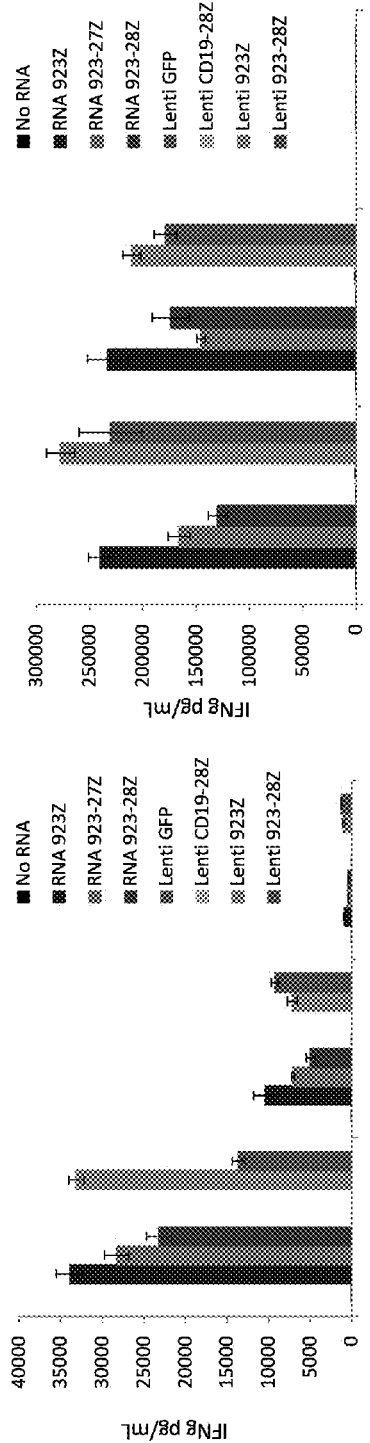
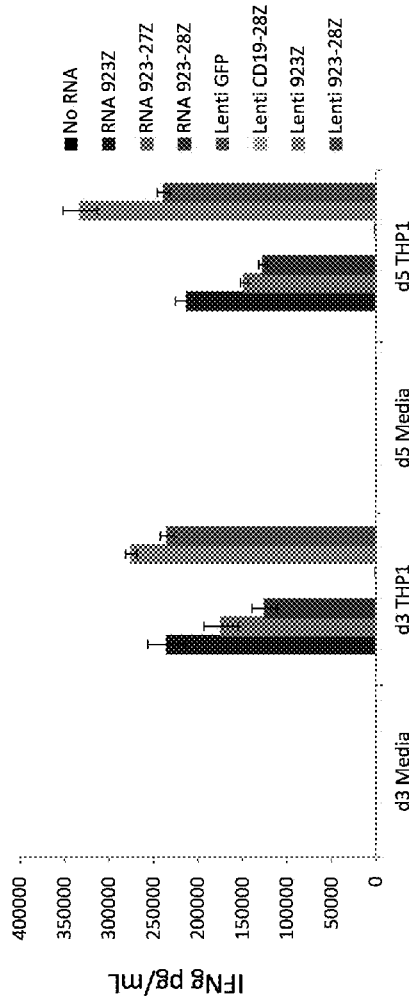
Figure 81A
Figure 81B
Figure 81C

CHIMERIC ANTIGEN RECEPTOR SPECIFIC FOR FOLATE RECEPTOR β

CROSS REFERENCE TO RELATED APPLICATION

The present application is entitled to priority under 35 U.S.C. §119(e) to U.S. Provisional Patent Application No. 61/793,279, entitled "Chimeric Antigen Receptor Specific of Folate Receptor Beta," filed on Mar. 15, 2013, which is hereby incorporated by reference in its entirety herein.

BACKGROUND OF THE INVENTION

The chimeric antigen receptor (CAR) provides a promising approach for adoptive T-cell immunotherapy for cancer. Commonly, CARs comprise a single chain fragment variable (scFv) of an antibody specific for a tumor associated antigen (TAA) coupled via hinge and transmembrane regions to cytoplasmic domains of T-cell signaling molecules. The most common lymphocyte activation moieties include a T-cell costimulatory (e.g. CD28, CD137, OX40, ICOS, and CD27) domain in tandem with a T-cell triggering (e.g. CD3ζ) moiety. The CAR-mediated adoptive immunotherapy allows CAR-grafted T cells to directly recognize the TAAs on target tumor cells in a non-HLA-restricted manner.

Most patients with acute myeloid leukemia (AML) are incurable with standard therapy; in addition, available treatment options are toxic. Redirecting T cells to recognize a target to which they had previously been blind may be one way to harness the power of the immune system to treat AML. Chimeric antigen receptor (CAR) modified autologous T cell (CART) therapy relies on redirecting T cells to a suitable cell-surface molecule on AML cells.

CAR therapies have been clinically successful in targeting CD19 for the control of B cell malignancy. However, therapeutic strategies for the treatment of myeloid leukemias are currently limited. Folate receptor beta (FRβ) is a GPI-anchored membrane protein with limited expression on normal tissues, restricted to a small population of mature hematopoietic subsets, but expressed on over 70% of primary Acute AML samples.

There is a need in the art for a CAR based therapy that targets folate receptor beta. The present invention addresses this unmet need in the art.

SUMMARY OF THE INVENTION

The invention includes compositions comprising at least one chimeric antigen receptor (CAR) specific to folate receptor beta (FRβ), vectors comprising the same, compositions comprising CAR vectors packaged in viral particles, and recombinant T cells comprising the FRβ CAR. The invention also includes methods of making a genetically modified T cell expressing a CAR (CART) wherein the expressed CAR comprises an FRβ binding domain.

In one aspect, the invention includes an isolated nucleic acid sequence encoding a chimeric antigen receptor (CAR), wherein the isolated nucleic acid sequence comprises the human nucleic acid sequence of a folate receptor beta (FRβ) binding domain, the nucleic acid sequence of an intracellular domain of a costimulatory molecule, and the nucleic acid sequence of a CD3 zeta signaling domain.

In another aspect, the invention includes an isolated chimeric antigen receptor (CAR) comprising a FRβ binding domain, an intracellular domain of a costimulatory molecule, and a CD3 zeta signaling domain.

In yet another aspect, the invention includes a genetically modified T cell comprising an isolated nucleic acid sequence encoding a chimeric antigen receptor (CAR), wherein the isolated nucleic acid sequence comprises the nucleic acid sequence of a folate receptor beta (FRβ) binding domain, the nucleic acid sequence of an intracellular domain of a costimulatory molecule, and the nucleic acid sequence of a CD3 zeta signaling domain.

An aspect of the invention includes a vector comprising an isolated nucleic acid sequence encoding a chimeric antigen receptor (CAR), wherein the isolated nucleic acid sequence comprises the nucleic acid sequence of a folate receptor beta (FRβ) binding domain, the nucleic acid sequence of an intracellular domain of a costimulatory molecule, and the nucleic acid sequence of a CD3 zeta signaling domain.

In various embodiments of the above aspects or any other aspect of the invention delineated herein, the invention includes a CAR comprising an amino acid sequence selected from the group consisting of SEQ ID NO: 2, SEQ ID NO: 4, SEQ ID NO: 6, SEQ ID NO: 8, SEQ ID NO: 10, and SEQ ID NO: 12. In one embodiment, the FRβ binding domain is selected from the group consisting of a murine antibody, a humanized antibody, a human antibody, a chimeric antibody, and an FRβ-binding fragment thereof. In another embodiment, the FRβ-binding fragment is a Fab or a scFv. In another embodiment, the invention further comprises the nucleic acid sequence of a transmembrane domain. In yet another embodiment, the isolated nucleic acid sequence comprises a nucleic acid sequence is selected from the group consisting of SEQ ID NO: 1, SEQ ID NO: 3, SEQ ID NO: 5, SEQ ID NO: 7, SEQ ID NO: 9, and SEQ ID NO: 11. In another embodiment, the vector is a lentiviral vector or a RNA vector or other gene delivery system including, but not limited to, retroviral, transposon, CRISPR, etc. Another embodiment includes the T cell having high affinity to FRβ. Yet another embodiment includes the T cell secreting high levels of at least one proinflammatory cytokine, such as IFNγ. Still yet another embodiment includes the T cell being capable of lysing FRβ+ cells. In another embodiment, the T cell is capable of eliminating tumor FRβ+ cells. In yet another embodiment, the T cell has limited toxicity toward healthy cells.

One aspect of the invention includes a method for providing anti-tumor immunity in a subject, the method comprising: administering to the subject an effective amount of a genetically modified T cell comprising an isolated nucleic acid sequence encoding a chimeric antigen receptor (CAR), wherein the isolated nucleic acid sequence comprises the nucleic acid sequence of a folate receptor beta (FRβ) binding domain, the nucleic acid sequence of an intracellular domain of a costimulatory molecule, and the nucleic acid sequence of a CD3 zeta signaling domain, thereby providing anti-tumor immunity in the subject.

Another aspect of the invention includes a method of treating a mammal having a disease, disorder or condition associated with expression of folate receptor beta (FRβ), the method comprising administering to the subject an effective amount of a genetically modified cell comprising an isolated nucleic acid sequence encoding a chimeric antigen receptor (CAR), wherein the isolated nucleic acid sequence comprises the sequence of a FRβ binding domain, the nucleic acid sequence of an intracellular domain of a costimulatory molecule, and the nucleic acid sequence of a CD3 zeta signaling domain.

In various embodiments of the above aspects or any other aspect of the invention delineated herein, the method includes further comprising administering a RXR agonist to the subject. In one embodiment, the RXR agonist is all-trans retinoic acid. In another embodiment, the CAR comprises an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

One embodiment the subject is a human. In another embodiment, the disease, disorder or condition associated with expression of FRβ is selected from the group consisting of chronic infection, cancer, autoimmune disease, and any combination thereof. In yet another embodiment, the CAR targeting a cancer cell is selected from the group consisting of a tumor-associated macrophage (TAM), a proinflammatory macrophage, and any combination thereof. In still yet another embodiment, the cancer is selected from the group of consisting of a solid tumor, a hematological cancer, and any combination thereof. In a further embodiment, the cancer is selected from the group consisting of AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and any combination thereof. In yet another embodiment, the autoimmune disease is selected from the group consisting of multiple sclerosis (MS), rheumatoid arthritis (RA), inflammatory bowel disease, psoriasis, Systemic Lupus Erythematosus (SLE), and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2H is an image showing degranulation of the cells.

FIG. 3B is a graph showing IFNγ secretion.

FIG. 3C is a graph showing viability of the cells.

FIG. 3D is a panel of graphs showing decreased FRβ expression on THP1 cells after coculture with FRb CAR Tcells.

FIG. 4A is a panel of graphs showing that ATRA increases FRβ expression on human AML cell lines.

FIG. 5A is an image demonstrating that FRβ was induced upon in vitro monocyte and demonstrating that FRβ CAR T cells recognize and respond to FRβ+ monocytes.

FIG. 14D is a panel of graphs showing m909-28Z CAR T cell (CD3+ cells, left graph, and CD8+ cells, right graph) accumulation in the periphery of treated THP1-tumor bearing NOD/SCID mice at 38 days.

FIG. 50A is a graph showing FRβ expression in $CD123^{hi}$ CD33(−) cells (early myeloid progenitors).

FIG. 50B is a graph showing FRβ expression in $CD123^{low}$ CD33+ $CD14^{low}$ (myeloid progenitors).

FIG. 50C is a graph showing FRβ expression in $CD123^{low}$ CD33+ $CD14^{hi}$ cells (123+ monocytes).

FIG. 50D is a graph showing FRβ expression in CD123 (−) CD33+ $CD14^{hi}$ cells (mature monocytes).

FIG. 50E is a graph showing FRβ expression in natural killer (NK) cells.

FIG. 67A is a panel of graphs showing viability 12 hours after RNA electroporation to transiently express m923 CAR in T cells.

FIG. 67B is a graph showing viability 12 hours after RNA electroporation to transiently express m923 CAR in T cells.

FIG. 68A is a panel of graphs showing CAR expression 3 days after RNA electroporation to transiently express m923 CAR in T cells.

FIG. 68B is a graph showing CAR expression 3 days after RNA electroporation to transiently express m923 CAR in T cells.

FIG. 69A is a panel of graphs showing viability 3 days after RNA electroporation to transiently express m923 CAR in T cells.

FIG. 69B is a graph showing viability 3 days after RNA electroporation to transiently express m923 CAR in T cells.

FIG. 70 is a graph showing total T cell numbers 3 days after RNA electroporation to transiently express m923 CAR in T cells.

FIG. 71A is a panel of graphs showing CAR expression 5 days after RNA electroporation to transiently express m923 CAR in T cells.

FIG. 71B is a graph showing CAR expression 5 days after RNA electroporation to transiently express m923 CAR in T cells.

FIG. 72A is a panel of graphs showing viability 5 days after RNA electroporation to transiently express m923 CAR in T cells.

FIG. 72B is a graph showing viability 5 days after RNA electroporation to transiently express m923 CAR in T cells.

FIG. 73 is a graph showing total T cell numbers 5 days after RNA electroporation to transiently express m923 CAR in T cells.

FIG. 74A is a panel of graphs showing CAR expression 8 days after RNA electroporation to transiently express m923 CAR in T cells.

FIG. 74B is a graph showing CAR expression 8 days after RNA electroporation to transiently express m923 CAR in T cells.

FIG. 75A is a panel of graphs showing viability 8 days after RNA electroporation to transiently express m923 CAR in T cells.

FIG. 75B is a graph showing viability 8 days after RNA electroporation to transiently express m923 CAR in T cells.

Figure 76:
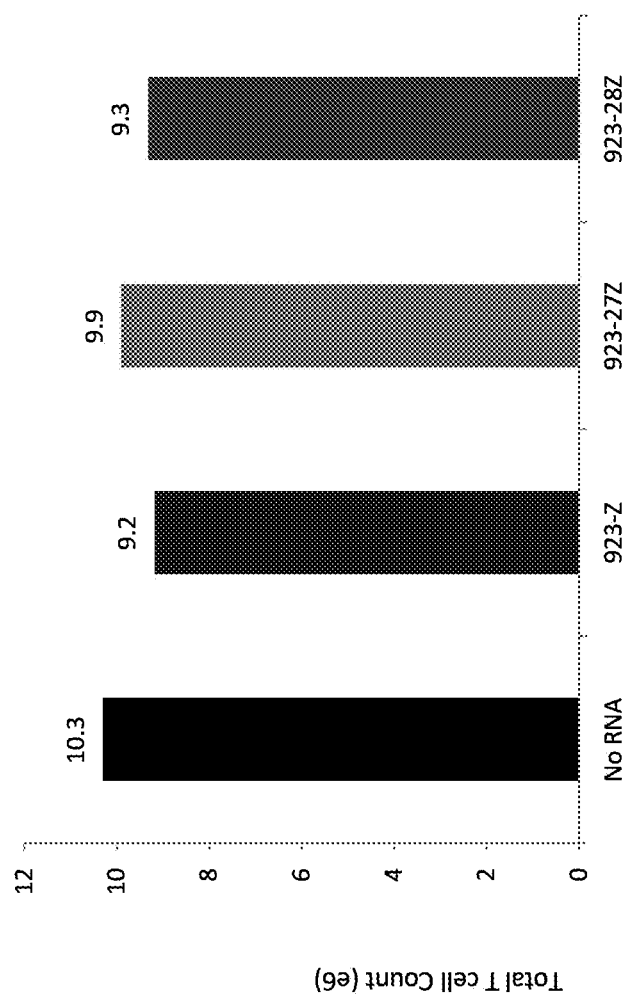

FIG. 76 is a graph showing total T cell numbers 8 days after RNA electroporation to transiently express m923 CAR in T cells.

FIG. 77 is a panel of graphs showing lysis of THP1 cells after 1, 5 and 8 days after RNA electroporation of m923 CAR in T cells.

Figure 78:
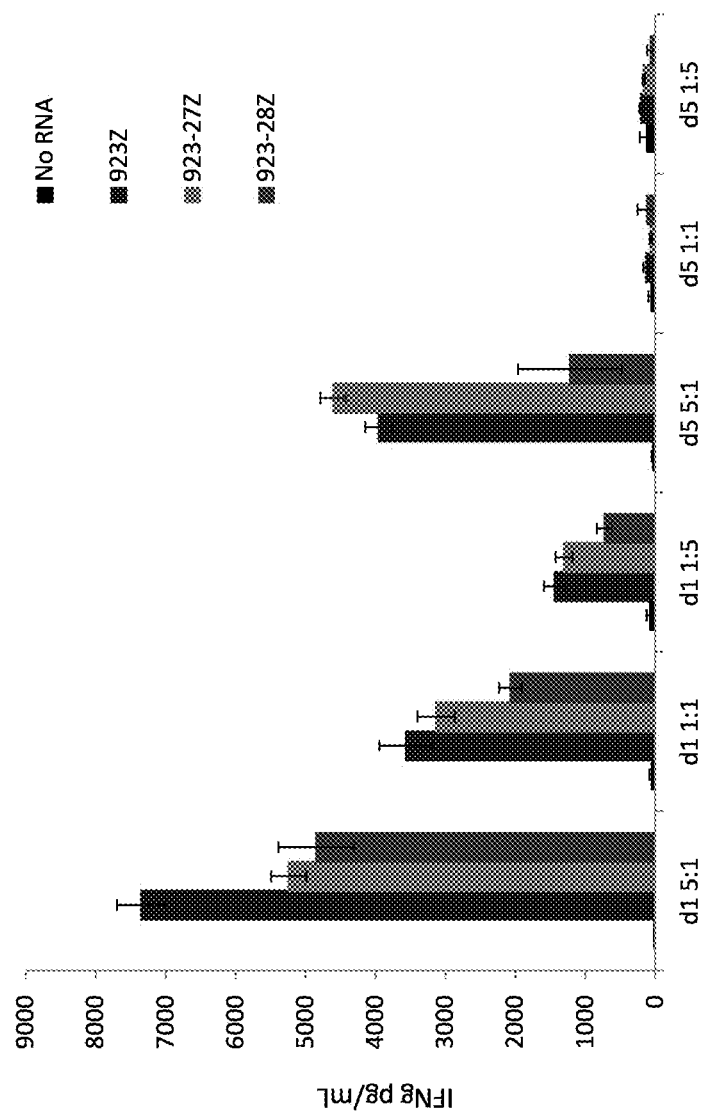

FIG. 78 is a graph showing IFNγ secretion 1 day after co-culture of day 1 and day 5 m923 CAR RNA electroporated T cells with THP1 cells.

Figure 79A:
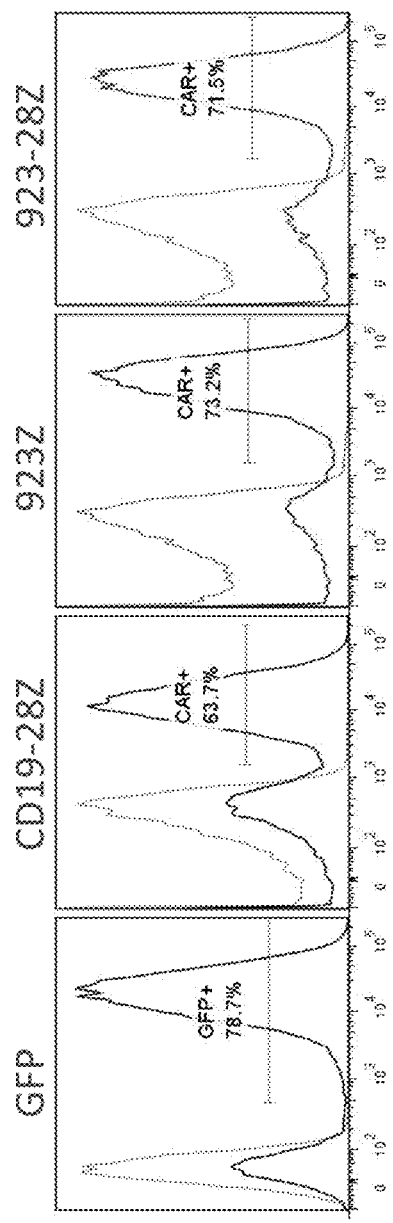

FIG. 79A is a panel of graphs showing lentivirus-based expression of m923 CAR 12 days after transduction in T cells.

Figure 79B:
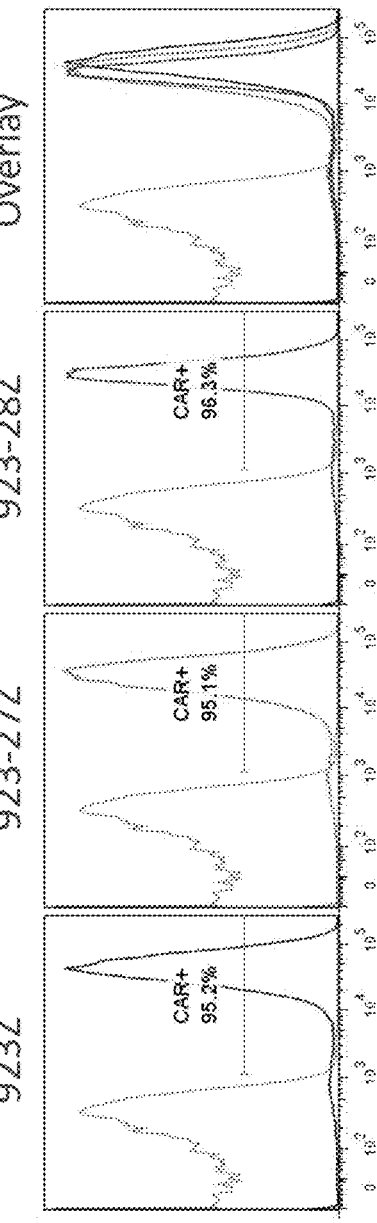

FIG. 79B is a panel of graphs showing RNA expression of m923 CAR 1 day after electroporation in T cells.

FIG. 80A is a graph showing lenti m923 CAR T cell specific lysis of THP1 cells.

FIG. 80B is a graph showing RNA m923 CAR T cell specific lysis of THP1 cells.

FIG. 80C is a graph showing lenti and RNA m923 CAR T cell specific lysis of THP1 cells.

FIG. 81A is a graph showing lenti and RNA m923 CAR T cell IFNγ secretion after 2 days in co-culture with THP1 cells.

FIG. 81B is a graph showing lenti and RNA m923 CAR T cell IFNγ secretion after 2 days in co-culture with THP1 or MV411 AML cells.

FIG. 81C is a graph showing lenti and RNA m923 CAR T cell IFNγ secretion after 3 and 5 days in co-culture with THP1 cells.

Figure 82:
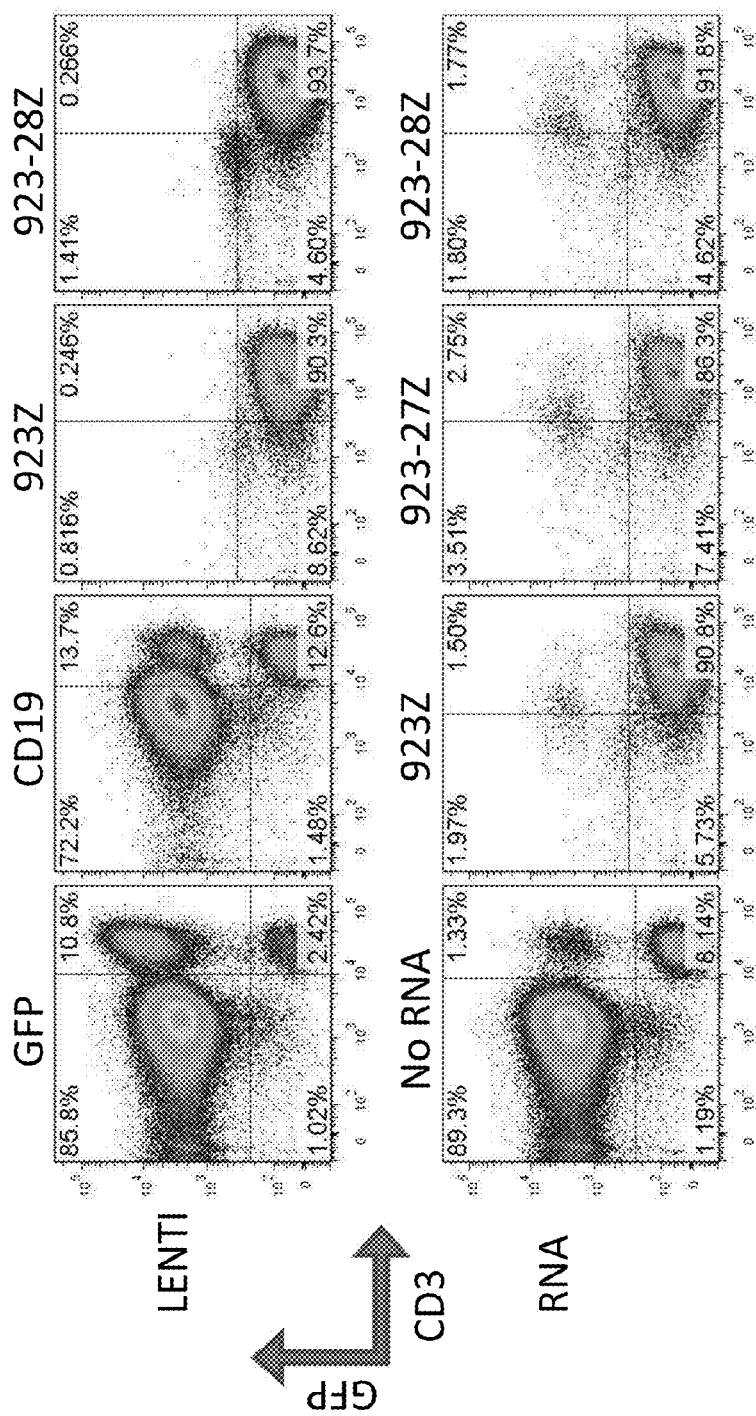

FIG. 82 is a panel of flow graphs showing loss of THP1 cells in lenti (upper graphs) and RNA (lower graphs) m923 CAR T cell co-cultures after 3 days.

Figure 83A:
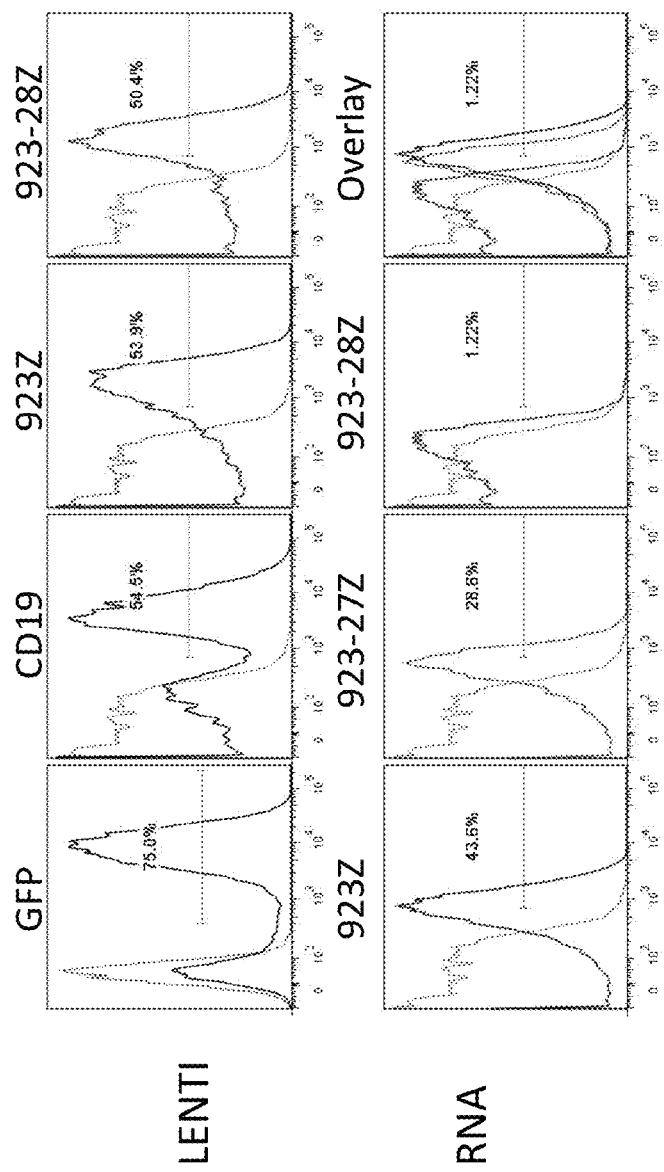

FIG. 83A is a panel of graphs showing CAR expression by lenti (upper graphs) and RNA (lower graphs) m923 CAR T cells (CD3+ cells) after 3 days in culture without stimulation.

Figure 83B:
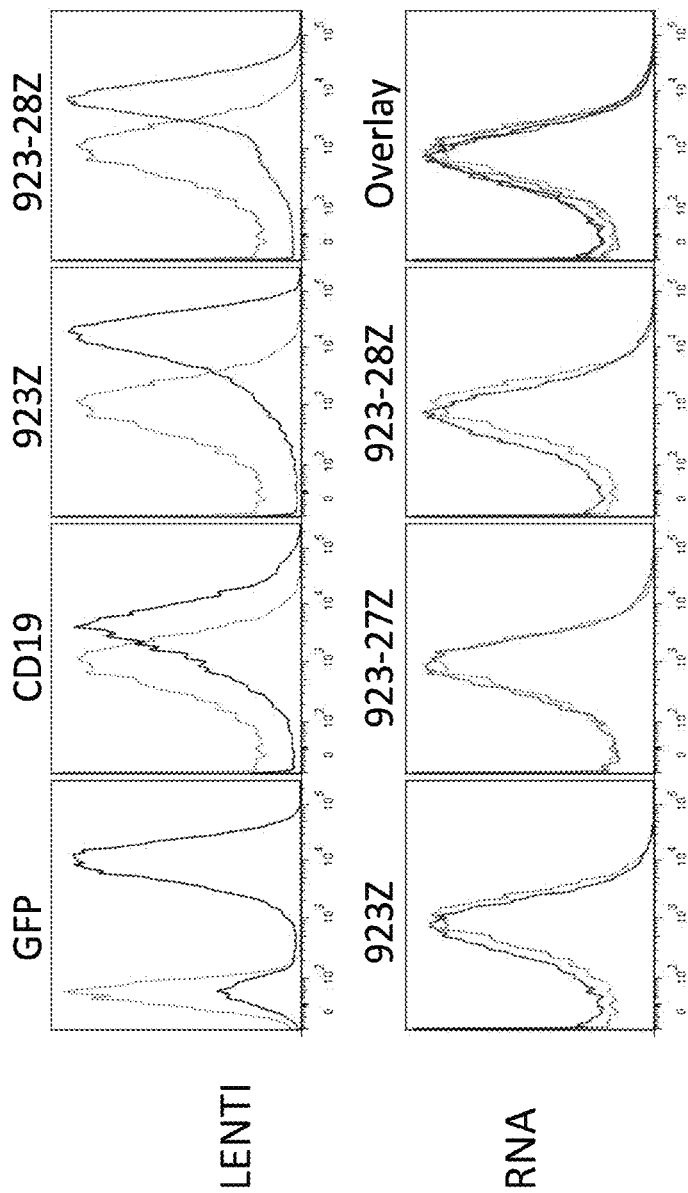

FIG. 83B is a panel of graphs showing CAR expression by lenti (upper graphs) and RNA (lower graphs) m923 CAR T cells (CD3+ cells) after 3 days in culture with THP1 cells.

Figure 84:
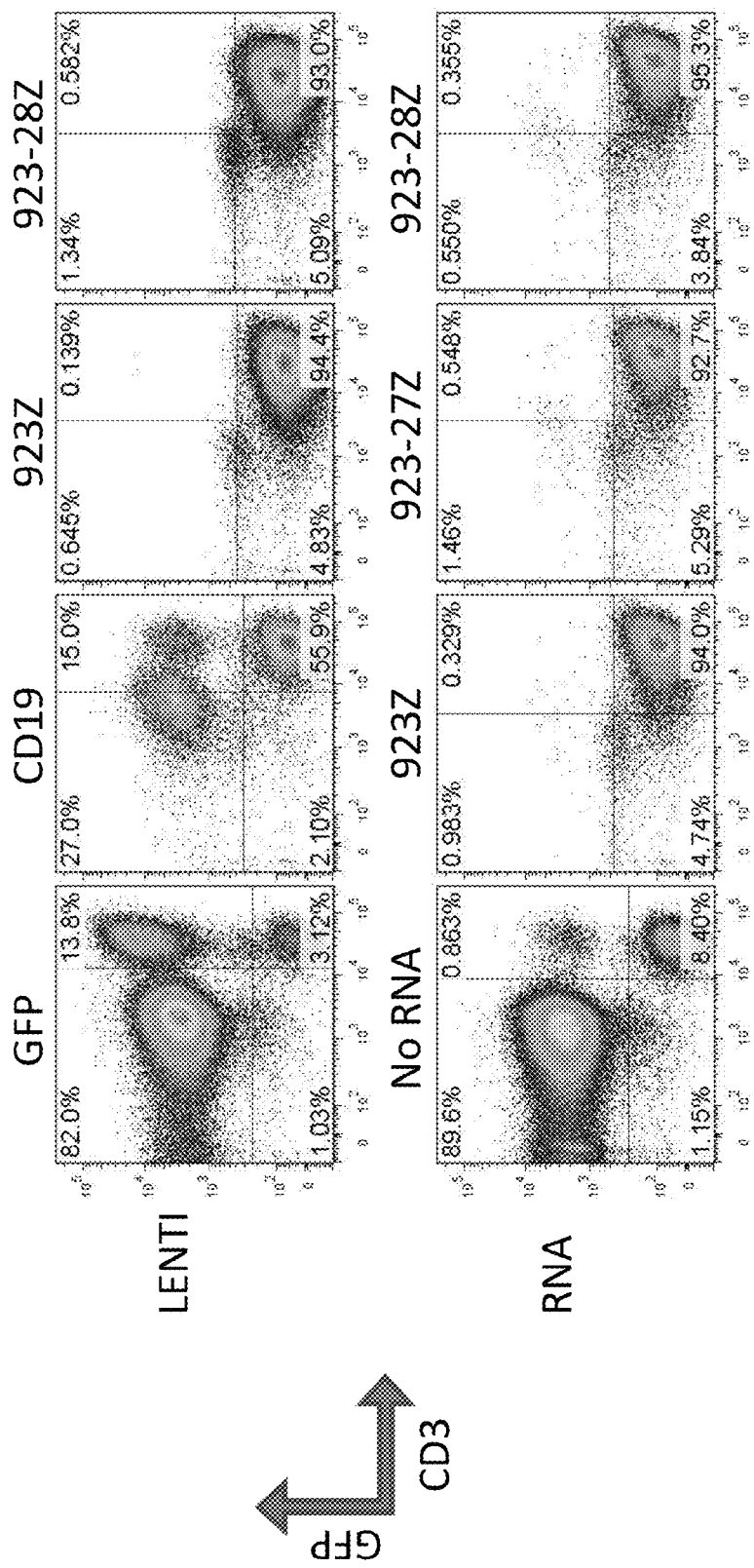

FIG. 84 is a panel of graphs showing loss of THP1 cells in lenti (upper graphs) and RNA (lower graphs) m923 CAR T cell co-cultures after 5 days.

Figure 85A:
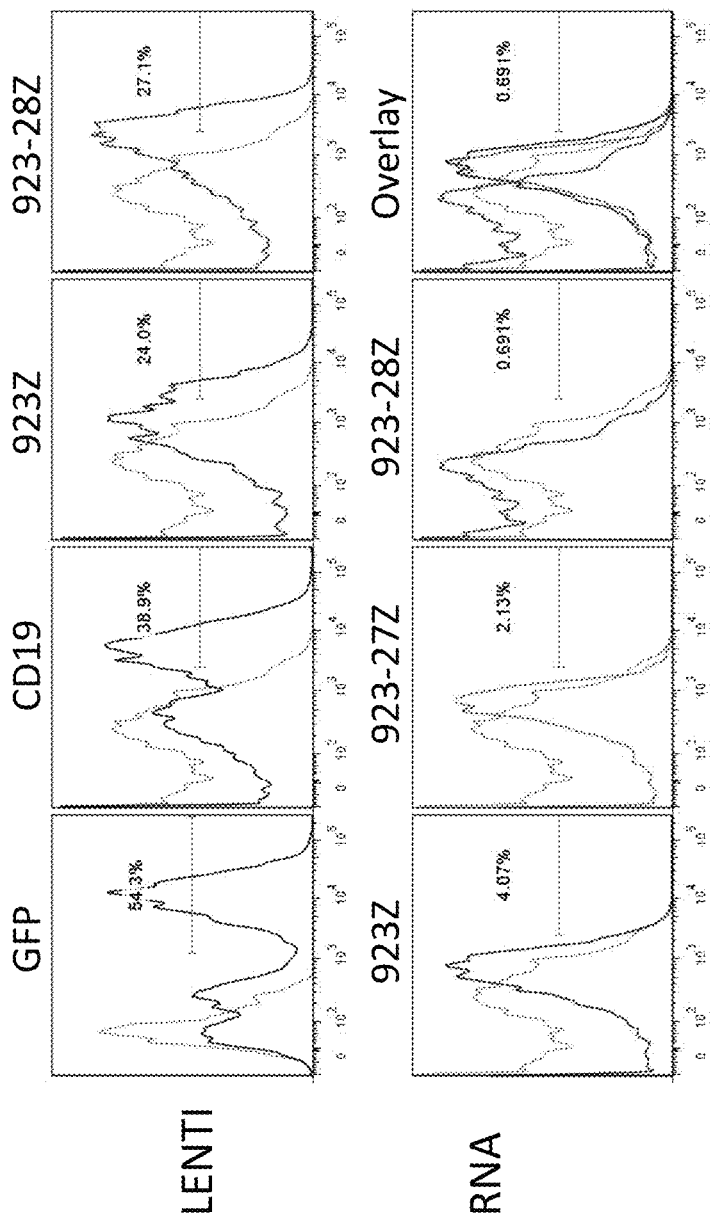

FIG. 85A is a panel of graphs showing CAR expression by lenti (upper graphs) and RNA (lower graphs) m923 CAR T cells (CD3+ cells) after 5 days in culture without stimulation.

Figure 85B:
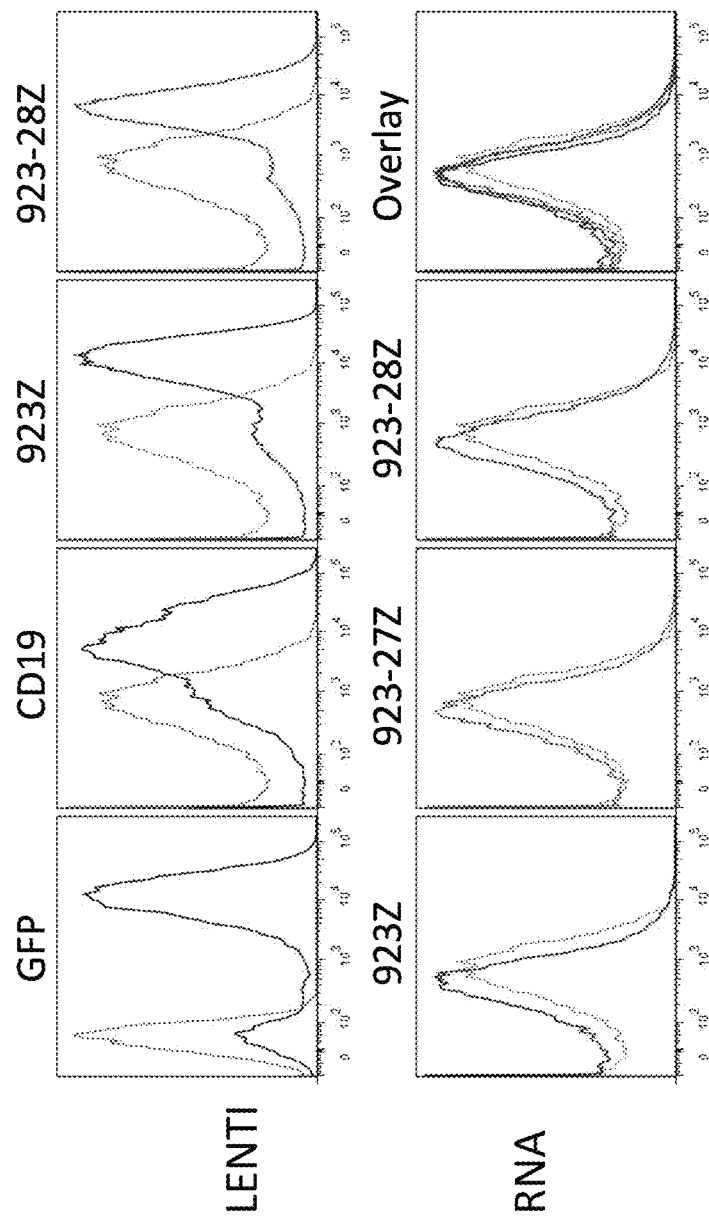

FIG. 85B is a panel of graphs showing CAR expression by lenti (upper graphs) and RNA (lower graphs) m923 CAR T cells (CD3+ cells) after 5 days in culture with THP1 cells.

DETAILED DESCRIPTION

The invention provides compositions comprising at least one Chimeric Antigen Receptor (CAR) specific to Folate receptor beta (FRβ), vectors comprising the same, compositions comprising CAR vectors packaged in viral particles, and recombinant T cells comprising the FRβ CAR. The invention also includes methods of making a genetically modified T cell expressing a CAR (CART) wherein the expressed CAR comprises an FRβ binding domain.

The present invention also relates generally to the use of T cells engineered to express a Chimeric Antigen Receptor (CAR) to treat a cancer associated with expression of FRβ. In one embodiment, the T cells expressing the CAR of the invention specifically bind to and kill FRβ expressing cells, but not normal or wild type FRβ expressing cells. In one embodiment, the FRβ expressing cell is a tumor cell. In another embodiment, the FRβ expressing cell is an activated macrophage including but not limited to a tumor associated macrophage (TAM), a proinflammatory macrophage that produce TNFα, and the like.

In one embodiment, the CARs of the invention combine an antigen recognition domain of a specific antibody with an intracellular signaling molecule. For example, in some embodiments, the intracellular signaling molecule includes, but is not limited to, CD3-zeta chain, 4-1BB and CD28 signaling modules and combinations thereof. Preferably, the antigen recognition domain binds to FRβ.

In one aspect, the FRβ CAR comprises the polypeptide sequence of any of SEQ ID NO: 2, SEQ ID NO: 4, SEQ ID NO: 6, SEQ ID NO: 8, SEQ ID NO: 10, and SEQ ID NO: 12.

In one embodiment, the antigen recognition domain is derived from a mouse anti-FRβ antibody or fragment thereof. In another embodiment, the antigen recognition domain is derived from a humanized anti-FRβ antibody or fragment thereof. In yet another embodiment, the antigen recognition domain is derived from a fully human anti-FRβ antibody or fragment thereof.

Accordingly, the invention provides an anti-FRβ-CAR engineered into a T cell and methods of their use for adoptive therapy. The CAR of the invention comprising an antigen recognition domain that binds to FRβ is sometimes referred herein as FRβ CAR or anti-FRβ CAR.

In one embodiment, the FRβ CAR of the invention is used for therapy against a disease, disorder or condition associated with FRβ expression including but is not limited to chronic infection, cancer, autoimmune disease, and any combination thereof.

In one embodiment, the FRβ CAR of the invention is used for treating an autoimmune disease (e.g., rheumatoid arthritis). In one embodiment, the therapy is to target the proinflammatory mononuclear cells associated with rheumatoid arthritis.

In one embodiment, the FRβ CAR of the invention is used for cancer therapy against cancers associated which express FRβ. In one embodiment, the cancer therapy is to regulate the tumor microenvironment by way of regulating TAMs.

In one embodiment, the FRβ CAR of the invention is used for cancer therapy against cancers associated which express FRβ. In one embodiment, the cancer is a hematologic cancer. In one aspect, the hematologic cancer is acute myeloid leukemia (AML).

The present invention relates generally to the treatment of a patient having a cancer associated with expression of FRβ, or at risk of having a cancer associated with expression of FRβ, using cellular infusion. In one embodiment, lymphocyte infusion, preferably autologous lymphocyte infusion is used in the treatment of the cancer.

In one embodiment, the invention provides a vector comprising an anti-FRβ CAR transgene. In one aspect, the vector is a retroviral vector. In one aspect, the vector is a self-inactivating lentiviral vector as described elsewhere herein. In one aspect, the vector comprises an anti-FRβ CAR transgene operably linked to a promoter capable of expression in a mammalian T cell.

In one aspect the anti-FRβ CAR transgene is expressed as an mRNA molecule. In one embodiment, the genetically modified CART cells of the invention can be generated by transfecting an RNA encoding the desired CARs into a T cell.

The present invention also provides compositions and methods for using the CAR T cells of the invention in combination with a retinoic acid receptor (RARs) agonist. An example of a RAR agonist is all-trans retinoic acid (ATRA). In one embodiment, a cell is contacted with an ATRA wherein the ATRA enhances the intensity of FRβ expression on the cell. The increase in FRβ expression increases immune recognition by FRβ CAR T cells.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The an antibody in the present invention may exist in a variety of forms where the antigen binding portion of the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to at least one portion of an intact antibody and refers to the antigenic determining variable regions of an intact antibody. Examples of antibody fragments include, but are not limited to, Fab, Fab', F(ab')2, and Fv fragments, linear antibodies, sdAb (either $V_L$ or $V_H$), camelid $V_{HH}$ domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "high affinity" as used herein refers to high specificity in binding or interacting or attraction of one molecule to a target molecule.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

The term "autoimmune disease" as used herein is defined as a disorder that results from an autoimmune response. An autoimmune disease is the result of an inappropriate and excessive response to a self-antigen. Examples of autoimmune diseases include but are not limited to, Addision's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, glioma, and the like.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the CDR regions of an antibody of the invention can be replaced with other amino acid residues from the same side chain family and the altered antibody can be tested for the ability to bind FRβ using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the terms "FRβ binding domain" may refer to any FRβ specific binding domain, known to one of skilled in the art. In one example, FRβ binding domain comprises a single-chain variable fragment (scFv) comprising the variable regions of the heavy ($V_H$) and light chains ($V_L$) of an antibody binding specifically to FRβ. In one embodiment, the FRβ binding domain is a homologue, a variant, an isomer, or a functional fragment of an anti-FRβ antibody. Each possibility represents a separate embodiment of the present invention.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, IL10 and IL-15), interferons (IFNγ), and tumor necrosis factors (TNFα and TNFβ).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "RAR agonist" as used herein refers to any compound, natural or synthetic, which results in an increased activation of the retinoic acid receptor.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, "tumor cells" or simply "tumor" refers to the tumor tissue as a whole, including different cell types that are present in a tumor environment. Tumor cells include cancer cells but also non-transformed host cells, or tumor-associated stroma cells. Examples of tumor-associated stroma cells include myeloid cells, in particular tumor-associated macrophages.

The term "tumor-associated macrophage" or "TAM" when used herein refers to a cell derived from a monocyte that can be found in the immune infiltrate associated with a tumor.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is partly based on the development of a CAR directed towards FRβ (FRβ CAR) for the targeting of AML. In addition, the invention is partly based on the discovery that treatment of AML cells with all-trans retinoic acid (ATRA), a vitamin A derivative currently part of standard of care regimens for AML subclass M3 (or APL), enhanced the intensity of FRβ expression on the AMLs, resulting in increased immune recognition by FRβ CAR T cells.

In one embodiment, the invention provides a method of treating a disease or disorder associated with the expression of FRβ in a mammal. In one embodiment, the method comprises administering FRβ CAR T cells in combination with a retinoic acid receptor (RARs) agonist. An example of an RAR agonist is a compound, natural or synthetic, which results in an increased activation of the retinoic acid receptor. The RAR agonist can be administered to the mammal in need thereof prior to, after or simultaneously with the FRβ CAR T cells.

In one embodiment the RAR agonist is a retinoid. Non-limiting examples of retinoids include retinols, retinoic acids, and retinyl esters. Retinol includes but is not limited to any isomers of retinol, e.g., all-trans-retinol, 13-cis-retinol, 11-cis-retinol, 9-cis-retinol, 3,4-didehydro-retinol. Examples of retinoic acids include all trans retinoic acid (ATRA) and 9-cis retinoic acid. Examples of retinyl esters include: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, and retinyl oleate.

The present invention is also partly based on the development of a CAR directed towards FRβ (FRβ CAR) for targeting macrophages, including but are not limited to activated macrophages, M2 tumor associated macrophages (TAMs) that suppress T cell responses, and proinflammatory macrophages that produce TNFα (e.g., in a person with rheumatoid arthritis). Accordingly, the FRβ CAR and cells expressing the FRβ CAR of the invention can be used to treat cancer by targeting anti-inflammatory/regulatory macrophages via FRβ CAR T cells in the tumor microenvironment. In another embodiment, the FRβ CAR and cells expressing the FRβ CAR of the invention can be used to treat diseases associated with proinflammatory macrophages that produce TNFα (e.g., rheumatoid arthritis) by targeting proinflammatory mononuclear cells in the subject thereby providing a clinical benefit.

In one embodiment, the invention provides a number of antibodies or fragments thereof engineered for enhanced binding to an FRβ protein expressed on a cell surface. In one embodiment, the FRβ antibody is a scFv antibody fragment. In one aspect such antibody fragments are functional in that they retain the equivalent binding affinity, i.e., they bind the same antigen with comparable efficacy, as the IgG antibody from which it was derived. In another embodiment such antibody fragments are functional in that they provide a biological response including but is not limited to, activation of an immune response, inhibition of signal-transduction origination from its target antigen, inhibition of kinase activity, and the like, as will be understood by a skilled artisan.

In some embodiments, the antibodies of the invention are incorporated into a chimeric antigen receptor (CAR). In one embodiment, the CAR comprises the polypeptide sequence shown in SEQ ID NO:1 or SEQ ID NO: 2. Furthermore, the present invention provides compositions and methods for treating, among other diseases, cancer or any malignancy or autoimmune disease in which expression of FRβ is expressed.

In one embodiment, the invention provides a cell (e.g., T cell) engineered to express a chimeric antigen receptor (CAR), wherein the CAR T cell exhibits an antitumor property. A preferred antigen is FRβ. In one embodiment, the antigen recognition domain of the CAR comprises a fully human anti-FRβ antibody. Accordingly, the invention provides a fully human anti-FRβ-CAR engineered into a T cell and methods of their use for adoptive therapy.

In one embodiment, the anti-FRβ-CAR comprises at least one intracellular domain selected from the group of a CD137 (4-1BB) signaling domain, a CD28 signaling domain, a CD3zeta signal domain, and any combination thereof. This is because the present invention is partly based on the discovery that CAR-mediated T-cell responses can be further enhanced with the addition of costimulatory domains.

Chimeric Antigen Receptor (CAR) Composition

The present invention encompasses a recombinant DNA construct comprising sequences of an antibody of the invention that binds specifically to FRβ, in one aspect, human FRβ, wherein the sequence of the antibody or a fragment thereof is operably linked to the nucleic acid sequence of an intracellular domain. The intracellular domain or otherwise the cytoplasmic domain comprises, a costimulatory signaling region and/or a zeta chain portion. The costimulatory signaling region refers to a portion of the CAR comprising the intracellular domain of a costimulatory molecule. Costimulatory molecules are cell surface molecules other than antigen receptors or their ligands that are required for an efficient immune response.

In one embodiment, the present invention encompasses a recombinant DNA construct comprising sequences of a CAR, wherein the sequence comprises the nucleic acid sequence of an FRβ binding domain operably linked to the nucleic acid sequence of an intracellular domain. An exemplary intracellular domain that can be used in the CAR includes but is not limited to the intracellular domain of CD3-zeta, CD28, 4-1BB, and the like. In some instances, the CAR can comprise any combination of CD3-zeta, CD28, 4-1BB, and the like.

In one embodiment, the present invention encompasses an isolated nucleic acid sequence comprising a nucleic acid sequence selected from the group consisting of SEQ ID NO: 1, SEQ ID NO: 3, SEQ ID NO: 5, SEQ ID NO: 7, SEQ ID NO: 9, and SEQ ID NO: 11.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering an antigen binding domain that specifically binds a desired antigen into the CAR. In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal.

In one embodiment, the antigen binding moiety portion of the CAR comprises an antigen binding domain that targets FRβ, including but not limited to human FRβ.

The antigen binding domain can be any domain that binds to the antigen including but not limited to antigen recognition domains derived from any one or more of monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof. Thus, in one embodiment, the antigen biding domain portion comprises a human antibody or a fragment thereof.

In some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

In some embodiments, the antibody is humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the present invention, the ability to bind human FRβ. However, using certain methods of humanization, the affinity and/or specificity of binding of the antibody for human FRβ may be increased using methods of "directed evolution," as described by Wu et al., J. Mol. Biol., 294:151 (1999), the contents of which are incorporated herein by reference herein in their entirety.

In one embodiment, the antigen binding moiety is characterized by particular functional features or properties of an antibody. For example, the antigen binding moiety binds specifically FRβ, including but is not limited to human FRβ. In one embodiment, the invention relates to an antigen binding moiety comprising an antibody or functional fragment thereof, wherein the antibody specifically binds to an FRβ protein or fragment thereof. In one embodiment, the present invention encompasses a CAR comprising an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

In one embodiment, the antibody fragment provided herein is a single chain variable fragment (scFv). In another embodiment, the antibodies of the invention may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)). In one embodiment, the antibodies and fragments thereof of the invention binds an FRβ protein with wild-type or enhanced affinity.

In one embodiment, an antibody of the invention comprises heavy and light chain variable regions comprising amino acid sequences that are homologous to the amino acid sequences of the preferred antibodies described herein, and wherein the antibodies retain the desired functional properties of the anti-FRβ antibodies of the invention.

In some embodiments, the antibody of the invention is further prepared using an antibody having one or more of the VH and/or VL sequences disclosed herein can be used as starting material to engineer a modified antibody, which modified antibody may have altered properties as compared to the starting antibody. In various embodiments, the antibody is engineered by modifying one or more amino acids within one or both variable regions (i.e., VH and/or VL), for example within one or more CDR regions and/or within one or more framework regions.

Transmembrane Domain

With respect to the transmembrane domain, in various embodiments, the CAR is designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the CAR. A glycine-serine doublet provides a particularly suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the cytoplasmic domain of the CAR is designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR of the invention may be linked to each other in a random or specified order. Optionally, a short oligo- or polypeptide linker, for example, between 2 and 10 amino acids in length may form the linkage. A glycine-serine doublet provides a particularly suitable linker.

Hematologic Cancer

Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Examination of peripheral blood smear and bone marrow is diagnostic. Existing treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic.

Remission induction rates range from 50 to 85%. Long-term disease-free survival reportedly occurs in 20 to 40% of patients and increases to 40 to 50% in younger patients treated with stem cell transplantation.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; favorable karyotypes include t(15; 17), t(8;21), and inv16 (p13;q22). Negative factors include increasing age, a preceding myelodysplastic phase, secondary leukemia, high WBC count, and absence of Auer rods.

Initial therapy attempts to induce remission and differs most from ALL in that AML responds to fewer drugs. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

The present invention provides for compositions and methods for treating cancer. In one aspect, the cancer is a hematologic cancer including but is not limited to leukemias (such as acute myelogenous leukemia, chronic myelogenous leukemia, acute lymphoid leukemia, chronic lymphoid leukemia and myelodysplastic syndrome) and malignant lymphoproliferative conditions, including lymphomas (such as multiple myeloma, non-Hodgkin's lymphoma, Burkitt's lymphoma, and small cell- and large cell-follicular lymphoma).

The present invention also provides methods for inhibiting the proliferation or reducing an FRβ-expressing cell population, the methods comprising contacting a population of cells comprising an FRβ-expressing cell with an FRβ CART cell of the invention that binds to the FRβ-expressing cell. In a specific embodiment, the present invention provides methods for inhibiting the proliferation or reducing the population of cancer cells expressing FRBβ, the methods comprising contacting the FRβ-expressing cancer cell population with an FRβ CART cell of the invention that binds to the FRβ-expressing cell. In one embodiment, the T cell has high affinity for FRβ. In another embodiment, the T cell secretes high levels of at least one proinflammatory cytokine, such as IFNγ. In yet another embodiment, the T cell is capable of lysing FRβ+ cells. The lysis of FRβ+ cells is one example of a mechanism by which the T cell eliminates FRβ+ tumor cells.

Moreover, it is useful in the context of the present invention that the T cell has limited toxicity toward healthy cells. By targeting the tumor or diseased cells, the T cell manifests no substantial negative biological effects, antitumor effects, or substantial negative physiological symptoms toward a healthy cell, non-tumor cell, non-diseased cell, non-target cell or population of such cells either in vitro or in vivo.

In another embodiment, the present invention provides methods for inhibiting the proliferation or reducing the population of cancer cells expressing FRβ, the methods comprising contacting the FRβ-expressing cancer cell population with an FRβ CART cell of the invention that binds to the FRβ-expressing cell. In certain embodiments, the FRβ CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with FRB-expressing cells relative to a negative control. In one aspect, the subject is a human.

The present invention also provides methods for preventing, treating and/or managing a disorder associated with FRβ-expressing cells (e.g., a hematologic cancer), the methods comprising administering to a subject in need an FRβ CART cell of the invention that binds to the FRβ-expressing cell. In one aspect, the subject is a human. Non-limiting examples of disorders associated with FRβ-expressing cells include autoimmune disorders (such as lupus), inflammatory disorders (such as allergies and asthma) and cancers (such as hematological cancers).

The present invention also provides methods for preventing, treating and/or managing a disease associated with FRβ-expressing cells, the methods comprising administering to a subject in need an FRβ CART cell of the invention that binds to the FRβ-expressing cell. In one aspect, the subject is a human. Non-limiting examples of diseases associated with FRβ-expressing cells include Acute Myeloid Leukemia (AML), myelodysplasia, B-cell Acute Lymphoid Leukemia, T-cell Acute Lymphoid Leukemia, hairy cell leukemia, blastic plasmacytoid dendritic cell neoplasm, chronic myeloid leukemia, hodgkin lymphoma, and the like.

The present invention provides methods for preventing relapse of cancer associated with FRβ-expressing cells, the methods comprising administering to a subject in need thereof an FRβ CART cell of the invention that binds to the FRβ-expressing cell. In another embodiment, the methods comprise administering to the subject in need thereof an effective amount of an FRβ CART cell of the invention that binds to the FRβ-expressing cell in combination with an effective amount of another therapy.

Targeting Activated Macrophages

The present invention is also partly based on the development of a CAR directed towards FRβ (FRβ CAR) for targeting macrophages, including but are not limited to activated macrophages, M2 tumor associated macrophages (TAMs) that suppress T cell responses, and proinflammatory macrophages that produce TNFα (e.g., in a person with rheumatoid arthritis). Accordingly, the FRβ CAR and cells expressing the FRβ CAR of the invention can be used to treat cancer by targeting anti-inflammatory/regulatory macrophages via FRβ CAR T cells in the tumor microenvironment. In another embodiment, the FRβ CAR and cells expressing the FRβ CAR of the invention can be used to treat diseases associated with proinflammatory macrophages that produce TNFα (e.g., rheumatoid arthritis) by targeting proinflammatory mononuclear cells in the subject thereby providing a clinical benefit.

In one embodiment, the FRβ CAR and cells expressing the FRβ CAR of the invention can be used to treat chronic infections, cancer and autoimmune diseases. In some embodiments, patients suffering from an autoimmune disorder, such as multiple sclerosis (MS), rheumatoid arthritis (RA), inflammatory bowel disease, psoriasis and Systemic Lupus Erythematosus (SLE), are treated by administering FRβ CAR T cells of the invention to the patent in need thereof.

(TAMs) are known to be important for tumor growth. TAMs originate from circulating monocytes and their recruitment into tumors is driven by tumor-derived chemotactic factors. TAMs promote tumor cell proliferation and metastasis by secreting a wide range of growth and proangiogenic factors. Consequently, many tumors with a high number of TAMs have an increased tumor growth rate, local proliferation and distant metastasis. In fact, the extent of TAM infiltration has been used as an inverse prognostic predictor in breast cancer, head and neck cancer, prostate and uterine cancer (R. D. Leek, R. Landers, S. B. Fox, F. Ng, A. L. Harris, C. E. Lewis, British journal of cancer 1998, 77, 2246; M. R. Young, M. A. Wright, Y. Lozano, M. M. Prechel, J. Benefield, J. P. Leonetti, S. L. Collins, G. J. Petruzzelli, International Journal of Cancer 1997, 74, 69; I. F. Lissbrant, P. Stattin, P. Wikstrom, J. E. Damber, L. Egevad, A. Bergh, International journal of oncology 2000, 17, 445; H. B. Salvesen, L. A. Akslen, International Journal of Cancer 1999, 84, 538). TAMs are also prominent in tumor tissues, comprising up to 80% of the cell mass in breast carcinoma.

In one embodiment, the invention provides methods of reducing tumor associated macrophages and methods of treating cancer with the FRβ CAR and cells expressing the FRβ CAR of the invention. The compositions of the invention can be used to target TAMs, thereby being able to reduce the density of TAMs in vitro and in vivo and reduce tumor growth in vivo as measured by tumor volume.

In one embodiment, the invention relates to a method of inhibiting tumor growth or tumor metastases in a mammal in need thereof comprising targeting TAMs using the FRβ CAR and cells expressing the FRβ CAR of the invention. In one embodiment, the method includes targeting TAM subpopulations linked to different intratumoral regions, such as hypoxic or normoxic regions of a solid tumor.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1a promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62L$^{hi}$, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun.

73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one embodiment, the invention pertains to a vector comprising an FRβ CAR operably linked to promoter for expression in mammalian T cells. In one embodiment, the invention provides a recombinant T cell expressing the FRβ CAR for use in treating FRβ-expressing tumors, wherein the recombinant T cell expressing the FRβ CAR is termed an FRβ CART. In one embodiment, the FRβ CART of the invention is capable of contacting a tumor cell with at least one FRβ CAR of the invention expressed on its surface such that the FRβ CART is activated in response to the antigen and the CART targets the tumor cell and growth of the tumor is inhibited.

In one embodiment, the invention pertains to a method of inhibiting growth of an FRβ-expressing tumor cell, comprising contacting the tumor cell with an anti-FRβ CAR T cell of the present invention such that the CART is activated in response to the antigen and targets the cancer cell, wherein the growth of the tumor is inhibited.

In another aspect, the invention pertains to a method of treating cancer in a subject. The method comprises administering to the subject an anti-FRβ CAR T cell of the present invention such that the cancer is treated in the subject. An example of a cancer that is treatable by the anti-FRβ CAR T cell of the invention includes but is not limited to AML, myelodysplastic syndrome, ALL, hairy cell leukemia, Pro-lymphocytic leukemia, Chronic myeloid leukemia, Hodgkin lymphoma, Blastic plasmacytoid dendritic cell neoplasm, and the like.

The present invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the CAR transduced T cells exhibit specific proinflammatory cytokine secretion and potent cytolytic activity in response to human cancer cells expressing the FRβ, resist soluble FRβ inhibition, mediate bystander killing and mediate regression of an established human tumor. For example, antigen-less tumor cells within a heterogeneous field of FRβ-expressing tumor may be susceptible to indirect destruction by FRβ-redirected T cells that has previously reacted against adjacent antigen-positive cancer cells.

In one embodiment, the fully-human CAR-modified T cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with expression of FRβ. In certain embodiments, the cells of the invention are used in the treatment of patients at risk for developing diseases, disorders and conditions associated with expression of FRβ. Thus, the present invention provides methods for the treatment or prevention of diseases, disorders and conditions associated with expression of FRβ comprising administering to a subject in need thereof, a therapeutically effective amount of the CAR-modified T cells of the invention. An example of a diseases, disorders and conditions associated with expression of FRβ includes but is not limited to AML, myelodysplastic syndrome, ALL, hairy cell leukemia, Pro-lymphocytic leukemia, Chronic myeloid leukemia, Hodgkin lymphoma, Blastic plasmacytoid dendritic cell neoplasm, and the like.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Targeting FRβ for CAR T Cell Therapy of Acute Myeloid Leukemia

Figure 1A:
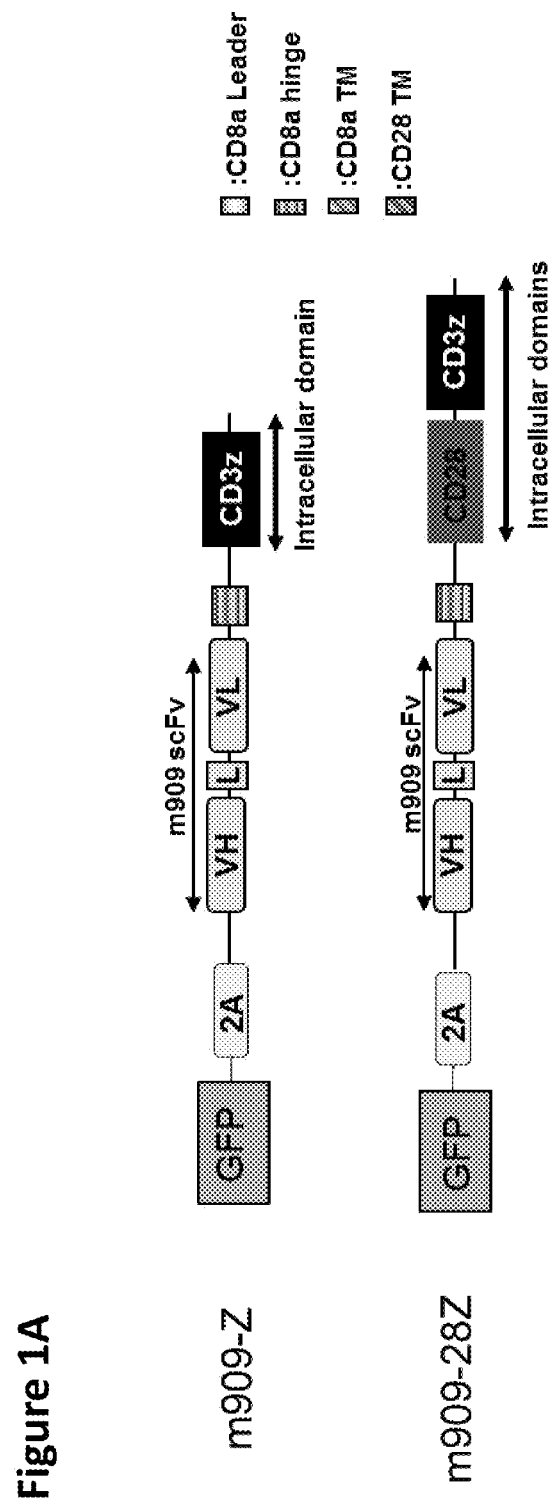
FIG. 1A is a schematic of the lentiviral constructs demonstrating the generation of anti-FRβ (m909) CAR and expression on lentivirally transduced T lymphocytes.
Figure 1B:
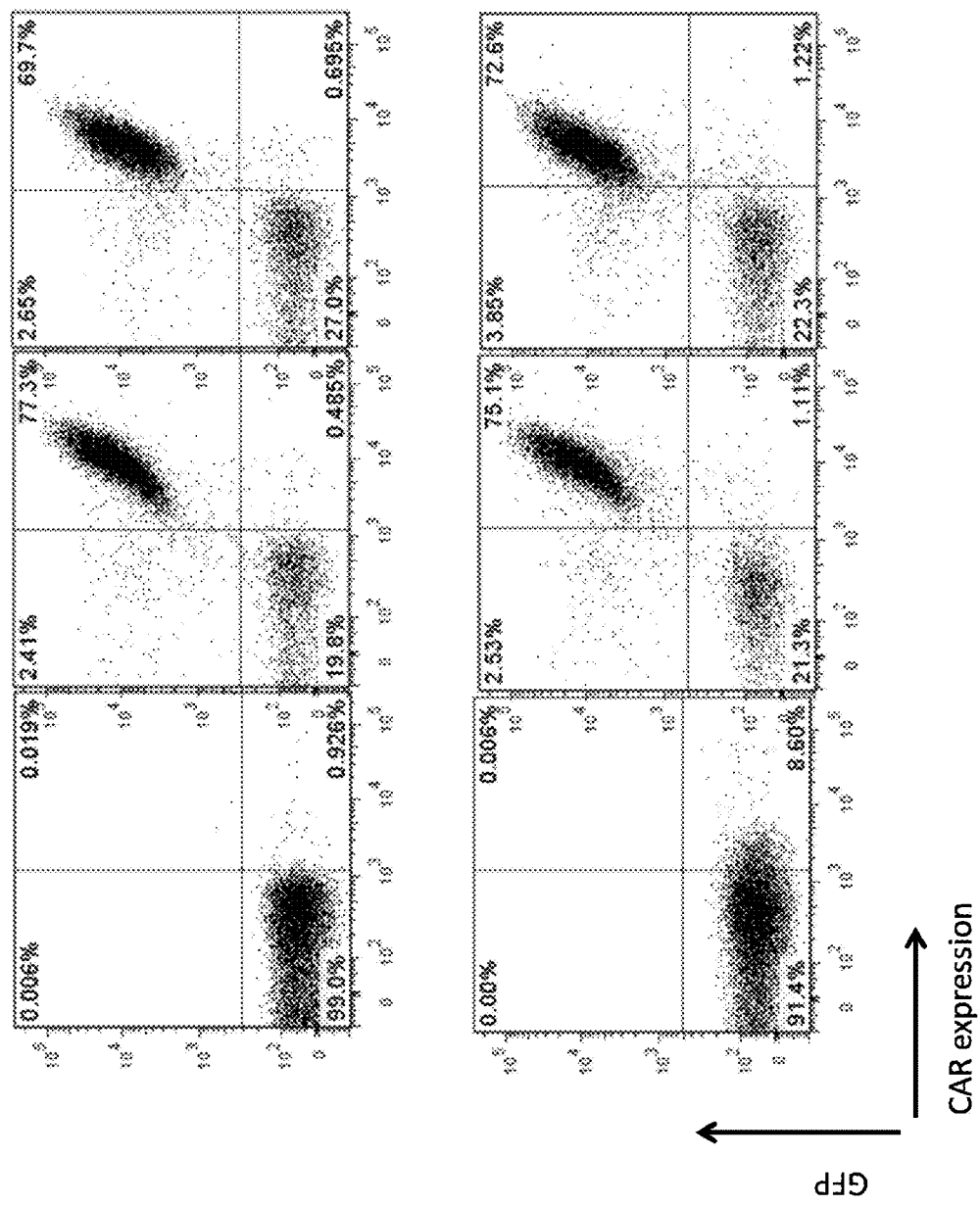
FIG. 1B is an image demonstrating the transduction of primary human T cells.

The results presented herein demonstrate the development of a CAR directed towards FRβ for the targeting of AML. Briefly, the m909 scFv specific for human FRβ was cloned into a lentiviral backbone containing CD3ζ and CD28 intracellular domains (FIG. 1A). High transduction of human CD4 and CD8 T cells was confirmed using GFP and an antibody specific for human IgG (FIG. 1B).

To assess the antigen-specific functional capability of the m909 CAR, the FRβ-negative human ovarian cancer cell line C30 was transduced with human FRβ cDNA (FIG. 2A). m909 CAR transduced T cells exhibited selective activation, proinflammatory cytokine secretion, and proliferation when co-cultured with FRβ+ C30 cells, but not parental C30 cells. m909 CAR T cells also mediated the specific lysis of FRβ+

C30 cells in a dose dependent manner. To assess the functionality of m909 CAR T cells in a more physiologically relevant model, human AML cell lines with and without FRβ expression were acquired. m909 CAR T cells showed specific reactivity towards the FRβ+ AML line THP1 but not HL60, which lacks detectable FRβ expression. Despite its broad expression in AML, FRβ antigen expression on AML cells is generally low and could present a potential obstacle to FRβ-mediated CAR therapy. However, treatment of AML cells with all-trans retinoic acid (ATRA), a vitamin A derivative currently part of standard of care regimens for AML subclass M3 (or APL), enhanced the intensity of FRβ expression, resulting in increased immune recognition by m909 CAR T cells.

Figure 2B:
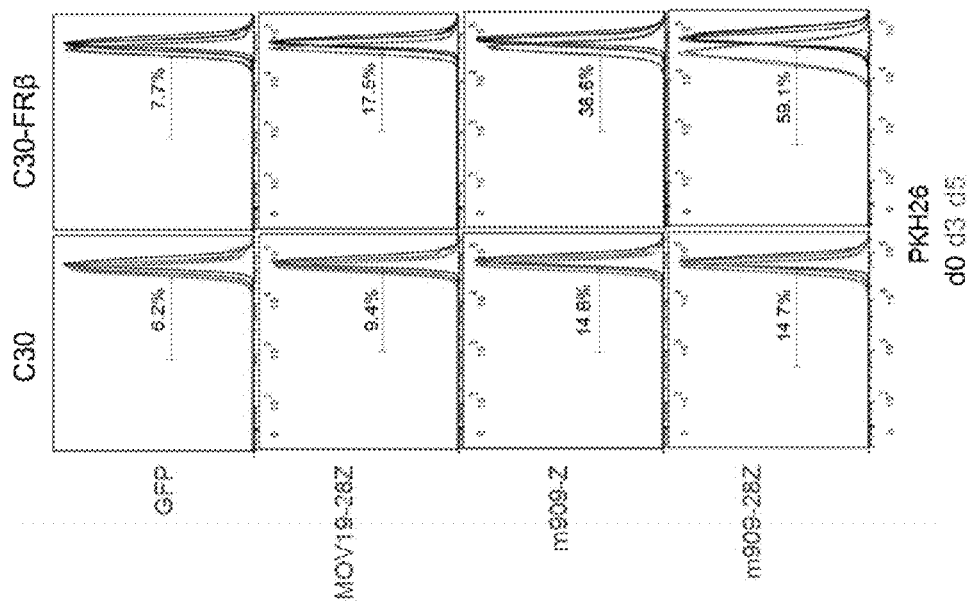
FIG. 2B shows antigen specific induction of proliferation of FRb CAR T cells.
Figure 2A:
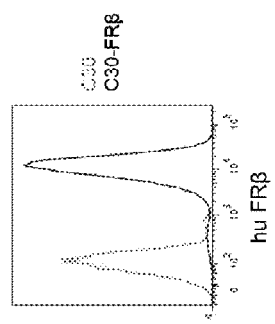
FIG. 2A is an image demonstrating the generation of C30-FRβ cells and that m909 CAR T cells exhibit specific reactivity against engineered FRβ positive C30 cells.
Figure 2C:
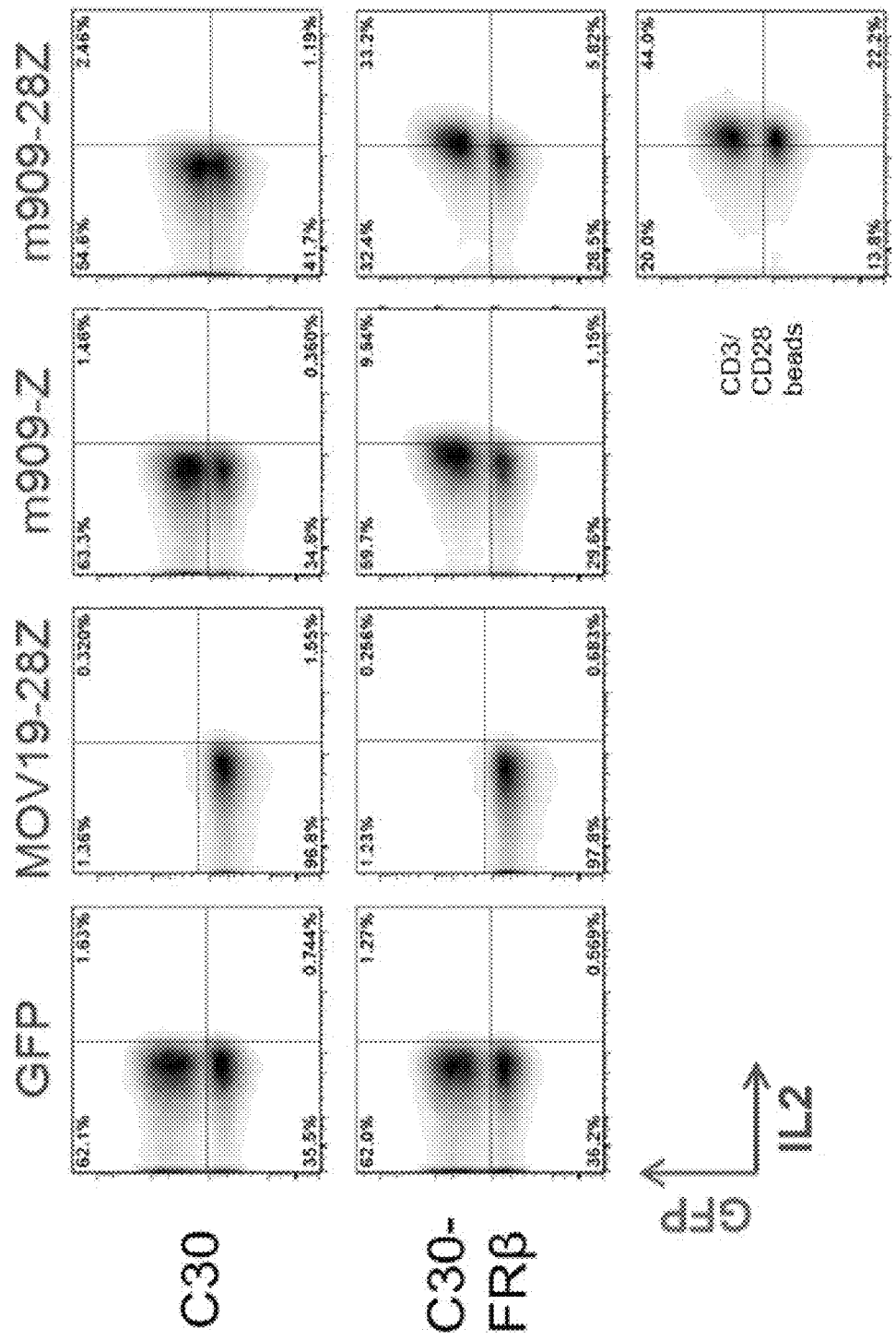
FIG. 2C is a panel of flow graphs showing the levels of intracellular cytokine, IL-2, by FRb CAR T cells after antigen stimulation.
Figure 2D:
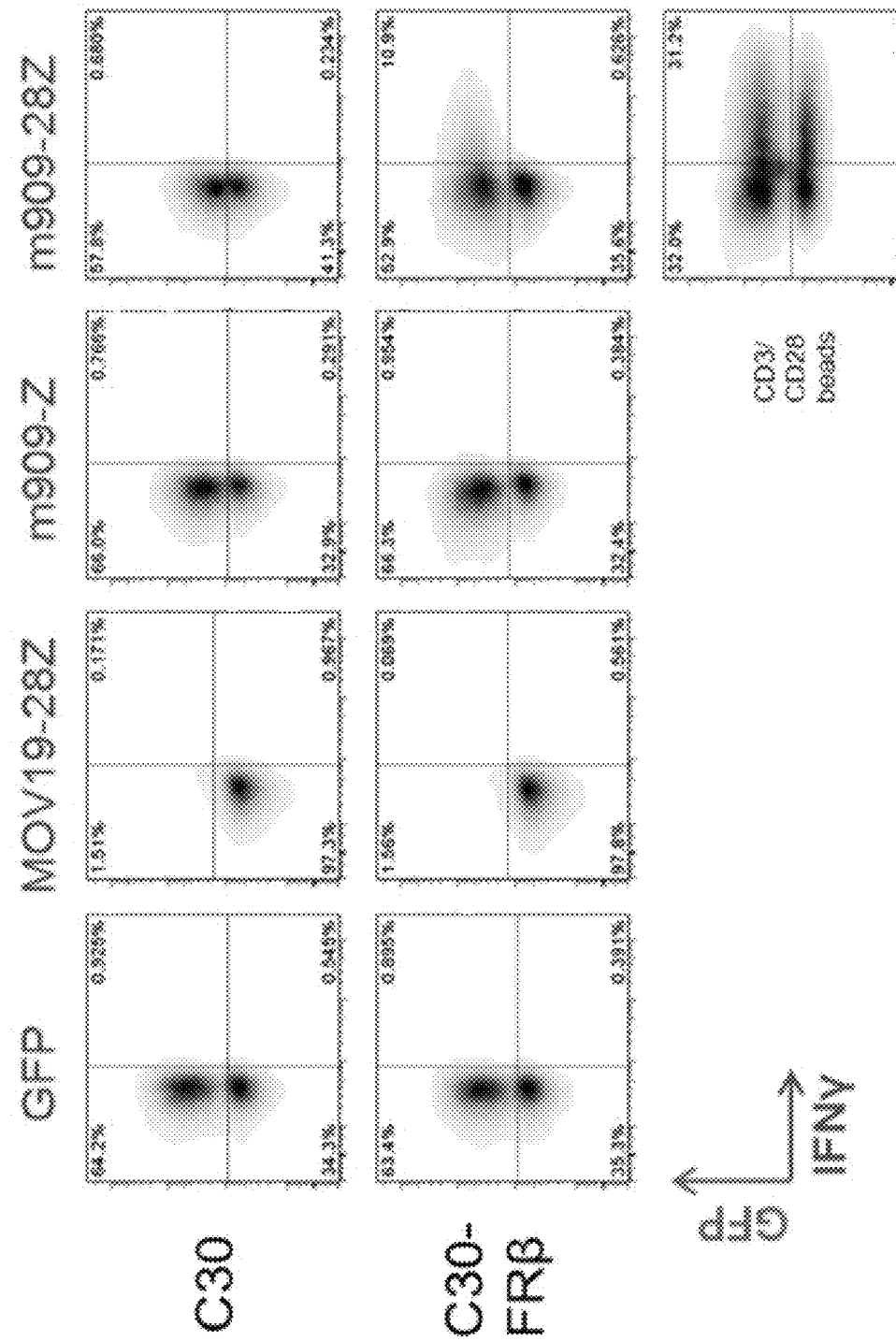
FIG. 2D is a panel of flow graphs showing the levels of intracellular cytokine, IFN-γ, by FRb CAR T cells after antigen stimulation.
Figure 2E:
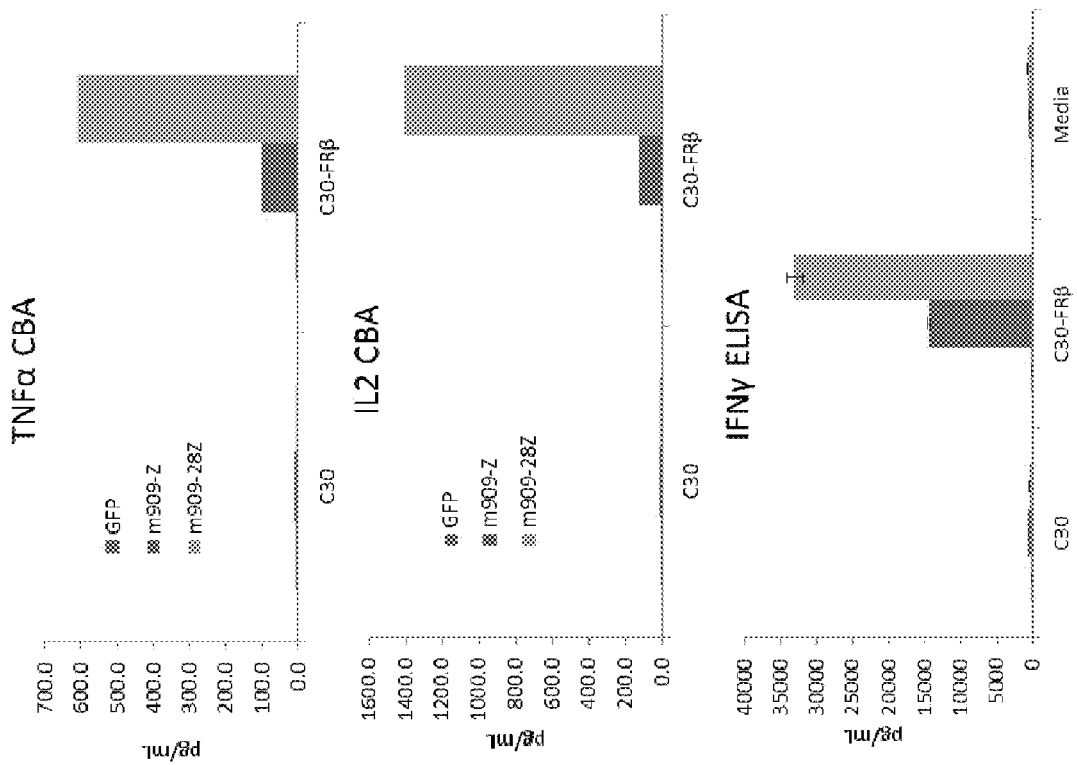
FIG. 2E is a panel of graphs showing the levels of cytokine secretion.
Figure 2F:
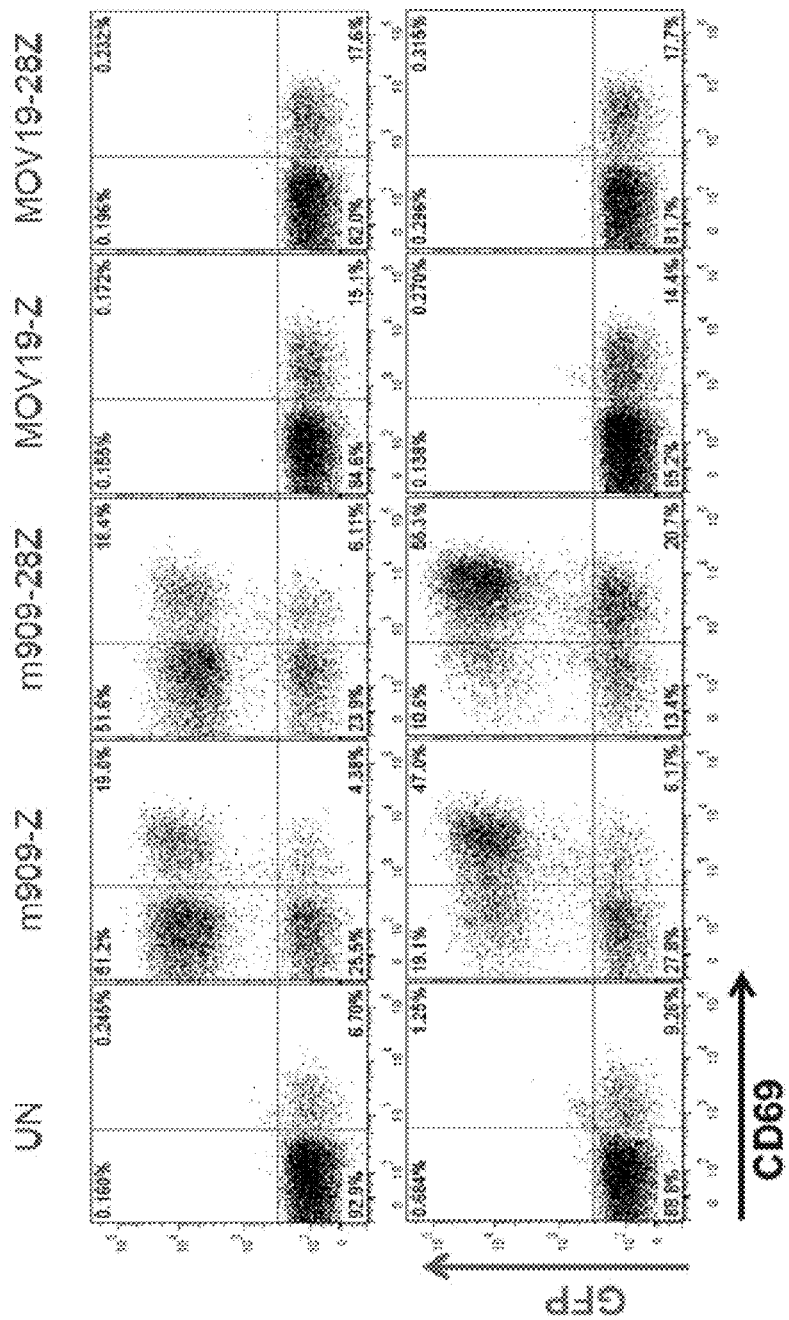
FIG. 2F is a panel of flow graphs showing the expression of CD69.
Figure 2G:
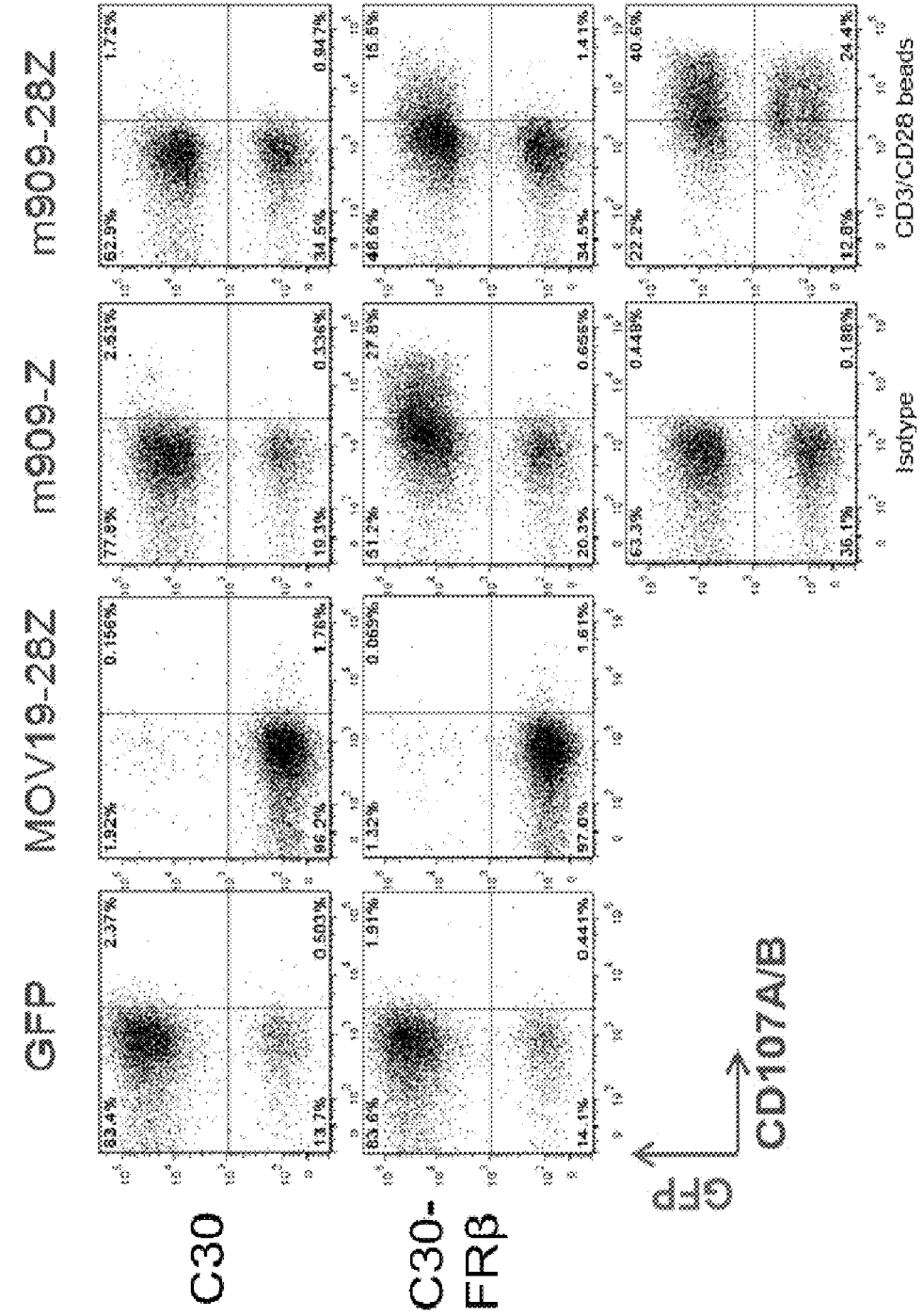
FIG. 2G is a panel flow graphs showing expression of CD107A/B.
Figure 2I:
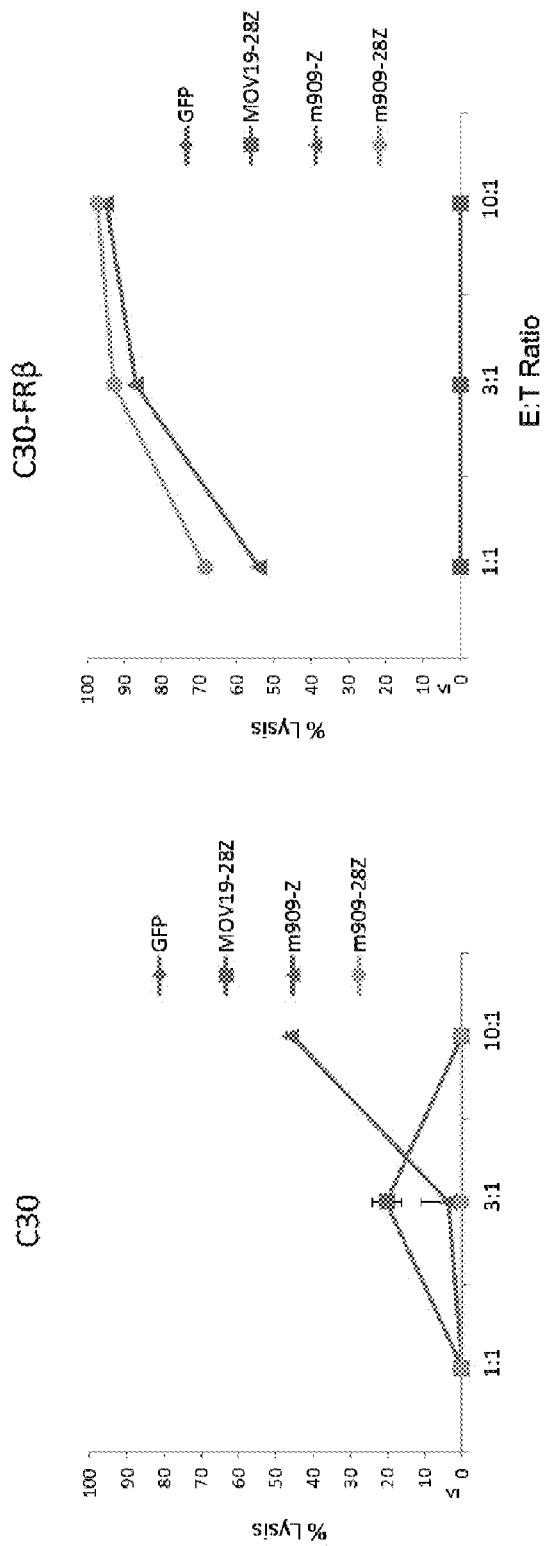
FIG. 2I is a panel of graphs showing lysis of target cells in an antigen-specific manner.

The results presented herein demonstrate that T cells were genetically modified to express an anti-human FRβ CAR using the m909 scFv linked to intracellular CD3 and CD28 (FIG. 2C). It was observed that m909 CAR T cells proliferate (FIG. 2B), secrete proinflammatory cytokines (FIGS. 2C, 2D and 2E), upregulate activation marker CD69 (FIG. 2F), degranulate (FIGS. 2G and 2H), and mediate lysis of target cells in an antigen-specific manner (FIG. 2H).

Figure 3A:
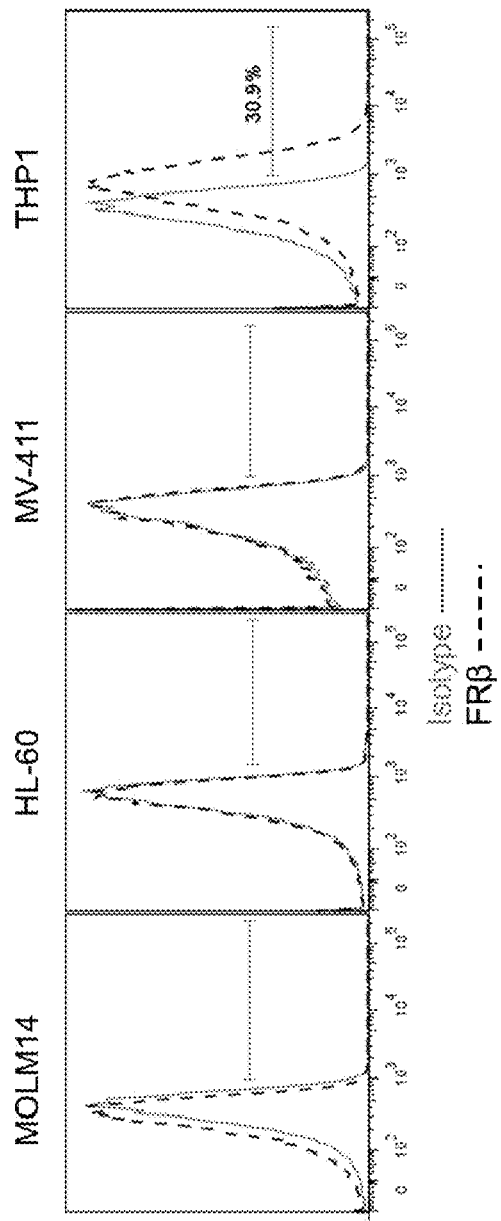
FIG. 3A is a panel of images showing FRβ expression on established human AML cell lines.
Figure 3B:
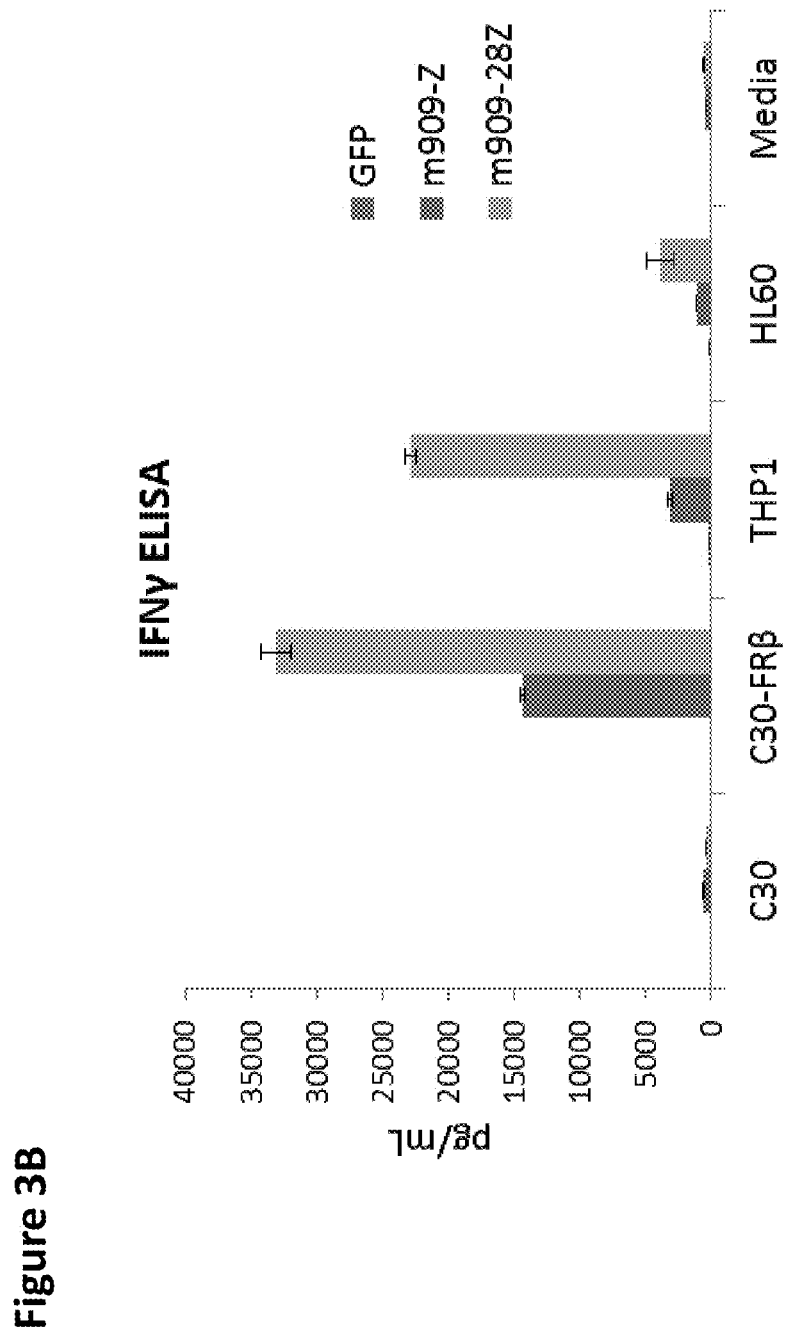
FIGS. 3B-3D demonstrate that m909 CAR T cells recognize endogenous FRβ expression on human AML cell lines.
Figure 3D:
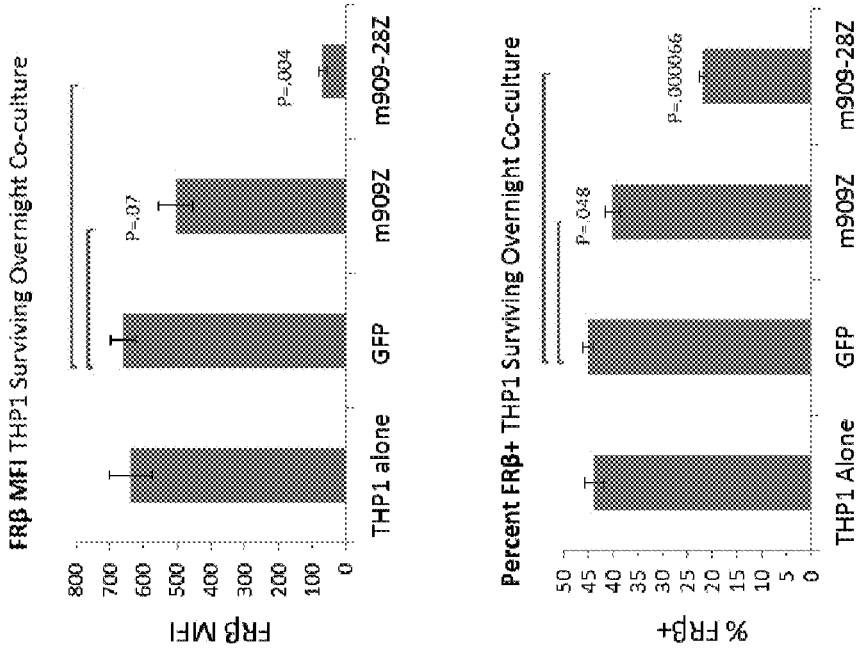
Figure 3C:
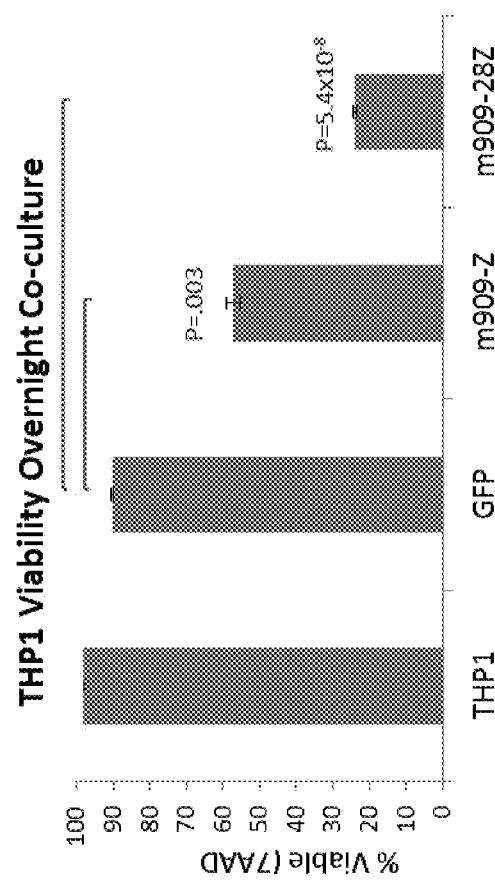
Figure 4B:
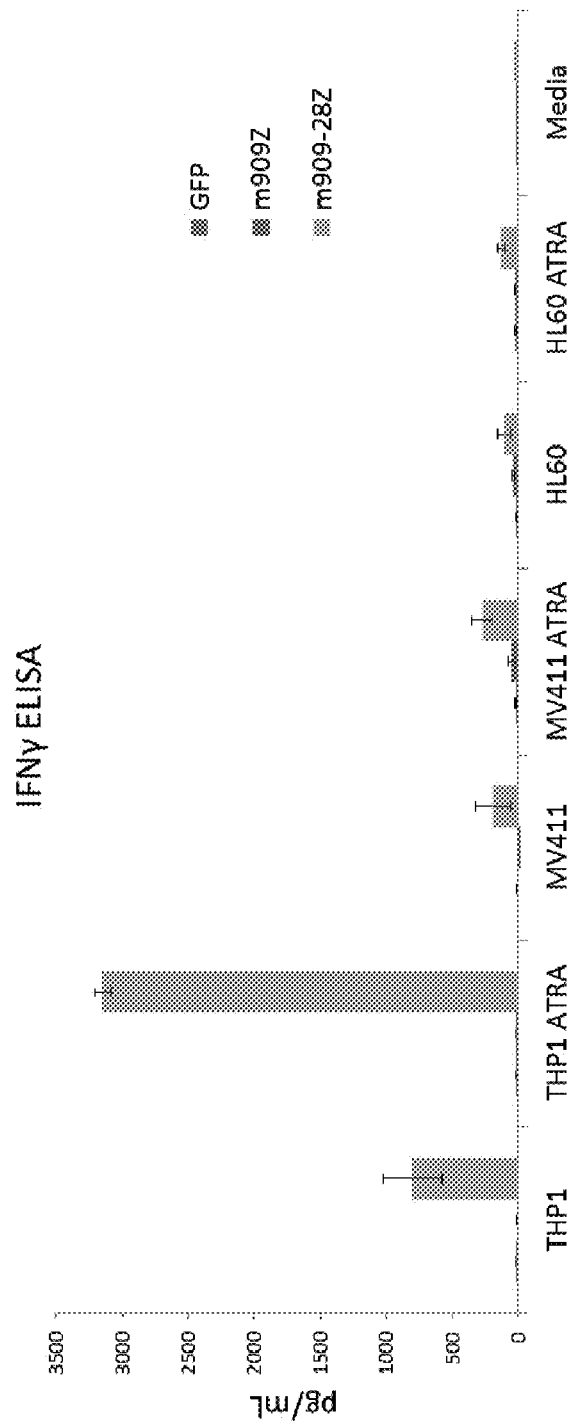
FIG. 4B is an image demonstrating that ATRA pretreatment of human AML enhances FRβ-mediated m909 CAR T cell recognition and IFNγ secretion.

FRβ is expressed on a subset of human AML cell lines and primary samples (FIG. 3A). It was observed that endogenous FRβ on AML cell line THP1 can trigger activation of m909 CAR T cells (FIGS. 3B, 3C and 3D). All-trans retinoic acid (ATRA) induced enhanced surface expression of FRβ on AML line THP1 (FIG. 4A). m909 CAR T cells exhibit enhanced recognition of ATRA-treated THP1 and enhanced IFNγ secretion (FIG. 4B). Without wishing to be bound by any particular theory, it is believed that that m909 CAR T cells are effective in eradicating human AML. This activity may be enhanced by co-treatment with ATRA.

Example 2

FRβ CAR T Cell Mediated Immune Attack of Proinflammatory Monocytes: Application for Use in Rheumatoid Arthritis and Immunomodulation of the Tumor Microenvironment Beyond AML, folate receptor beta (FRβ) expression is also detected on proinflammatory macrophages within rheumatoid arthritis synovial tissues (Nagayoshi et al., 2005 Arthritis Rheum, 52:2666-75). By antibody based detection, FRβ-expressing cells were not present in peripheral blood leukocytes and their activated cells. In all tissues examined, most FRβ-expressing cells were CD163+ macrophages. An anti-FRb immunotoxin significantly induced the apoptosis of FRβ-transfected macrophages and adherent rheumatoid arthritis (RA) synovial mononuclear cells and inhibited TNFα production by adherent RA synovial mononuclear cells. These results suggest that targeted elimination of proinflammatory mononuclear cells in rheumatoid arthritis may provide clinical benefit.

Additionally, experiments were designed to evaluate whether targeted elimination of anti-inflammatory/regulatory macrophages via FRβ CAR T cells in the tumor microenvironment would invigorate anti-tumor immune responses. FRβ CAR T cells were tested for their capacity to recognize and respond to FRβ+ monocytes. As previously reported (Puig-Kroger et al., 2009 Cancer Res. 69:9395-403), it was observed that FRβ was induced upon in vitro monocyte differentiation in the presence of 10 ng/mL M-CSF over the course of 7 days (FIG. 5A). FRβ expression was assessed with biotin-labeled m909 IgG (black dotted line) and biotin-human IgG isotype control (solid dark grey line) followed by SA-APC. Also shown is unstained (solid light grey line) and SA-APC only (grey dashed line). Gates represent the percentage of cells shift compared to isotype. Shown here are results from two independent donors (healthy donor ND340 and ovarian cancer patient UPCC-19809-305).

Figure 5B:
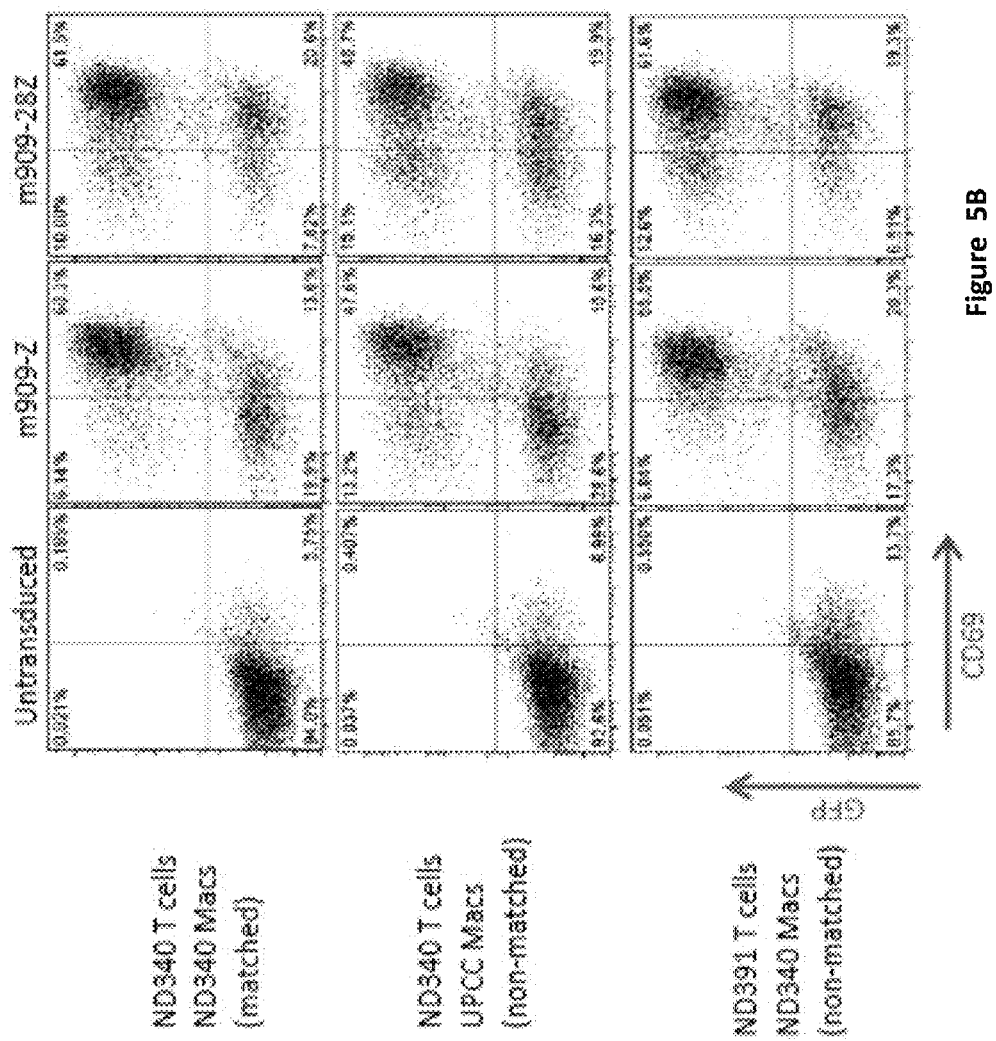
FIG. 5B is an image showing that day 8 M-CSF differentiated macrophages induced CD69 expression on FRβ CAR T cells therefore demonstrating that FRβ CAR T cells were activated upon encounter with FRβ expressing macrophages.

Day 8 M-CSF differentiated macrophages (from FIG. 5A) were co-cultured with m909 FRβ CAR transduced human T cells overnight at 1:1 ratio. Untransduced T cells were used as a control. After 24 hr, T cells were stained for surface expression of the activation induced molecule CD69 and assessed by flow (FIG. 5B). GFP was used as a marker for the m909 CAR+ T cells. CAR T cells were derived from two different healthy donors. ND340 was chosen to assess the effects of autologous versus allogeneic CAR T cell/Macrophage interactions. Both allogeneic (unmatched) and autologous (matched) donor macrophages induce CD69 expression on m909 CAR T cells. CD69 was preferentially expressed by CAR+ (GFP+) T cells while untransduced T cells exhibited no significant upregulation of CD69 after culture with allogeneic or autologous macrophages. Thus, FRβ CAR T cells were activated upon encounter with FRβ expressing macrophages.

Figure 5C:
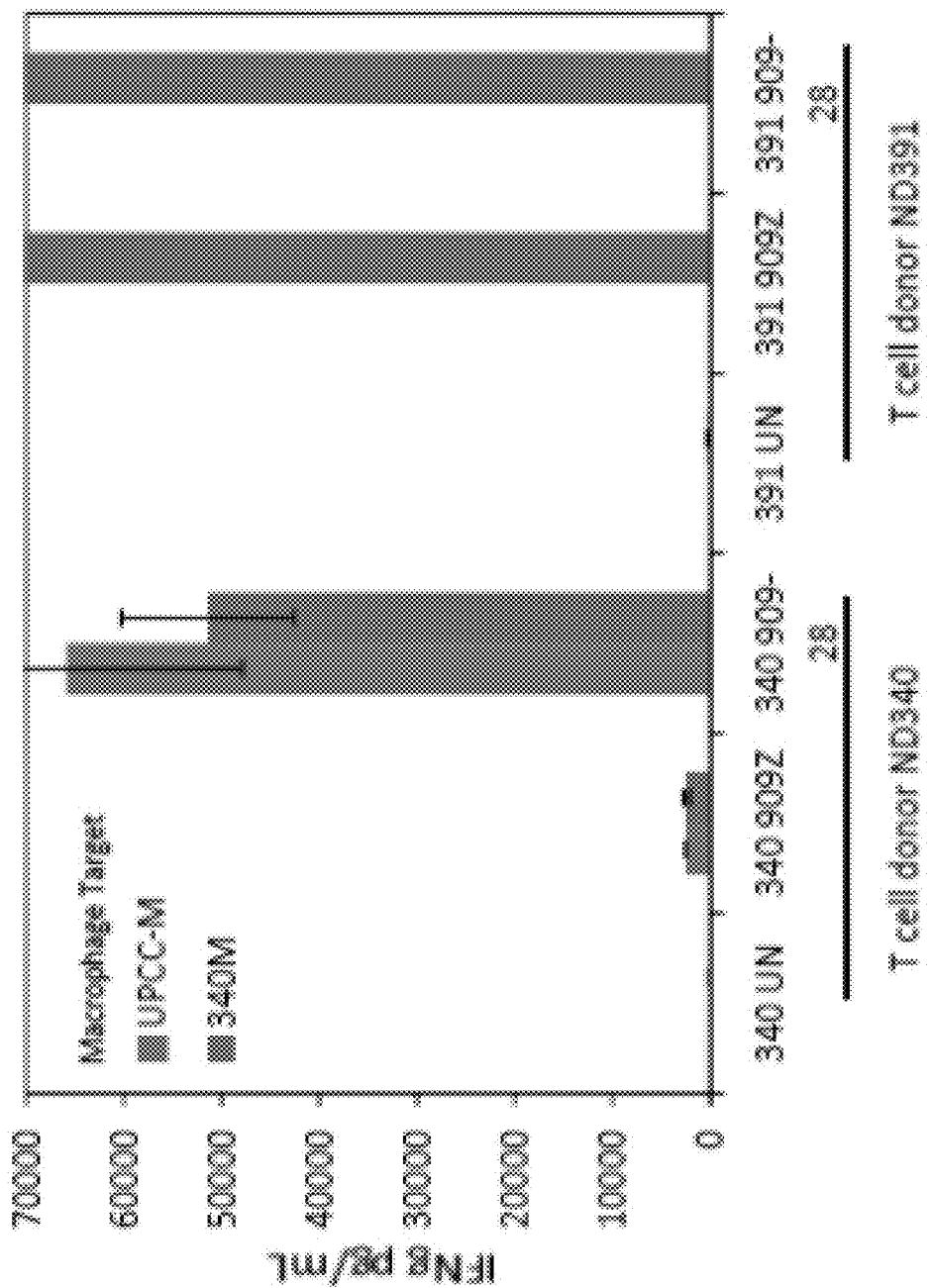
FIG. 5C is an image demonstrating that high levels of IFNγ were secreted by FRβ CAR T cells exposed to either allogeneic or autologous M-CSF-differentiated macrophages.

After 24 hrs in co-culture, culture supernatants from the above assays were removed for measurement of T cell IFNγ production in response to FRβ macrophages via ELISA (FIG. 5C). High levels of IFNγ were secreted by m909 CAR T cells exposed to either allogeneic or autologous M-CSF-differentiated macrophages. Untransduced T cells did not produce IFNγ. CD28-costimulated CARs were able to secrete higher IFNγ secretion as compared to CARs bearing TCR CD3Z domain alone. No significant differences were seen in IFNγ production by ND340 CAR T cells in response to auto (ND340-M) vs allo (UPCC-M) macrophages, indicating that responses were not allogeneic in nature and that CAR redirection is functional in both the allogeneic and autologous settings. In this line, Unmatched ND391 m909 CAR T cells also produced high levels of IFNγ in response to allogeneic ND340M macrophages. No IFNγ was produced from either T cells or macrophages in culture alone (data not shown). The results presented herein demonstrate that that FRβ+ MCSF-differentiated macrophages activate allogeneic and autologous donor m909 T cells, and this activation is CAR-dependent.

Example 3 m909-Z CAR Sequences (Nucleic Acid Sequence is
SEQ ID NO: 1, Amino Acid Sequence SED ID
NO: 2)

```
              M  A  L  P  V  T  A •
5501          ATGGCCTTAC CAGTGACCGC              CD8a Leader
              TACCGGAATG GTCACTGGCG

• L  L  L  P  L  A  L  L  L  H  A  A  R  P  G  S  A •
5551   CTTGCTCCTG CCGCTGGCCT TGCTGCTCCA CGCCGCCAGG CCGGGATCAG
       GAACGAGGAC CGCGACCGGA ACGACGAGGT GCGGCGGTCC GGCCCTAGTC

• E  V  Q  L  V  Q  S  G  A  E  V  K  K  P  G  A
5601    CCGAAGTGCA GCTGGTGCAG TCTGGGGCTG AGGTGAAGAA GCCTGGGGCC
        GGCTTCACGT CGACCACGTC AGACCCCGAC TCCACTTCTT CGGACCCCGG

S  V  K  V     S  C  K     A  S  G     Y  T  F  T     S  Y  A •
5651 TCAGTGAAGG TTTCCTGCAA CGCTTCTGGA TACACCTTCA CTAGCTATGC
     AGTCACTTCC AAAGGACGTT CGAAGACCT ATGTGAAGT GATCGATACG

• M  H  W     V  R  Q  A     P  G  Q     R  L  E     W  M  G  W •
5701   TATGCATTGG GTGCGCCAGG CCCCCGGACA AAGGCTTGAG TGGATGGGAT        m909 vHC
       ATACGTAACC CACGCGGTCC GSGGGCCTGT TTCCGAACTC ACCTACCCTA

• I  N  A     G  N  G     N  T  K  Y     S  Q  K     F  Q  G
5751   GGATCAACGC TGGCAATGGT AACACAAAAT ATTCACAGAA GTTCCAGGGC
       CCTAGTTGCG ACCGTTACCA TTGTGTTTTA TAAGTGTCTT CAAGGTCCCG

R  V  T  I     T  R  D     T  S  A     S  T  A  Y     M  E  L •
5801 AGAGTCACCA TTACCAGGCA CACATCCGCG AGCACAGCCT ACATGGAGCT
     TCTCAGTGGT AATGGTCCCT GTGTAGGCGC TCGTGTCGGA TGTACCTCGA

• S  S  L     R  S  E  D     T  A  V     Y  Y  C     A  R  D  I •
5851   GAGCAGCCTG AGATCTGAAG ACACGGCTGT GTATTACTGT GCGAGAGACA
       CTCGTCGGAC TCTAGACTTC TGTGCCGACA CATAATGACA CGCTCTCTGT

• S  Y  G     S  F  D     Y  W  G  Q     G  T  L     V  T  V
5901   TCAGCTATGG TTCGTTTGAC TACTGGGGCC AGGGAACCCT GGTCACCGTC
       AGTCGATACC AAGCAAACTG ATGACCCCGG TCCCTTGGGA CCAGTGGCAG

S  S  G  G     G  G  S     G  G  G     G  S  G  G     G  G  S •
5951 TCCTCAGGTG GAGGCGGTTC AGGCGGAGGT GGCTCTGGCG GTGGCGGATC
     AGGAGTCCAC CTCCGCCAAG TCCGCCTCCA CCGAGACCGC CACCGCCTAG        m909 Linker

• S  S  E     L  T  Q  D     P  A  V     S  V  A     L  G  Q  T •
6001   ATCTTCTGAG CTGACTCAGG ACCCTGCTGT GTCTGTGGCC TTGGGACAGA
       TAGAAGACTC GACTGAGTCC TGGGACGACA CAGACACCGG AACCCTGTCT

• V  R  I     T  C  Q     G  D  N  L     R  S  Y     Y  A  S
6051   CAGTCAGGAT ACACATGCCA GGAGACAACC TCAGAAGCTA TTATGCAAGC
       GTCAGTCCTA GTGTACGGTT CCTCTGTTGG AGTCTTCGAT AATACGTTCG

W  Y  R  Q     K  S  G     Q  A  P     V  L  V  I     Y  G  K •
6101 TGGTACCGGC AGAAGTCAGG ACAGGCCCCT GTACTTGTCA TCTATGGTAA
     ACCATGGCCG TCTTCAGTCC TGTCCGGGGA CATGAACAGT AGATACCATT        m909 vLC

• N  N  R     P  S  G  I     P  D  R     F  S  H     S  S  S  G •
6151   AAACAACCGG CCCTCAGGGA TCCCAGACCG ATTCTCTGGC TCCAGCTCAG
       TTTGTTGGCC GGGAGTCCCT AGGGTCTGGC TAAGAGACCG AGGTCGAGTC

• N  T  A     S  L  T     I  T  A  A     Q  A  E     D  E  A
6201   GAAACACAGC TTCCTTGACC ATCACTGCGG CTCAGGCGGA AGATGAGGCT
       CTTTGTGTCG AAGGAACTGG TAGTGACGCC GAGTCCGCCT TCTACTCCGA

D  Y  Y  C     H  S  R     K  S  R     G  N  H  L     L  F  G •
6251 GACTATTACT GTCACTCCCG GAAAAGCCGC GGTAACCATC TGCTATTCGG
     CTGATAATGA CAGTGAGGGC CTTTTCGGCG CCATTGGTAG ACGATAAGCC

• G  G  T     K  L  T  V     L  G  Q     A  S  T     T  T  P  A •
6301   CGGAGGGACC AAGCTGACCG TCCTAGGCCA GGCTAGCACC ACGACGCCAG
       GCCTCCCTGG TTCGACTGGC AGGATCCGGT CCGATCGTGG TGCTGCGGTC
```

```
          • P  R  P    P  T  P    A  P  T  I    A  S  Q    P  L  S
     6351 CGCCGCGACC ACCAACACCG GCGCCCACCA TCGCGTCGCA GCCCCTGTCC
          GCGGCGCTGG TGGTTGTGGC CGCGGGTGGT AGCGCAGCGT CGGGGACAGG

L  R  P  E    A  C  R    P  A  A    G  G  A  V    H  T  R •
     6401 CTGCGCCCAG AGGCGTGCCG GCCAGCGGCG GGGGGCGCAG TGCACACGAG
          GACGCGGGTC TCCGCACGGC CGGTCGCCGC CCCCCGCGTC ACGTGTGCTC

• G  L  D    F  A  C  D    I  Y  I    W  A  P    L  A  G  T •
     6451 GGGGCTGGAC TTCGCCTGTG ATATCCACAT CTGGACGCCC TTGGCCGGGA
          CCCCGACCTG AAGCGGACAC TATAGATGTA GACCTGCGGG AACCGGCCCT

• C    G  V    L  L  L    S  L  V  I    T  L  Y    C  R  V
     6501 CTTGTGGGGT CCTTCTCCTG TGACTGCTTA TCACCCCTTA CTGCAGAGTG
          GAACACCCGA CCAAGACCAC AGTGACCAAT AGTGCAACAT GACGTCTCAC
```
CD8a Hinge CD8a Transmembrane

```
          K  F  S  R    S  A  D    A  P  A    Y  Q  Q  G    Q  N  Q •
     6551 AAGTTCAGCA GGAGCGCAGA CGCCCCCGCG TACCAGCAGG GCCAGAACCA
          TTCAAGTCGT CCTCGCGTCT GCGGGGGCGC ATGGTCGTCC CGGTCTTGGT

• L  Y  N    E  L  N  L    G  R  R    E  E  Y    D  V  L  D •
     6601 CCTCTATAAC GAGCTCAATC TACGACCAAG ACACGAGTAC CATGTTTTGG
          CGAGATATTG CTCGAGTTAG ATCCTGCTTC TCTCCTCATG CTACAAAACC

• K  R  R    G  R  D    P  E  M  G    G  K  P    R  R  K
     6651 ACAAGAGACG TGGCCGGGAC GCTGAGATGG GGGGAAAGCC GAGAAGGAAG
          TGTTCTCTGC ACCGGCCCTG CGACTCTACC CCCCTTTCGG CTCTTCCTTC

N  P  Q  E    G  L  Y    N  E  L    Q  K  D  K    M  A  E •
     6701 AACCCTCAGG AAGGCGTGTA CAATGAACTG CAGAAAGATA AGATGCCGCA
          TTGGGAGTCC TTCCGCACAT GTTACTTGAC GTCTTTCTAT TCTACGGCGT

• A  Y  S    E  I  G  M    K  G  E    R  R  R    G  K  G  H •
     6751 GCCCTACAGT CACATTCGCA TCAAACGCGA CCCCCGCACG GCCAACGCGC
          CGGGATGTCA GTGTAAGCGT AGTTTGCGCT GGGGGCGTGC CGGTTGCGCG

• D  G  L    Y  Q  G    L  S  T  A    T  K  D    T  Y  D
     6801 ACGATGGCCT TTACCAGGGT CTCAGTACAG CCACCAAGGA CACCTACGAC
          TGCTACCGGA AATGGTCCCA GAGTCATGTC GGTGGTTCCT GTGGATGCTG

A  L  H  M    Q  A  L    P  P  R    *
     6851 GCCCTTCACA TGCAGGCCCT GCCCCCTCGC TAA
          CGGGAAGTGT ACGTCCGGGA CGGGGAGCG ATT
```
CD3 Zeta

Example 4 m909-28Z CAR Sequence (Nucleic Acid Sequence is SEQ ID NO: 3, Amino Acid Sequence SED ID NO: 4)

```
             M   A  L  P   V  T  A   L  L  L   P •
6301         A TGGCCTTACC AGTGACCGCC TTGCTCCTGG
             A ACCGGAATGG TCACTGGCGG AACGAGGACG    [CD8a Leader]

• L  A  L   L  L  H   A  A  R   P  G  S   A  E  V  Q
6351   CGCTGGCCTT GCTGCTCCAC GCCGCCAGGC CGGGATCAGC CGAAGTGCAG
       GCGACCGCAA CGACCACGTG CGGCGGTCCG GCCCTAGTCG GCTTCACCTC

L  V  Q  S   G  A  E   V  K  K   P  G  A   S  V  K  V •
6401 CTCGTGCACT CTGCGCCTGA CGTGAACAAG CCTCGCGCCT CACTCAAGGT
     GACCACGTCA GACCCCGACT CCACTTCTTC GGACCCCGGA GTCACTTCCA

• S  C  K   A  S  G  Y   T  F  T   S  Y  A   M  H  W  V •
6451   TTCCTGCAAG GCTTCTGGAT ACACCTTCAC TAGCTATGCT ATGCATTGGG
       AAGGACGTTC CCAAGACCTA TGTGGAAGTG ATCCATACGA TACGTAACCC

• R  Q  A   P  G  Q   R  L  E  W   M  G   W  I  N  A
6501 TGCGCCAGGC CCCCGGACAA AGGCTTGAGT GGATGGGATG GATCAACGCT     [m090 vHC]
     ACGCGGTCCG GGGGCCTGTT TCCGAACTCA CCTACCCTAC CTAGTTGCGA

G  N  G  N   T  K  Y   S  Q  K   F  Q  G   R  V  T  I •
6551 GGCAATGGTA ACACAAAATA TTCACAGAAG TTCCAGGGCA CAGTCACCAT
     CCGTTACCAT TGTGTTTTAT AAGTGTCTTG AAGCTCCCGT GTCAGTGGTA

• T  R  D   T  S  A  S   T  A  Y   M  E  L   S  S  L  R •
6601 TACCAGGGAC ACATCCGCGA GCACAGCCTA CATGGAGCTG AGCAGCCTGA
     ATCGTCCCTG TGTAGGCGCT CGTGTCGGAT GTACCTCCAC TCGTCGGACT

• S  E  D   T  A  V   Y  Y  C   A  R  D   I  S  Y  G
6651 GATCTGAAGA CACGGCTGTG TATTACTGTG CGAGAGACAT CAGCTATGGT
     CTAGACTTCT GTGCCACAC ATAATGACAC GCTCTCTGTA GTCGATACCA

S  F  D  Y   W  G  Q   G  T  L   V  T  V   S  G  G •
6701 TCGTTTGACT ACTGGGGCCA GGGAACCCTG GTCACCGTCT CCTCAGGTGG
     AGCAAACTGA TGACCCCGGT CCCTTGGGAC CAGTGGCAGA GGAGTCCACC    [m909 Linker]

• G  G  S   G  G  G  G   S  G  G   G  G  S   S  S  E  L •
6751   AGGCGGTTCA GGCGGAGGTG GCTCTGGCGG TGGCGGATCA TCTTCTGAGC
       TCCGCCAAGT CCGCCTCCAC CGAGACCGCC ACCGCCTAGT AGAAGACTCG

• T  Q  D   P  A  V   S  V  A  L   G  Q  T   V  R  I
6801 TGACTCAGGA CCCTGCTGTG TCTGTGGCCT TGGGACAGAC AGTCAGGATC
     ACTGAGTCCT GGGACGACAC AGACACCGGA ACCCTGTCTG TCAGTCCTAG

T  C  Q  G   D  N  L   R  S  Y   Y  A  S  W   Y  R  Q •
6851 ACATGCCAAG GAGACAACCT CAGAAGCTAT TATGCAAGCT GGTACCGGCA
     TGTACGGTTC CTCTGTTGGA GTCTTCGATA ATACGTTCGA CCATGGCCGT

• K  S  G   Q  A  P   V  L  V   I  Y  G   K  N  N  R  P •
6901 GAAGTCAGGA CAGGCCCCTG TACTTGTCAT CTATGGTAAA AACAACCGGC   [m909 vLC]
     CTTCAGTCCT GTCCGGGGAC ATGAACAGTA GATACCATTT TTGTTGGCCG
```

```
                • S  G  I    P  D  R   F  S  G  S    S  S  G   N  T  A
        6951 CCTCAGGGAT CCCAGACCGA TTCTCTGGCT CCAGCTCAGG AAACACAGCT
             GGAGTCCCTA GGGTCTGGCT AAGAGACCGA GGTCGAGTCC TTTGTGTCGA

S  L  T  I    T  A  A   Q  A  E    D  E  A  D   Y  Y  C •
        7001 TCCTTGACCA TCACTGCGGC TCAGGCGGAA GATGAGGCTG ACTATTACTG
             AGGAACTGGT AGTGACGCCG AGTCCGCCTT CTACTCCGAC TGATAATGAC

• H  S  T    K  S  R  G   N  H  L    L  F  G   G  G  T  K •
        7051 TCACTCCCGG AAAAGCCGCG GTAACCATCT GCTATTCGGC GGAGGGACCA
             AGTGAGGGCC TTTTCGGCGC CATTGGTAGA CGATAAGCCG CCTCCCTGGT

• L  T  V    L  G  Q   A  S  T  T    T  P  A   P  R  P
        7101 AGCTGACCGT CCTAGGCCAG GCTAGCACCA CGACGCCAGC GCCGCGACCA       ┌──────────┐
             TCGACTGGCA GGATCCGGTC CGATCGTGGT GCTGCGGTCG CGGCGCTGGT       │ CD8a Hinge│
                                                                         └──────────┘
                  P  T  P  A    P  T  I   A  S  Q    P  L  S   L  R  P •
        7151 CCAACACCGG CGCCCACCAT CGCGTCGCAG CCCCTGTCCC TGCGCCCAGA
             GGTTGTGGCC GCGGGTGGTA GCGCAGCGTG GGGGACAGGG ACGCGGGTCT

• A  C  R    P  A  A  G   G  A  V    H  T  R   G  L  D  F •
        7201 GGCGTGCCGG CCAGCGGCGG GGGGCGCAGT GCACACGAGG GGGCTGGACT
             CCGCACGGCC GGTCGCCGCC CCCCGCGTCA CGTGTGCTCC CCCGACCTGA

• A  C  D    F  W  V   L  V  V  V    G  G  V   L  A  C
        7251 TCGCCTGTGA TTTTTGGSTG CTGGTGGTGG TTGGTGGAGT CCTGGCTTGC
             AGCGGACACT AAAAACCCAC CACCACCACC AACCACCTCA GGACCGAACG

Y  S  L  L    V  T  V   A  F  I    I  F  W  V   R  S  K •
        7301 TATAGCTTGC TAGTAACAGT GGCCTTTATT ATTTTCTGGG TGACCACCAA        ┌──────────────┐
             ATATCGAACG ATCATTGTCA CCGGAAATAA TAAAAGACCC ACTCCTCATT       │ CD28         │
                                                                         │ Transmembrane│
                • R  S  R    L  L  H  S   D  Y  M    N  M  T   P  R  R  P • └──────────────┘
        7351 GACGAGCAGG CTCCTCCACA CTGACTACAT GAACATCACT CCCCGCCGCC       ┌──────────┐
             CTGCTCGTCC GACGAGGTGT CACTGATGTA CTTGTAGTGA GGGGCGGCGG       │ CD28 ICD │
                                                                         └──────────┘
                   G  P  T    R  K  H   Y  Q  P  Y    A  P  P   R  D  F
        7401 CCGGGCCCAC CCGCAAGCAT TACCAGCCCT ATGCCCCACC ACGCGACTTC
             GGCCCGGGTG GGCGTTCGTA ATGGTCGGGA TACGGGGTGG TGCGCTGAAG A  A  Y  R    S  I  D   R  V  K    F  S  R  S   A  D  A •
        7451 GCAGCCTATC GCTCCATCGA TAGAGTGAAG TTCAGCAGGA GCGCAGACGC
             CGTCGGATAG CGAGGTAGCT ATCTCACTTC AAGTCGTCCT CGCGTCTGCG

• P  A  Y    Q  Q  G  Q   N  Q  L    Y  N  E   L  N  L  G •
        7501 CCCCGCGTAC CAGCAGGCCC AGAACCAGCT CTATAACGAG CTCAATCTAG
             GGGGCGCATG GTCGTCCGGG TCTTGGTCGA GATATTGCTC GAGTTAGATC

• R  R  E    E  Y  D   V  L  D  K    R  R  G   R  D  P
        7551 GACGAAGAGA GGAGTACGAT GTTTTGGACA AGAGACGTGG CCGGGACCCT
             CTGCTTCTCT CCTCATGCTA CAAAACCTGT TCTCTGCACC GGCCCTGGGA

E  M  G  G    K  P  R   R  K  N    P  Q  E  G   R  D  P
        7601 GAGATGGGGG GAAAGCCGAG AAGGAAGAAC CCTCAGGAAG GCCTGTACAA
             CTCTACCCCC CTTTCGGCTC TTCCTTCTTG GGAGTCCTTC CGGACATGTT       ┌──────────┐
                                                                         │ CD3 Zeta │
                • E  L  Q    K  D  K  M   A  E  A    Y  S  E   I  G  M  K • └──────────┘
        7651 TGAACTGCAG AAAGATAAGA TGGCGGAGGC CTACAGTGAG ATTGGGATGA
             ACTTGACGTC TTTCTATTCT ACCGCCTCCG GATGTCACTC TAACCCTACT

• G  E  R    R  R  G   K  G  H  D    G  L  Y   Q  G  L
        7701 AAGGCGAGCG CCGGAGGGGC AAGGGGCACG ATGGCCTTTA CCATGGTCTC
             CTGCTTCTCT CCTCATGCTA CAAAACCTGT TCTCTGCACC GGCCCTGGGA
```

```
           • G E R   R R G   K G H D   G L Y   Q G L
7701 AAGCCCACCG CCGGAGGGGC AAGCGCCACC ATGGCCTTTA CCAGGCTCTC
     TTCCGCTCGC GGCCTCCCCG TTCCCCGTGT ACCGGAAAT  GGTCCCAGAG

S   T A T   K D T   Y D A   L H M Q   A L P •
7751 AGTACAGCCA CCAAGGACAC CTACGACGCC CTTCACATGC AGGCCCTGCC
     TCATGTCGGT GGTTCCTGTG GATGCTGCGG GAAGTGTACG TCCGGGACGG

• P R *
7801 CCCTCGC TAA
     GGGAGCG ATT
```

Example 5

Targeting FRβ for Immunotherapy of Cancer

FRβ is a GPI-anchored membrane protein with limited expression on normal tissues, restricted to a small population of mature hematopoietic subsets. However, FRβ is expressed on over 70% of primary Acute Myeloid Leukemias (AML) samples as well as inhibitory tumor associated macrophages (TAMs) in cancer of multiple tissue origins. The following outlines the progress in creating and testing chimeric antigen receptors (CARs) directed against folate receptor beta (FRβ).

The materials and methods employed in these experiments are now described.

CAR Construction:

The plasmid containing the anti-FRβ scFv m909 was used as a template for PCR amplification of a 750-bp m909 fragment using the following primers: 5'-TATTGATCAGCCGAAGTGCAGCTGGTGCAGTCTGG-3' (BclI is underlined) and 5'-TAT GCTAGCCTGGCCTAGGACGGTCAGCTTGGTC-3' (NheI is underlined). The resulting PCR product was digested with the relevant enzymes. Third generation self-inactivating lentiviral expression vectors pELNS were digested with BamHI and NheI to create compatible cohesive ends and gel purified. The digested PCR product was then inserted into the pELNS-GFP-2A vectors containing CD3z or CD28-CD3z T cell signaling domains in which transgene expression is driven by the elongation factor-1α (EF-1α) promoter. The resulting construct (FIG. 7) was designated pELNS-GFP-2A-m909-Z/28Z. pELNS vectors encoding GFP alone, MOV19-Z and 28Z, specific for folate receptor α, or CD19-28Z have been previously described.

Lentivirus Production:

High-titer replication-defective lentiviral vectors were produced and concentrated. 293T human embryonic kidney cells were seeded at 12×10⁶ per T150 tissue culture flask 24 hours before transfection. All plasmid DNA were purified using the QIAGEN Endo-free Maxi prep kit. Cells were transfected with 7 μg pVSV-G, 18 μg of μg pRSV.REV, 18 μg of pMDLg/p.RRE, and 15 μg of pELNS transfer plasmid using Express Inn (Open Biosytems). The viral supernatant was harvested at 24 and 48 hours post-transfection and combined. Viral particles were concentrated by ultracentrifugation for 3 hours at 28,000 rpm with a Beckman SW32TI rotor (Beckman Coulter) and resuspended in 0.5 mL. Resuspended viral particles were stored at −80 C in individual aliquots until use.

T Cells:

Primary human CD4+ and CD8+ T cells were isolated from healthy volunteer donors after leukapheresis by negative selection and purchased from the Human Immunology Core at University of Pennsylvania. All specimens were collected under a University Institutional Review Board-approved protocol, and written informed consent was obtained from each donor in accordance with the Declaration of Helsinki CD4+ and CD8+ T cells were mixed at a 1:1 ratio and activated with anti-CD3 and anti-CD28 mAb-coated beads (Invitrogen) as described. T cells were cultured in complete media (RPMI 1640-GlutaMAX supplemented with 10% heat-inactivated FBS, 100 U/mL penicillin, 100 μg/mL streptomycin sulfate). At 20 hours after activation, cells were transduced with lentiviral vectors at MOI of ~5-10. T cells were then expanded in the presence of human recombinant IL2 (Novartis) at a final concentration of 50 IU/mL, maintaining a cell density of 0.5-1×10⁶ cells/mL. After ~2 weeks, rested T cells (cell size <300 fL) were then adjusted to equalize the frequency of transgene expressing cells before use in functional assays.

Cell Lines:

Lentivirus packaging was performed in the immortalized normal fetal renal 293T cell line purchased from ATCC. The FR-negative human ovarian cancer cell line, C30, was transduced with lentivirus encoding human FRβ cDNA (Origene) to generate C30-FRβ. Human AML cell lines THP1, MV411, and HL60 were kindly provided by Gwenn Danet-Desoyners (University of Pennsylvania). All cell lines were grown in complete media. For in vivo bioluminescence and luciferase-based lytic assays, C30, C30-FRβ, and THP1 cell lines were transduced with lentivirus encoding GFP and firefly luciferase. Flow cytometric analysis was used to confirm GFP expression, and cells were sorted to produce 100% positive lines if necessary.

T Cell Activation (CD69) and Cytokine Release Assays:

These assays were performed by co-culture of 10⁵ CAR+ T cells with 10⁵ target cells per well (or media alone) in triplicate in 96-well plates in a 200 μL volume of complete media. After ~24 hours, plates were centrifuged at 1200 RPM to pellet the cells, and co-culture supernatants were removed and assayed for the presence of IFN-γ by ELISA (Biolegend). Values represent the mean of triplicate wells. IL-2, IL-4, IL-10, IFN-γ, and TNF-α cytokines were measured by flow cytometry with Cytometric Bead Array (BD Biosciences). The cell pellets were then labeled with antibodies for CD3 and CD69, and assessed by flow cytometry. Live, CD3+ gates were used for analysis of CD69 upregulation. For m909 CAR T cells, GFP was used as a marker for CAR+ cells. In some cases cell pellets were labeled for FRβ surface expression following co-cultures.

T-Cell Proliferation:

T cells were labeled with 2.5 μM PKH26 (red fluorescent for general cell membrane labeling, Sigma) according to the manufacturer's protocol. Labeled cells were co-cultured with tumor cells (or media alone) at 1:1 ratio in the absence of exogenous IL-2. After 5 days, cells were stained with CD3 and analyzed for PKH26 dilution by flow cytometry. A live, CD3+ gate was used for analysis. The percent of cells showing PKH26 dilution at d5 compared to d0 was quantified. Graphs represent the mean from triplicate wells.

Degranulation Assay:

$10^5$ CAR+ T cells were co-cultured with $10^5$ target cells in 200 uL per well in a 96-well plate in triplicate in the presence of APC-conjugated anti-CD107a and anti-CD107b antibodies (10 μl per well) or control IgG1 conjugated to APC (BD Biosciences) and monensin (BD biosciences). Co-cultures were incubated for 5-6 hours at 37° C. Additional wells were co-cultured with anti-CD3/anti-CD28 coated beads as a positive control for the assay. Cells were washed two times with PBS, labeled for CD3, and analyzed by flow cytometry. Live, CD3+ gates were used for analysis of surface CD107a/b expression. For m909 CAR T cells, GFP was used as a marker for CAR+ cells. The percent of CAR+ cells with CD107a/b+ labeling was quantified. Graphs represent the mean values from triplicate wells.

Cytotoxicity Assays:

For luciferase-based lysis assays, cell lines (C30, C30-FRβ, THP1) were transduced to stably express firely luciferase. Target cells were plated at $10^4$ per well in triplicate in white 96-well tissue culture plates (Bioexpress). CAR+ T cells were added at the indicated E:T (effector: target) cell ratios. Co-cultures were incubated overnight at 37 degrees in phenol-free complete media. The Extended-Glow Bioluminescent Reporter Gene Assay (Applied Biosystems) was used in conjunction with an Ascent microplate luminometer (Thermo) to measure residual luciferase activity from remaining target cells. Average signal from six untreated target wells was used to determine percent lysis according to the following equation:

$$\text{Percent Lysis} = 100 - \left( \frac{\text{(Average Signal from } T \text{ cell treated wells)}}{\text{(Average Signal from untreated target wells)}} \times 100 \right)$$

For flow-based lysis assays, (human peripheral blood monocytes or in vitro polarized macrophages) were isolated from healthy volunteer donors after leukapheresis by negative selection and purchased from the Human Immunology Core at University of Pennsylvania. $3 \times 10^4$ cryopreserved monocytes (thawed, rested 4 hr at 37 degrees) were plated per well in 96 well plates. CAR+ T cells were added at 3:1 or 1:3 E:T (effector:target) ratios in triplicate and co-cultured 4 hrs (or 18 hr) at 37 degrees. Cells were then moved to FACS tubes and labeled with CD3 and CD33 antibodies. 20 uL (20,000) CountBright absolute counting beads (invitrogen) were added to each tube. Flow cytometry was used to quantify the absolute number of live, CD3(-), CD33(+) monocytes in each sample. Mean values were calculated from six untreated target wells or three experimental wells, and percent lysis was defined according to the following equation:

$$\text{Percent Lysis} = 100 - \left( \frac{\text{(Average Number from } T \text{ cell treated wells)}}{\text{(Average Number from untreated target wells)}} \times 100 \right)$$

CFU Assay:

Bone marrow CD34+ HSCs were isolated from healthy donors by magnetic bead selection by the University of Pennsylvania Stem Cell and Xenograft core. 2000 CD34+ cells were co-cultured with 2000 CAR+ T Cells (1:1 E:T) in V-bottom 96 well plates. After 4 hrs, all cells were diluted in methylcellulose and plated in duplicate. Colonies were allowed to grow for 14 days and were then counted/scored as CFU-GEMM, GM, G, M, or BFU-E. Control untreated CD34+ were cultured in the absence of T cells.

qRT-PCR:

For quantification of human FRβ mRNA in AML cell lines, total RNA was extracted from $5 \times 10^6$ viable tumor cells using the RNeasy Mini kit (Qiagen) with on-column DNAse digestion. RNA quantity and quality ($A_{260/280}$=2.0-2.1) were verified using a Nanodrop 2000 spectrophotometer (Thermo). cDNA was generated from 1 ug total RNA using the High-Capacity-RNA-to-cDNA kit (Applied Biosystems). cDNA quantity (2.05 ug/uL) and quality ($A_{260/280}$=1.82) were verified to be equal for all samples. Human FRβ mRNA copy number was calculated using the standard curve method and ViiA7 real time PCR system (Applied Biosystems). 200 ng cDNA template was added to SYBR green PCR master mix (Applied Biosystems) and 200 nM PrimeTime qPCR Primers (IDT) specific for hFOLR2. Samples were plated in 5 replicate wells. Known quantities of plasmid-FRβ cDNA were used to construct a 6-point standard curve. Amplification was detected in all wells. The standard curve was used to calculate FRβ mRNA copy number. Absolute or relative mRNA copy numbers are represented as indicated.

ATRA Pre-Treatment:

AML cell lines were plated on d0 at $2.5 \times 10^5$ per mL in complete media with final concentration 10 nM ATRA. On d3 fresh media with 10 nM ATRA was added to keep cells at $2.5 \times 10^5$ per mL. On d5 viable AML cells were washed and counted with trypan blue exclusion. Cells were then stained for FRβ surface expression and analyzed by flow cytometry, processed for RNA extraction, or used in co-cultures for functional assays.

ATRA Co-Treatment:

Cell lines and CAR+ T cells were prepared as above (for cytokine release assays). In indicated samples 10 nM ATRA was included fresh in the co-culture preparation. Target cells and T cells were co-cultured for 3d in the presence of ATRA. Culture supernatants were then collected and analyzed for cytokines as described.

Flow Cytometric Analysis:

All samples for flow cytometry were labeled in 100 uL total volume FACS Buffer (PBS, 2% FBS). Cells were processed on a BD FACS-Canto flow cytometer, and results were analyzed with FlowJo 7.6.5. The following mAbs were used for phenotypic analysis: APC-Cy7 mouse anti-human CD3; PE-Cy7-anti-human CD3; PE-anti-human CD4; APC-anti-human CD8; PE-anti-human CD45; APC-anti-human CD34; PE-anti-human CD19; PE-anti-human CD69 (all Biolegend) and APC-anti-human CD33; APC-anti-human CD107a; APC-anti-human CD107b (BD). 7AAD was used to assess viable cells. In in vivo T cell transfer experiments, blood was obtained from treated mice via retro-orbital bleeding and stained for the presence of human CD45, CD3, and CD8 T cells. Human CD45+-gated, CD3+, and CD8+ subsets were quantified with TruCount tubes (BD Biosciences) per manufacturer's instructions. Spleens from individual mice were homogenized in RPMI cell culture medium. RBCs were lysed by adding ACK Lysing Buffer (Gibco). Cells were washed and 1×10⁶ cells per sample were labeled with CD3 and quantified using CountBright absolute counting beads (Invitrogen).

Tumor cell surface expression of FRβ was detected by m909-IgG antibody (Dimiter Dimitrov) conjugated to biotin (EZ-Link Biotinylation Kit, Thermo). To block Fc receptor binding, tumor cells were incubated with 50 ug/mL unlabeled human IgG (Jackson ImmunoResearch) for 10 min. 3-5 ug/mL m909-biotin or human IgG-biotin isotype control was added, and cells were labeled for 30 min at 4 degrees, washed with FACS buffer, and labeled with Streptavidin-APC (BD) for 25 min at 4 degrees. Cells were washed, resuspended with 7AAD, and analyzed by flow cytometry.

m909 CAR expression was detected by biotin-labeled rabbit-anti-human IgG H+L (Jackson ImmunoResearch). MOV19 CAR expression was detected by biotinylated-FRα recombinant protein (R&D). CD19 CAR expression was detected by biotin-proteinL (GenScript). Secondary labeling with Streptavidin-APC (BD) was used for all CARs.

Xenograft Model of AML:

(NOD/SCID)/γ-chain−/− (NSG) mice were obtained from the University of Pennsylvania Stem Cell and Xenograft core. 6-12 week old female mice were bred, treated, and maintained under pathogen-free conditions in-house under University of Pennsylvania IACUC-approved protocols. 5×10⁶ THP1-GFP-fLuc tumor cells were inoculated subcutaneously on day 0.5 mice per group were injected IP with 5×10⁶ CAR+ T cells on d8 and d10 following tumor inoculation. Tumor growth was assessed by weekly imaging and caliper measurements. fLuc+ tumor radiance was calculated using Living Image software. Tumor volumes were calculated using the following formula: $V=\frac{1}{2}(length \times width)$, where length is greatest longitudinal diameter and width is greatest transverse diameter.

Bioluminescence Imaging:

Tumor growth was also assessed using bioluminescence imaging of fLuc+ tumor cells. Imaging was performed with the Xenogen IVIS imaging system and the photons emitted from fLuc+ cells within the animal body were quantified with the Living Image Version 3.0 software (Xenogen). To summarize in brief, mice bearing THP1 fLuc+ tumor cells were injected intraperitoneally with D-luciferin (150 mg/kg stock, 100 μL of D-luciferin per 10 g of mouse body weight) suspended in PBS, and imaged under isoflurane anesthesia after ~10 minutes. Consecutive images were taken until >2 mice/group had decreasing signal. The peak signal was determined for each mouse using Living Image software. Average radiance was calculated for each mouse at each indicated time point. Pseudocolor images (scale $1 \times 10^6 - 10^8$) representing light intensity (blue, least intense; red, most intense) were generated with Living Image.

Statistical Analysis:

The data are reported as means and SEM. Statistical analysis was performed using unpaired 2-tail student t test. GraphPad Prism 6.0 (GraphPad Software) was used for the statistical calculations. $P<0.05$ was considered significant.

The results of the experiments are now described.

m909 CAR

Figure 6:
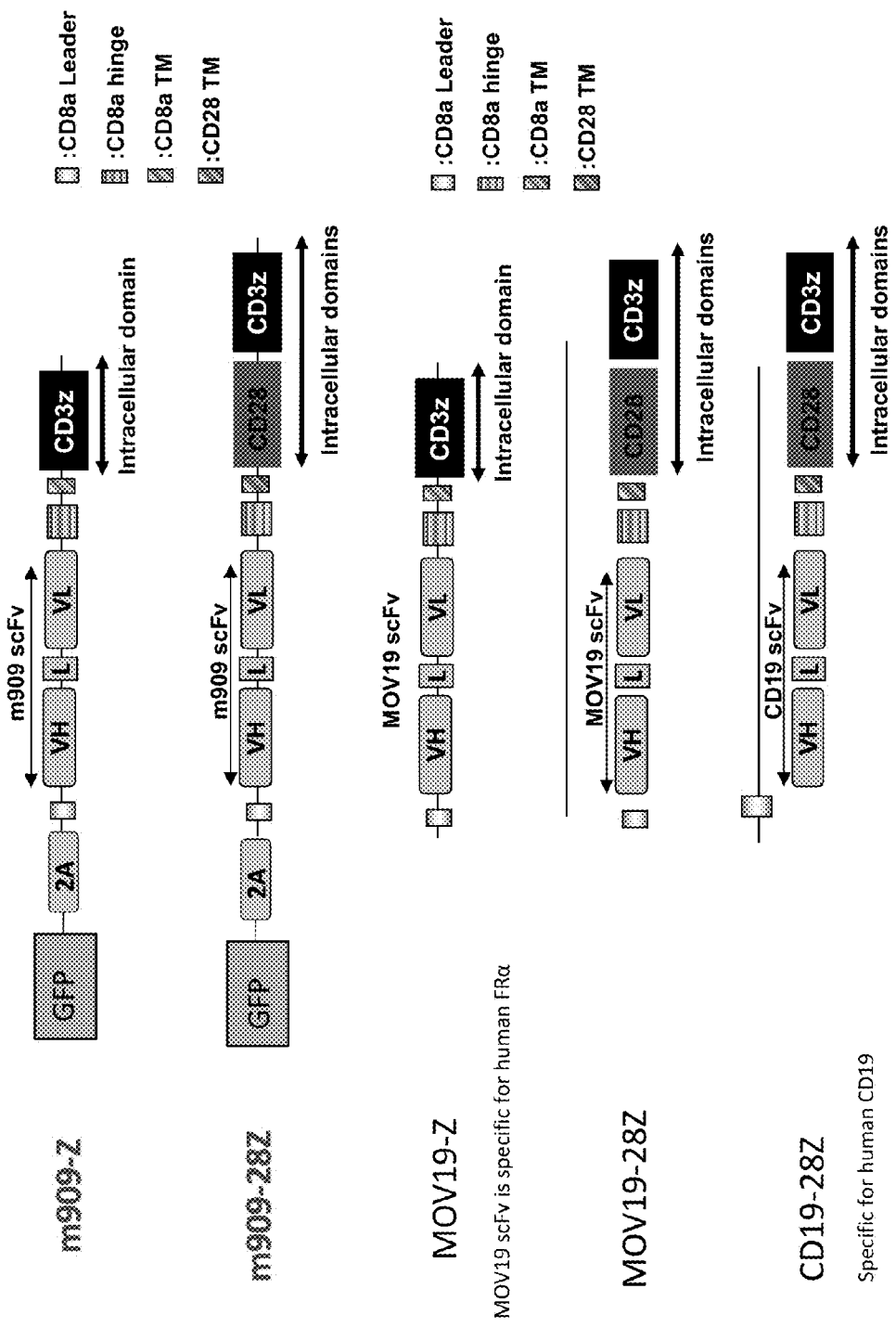
FIG. 6 is a schematic representation of anti-FRβ specific CAR in lentivirus vectors.
Figure 7:
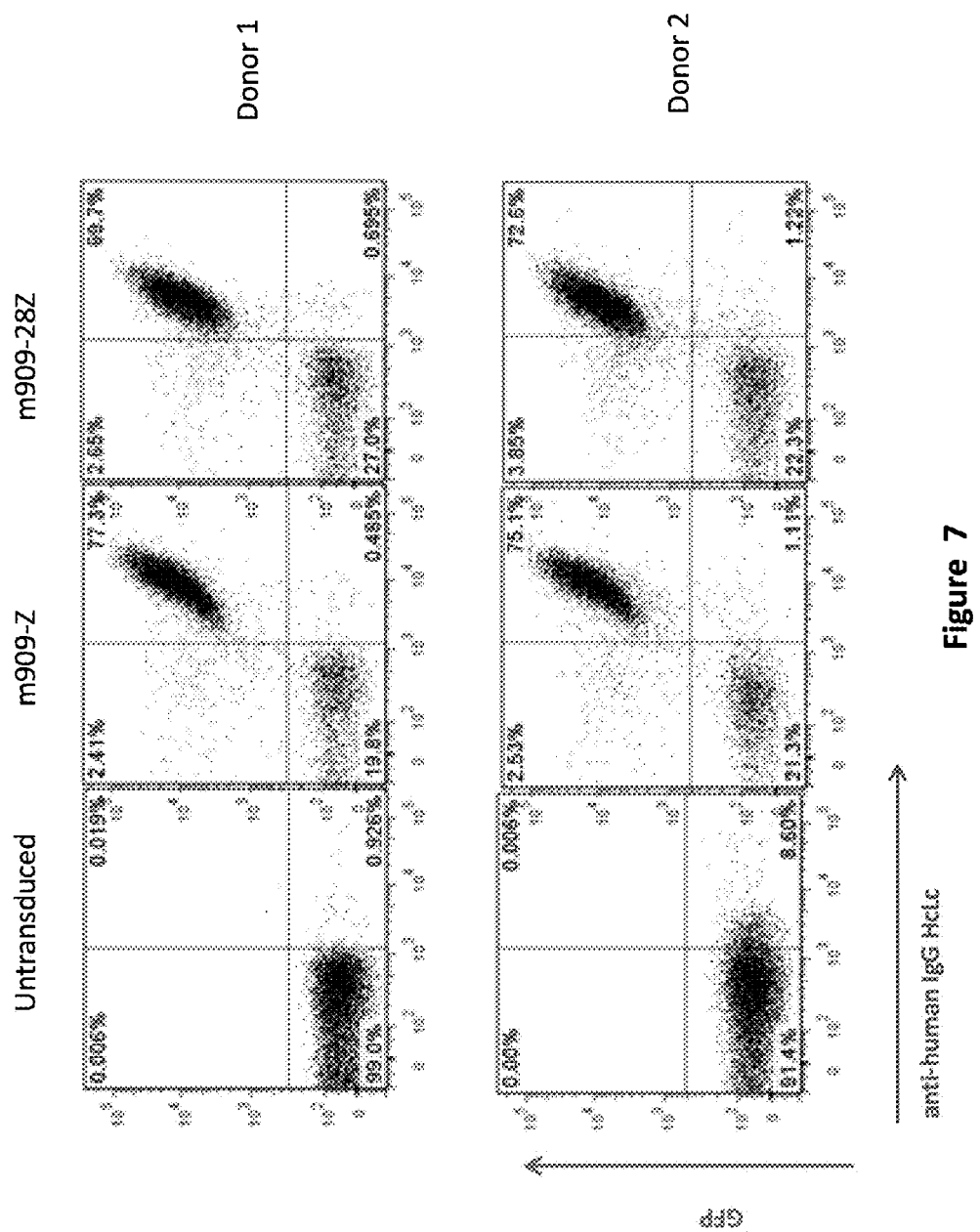
FIG. 7 is a panel of flow diagrams showing transduction of human T cells with m909.
Figure 8A:
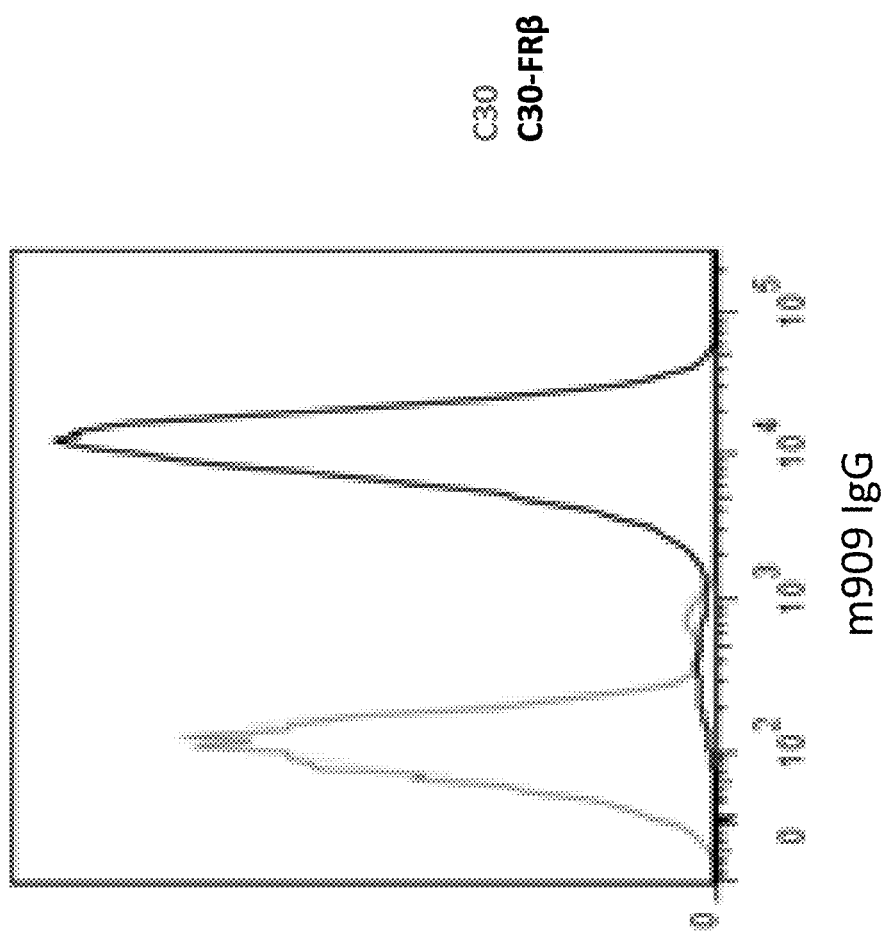
FIG. 8A is a graph showing the FRβ-negative human ovarian cancer cell line C30 was stably transduced with human FRβ cDNA.
Figure 8B:
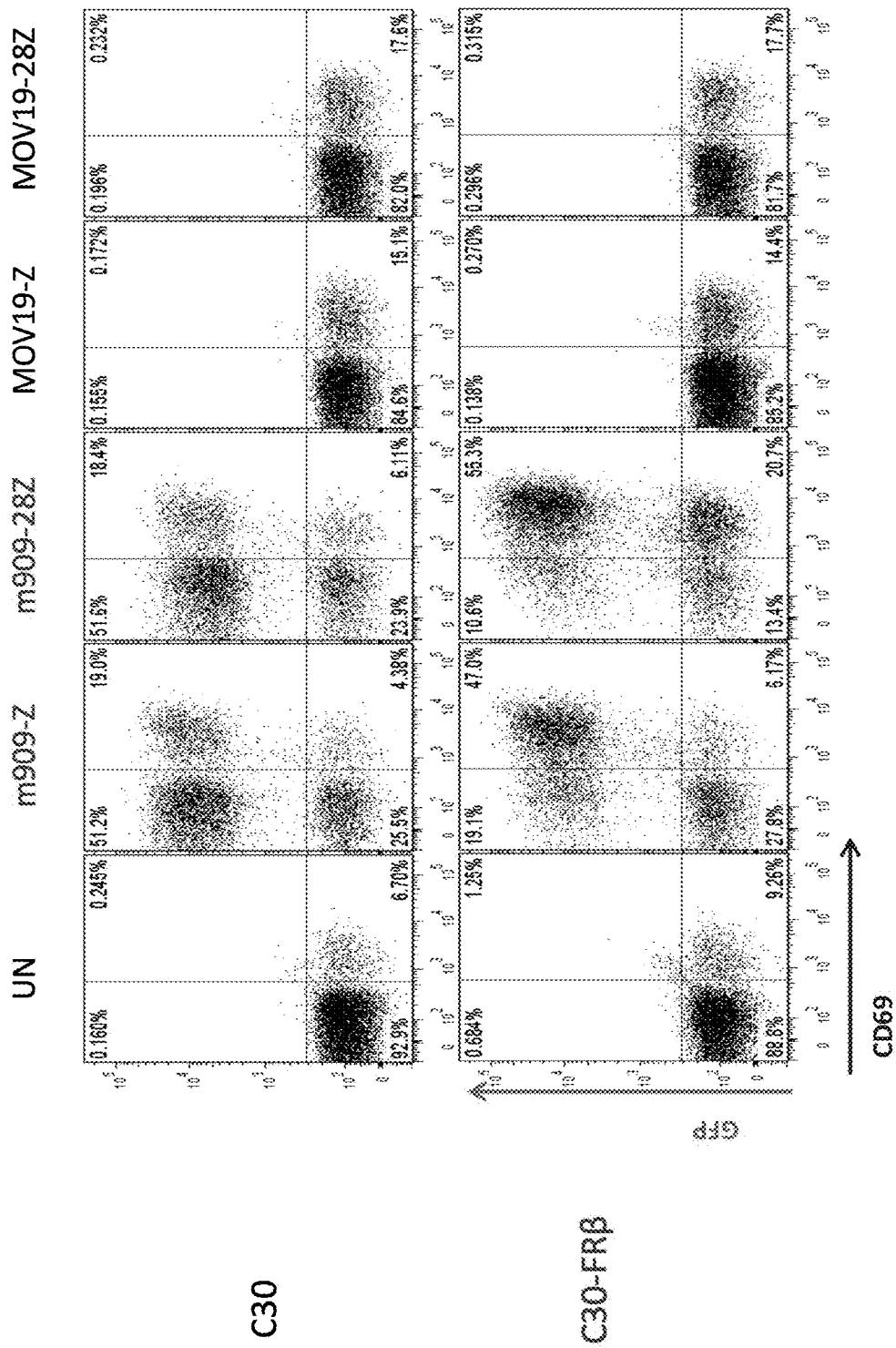
FIG. 8B is a panel of graphs showing m909 CAR T cells exhibit reactivity towards engineered C30 cells transduced with human FRβ.
Figure 8C:
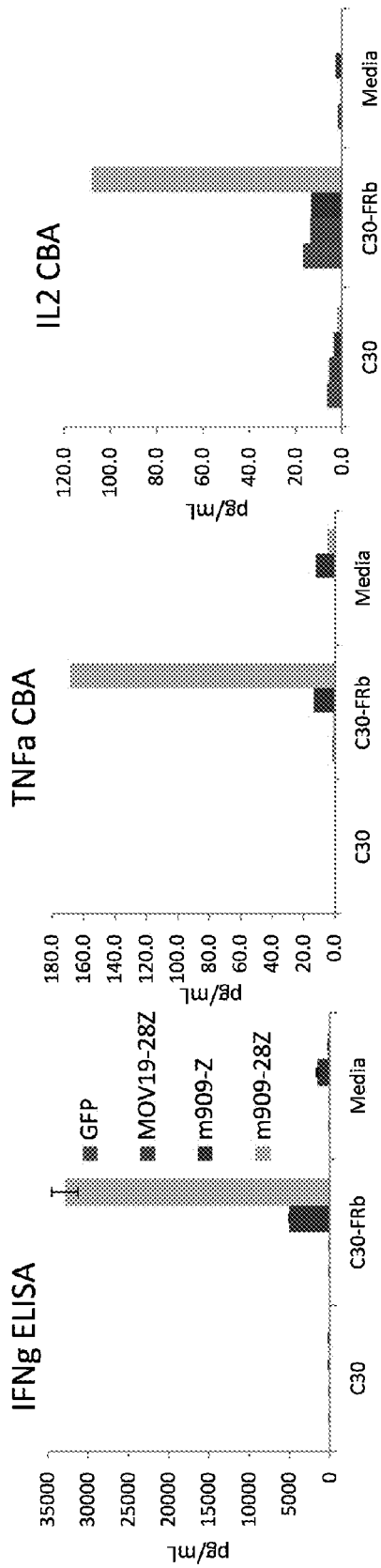
FIG. 8C is a panel of graphs showing m909 CAR T cells produce proinflammatory cytokines in response to engineered C30-FRβ.
Figure 8D:
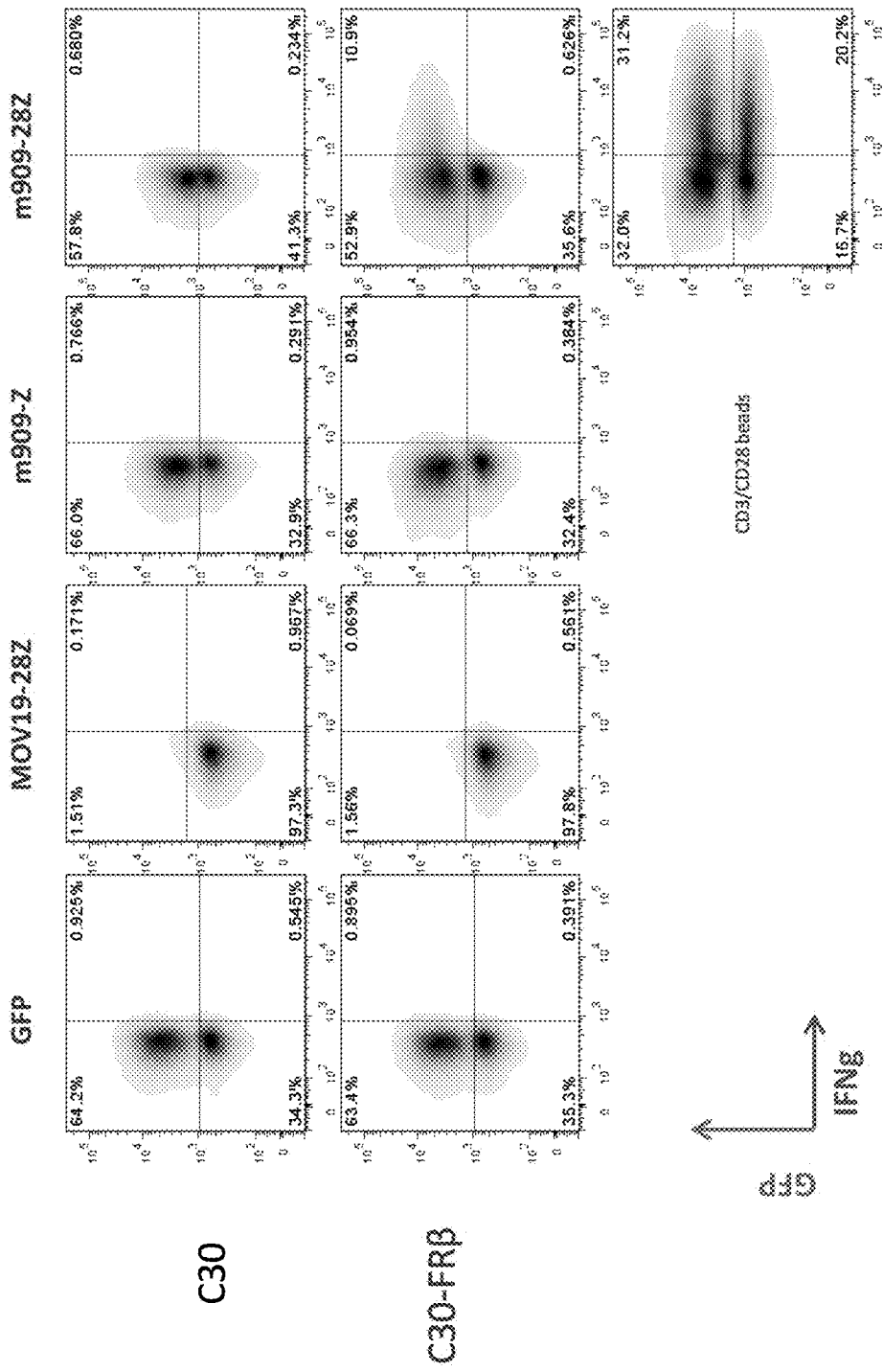
FIG. 8D is a panel of graphs showing m909 CAR T cells produce proinflammatory cytokine, IFNγ, in response to engineered C30-FRβ.
Figure 8E:
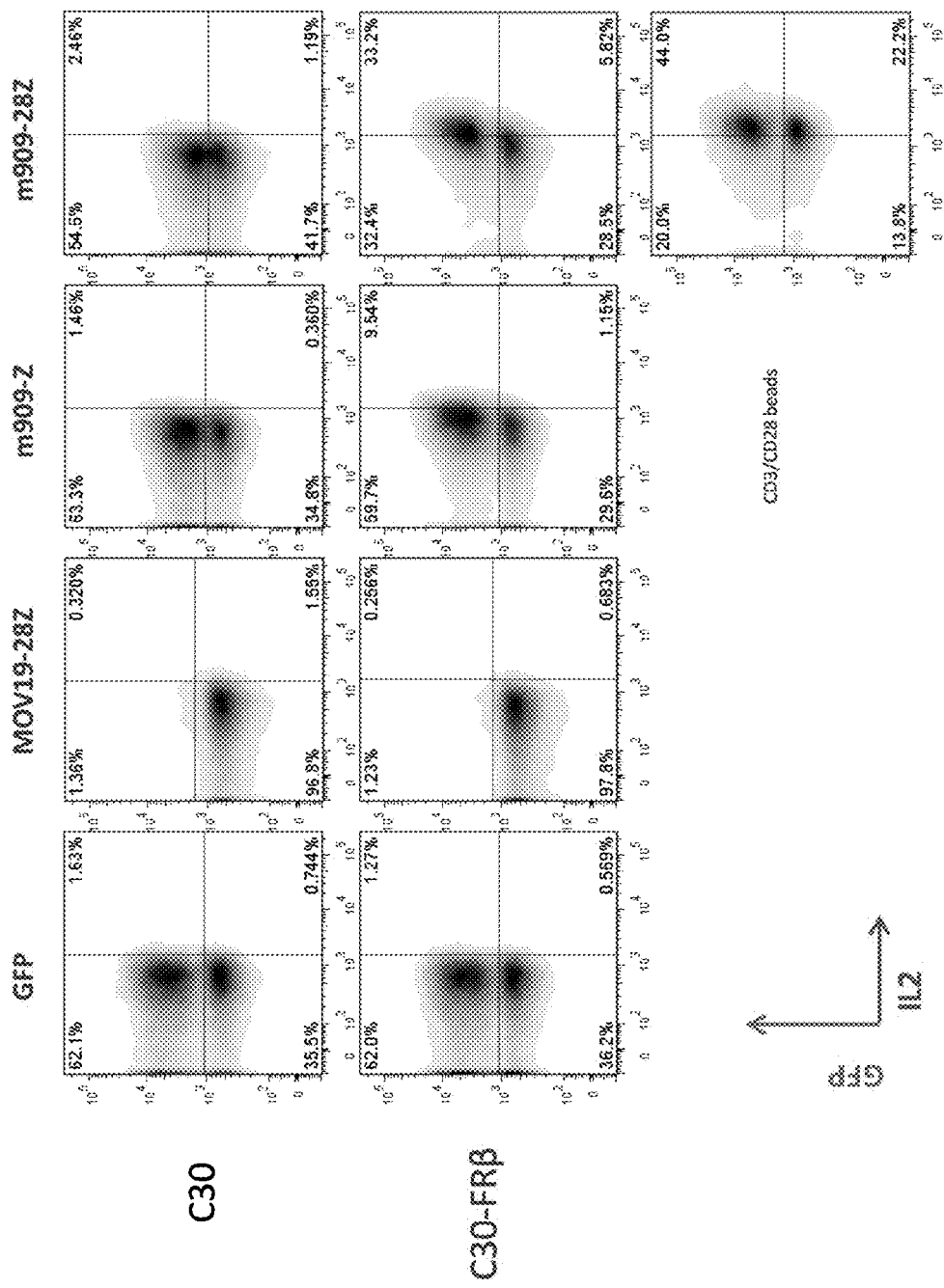
FIG. 8E is a panel of graphs showing m909 CAR T cells produce proinflammatory cytokine, IL-2, in response to engineered C30-FRβ.
Figure 8F:
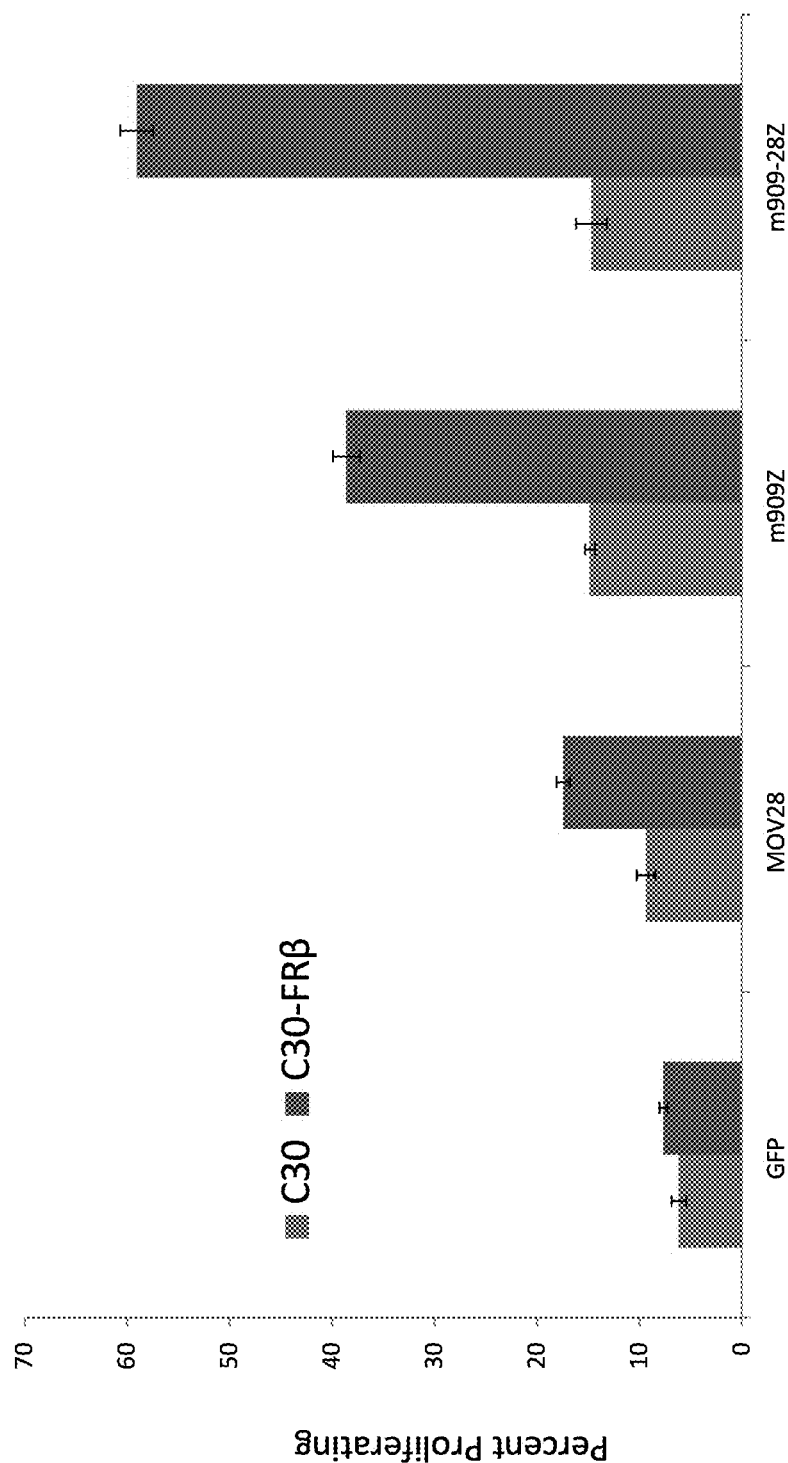
FIG. 8F is a graph showing m909 CAR T cells proliferate in response to C30-FRβ.
Figure 9A:
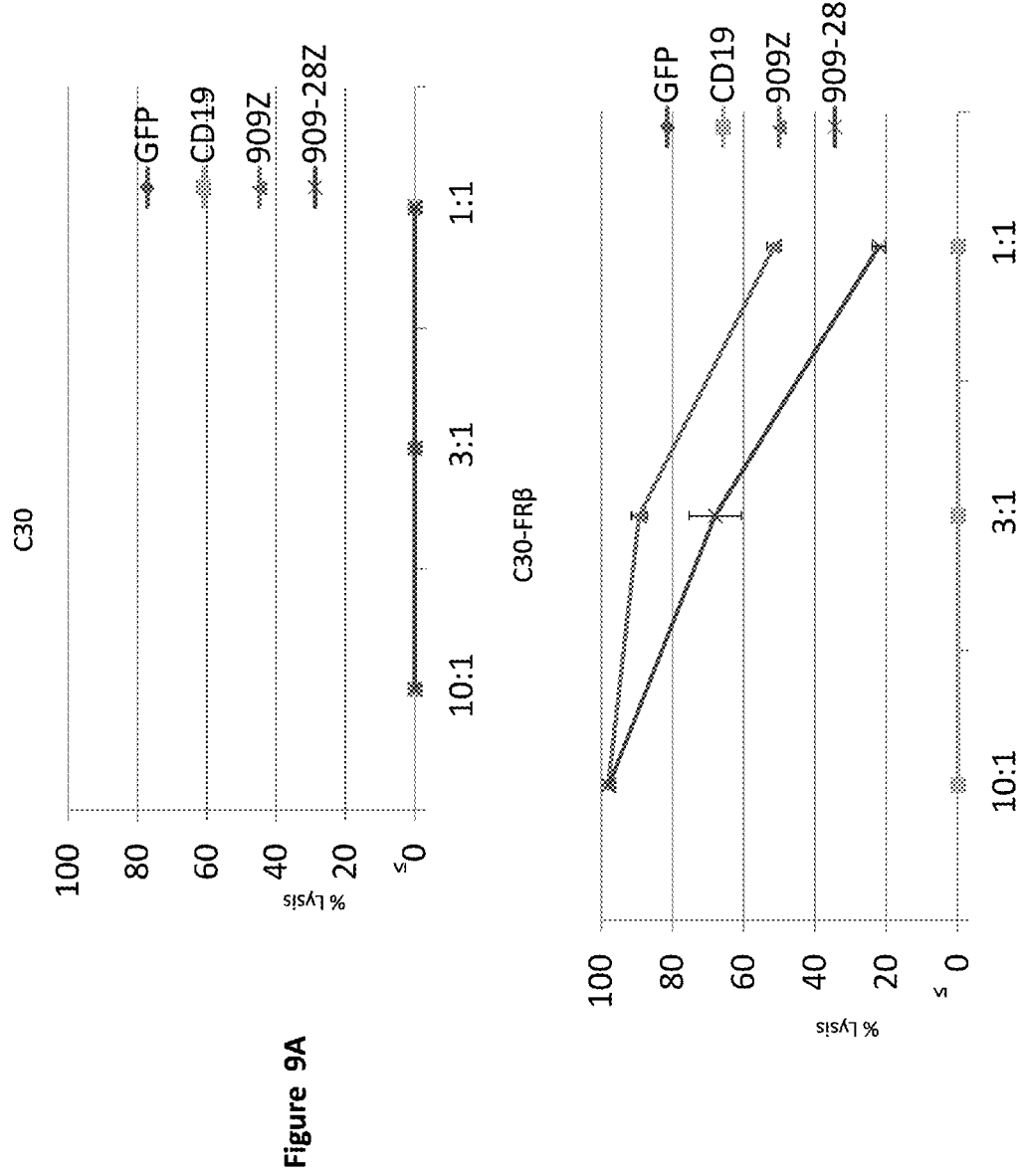
FIG. 9A is a panel of graphs showing m909 CAR T cells exhibiting lytic activity towards C30-FRβ cells.
Figure 9B:
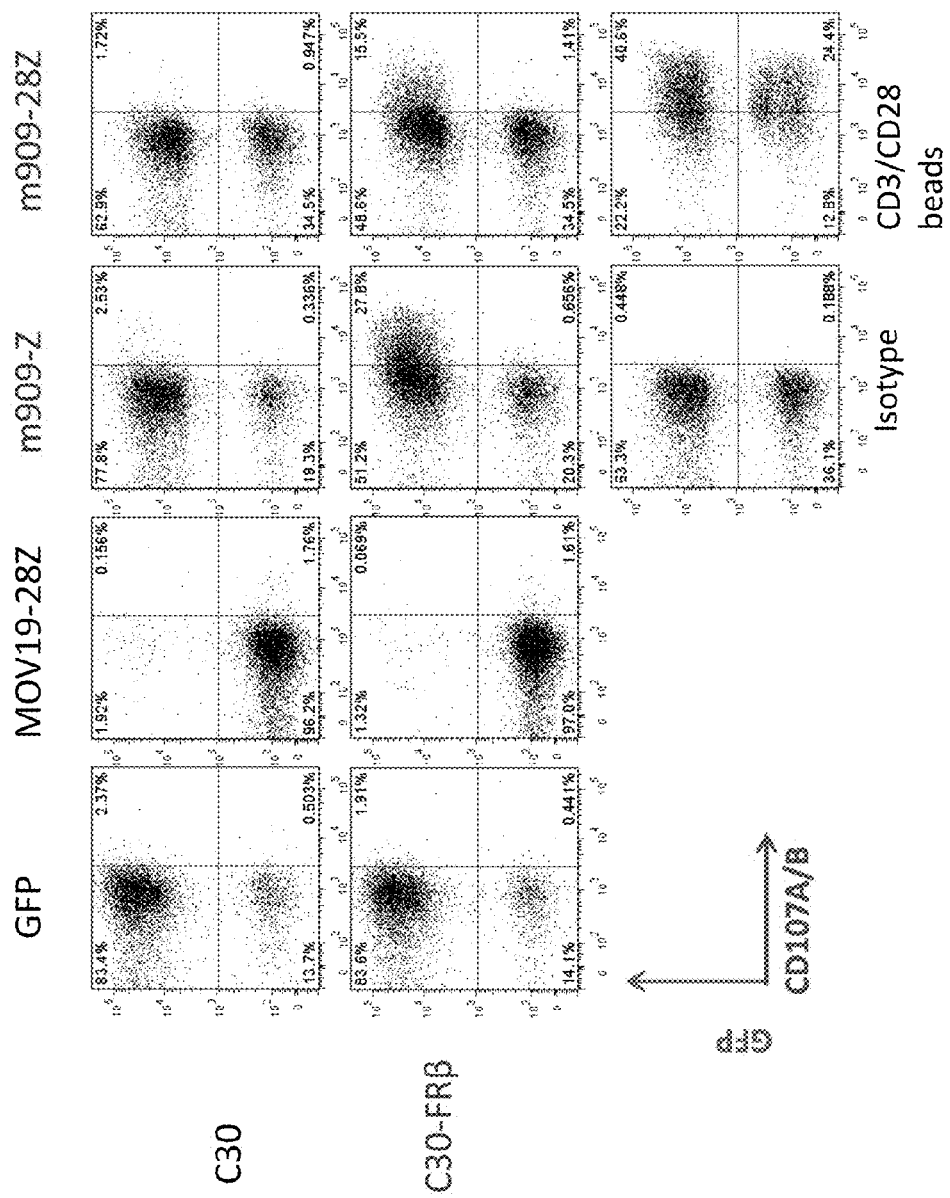
FIG. 9B is a panel of flow graphs showing degranulation, CD107, of the cells after 5 hours in culture.
Figure 9C:
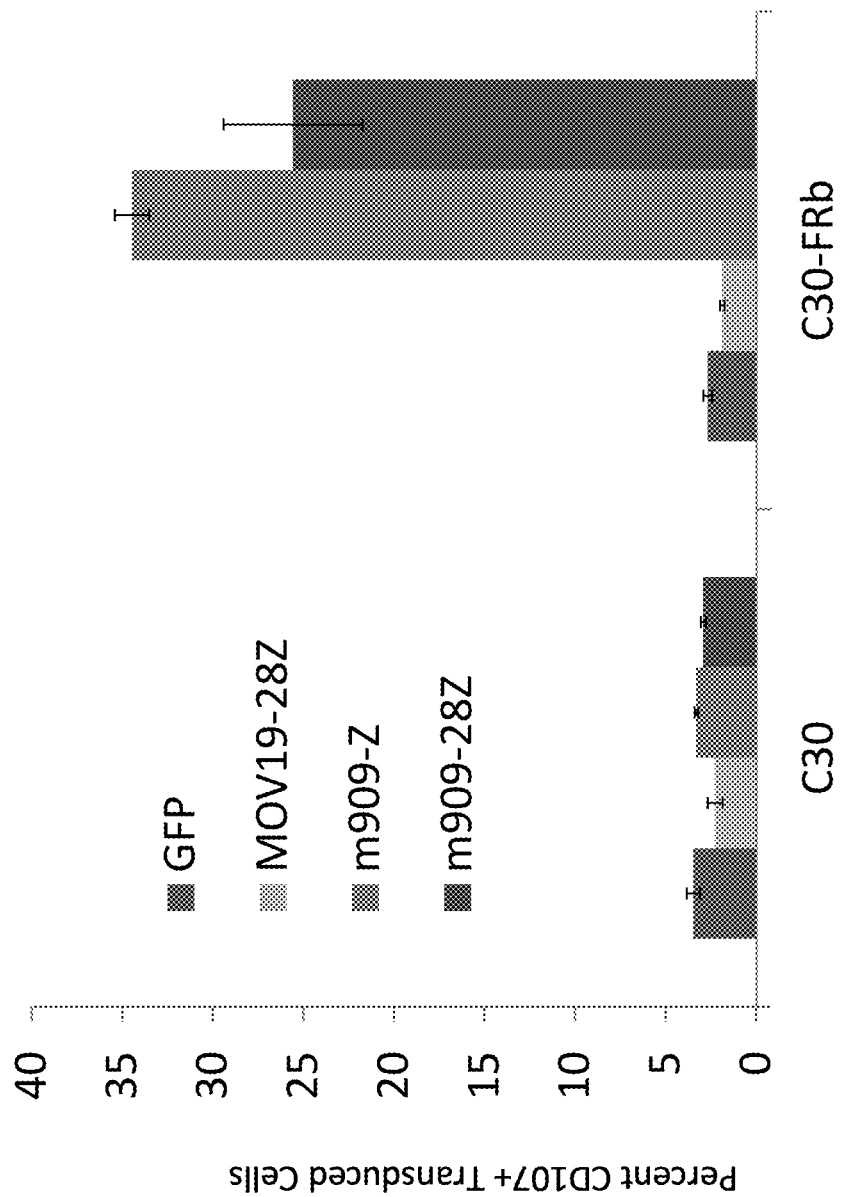
FIG. 9C is a graph showing the percentage of cells showing degranulation by expression of CD107.

The first FRβ CAR was designed using the m909 scFv specific for human FRβ (FIG. 6). The m909 was cloned into a lentiviral backbone containing CD3ζ and CD28 intracellular domains. High transduction of human CD4 and CD8 T cells was confirmed using GFP and an antibody specific for human IgG (FIG. 7). To assess the antigen-specific functional capability of the FRβ CARs, the FRβ-negative human ovarian cancer cell line C30 was stably transduced with human FRβ cDNA (FIG. 8A). m909 CAR transduced T cells exhibited selective activation (FIG. 8B), proinflammatory cytokine secretion (FIGS. 8C, 8D and 8E), and proliferated when co-cultured with FRβ+C30 cells (FIG. 8F), but not parental C30 cells. m909 CAR T cells also mediated the specific lysis of FRβ+ C30 cells in a dose dependent manner (FIGS. 9A, 9B and 9C).

Figure 10A:
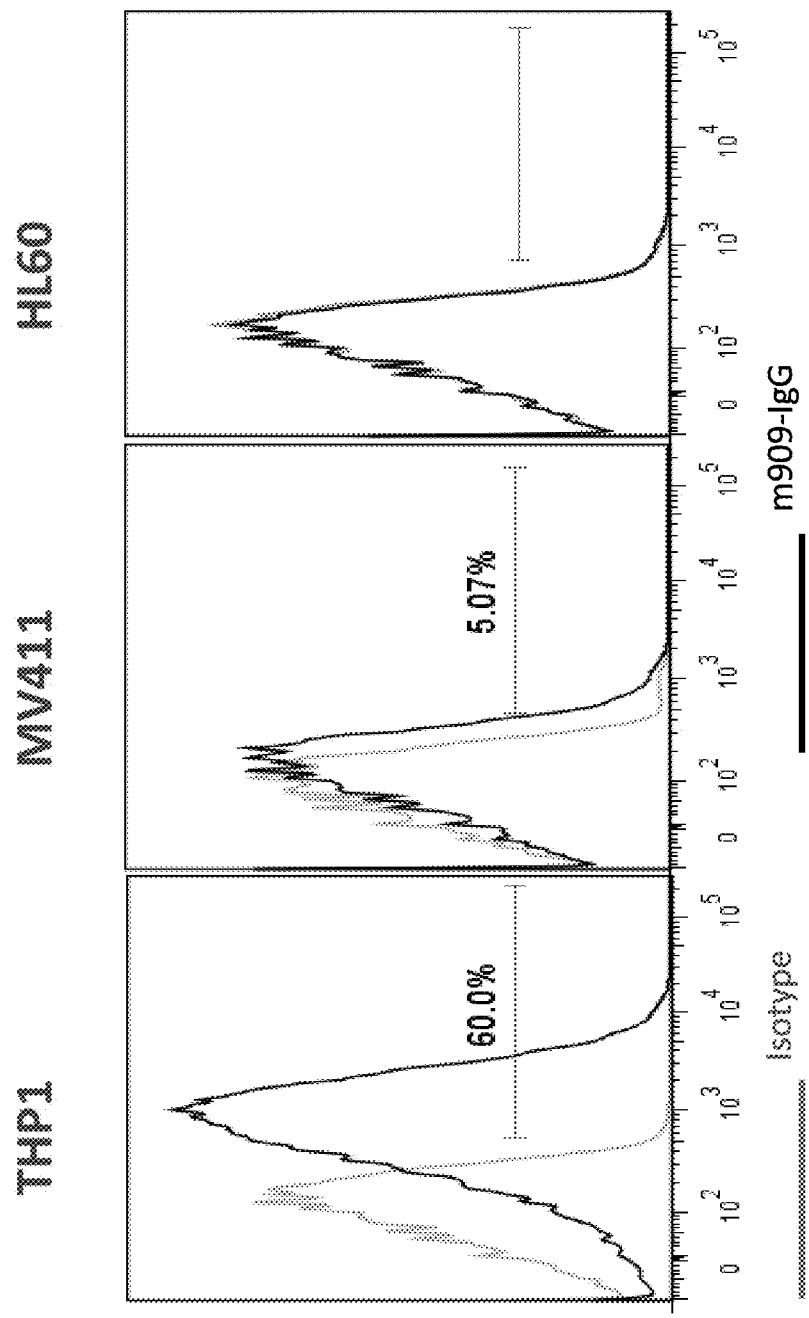
FIG. 10A is a panel of images showing FRβ expression on acute myeloid leukemia (AML) cell lines.
Figure 10B:
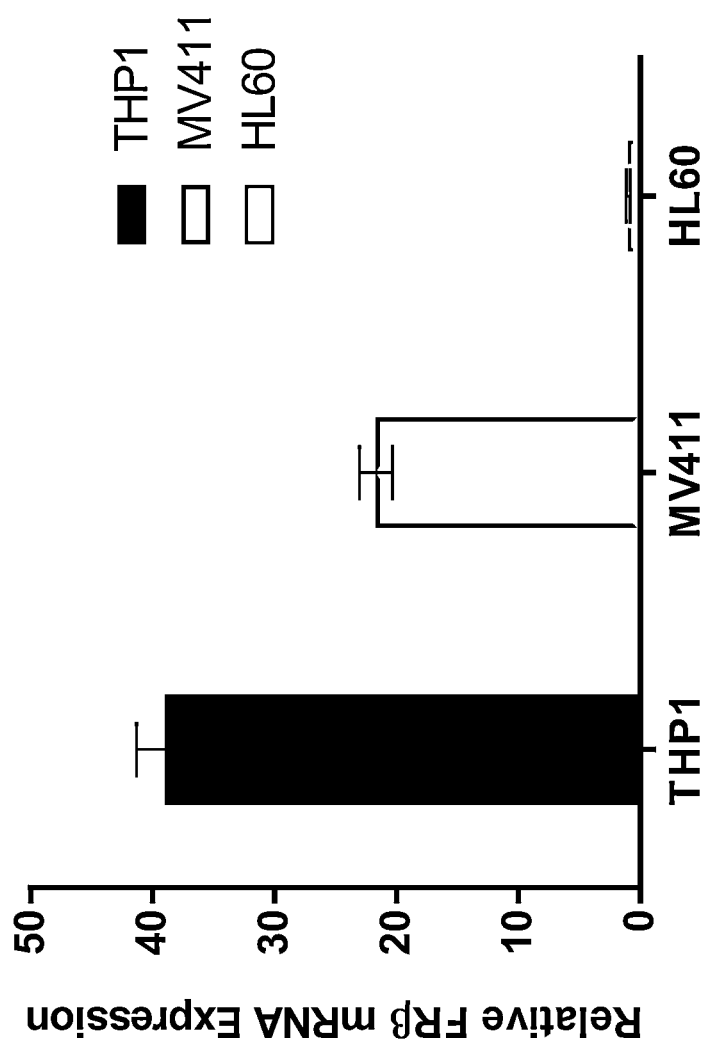
FIG. 10B is a graph showing relative FRβ mRNA expression on acute myeloid leukemia (AML) cell lines.
Figure 10C:
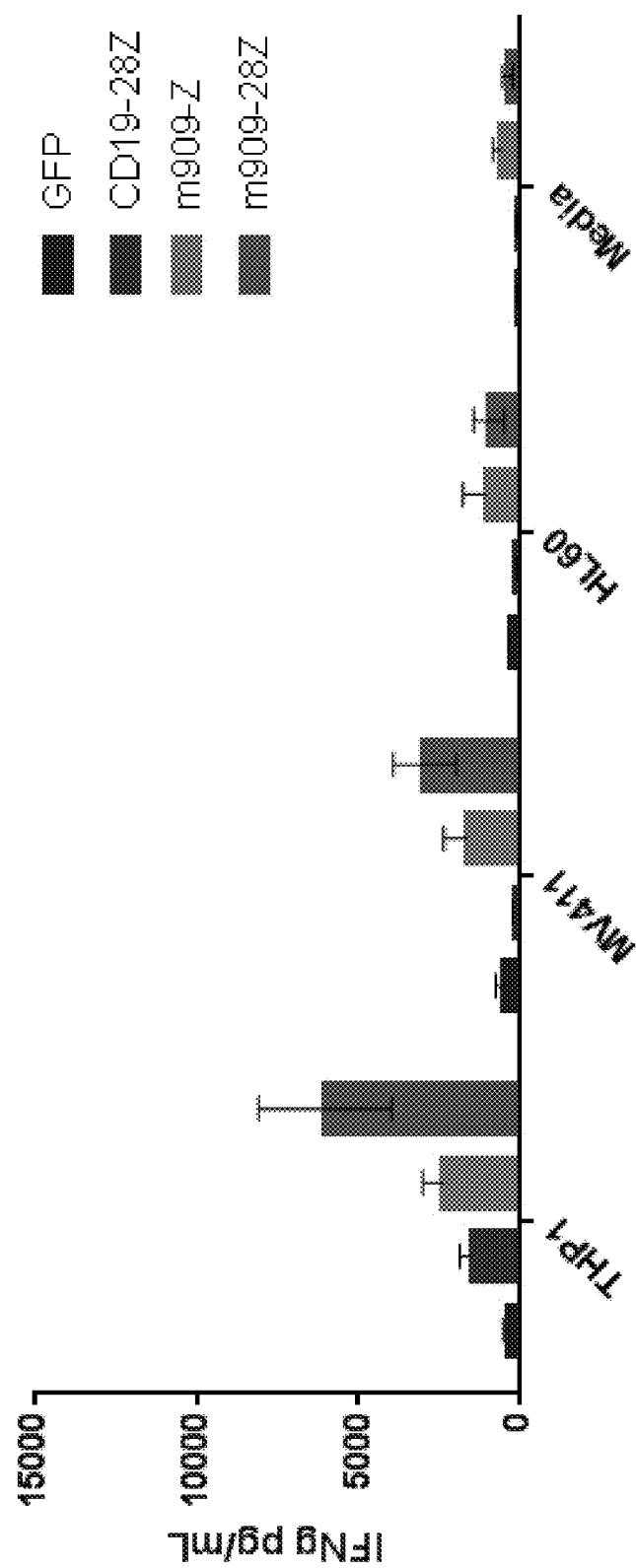
FIG. 10C is a graph showing CAR T cells produce proinflammatory cytokine, IFNγ, in response to engineered C30-FRβ.
Figure 10D:
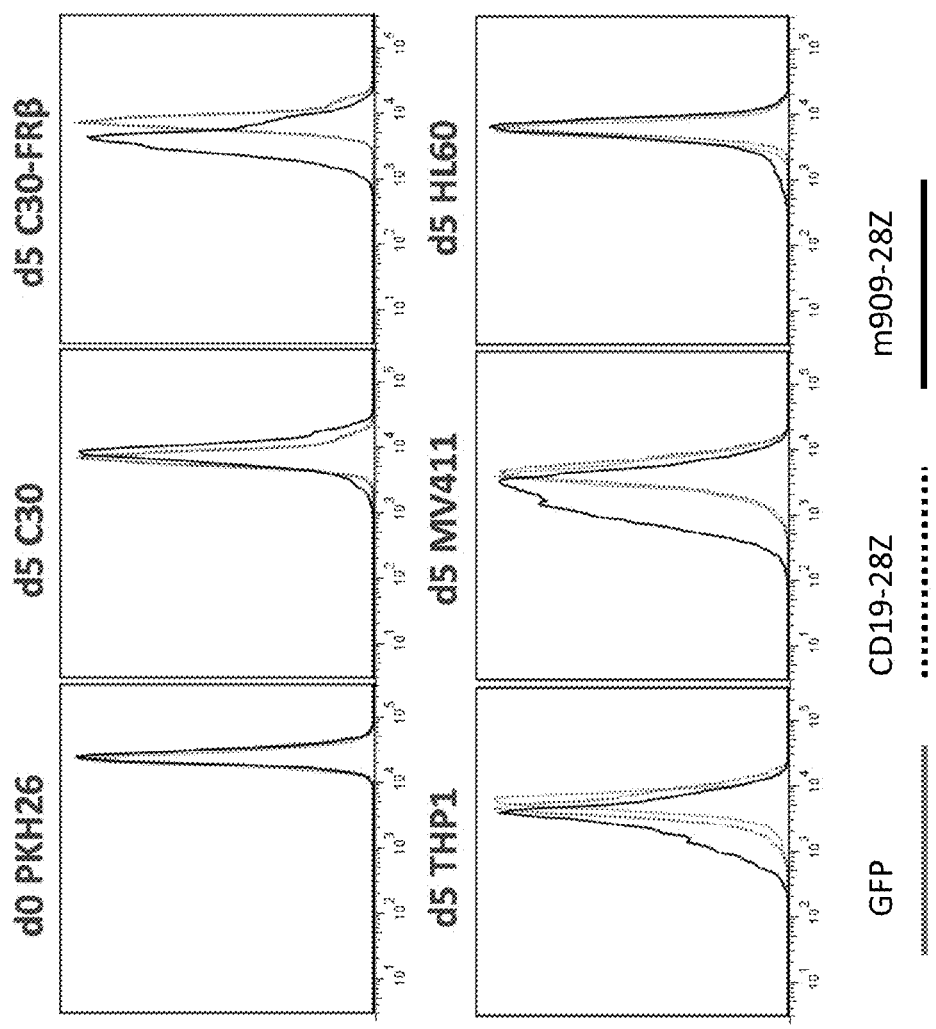
FIG. 10D is a panel of graphs showing CAR T cells exhibiting functional reactivity, as measured by proliferation after 5 days, towards human FRβ+ AML cell lines.
Figure 10E:
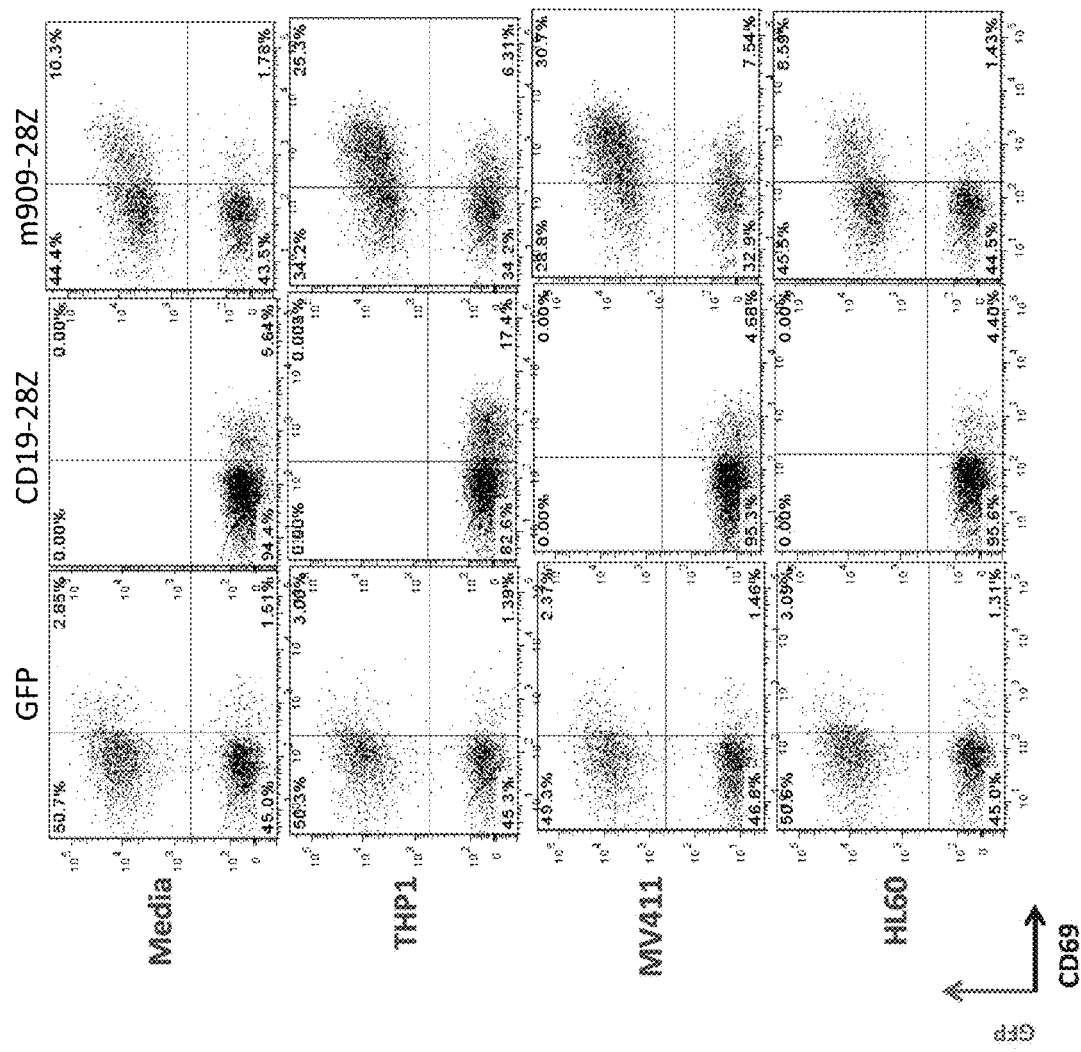
FIG. 10E is a panel of graphs showing CAR T cells exhibiting functional reactivity, as measured by CD69 expression, towards human FRβ+ AML cell lines.
Figure 11A:
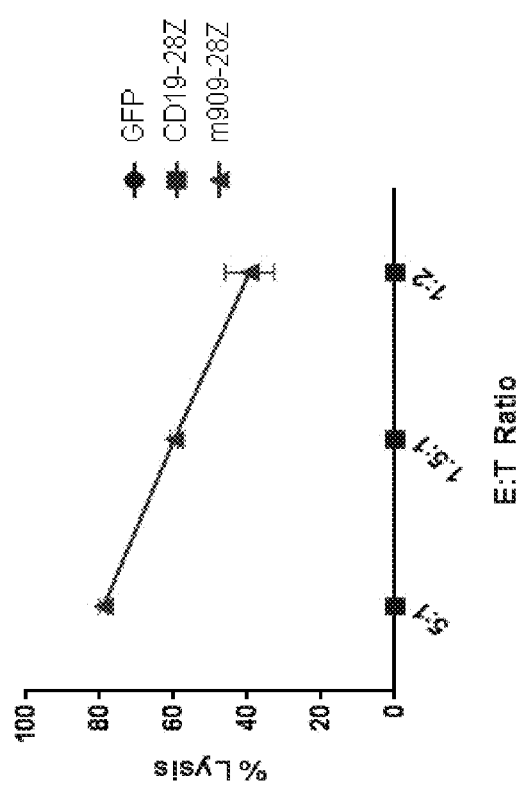
FIG. 11A is a graph showing m909 CAR T cells exhibiting antigen-specific lysis of human FRβ+ AML cell line, THP1.
Figure 11B:
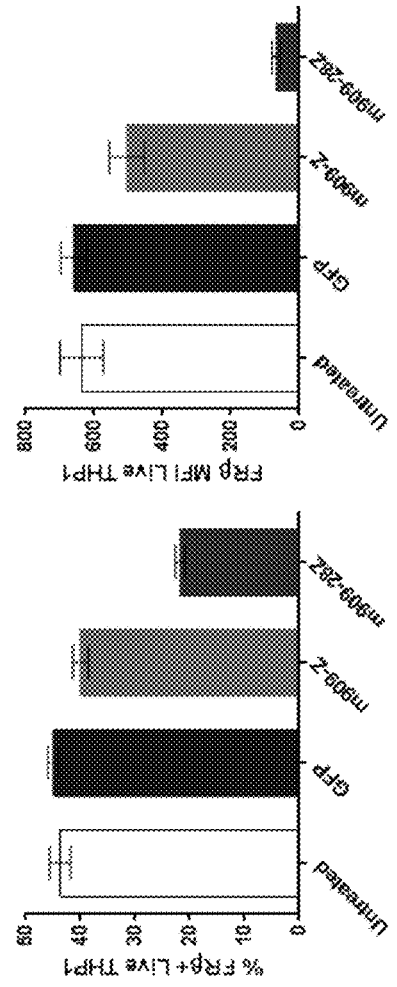
FIG. 11B is a panel of graphs showing m909 CAR T cells exhibiting antigen-specific lysis of human FRβ+ AML cell line, THP1, by measuring percentage of live FRβ+ cells.

To assess the functionality of m909 CAR T cells in a more physiologically relevant model, human AML cell lines with and without FRβ expression were acquired. m909 CAR T cells showed specific reactivity towards the FRβ+ AML line THP1 but not HL60, which lacks detectable FRβ expression. Despite its broad expression in AML, FRβ antigen expression on AML cells is generally low (FIGS. 10A and 10B) and could present a potential obstacle to FRβ-mediated CAR therapy. Treatment of AML cells m909 CAR T cells resulted in immune recognition by the m909 CAR T cells (FIGS. 10C, 10D and 10E). m909 CAR T cells also mediated the specific lysis of THP1 cells in (FIGS. 11A and 11B).

Figure 12A:
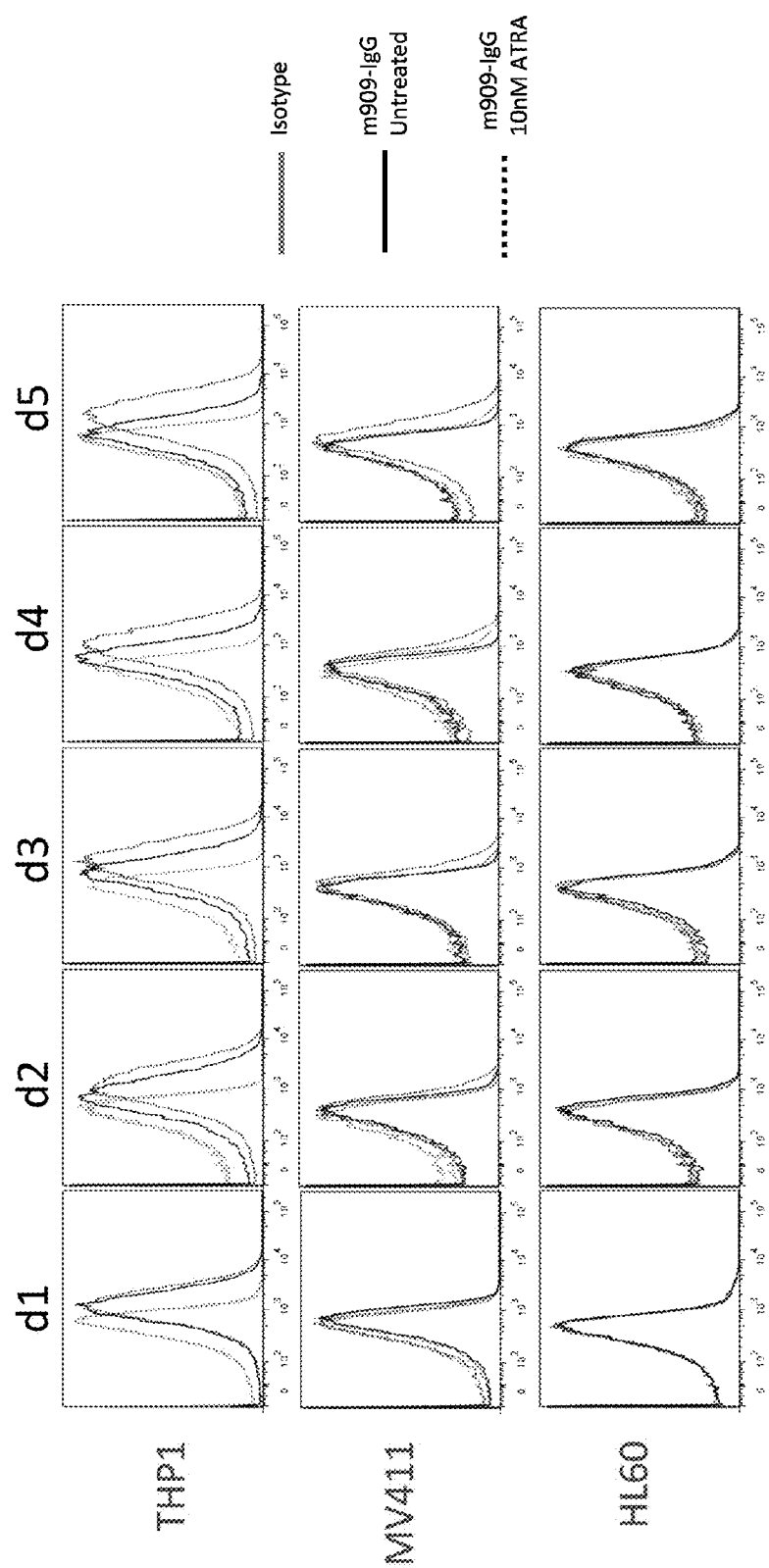
FIG. 12A is a panel of images showing FRβ expression on acute myeloid leukemia (AML) cell lines after 10 nM ATRA 5 day treatment.
Figure 12B:
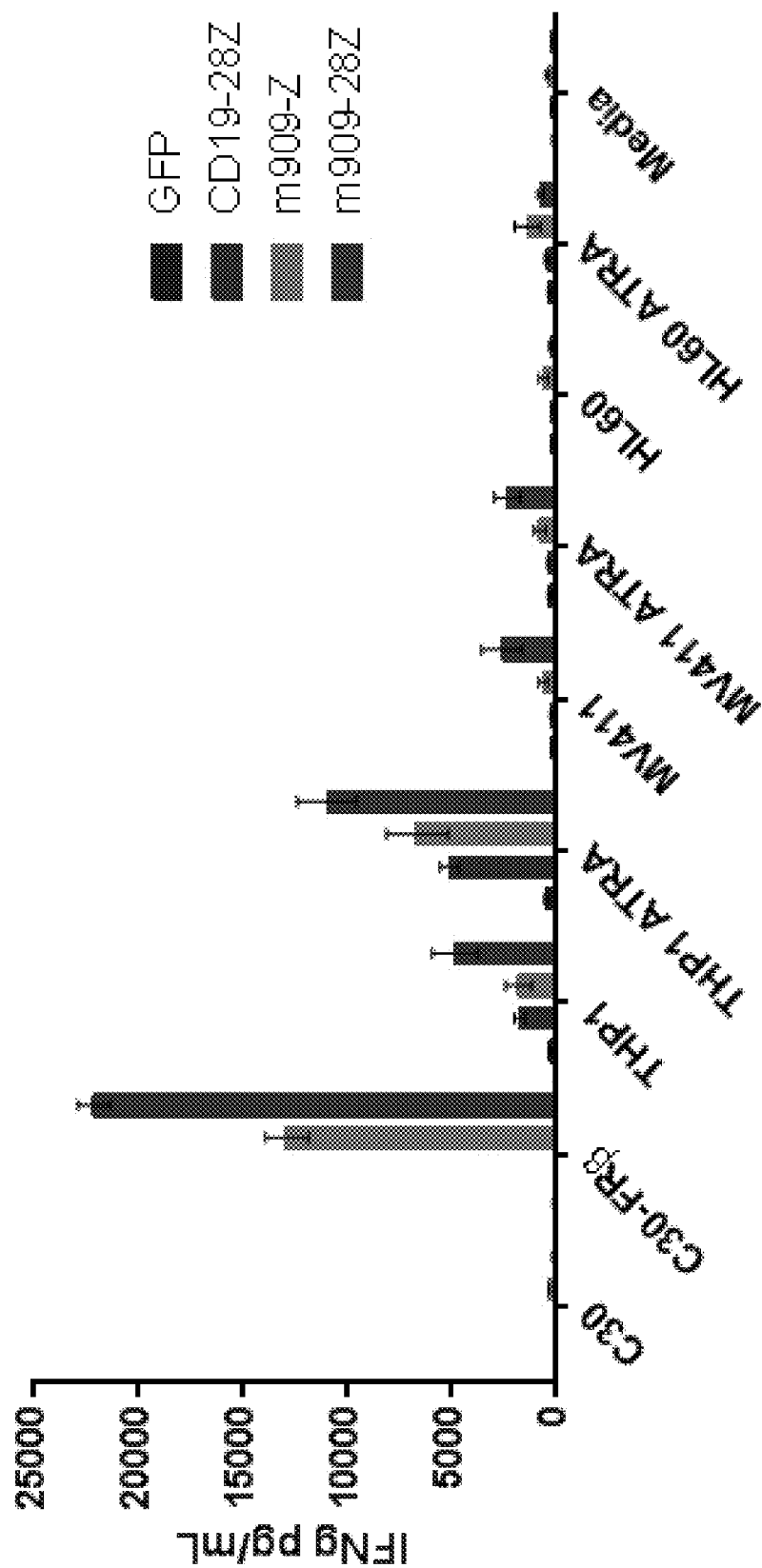
FIG. 12B is a graph showing ATRA treatment induced FRβ upregulation and IFNγ production after overnight co-culture with acute myeloid leukemia (AML) cell lines.
Figure 12C:
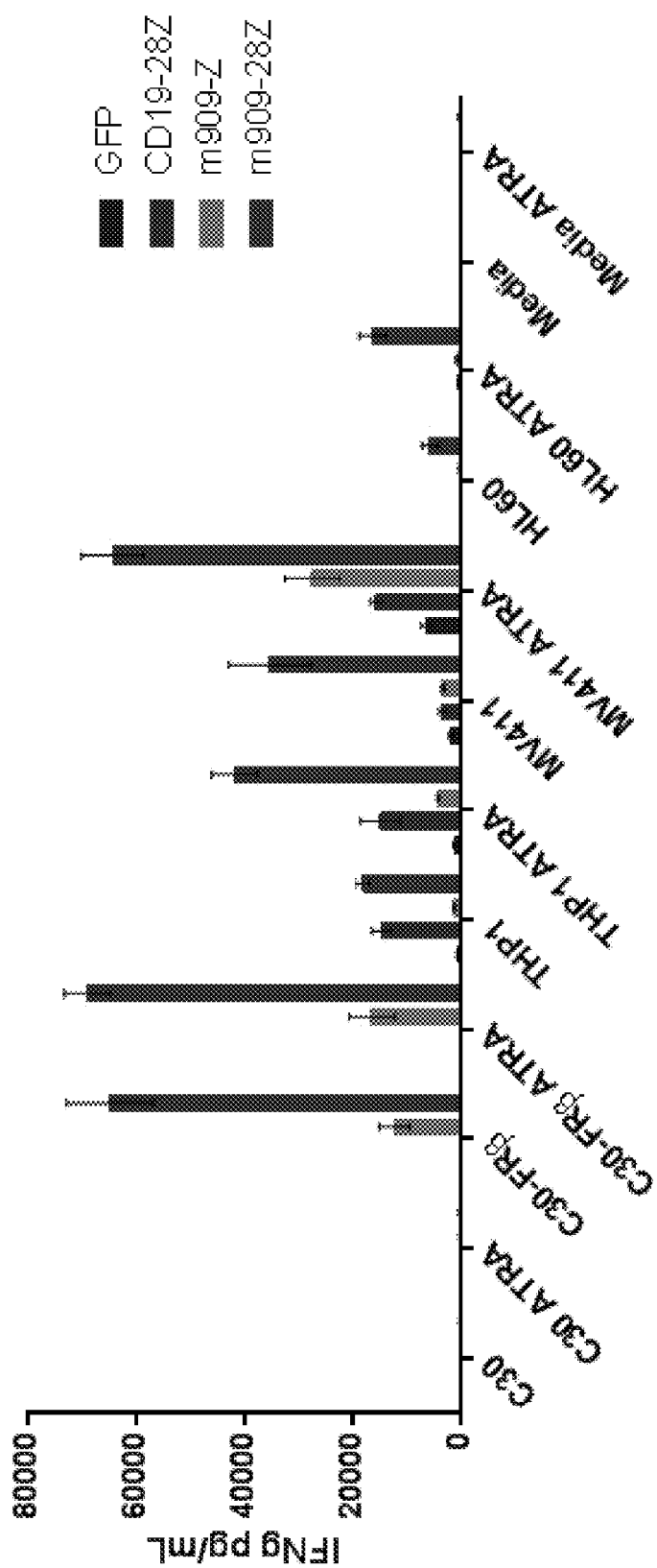
FIG. 12C is a graph showing ATRA treatment induced FRβ upregulation by acute myeloid leukemia (AML) cell lines increases immune recognition and IFNγ production by FRb CAR T cells after 3 day co-culture.
Figure 13:
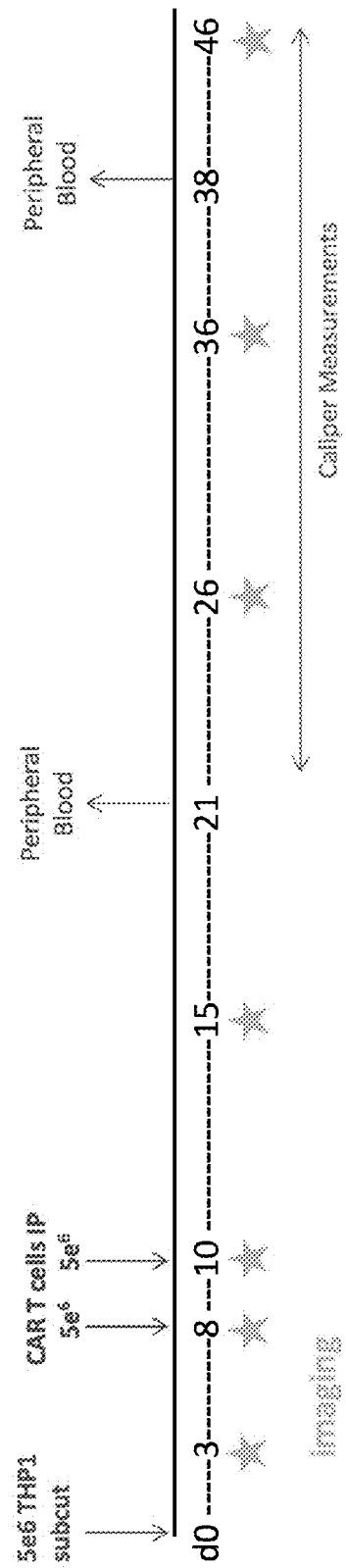
FIG. 13 is a diagram showing the in vivo experimental design for early treatment model.

However, treatment of AML cells with all-trans retinoic acid (ATRA), a vitamin A derivative currently part of standard of care regimens for AML subclass M3 (or APL), enhanced the intensity of FRβ expression (FIG. 12A), resulting in increased immune recognition by m909 CAR T cells (FIGS. 12B and 12C).

Figures 14A, 14B:
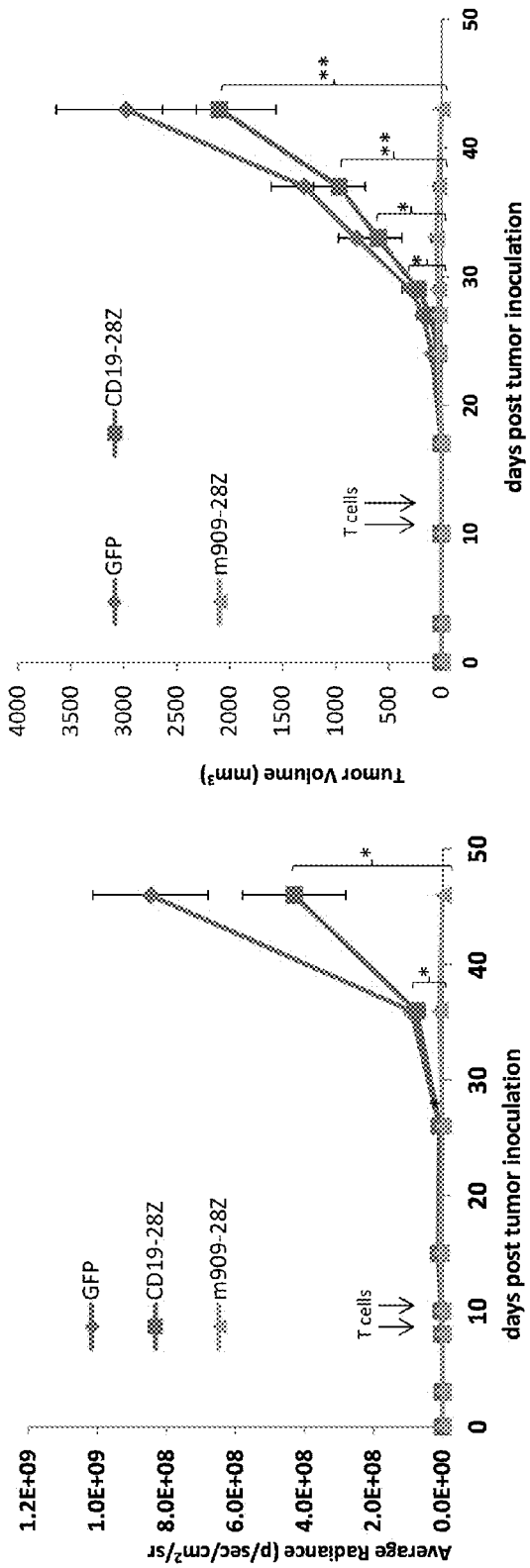
FIG. 14A is a graph showing THP1 tumor luminescence after m909-28Z CAR treatment in NOD/SCID mice.
FIG. 14B is a graph showing THP1 tumor volume after m909-28Z CAR treatment in NOD/SCID mice.
Figure 14C:
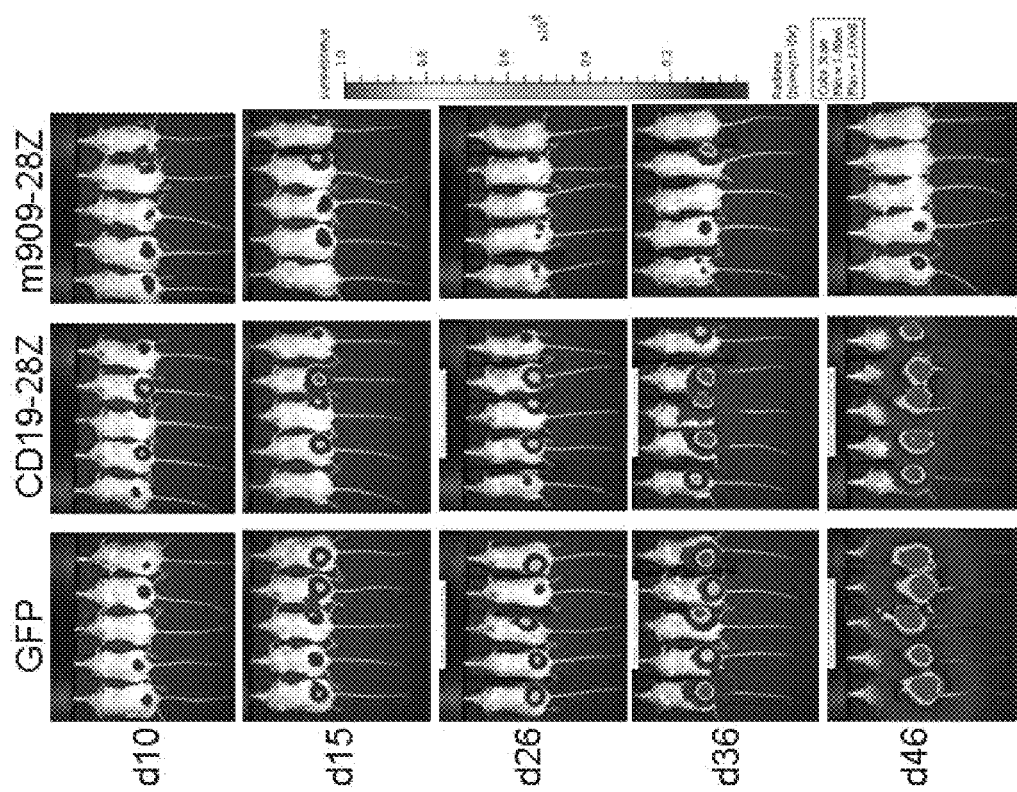
FIG. 14C is an image showing THP1 tumor luminescence in mice after m909-28Z CAR treatment of NOD/SCID mice.
Figure 14E:
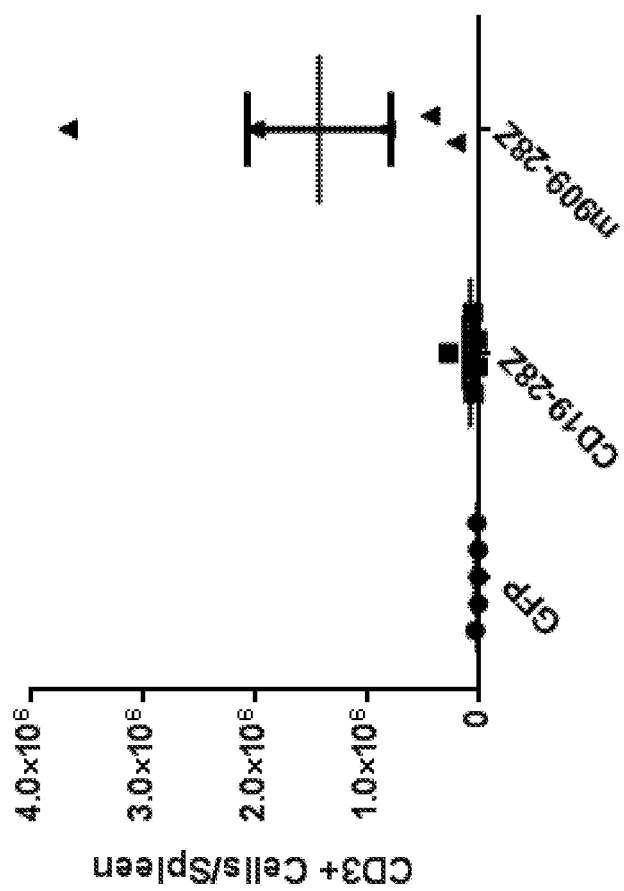
FIG. 14E is a panel of graphs showing m909-28Z CAR T cell (CD3+) accumulation in the spleen of treated THP1-tumor bearing NOD/SCID mice at 48 days.

Finally, the efficacy of m909 CAR T cells was tested in an in vivo mouse model of human AML using THP1 engrafted in NSG mice. Three treatment groups were analyzed, GFP transduced T cells, CD19-28Z transduced T cells, and GFP-m909-28Z transduced T cells. m909-28Z CAR T cells significantly decreased THP1 tumor growth (FIGS. 14A, 14B and 14C) when CAR T cells were given 8-10 days following tumor inoculation. An increase in peripheral T cell numbers was observed in m909 CAR T cell treated mice as compared to control T cells, indicative of antigen-specific proliferation in vivo.

m923 CAR

Figure 15:
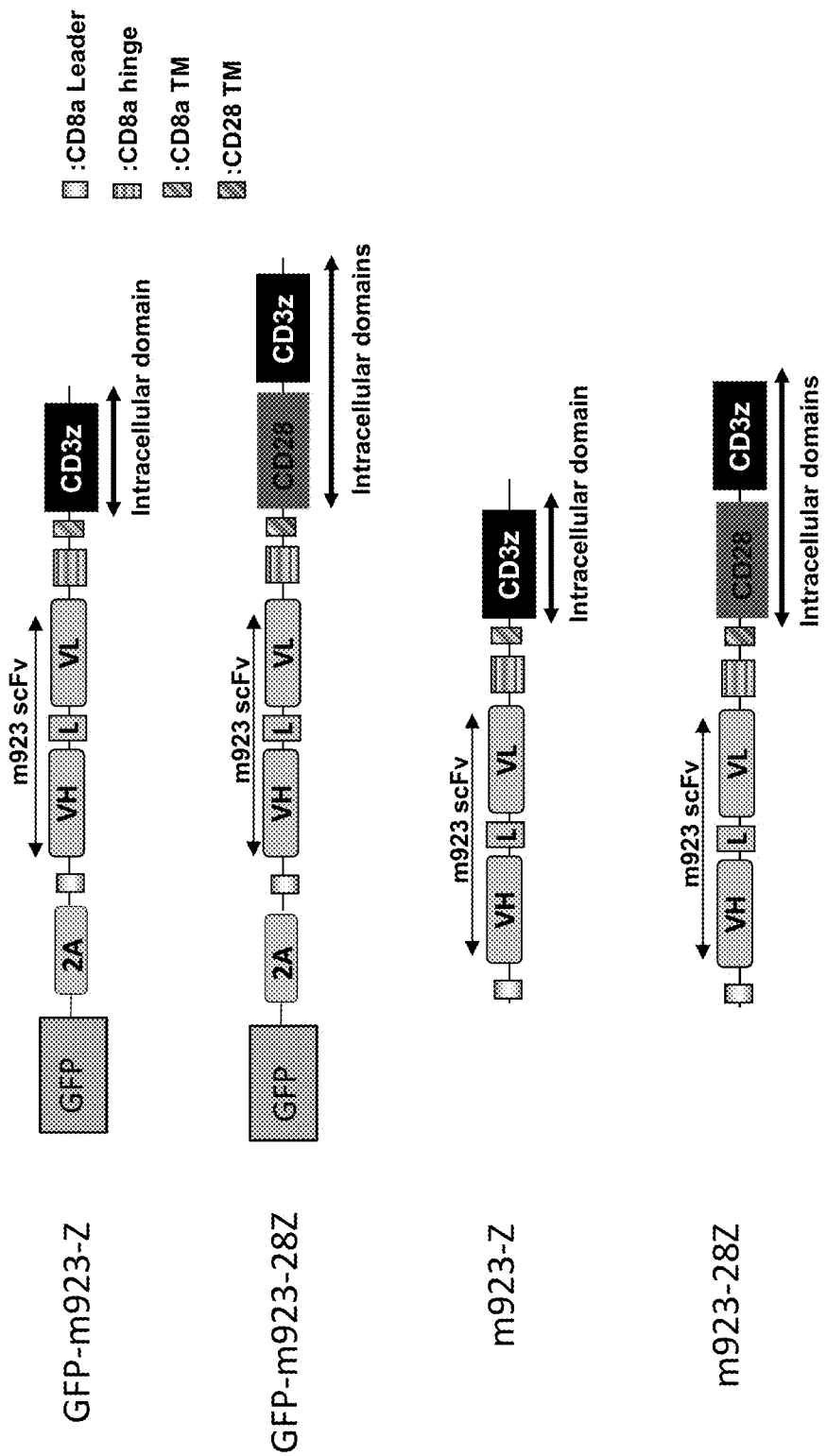
FIG. 15 is a diagram illustrating the FRβ specific m923 CARconstructs.
Figure 16:
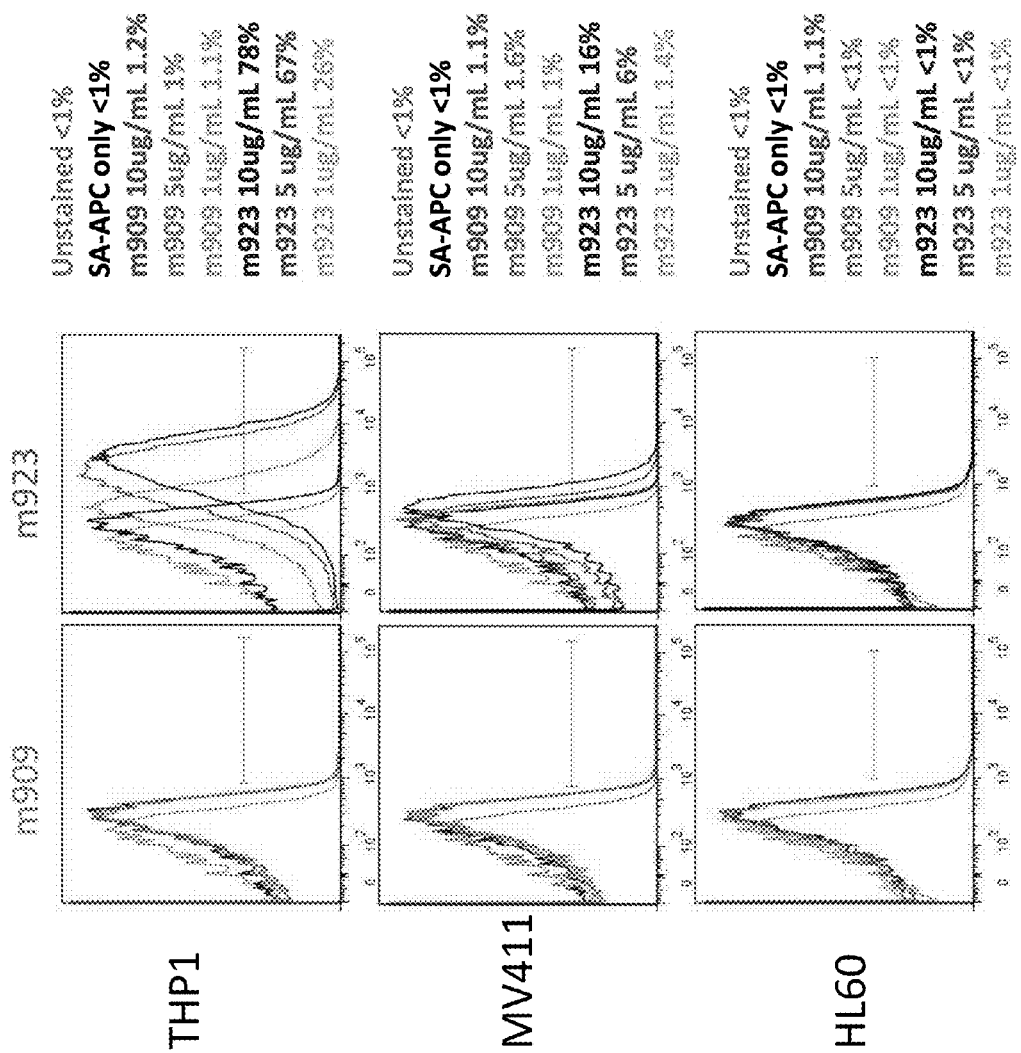
FIG. 16 is a panel of graphs showing m932-scFv exhibited increased affinity to FRβ.

A higher affinity scFv, m923 (FIG. 15) was used in the following experiments, and testing began on the hypothesis that the higher affinity m923 CARs (FIG. 16) will have more potent reactivity for FRβ+ target cells.

Figure 17:
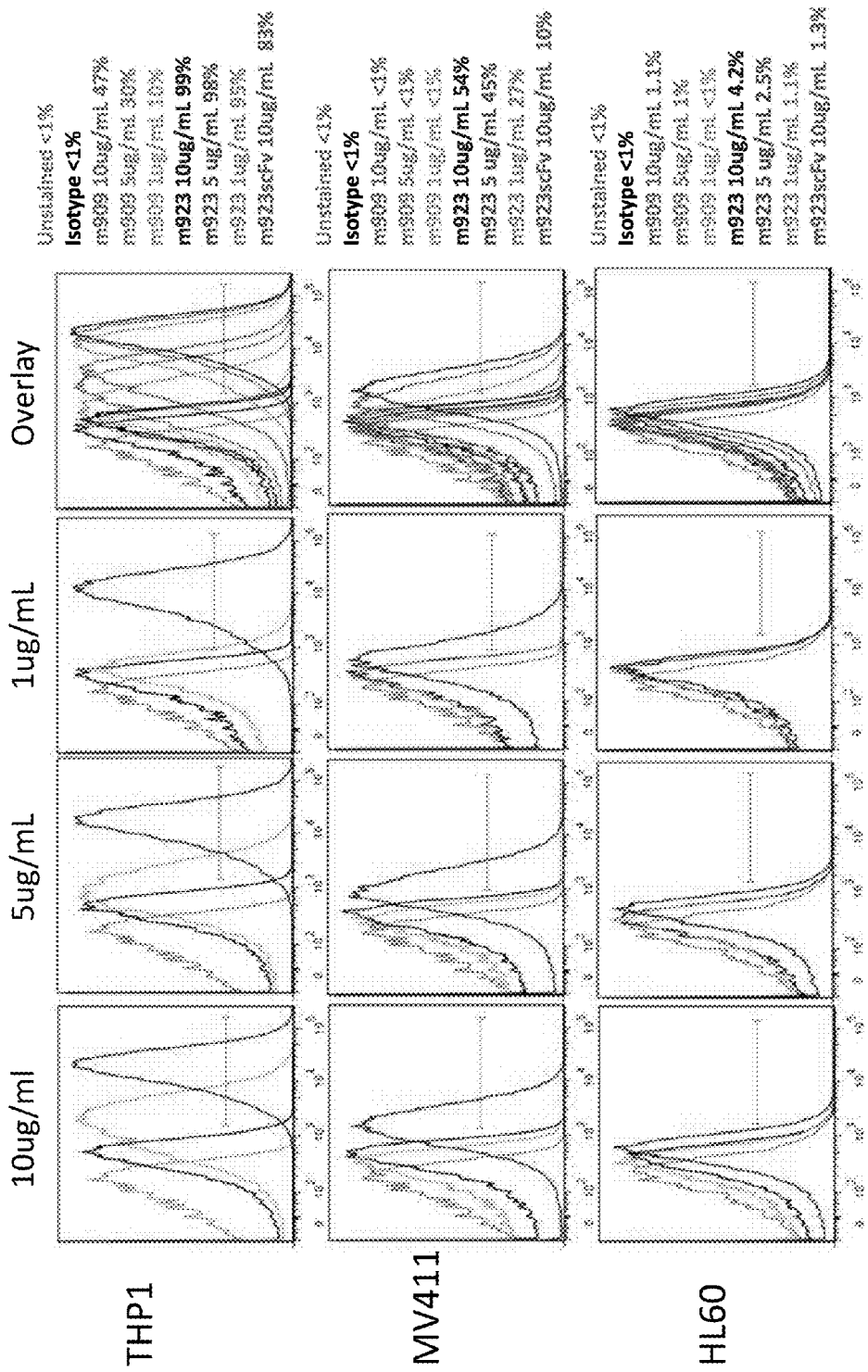
FIG. 17 is a panel of graphs showing m932-IgG exhibited increased affinity to FRβ as compared to m909.
Figure 18:
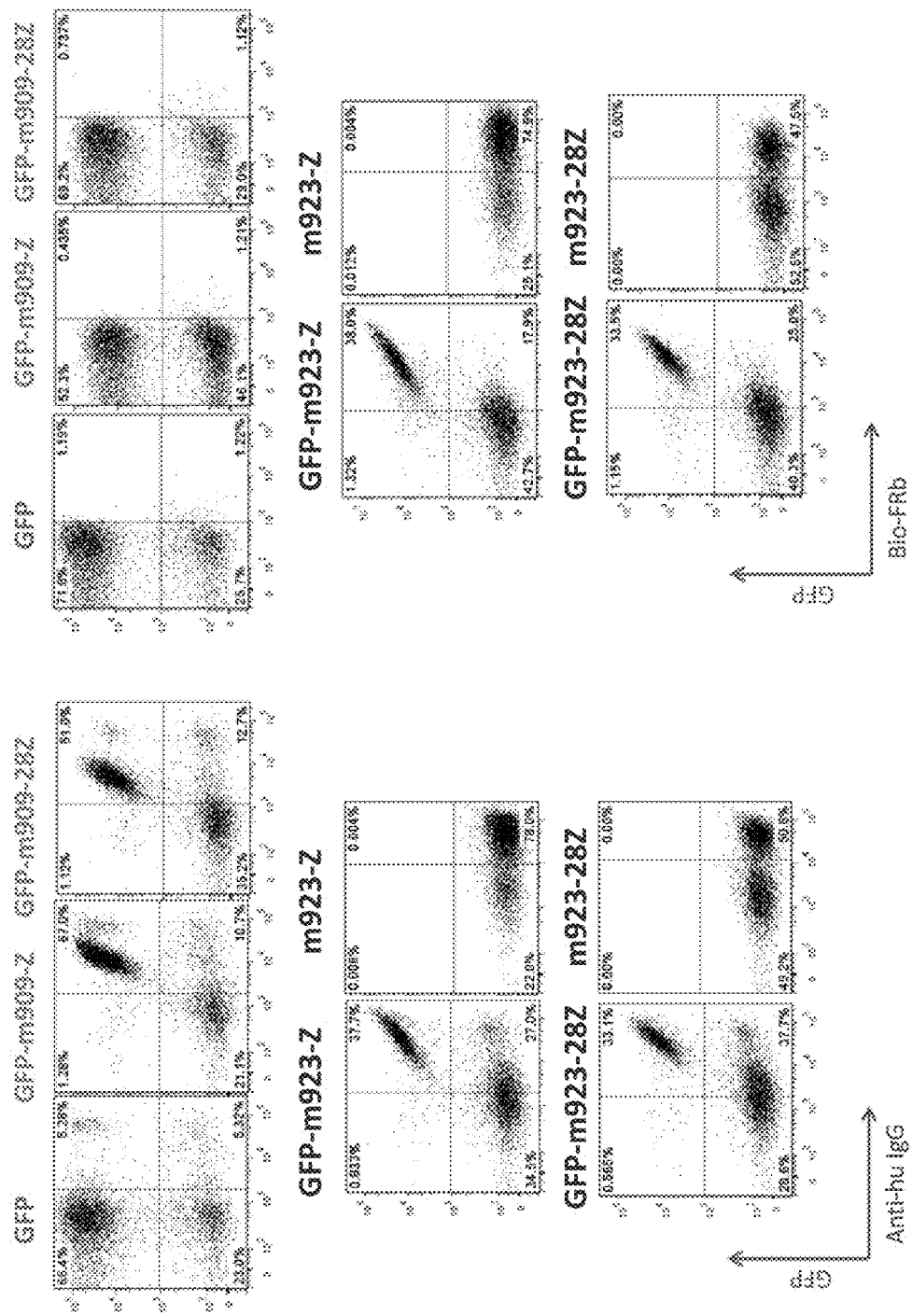
FIG. 18 is a panel of flow diagrams showing robust surface expression of m932 CARs on human T cells.
Figure 19:
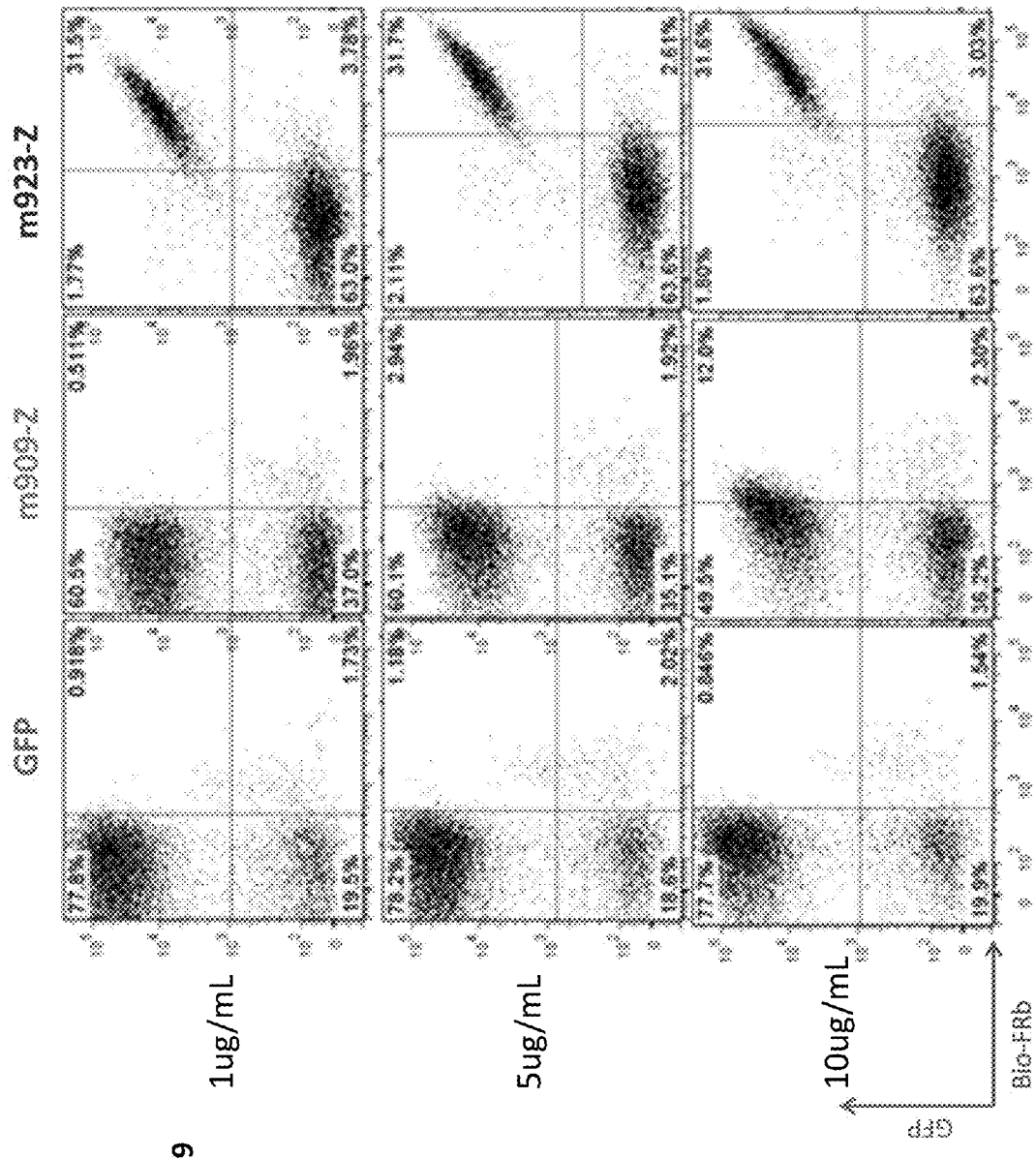
FIG. 19 is a panel of flow diagrams showing m932 CARs exhibited higher affinity for recombinant human FRβ protein.
Figure 20:
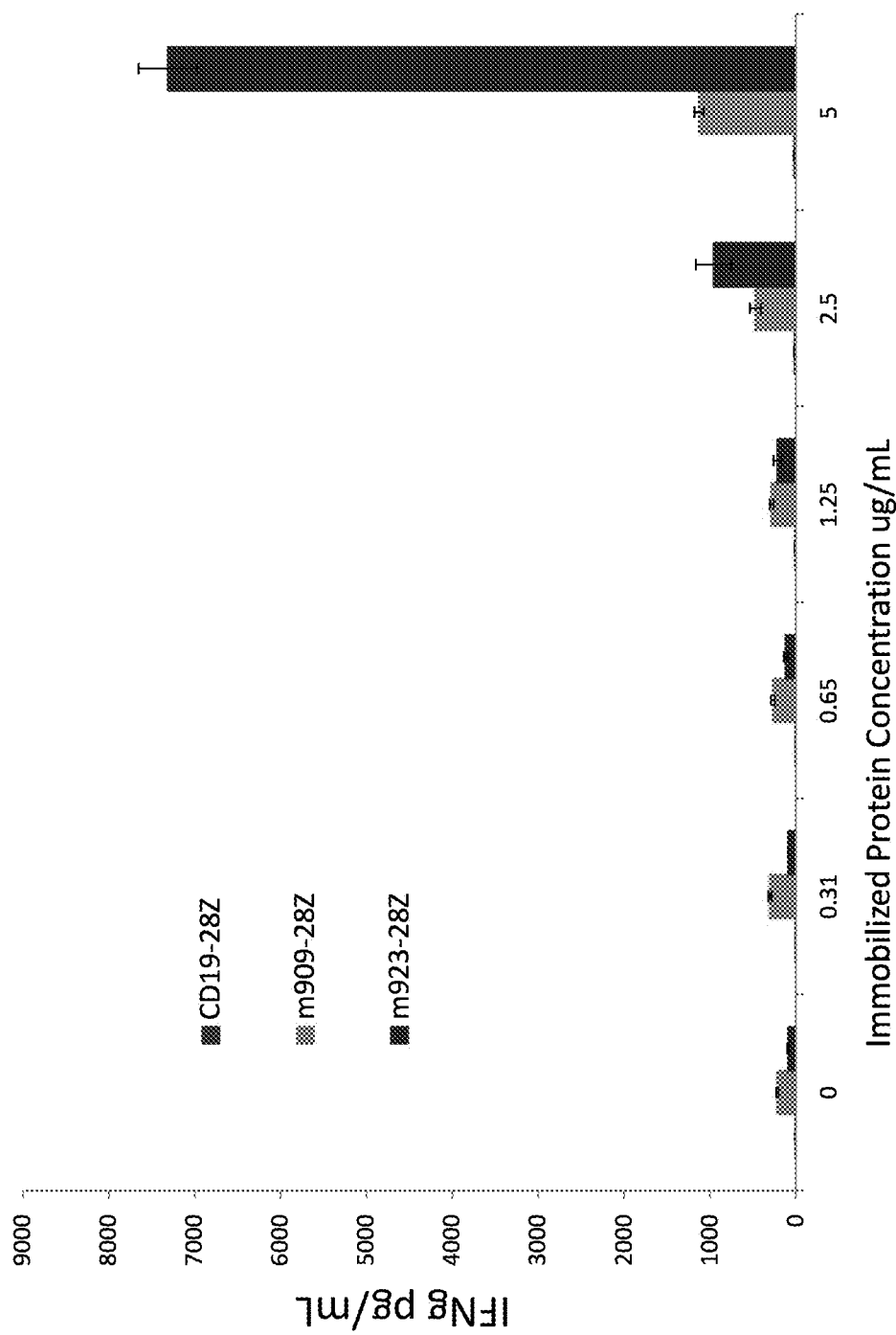
FIG. 20 is a graph showing m932 CARs exhibited higher affinity than m909 for immobilized recombinant human FRβ protein.
Figure 21A:
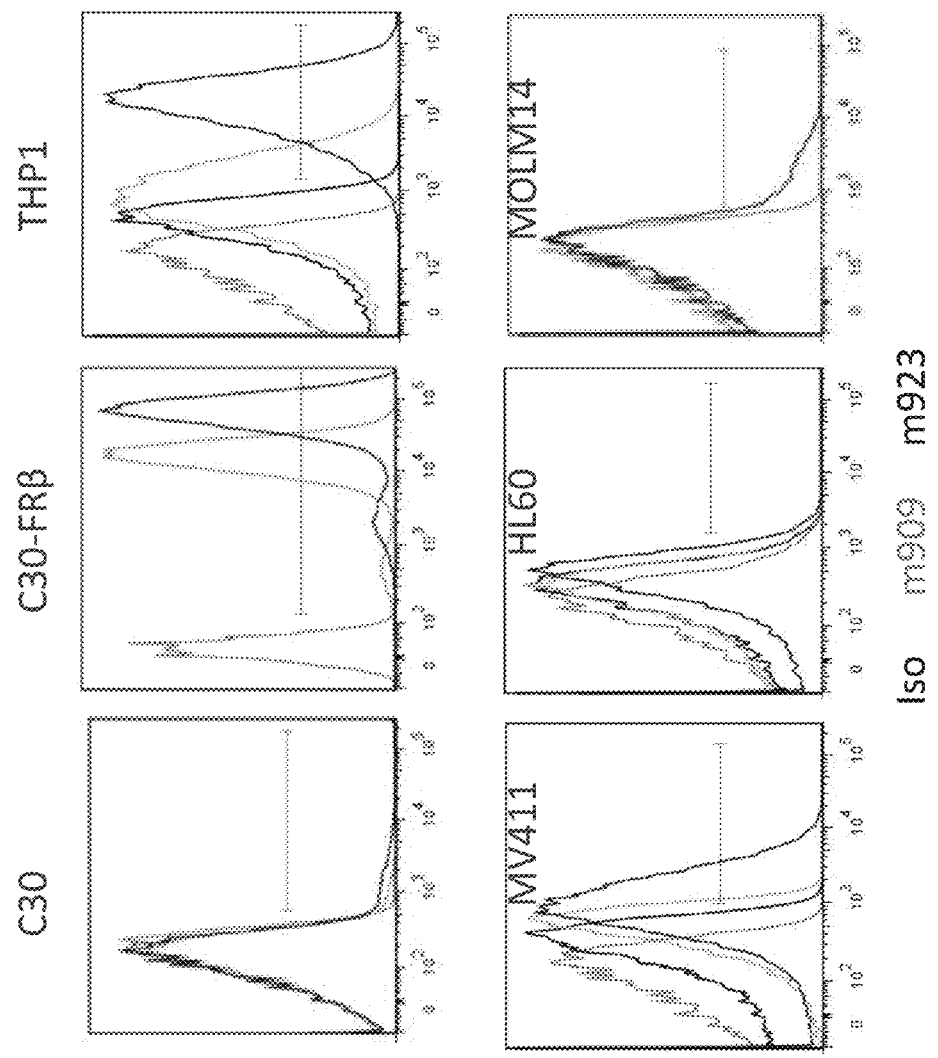
FIG. 21A is a panel of graphs showing FRβ expression by engineered and endogenous FRβ-expressing cell lines detected using anti-FRb antibodies in upper row or scFvs in lower row.
Figures 21B, 21C:
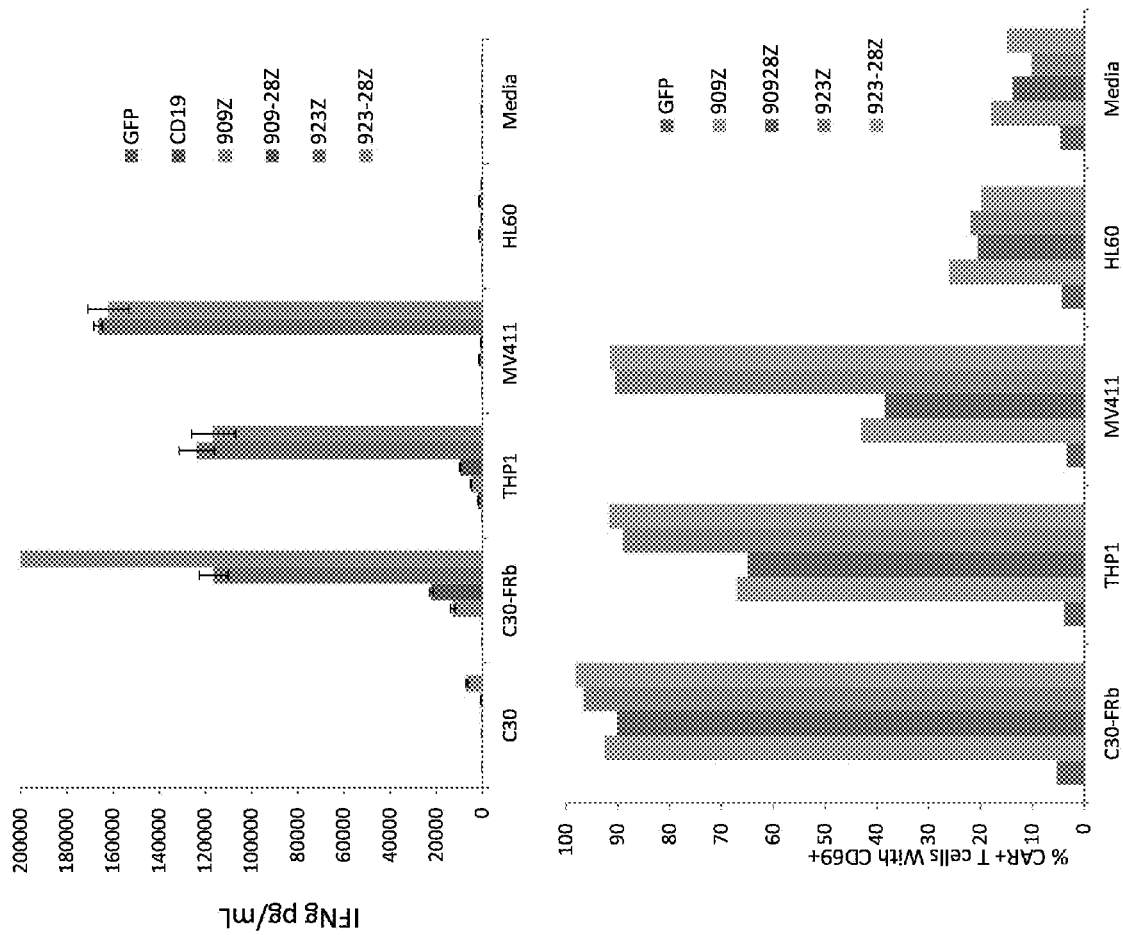
FIG. 21B is a graph showing increased IFNγ secretion by m932 CARs in response to FRβ-expressing cell lines.
FIG. 21C is a graph showing increased CD69 expression by m932 CARs in response to FRβ-expressing cell lines.
Figure 21D:
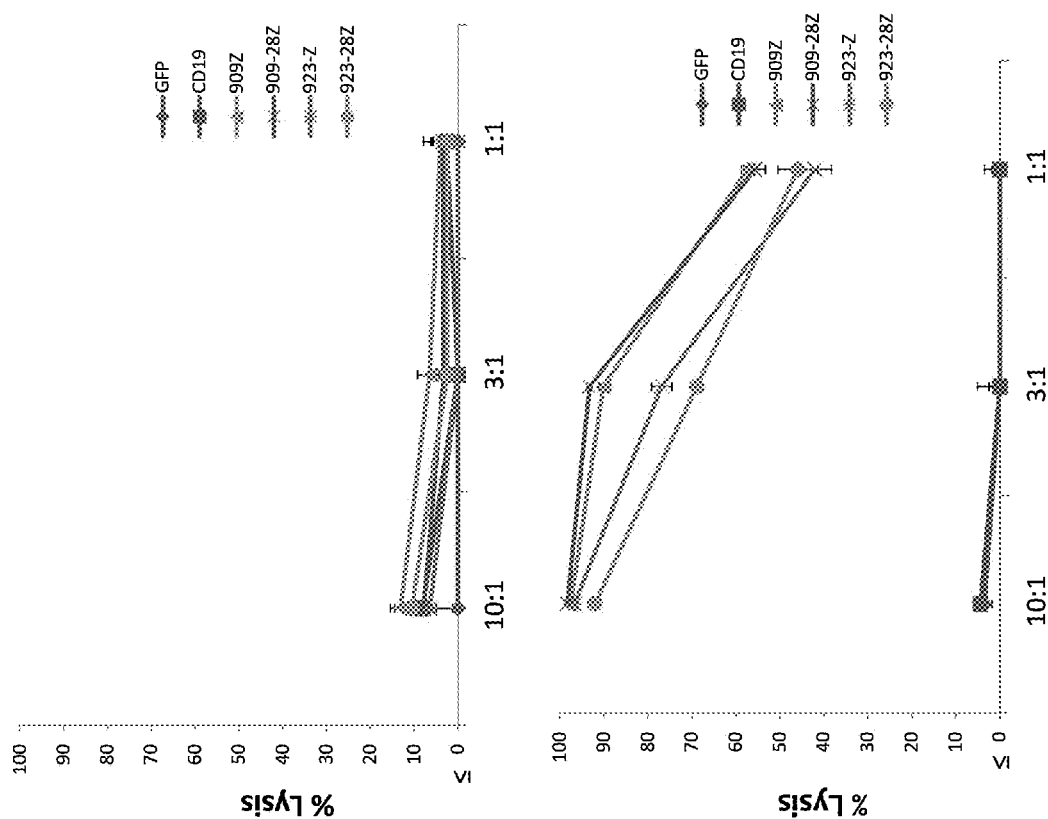
FIG. 21D is a panel of graphs showing m932 CAR T cells lyse engineered C30-FRβ cell lines.
Figure 21E:
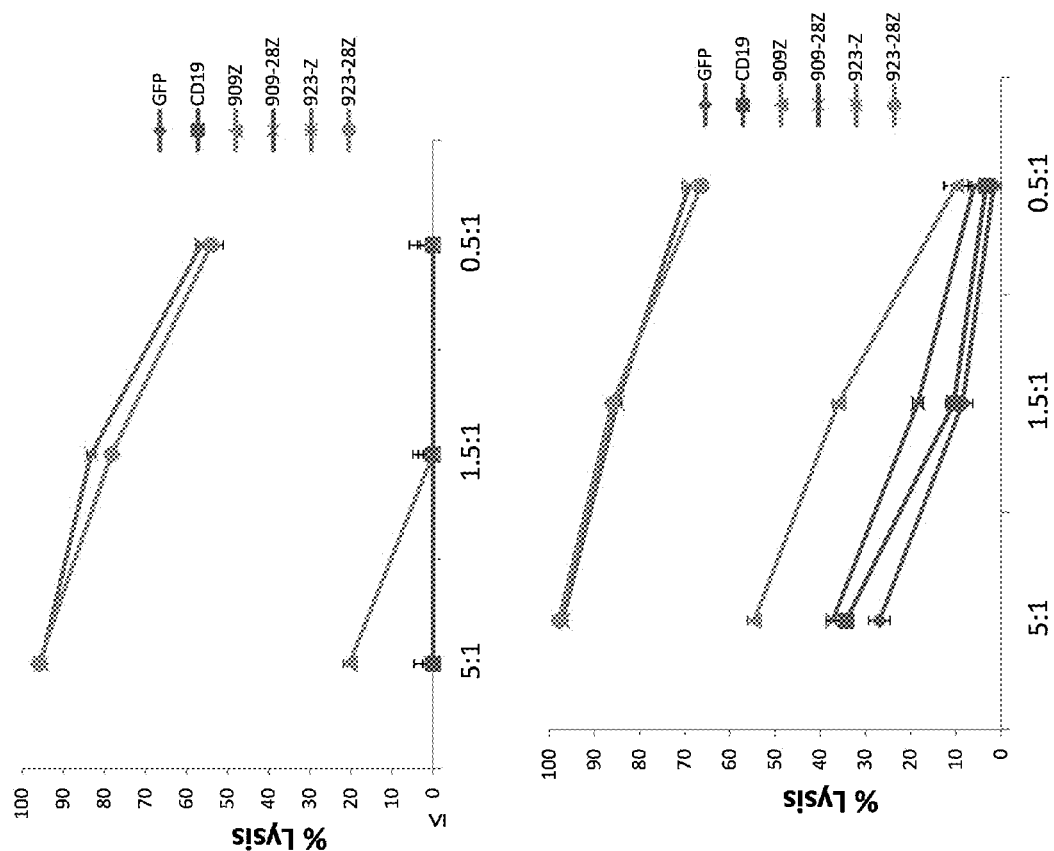
FIG. 21E is a panel of graphs showing m932 CAR T cells specifically lysed THP1 cells.

Increased labeling of FRβ on cell lines was observed when using m923 antibody as compared to m909 (FIGS. 17 and 18). Also, increased binding of m923 CAR T cells to recombinant FRβ was observed by flow cytometry (FIG. 19) and reactivity against immobilized protein (FIG. 20). m923 CAR T cells showed significant improvement over m909 CAR T cells in targeting FRβ+ human AML cell lines (FIG. 21A) when measuring increased cytokine secretion (FIG. 21B), CD69 expression (FIG. 21C), and target cell lysis (FIGS. 21D and 21E).

Figure 22:
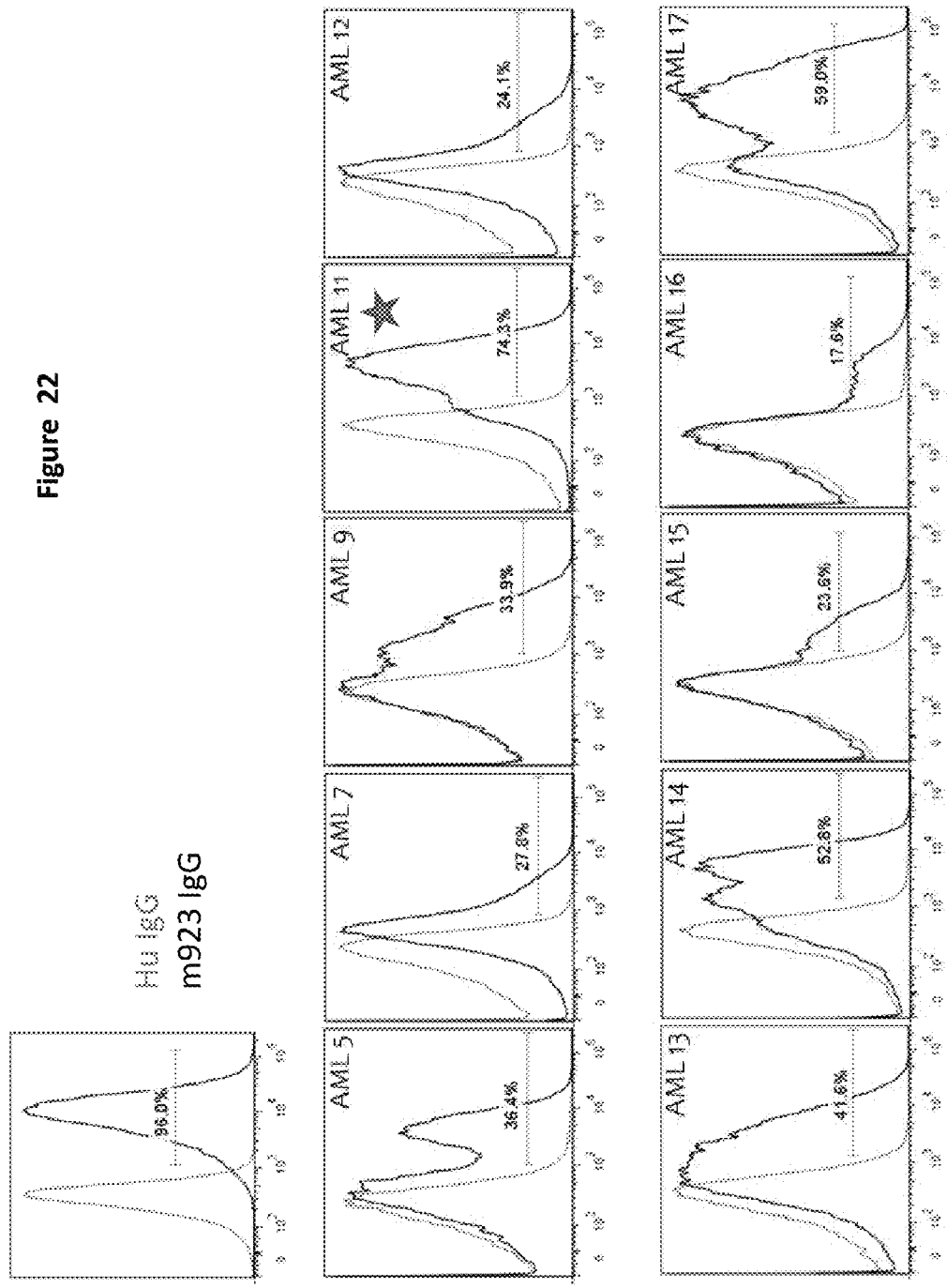
FIG. 22 is a panel of graphs showing FRβ expression detection in primary AML samples using m932 antibody.
Figure 23:
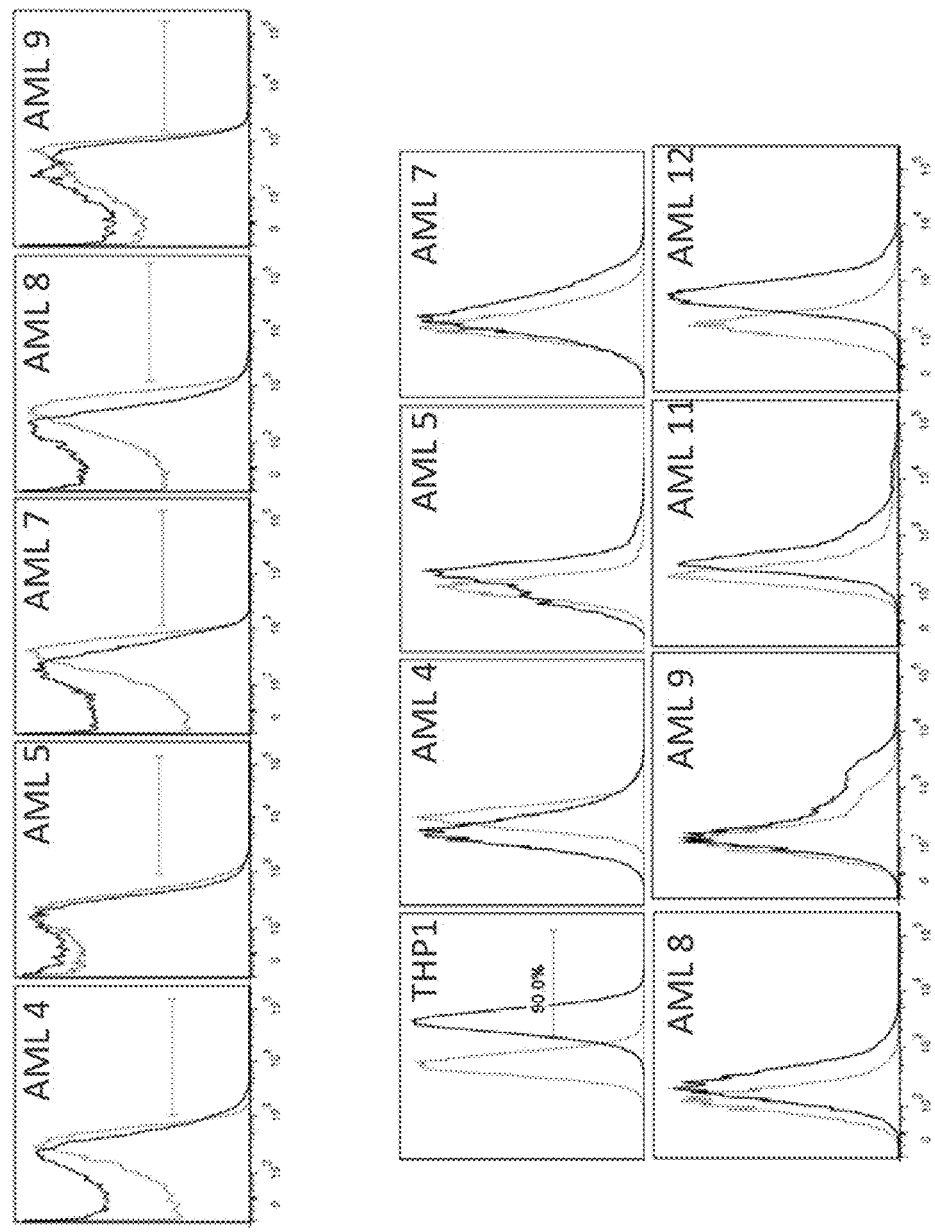
FIG. 23 is a panel of graphs showing lack of FRβ expression detection in primary AML samples using m909 antibody.
Figure 24A:
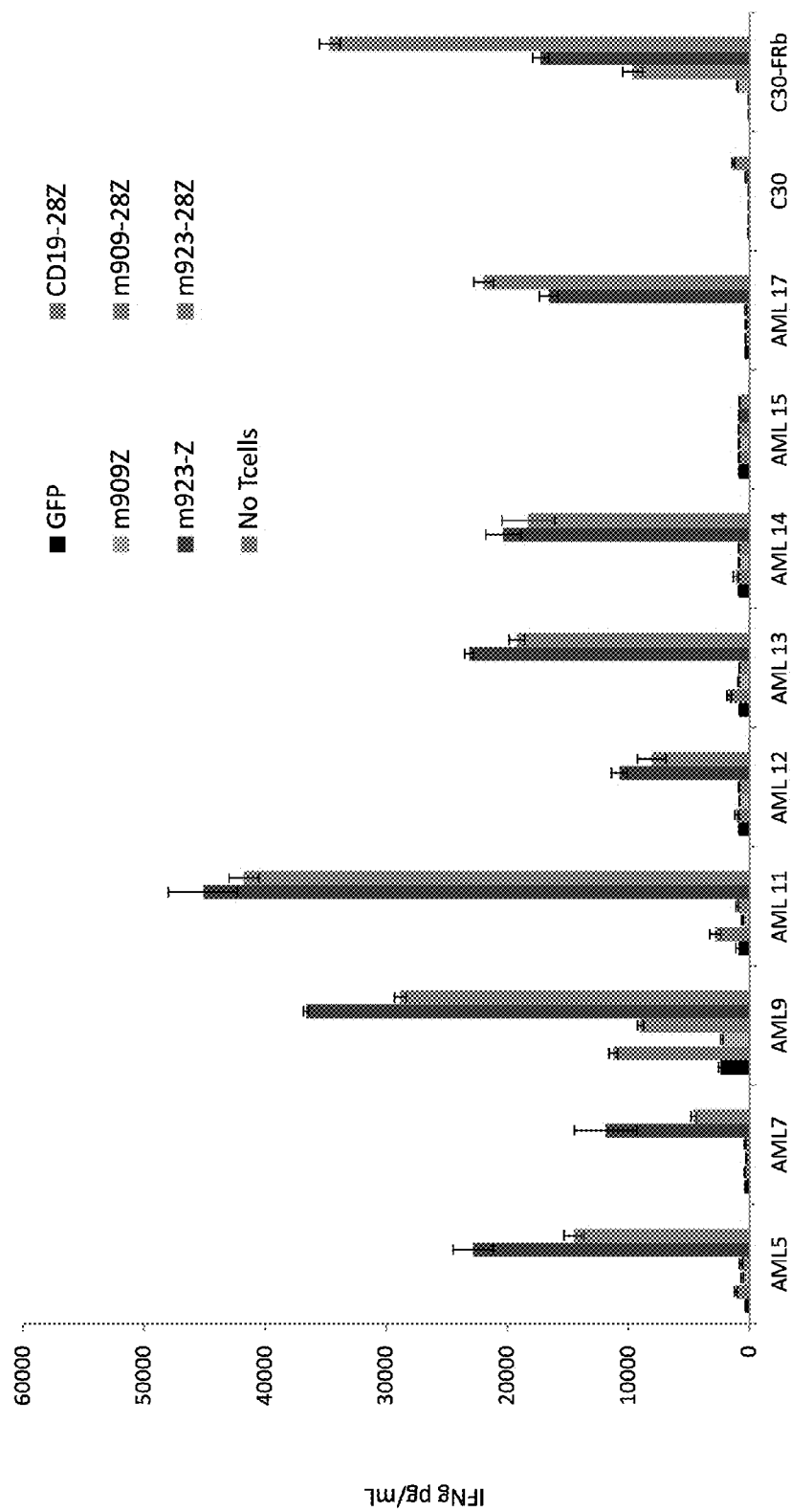
FIG. 24A is a graph showing IFNγ secretion from m923 CARs after coculture with FRβ expressing primary AML samples.
Figure 24B:
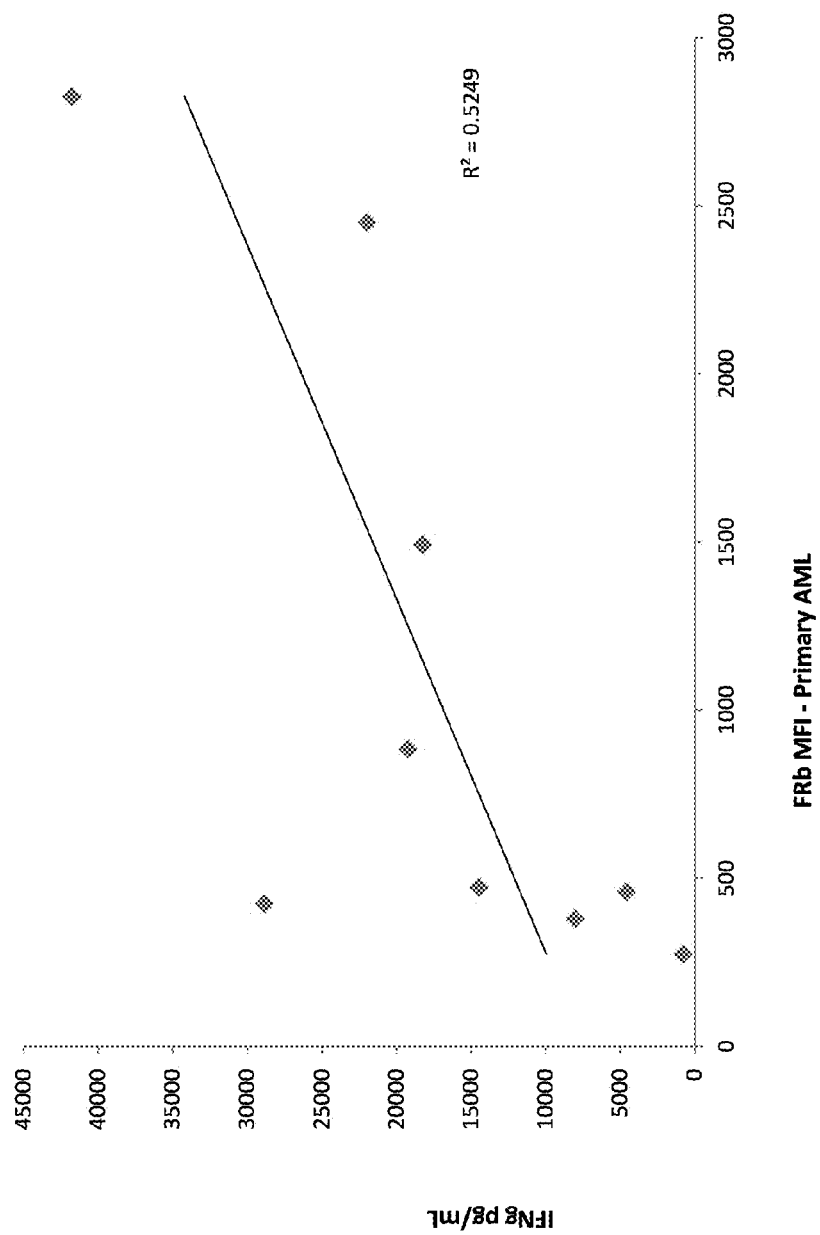
FIG. 24B is a graph showing the correlation of IFNγ secretion from m923 CARs with FRβ expression in primary AML samples.
Figure 24C:
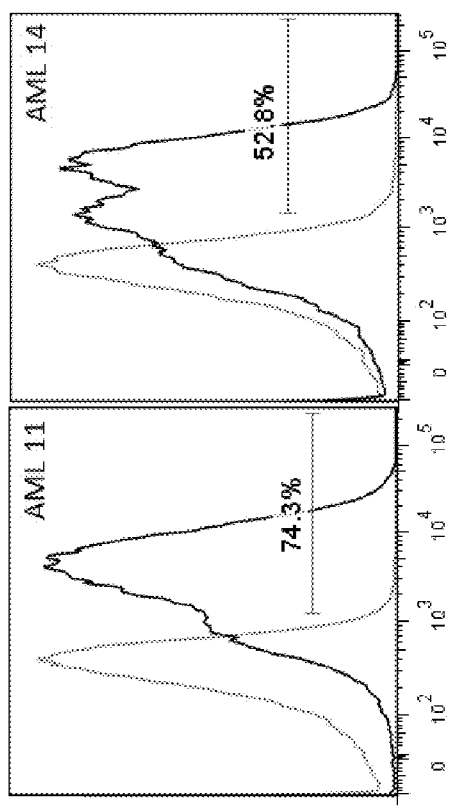
FIG. 24C is a panel of graphs showing FRβ expression by two primary AML samples using m923 antibody.
Figure 24D:
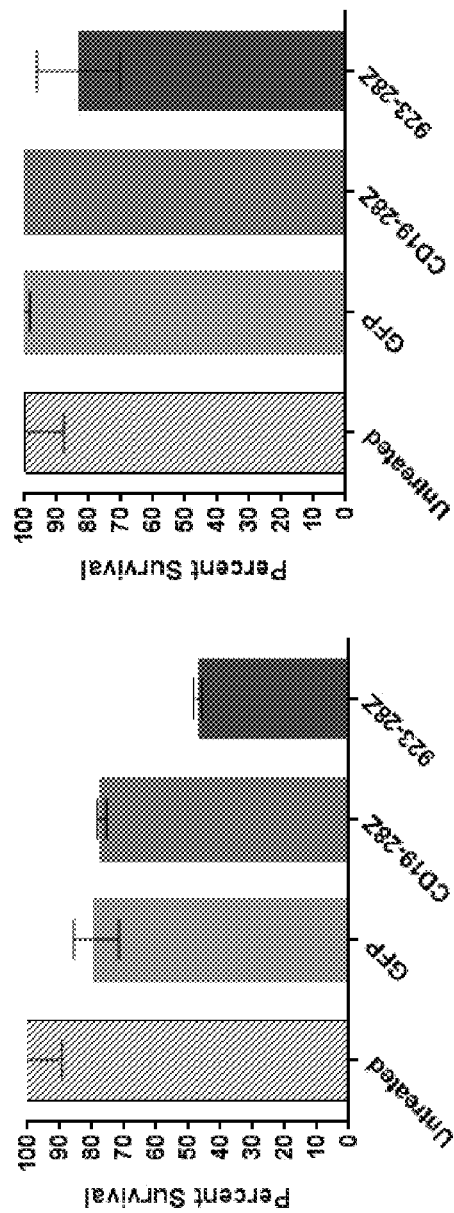
FIG. 24D is a panel of graphs showing m923 CAR T cells displayed specific lysis of primary AML samples.
Figure 24E:
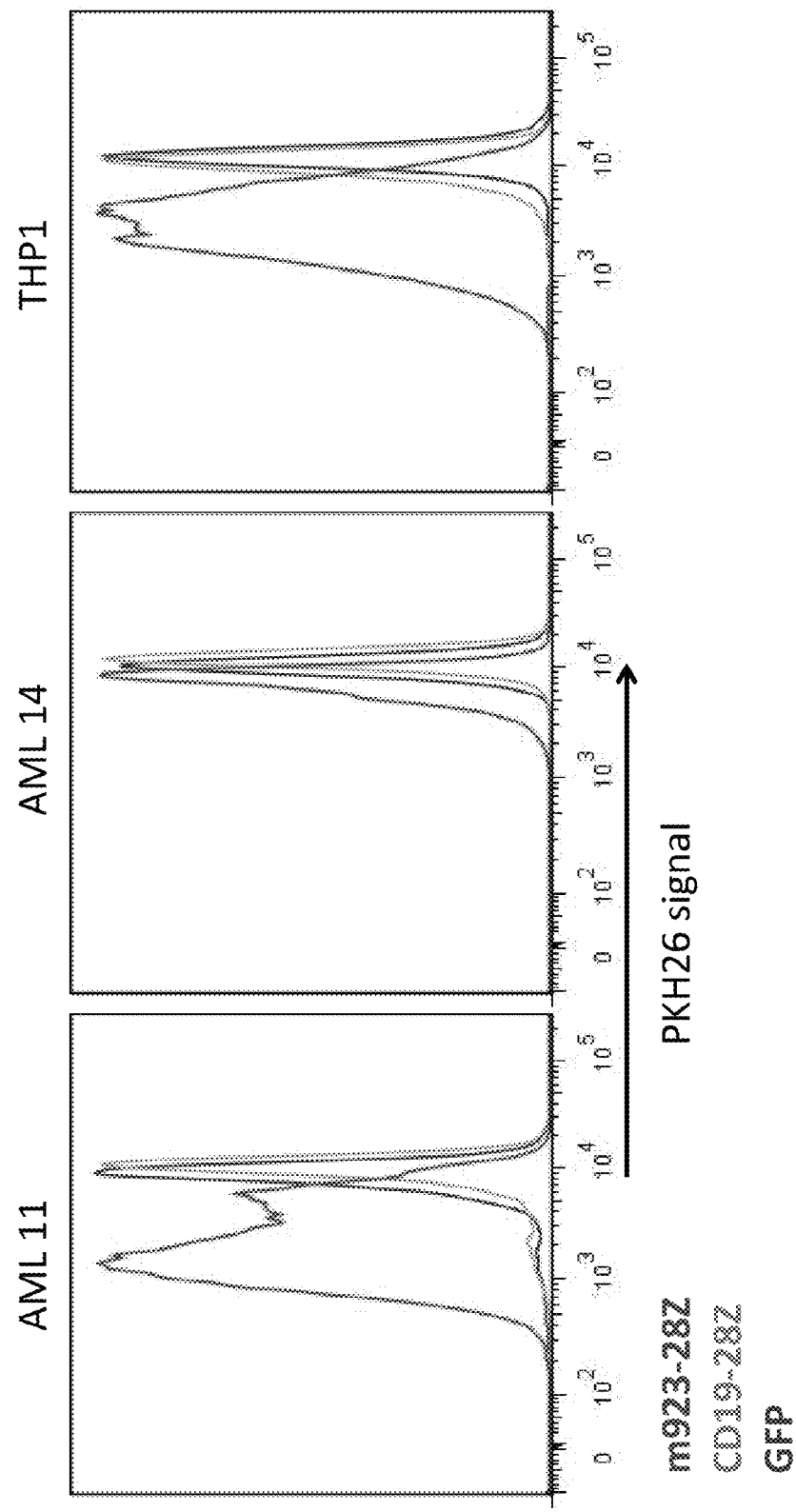
FIG. 24E is a panel of graphs showing proliferation of m923 CAR T cells in response to primary AML samples after 5 days.

In addition, m923 IgG was able to detect low levels of FRβ on primary human AML samples (FIG. 22), whereas m909 was not as sensitive (FIG. 23). Upon co-culture, m923 CARs secreted high levels of IFNγ (FIGS. 24A and 24B), suggesting an ability to target primary AML. In addition, m923 CAR T cells lysed FRβ+ primary human CD33+ AML blasts in vitro (FIGS. 24C and 24D) and underwent significant proliferation upon co-culture (FIG. 24E).

Figure 25:
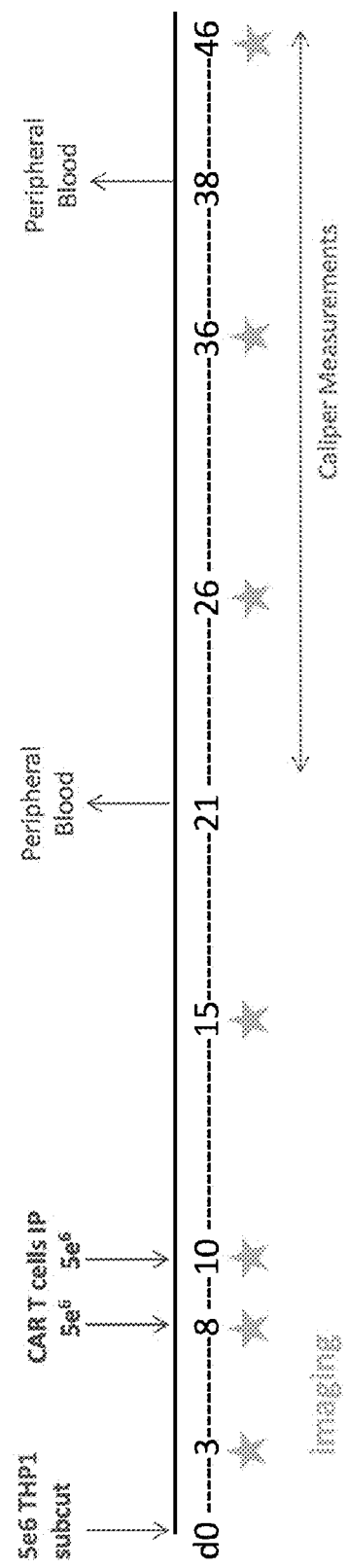
FIG. 25 is a diagram showing the in vivo experimental design for early treatment model.
Figure 26:
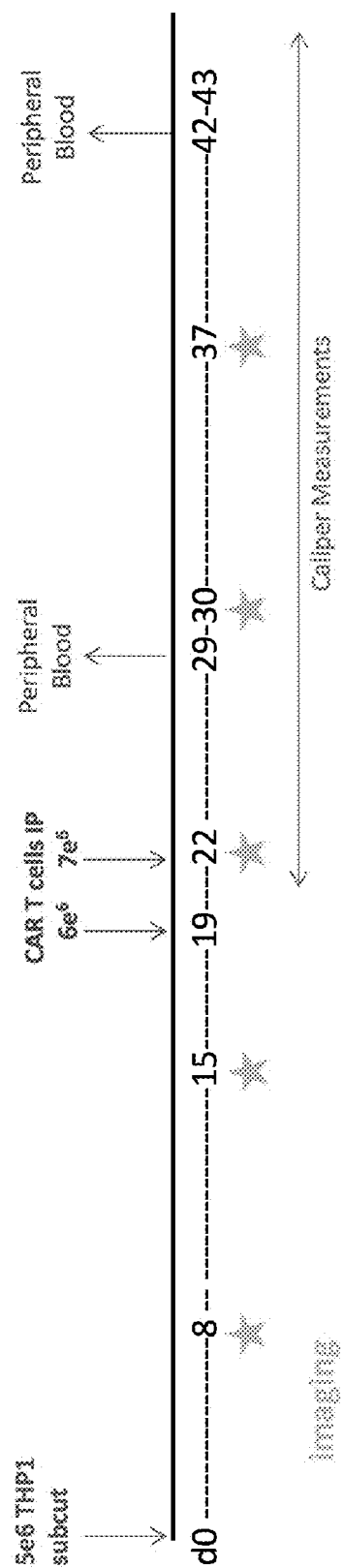
FIG. 26 is a diagram showing the in vivo experimental design for late treatment model.
Figure 27:
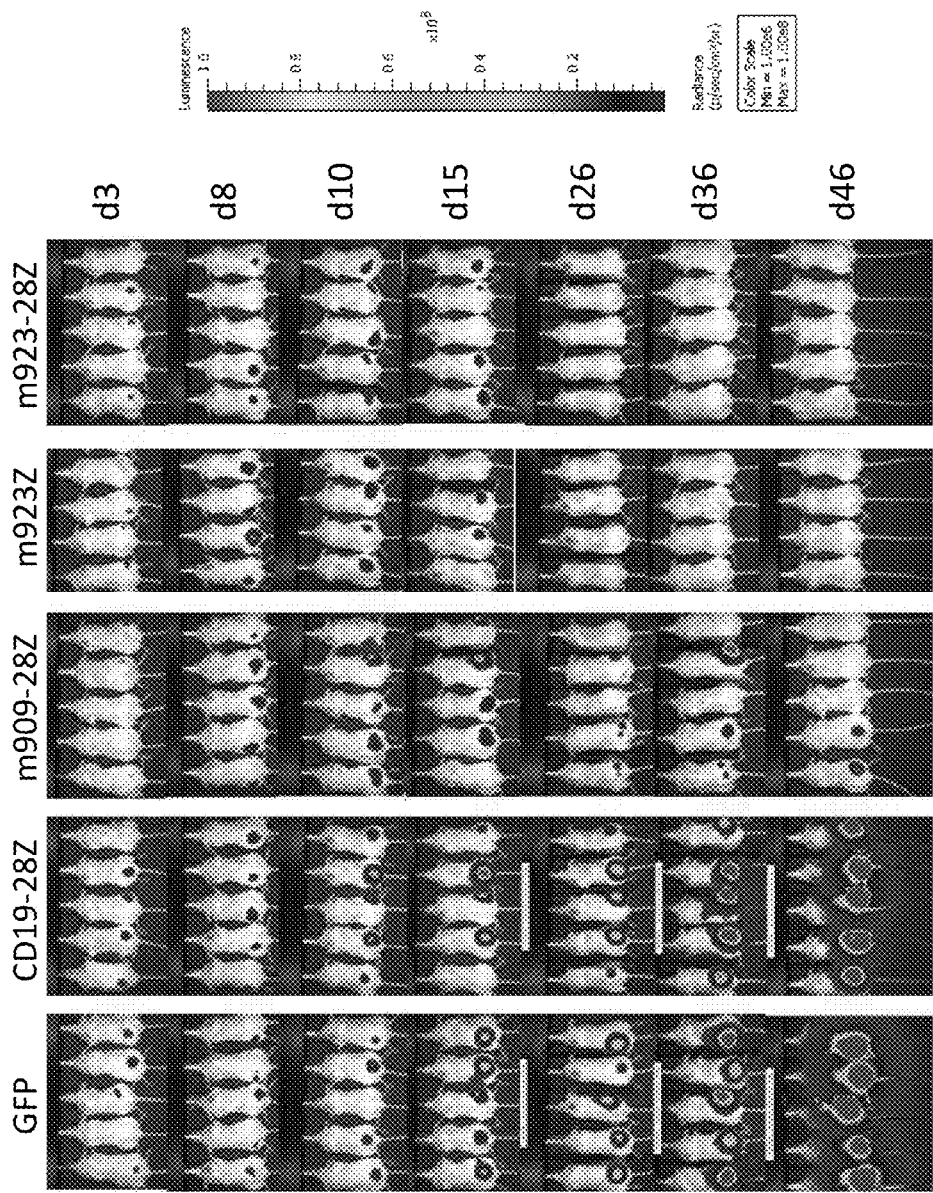
FIG. 27 is an image showing tumor luminescence in the early treatment model in mice after m909 and m923 CAR treatment of NOD/SCID mice.
Figure 28:
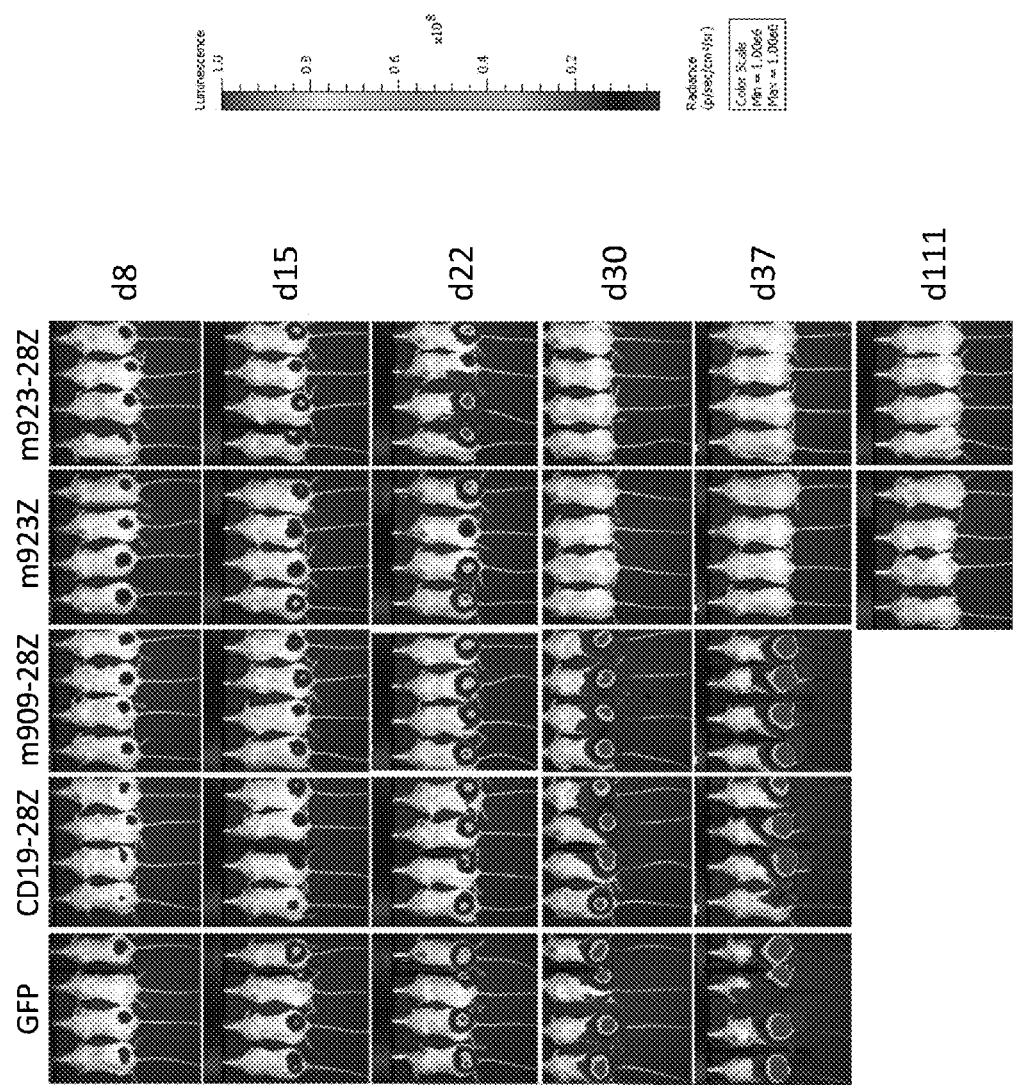
FIG. 28 is an image showing tumor luminescence in the late treatment model in mice after m909 and m923 CAR treatment of NOD/SCID mice.
Figure 29:
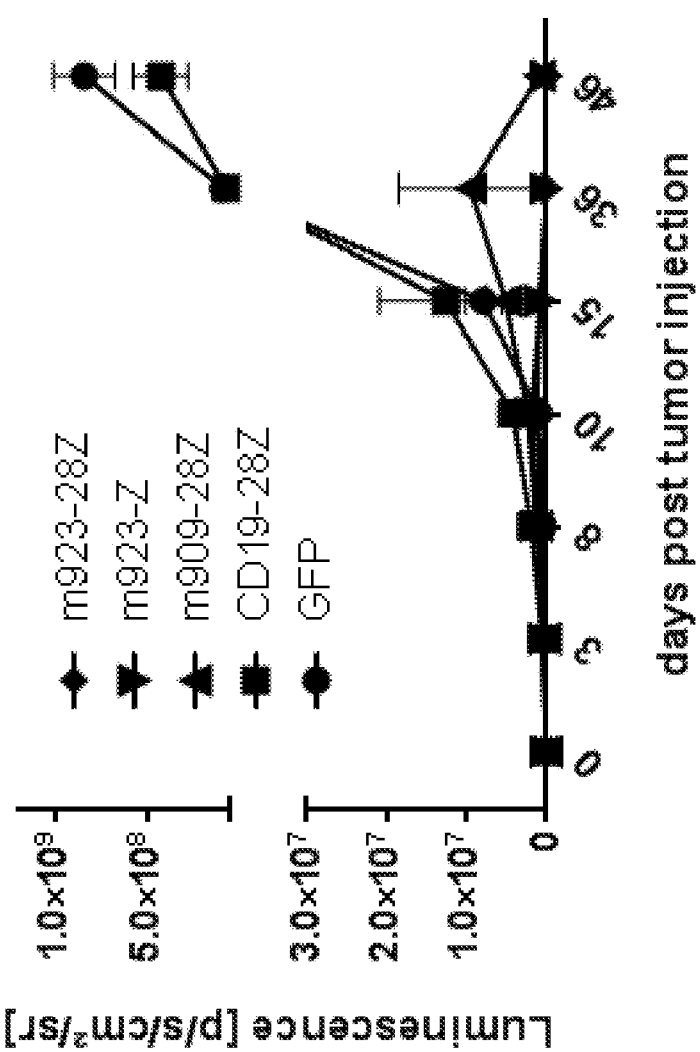
FIG. 29 is a graph showing tumor luminescence in the early treatment model in mice after m909 and m923 CAR treatment of NOD/SCID mice.
Figure 30:
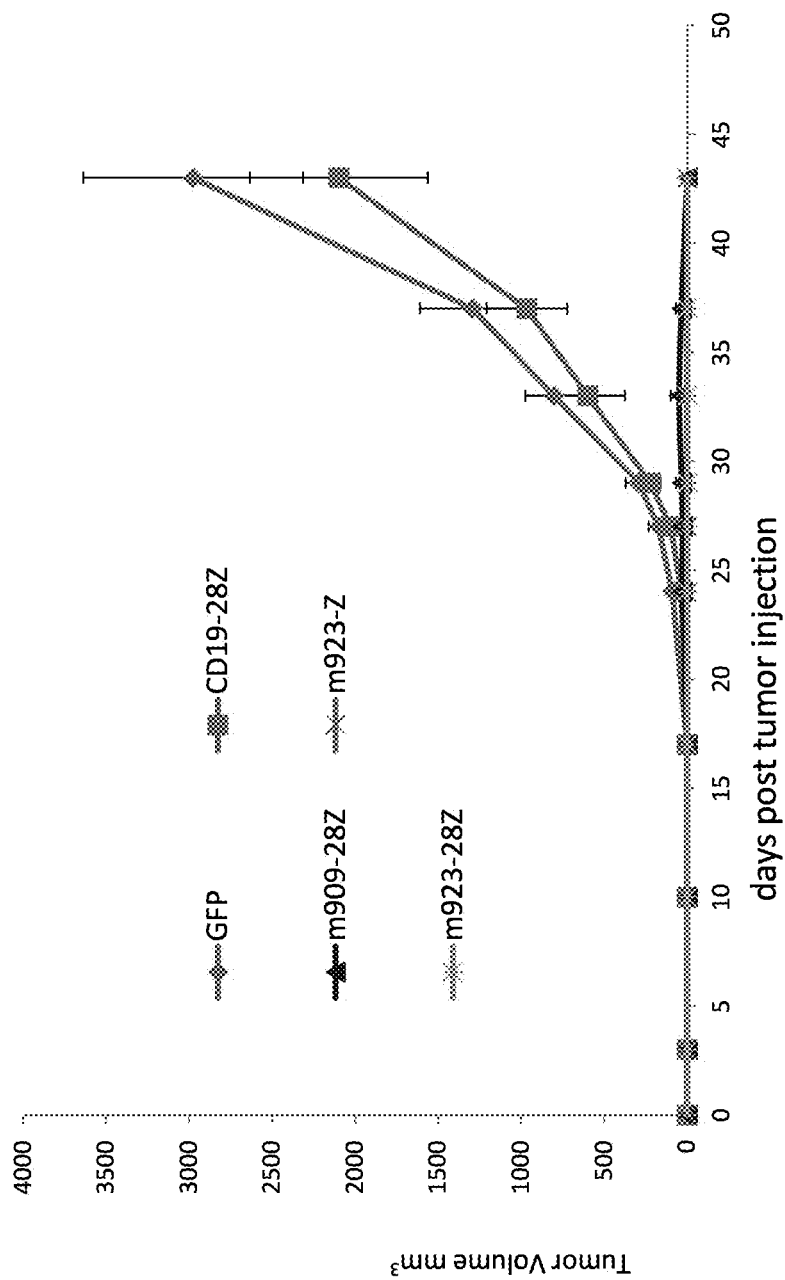
FIG. 30 is a graph showing tumor volume in the early treatment model in mice after m909 and m923 CAR treatment of NOD/SCID mice.
Figure 31:
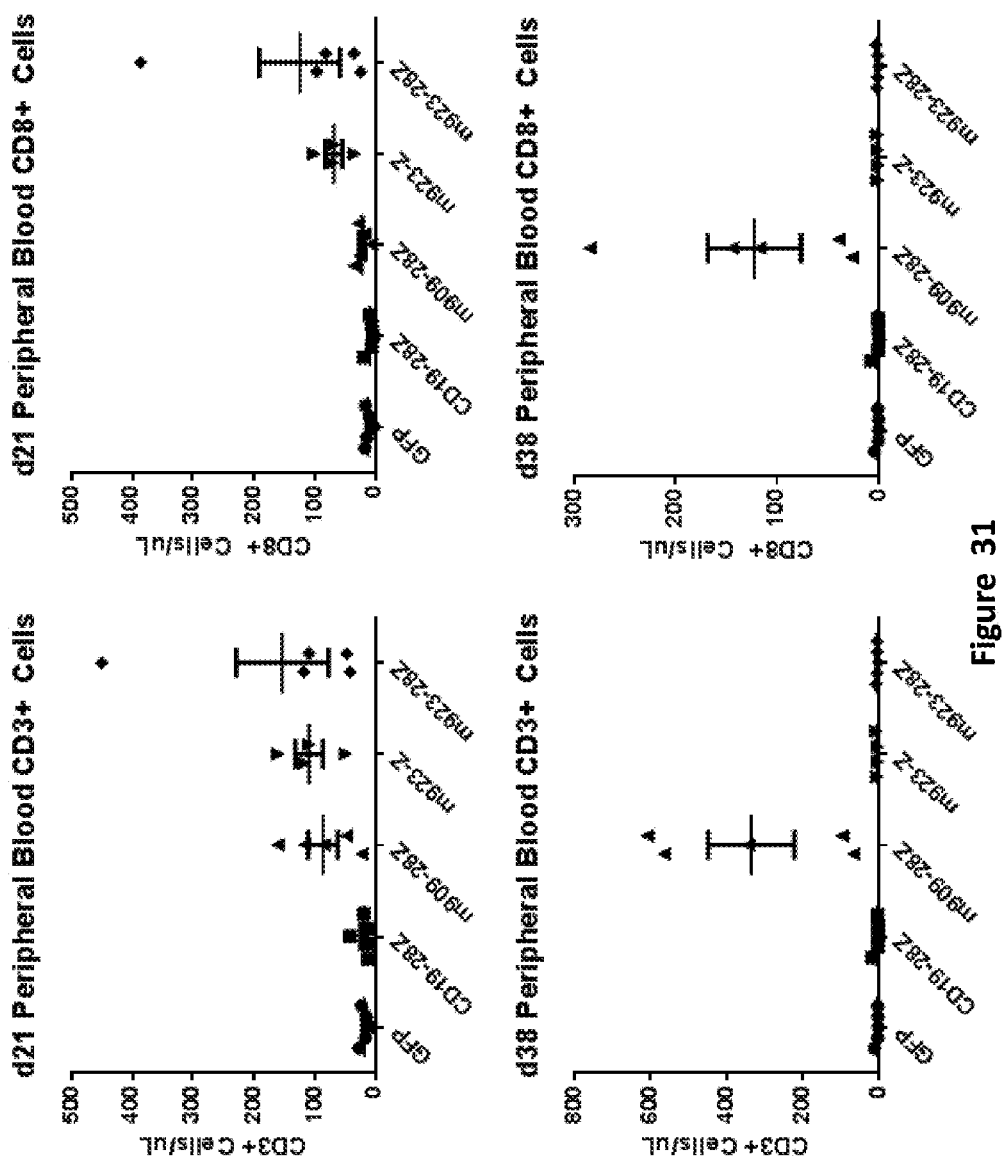
FIG. 31 is a panel of graphs showing human CD3+ cell (left graphs), and CD8+ cell (right graphs) accumulation in the periphery of m909 and m923 CAR T cell treated THP1-tumor bearing NOD/SCID mice at 21 and 38 days.
Figure 32:
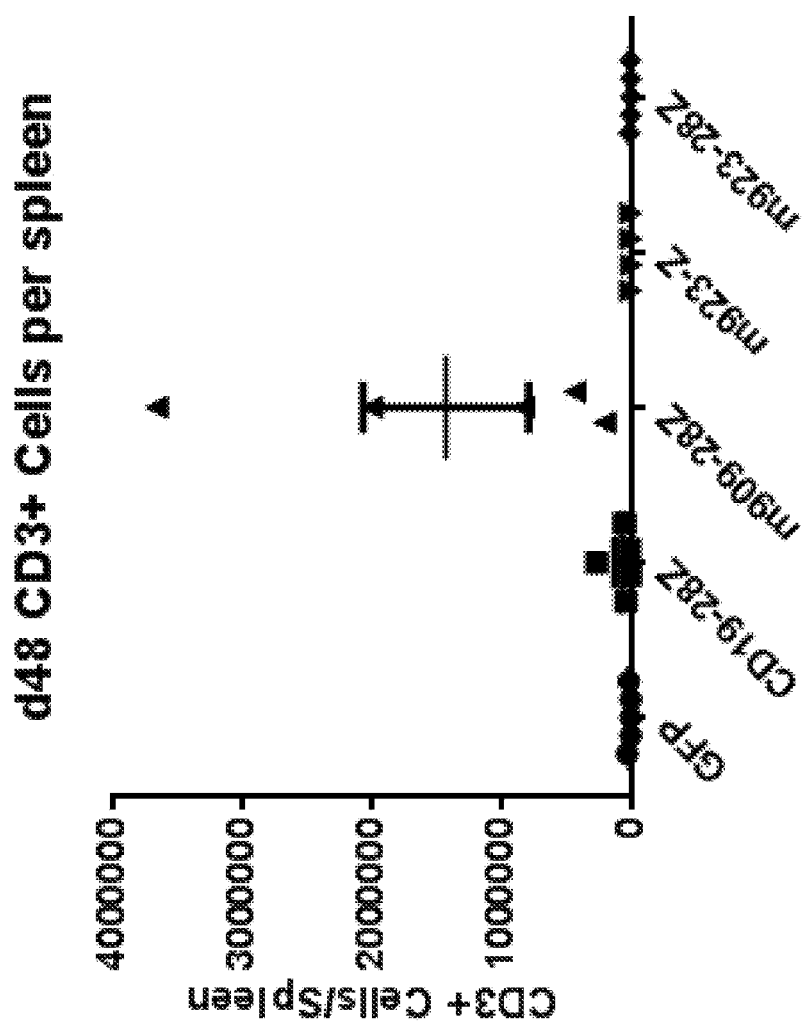
FIG. 32 is a graph showing m909 and m923 CAR T cell (CD3+) accumulation in the spleen of treated THP1-tumor bearing NOD/SCID mice at 48 days.
Figure 33:
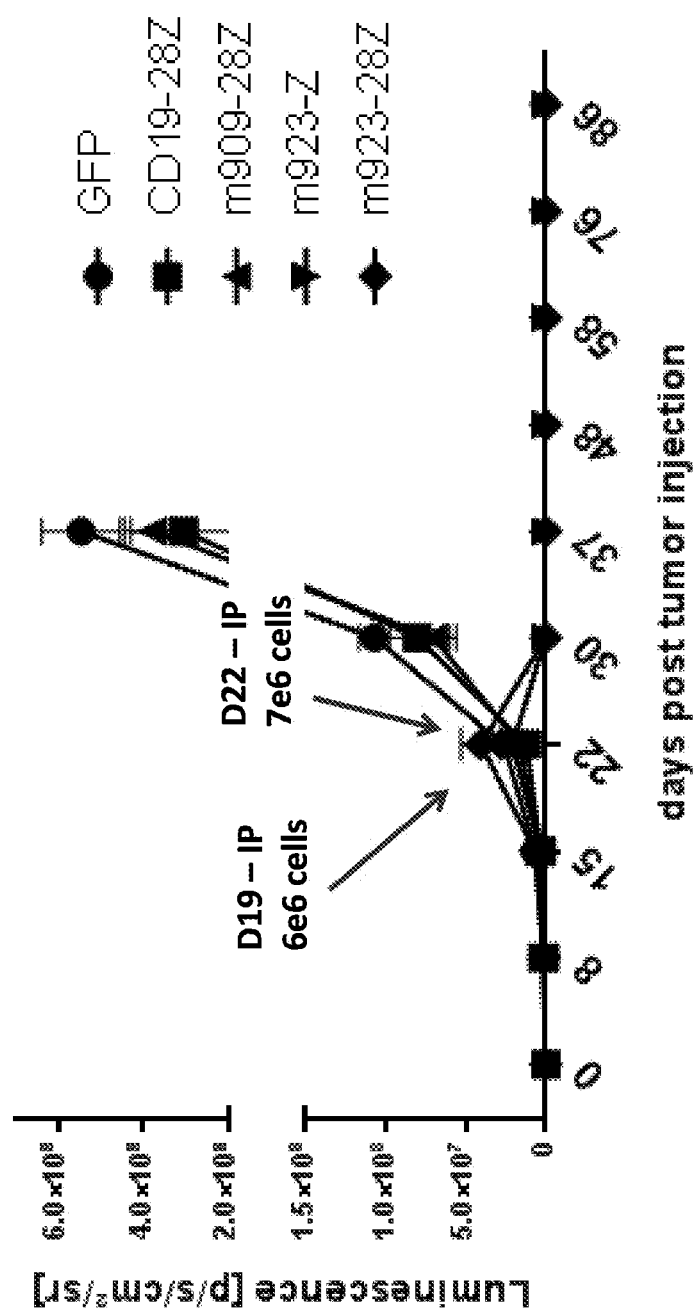
FIG. 33 is a graph showing tumor luminescence in the late treatment model in mice after m909 and m923 CAR treatment of THP1-tumor bearing NOD/SCID mice.
Figure 34:
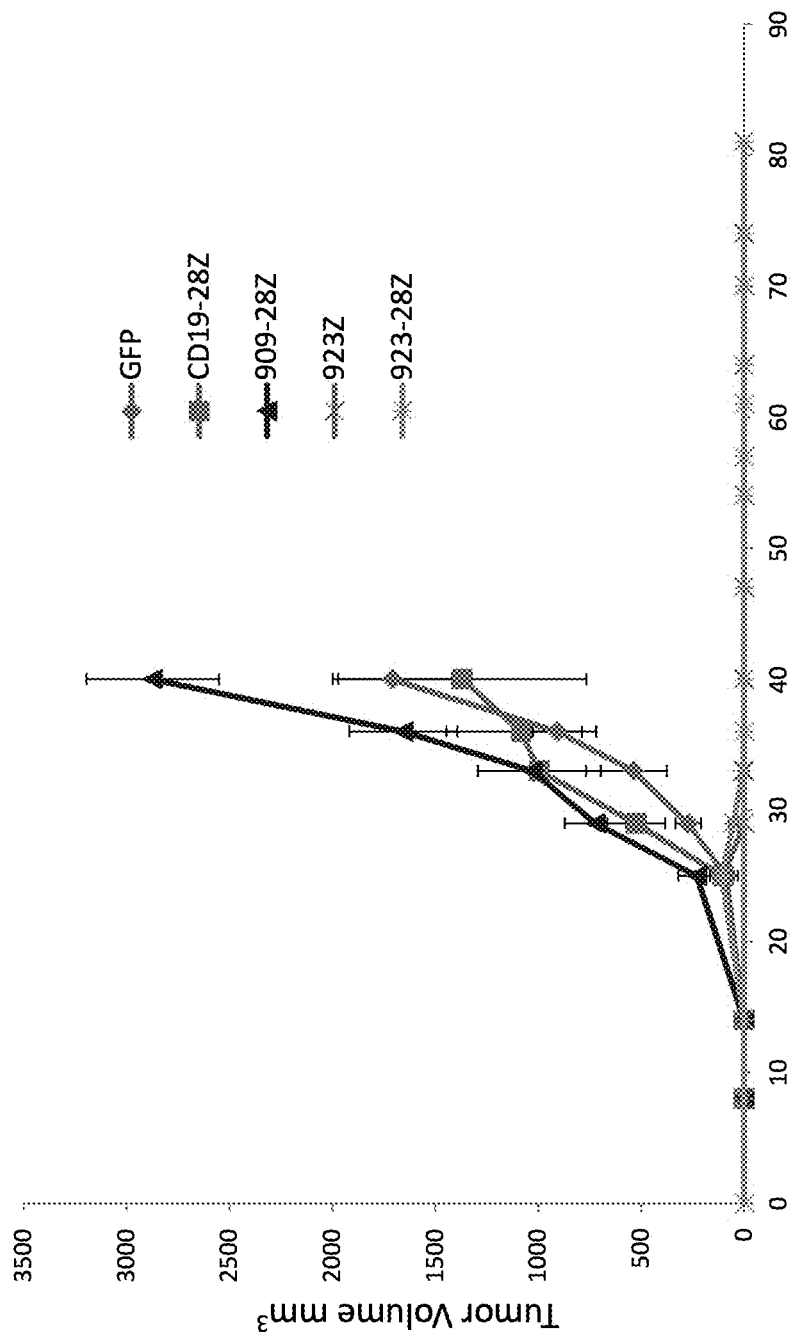
FIG. 34 is a graph showing tumor volume in the late treatment model in mice after m909 and m923 CAR treatment of THP1-tumor bearing NOD/SCID mice.
Figure 35:
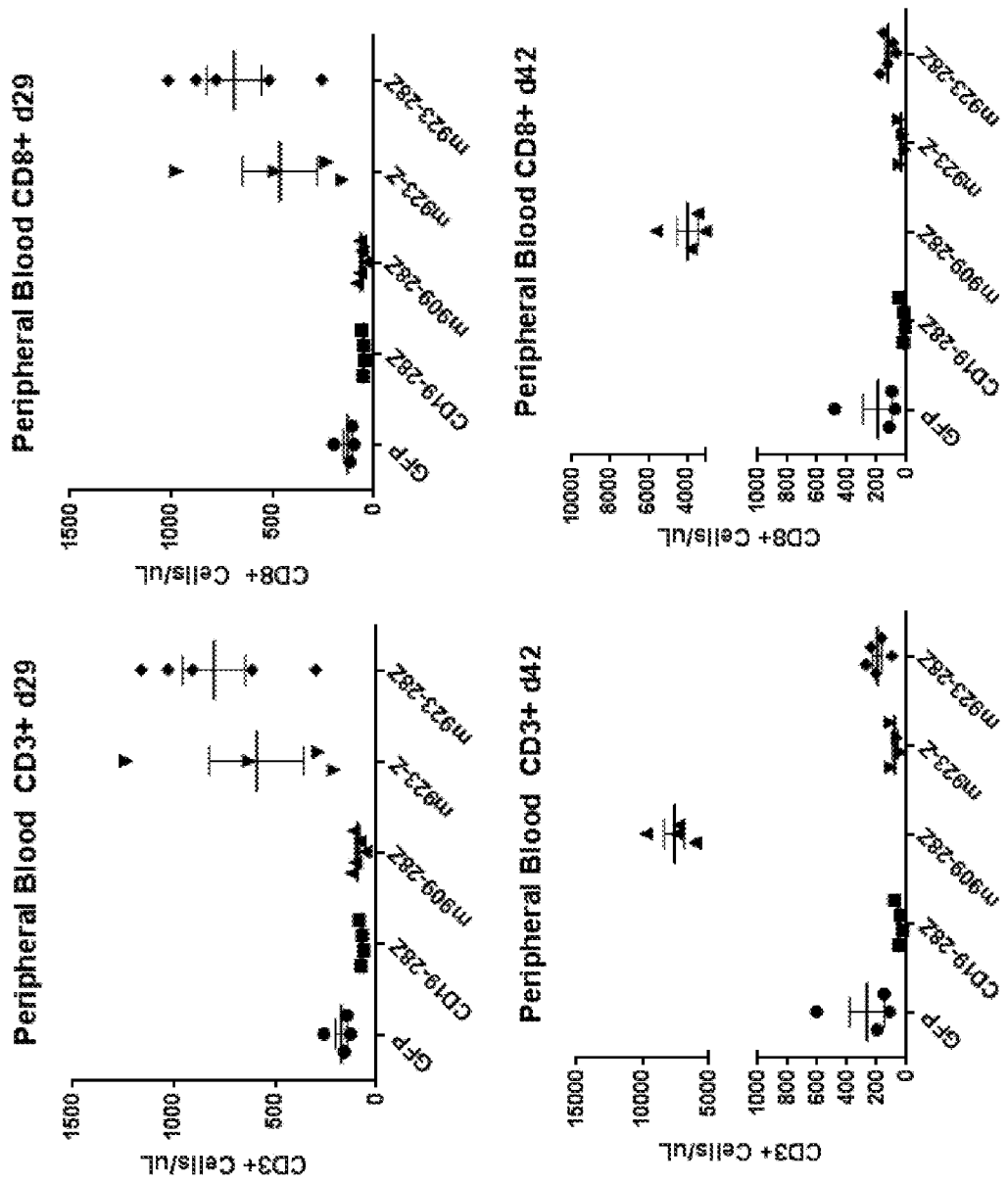
FIG. 35 is a panel of graphs showing human CD3+ cell (left graphs), and CD8+ cell (right graphs) accumulation in the periphery of m909 and m923 CAR T cell treated THP1-tumor bearing NOD/SCID mice at 29 and 42 days.
Figure 36:
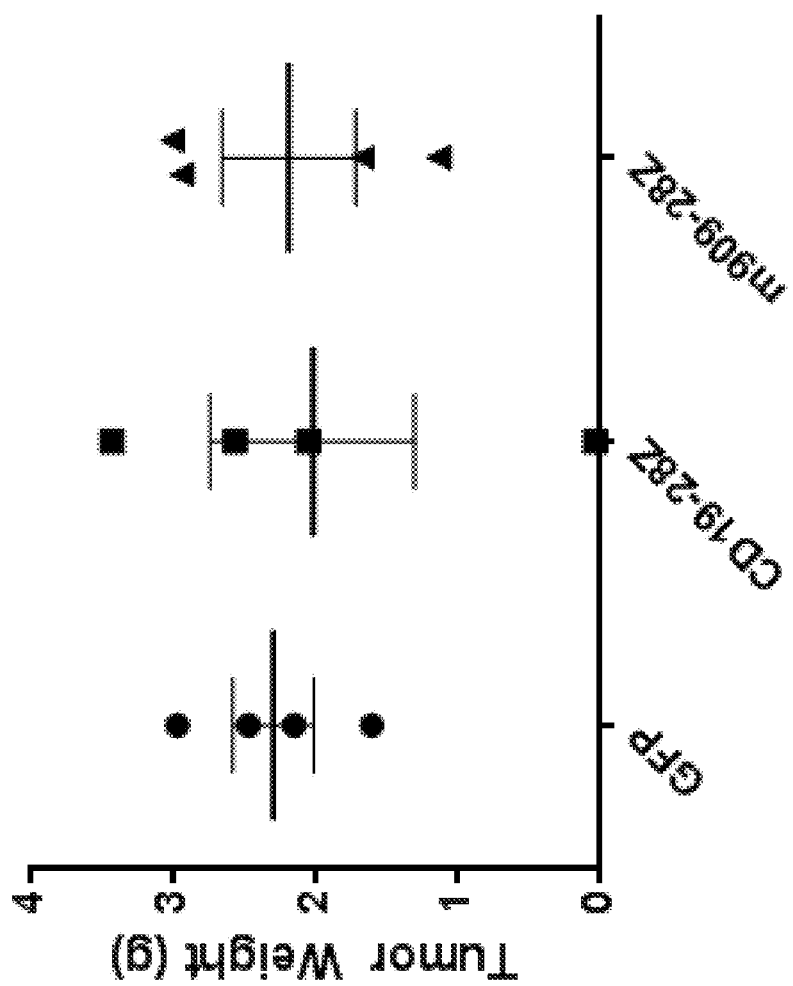
FIG. 36 is a graph showing tumor weight in treated THP1-tumor bearing NOD/SCID mice at 43 days.
Figure 37:
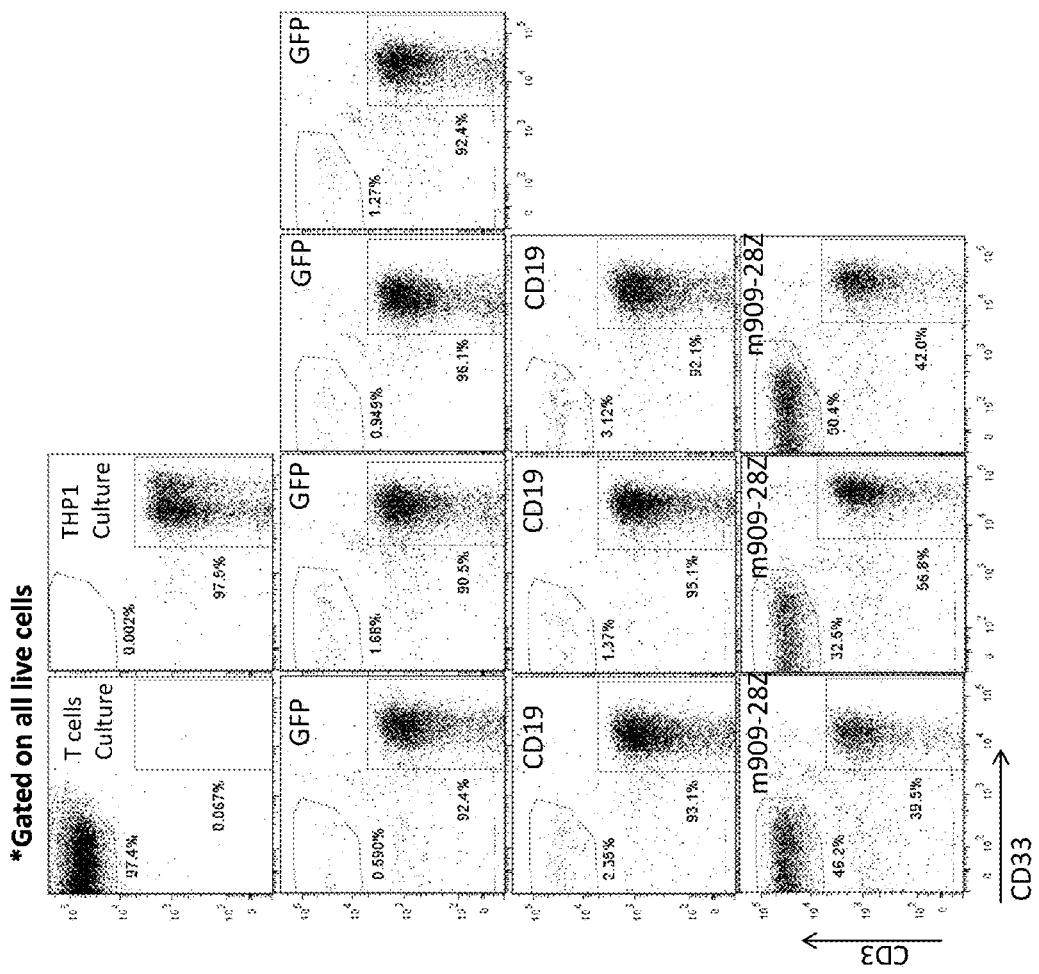
FIG. 37 is a panel of graphs showing m909-28Z CAR T cell expansion in THP1 tumors.
Figure 38:
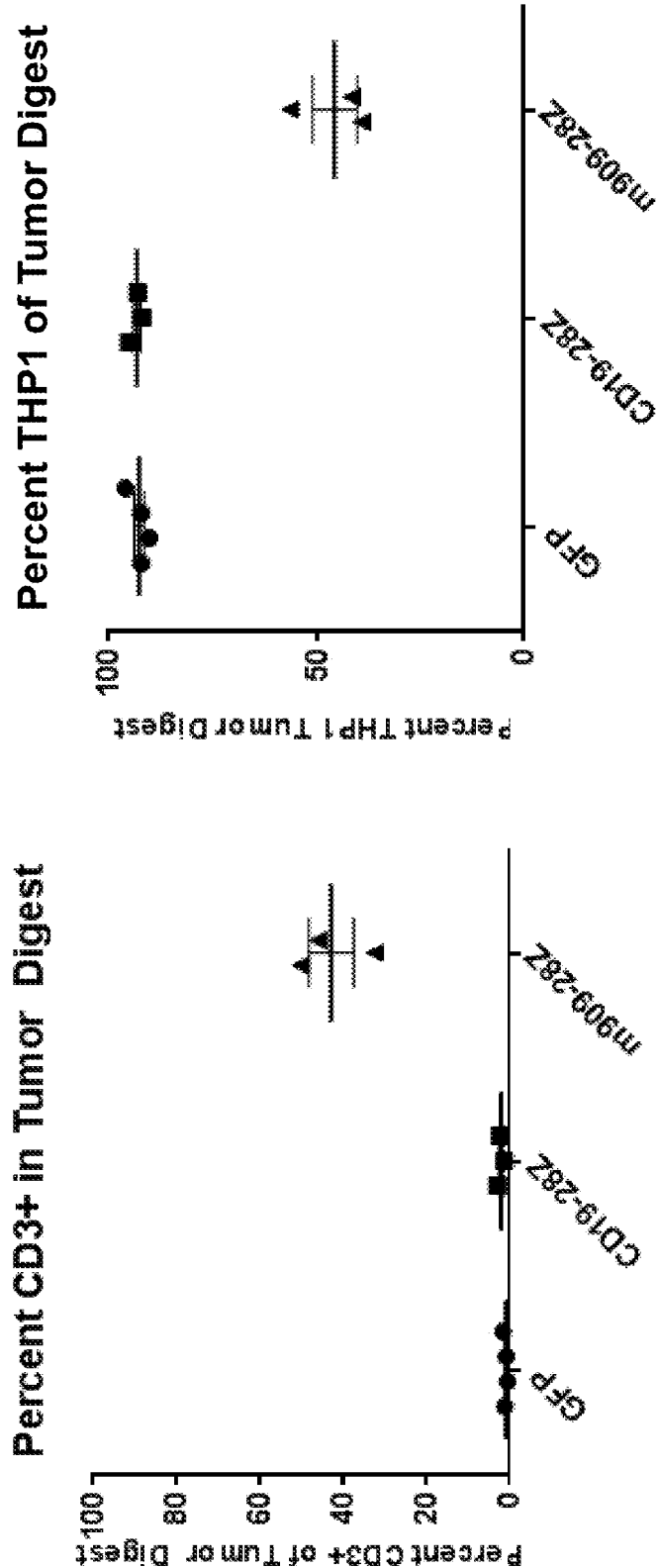
FIG. 38 is a panel of graphs showing the percentage of intratumoral CD3+ cells (left graph) and percentage of tumor cells (right graph) present after treatment in digested resected tumor.
Figure 39:
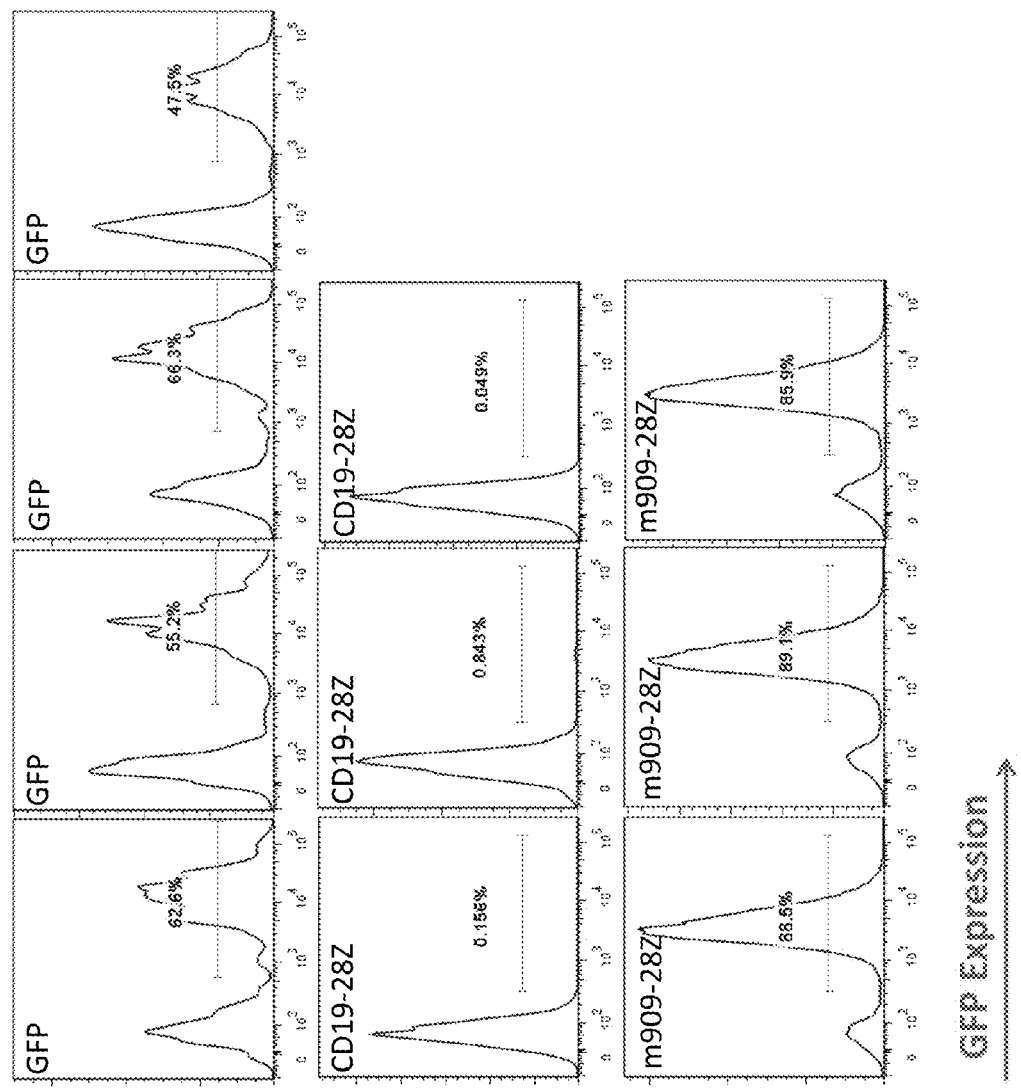
FIG. 39 is a panel of graphs showing the selective expansion of m909 CAR T cells in THP1 tumors
Figure 40:
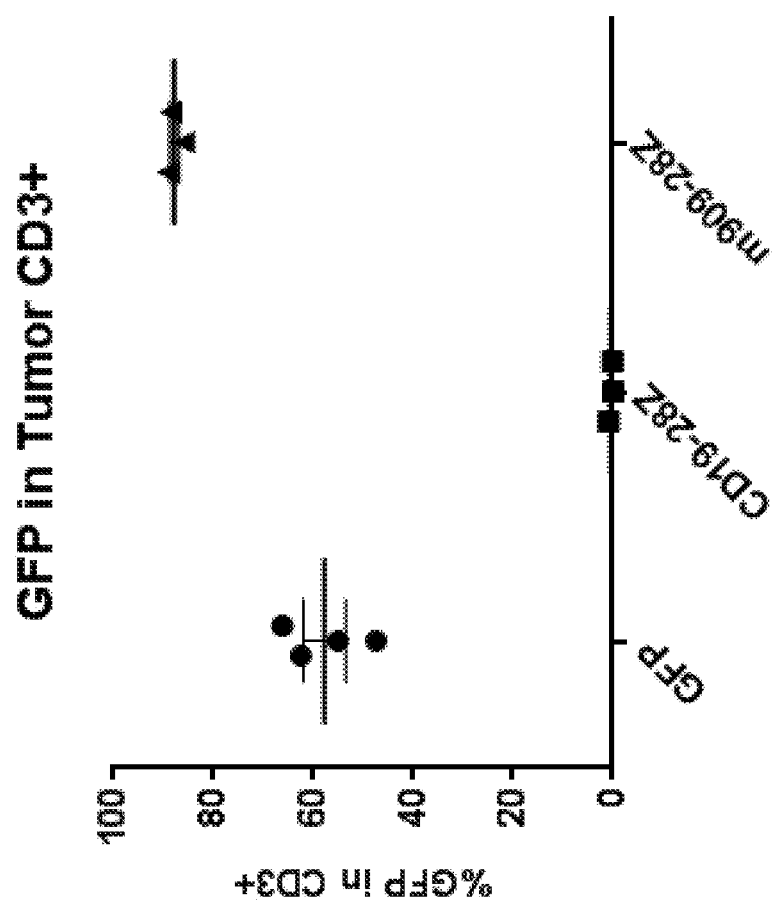
FIG. 40 is a graph showing the selective expansion of m909 CAR T cells in THP1 tumors
Figure 41:
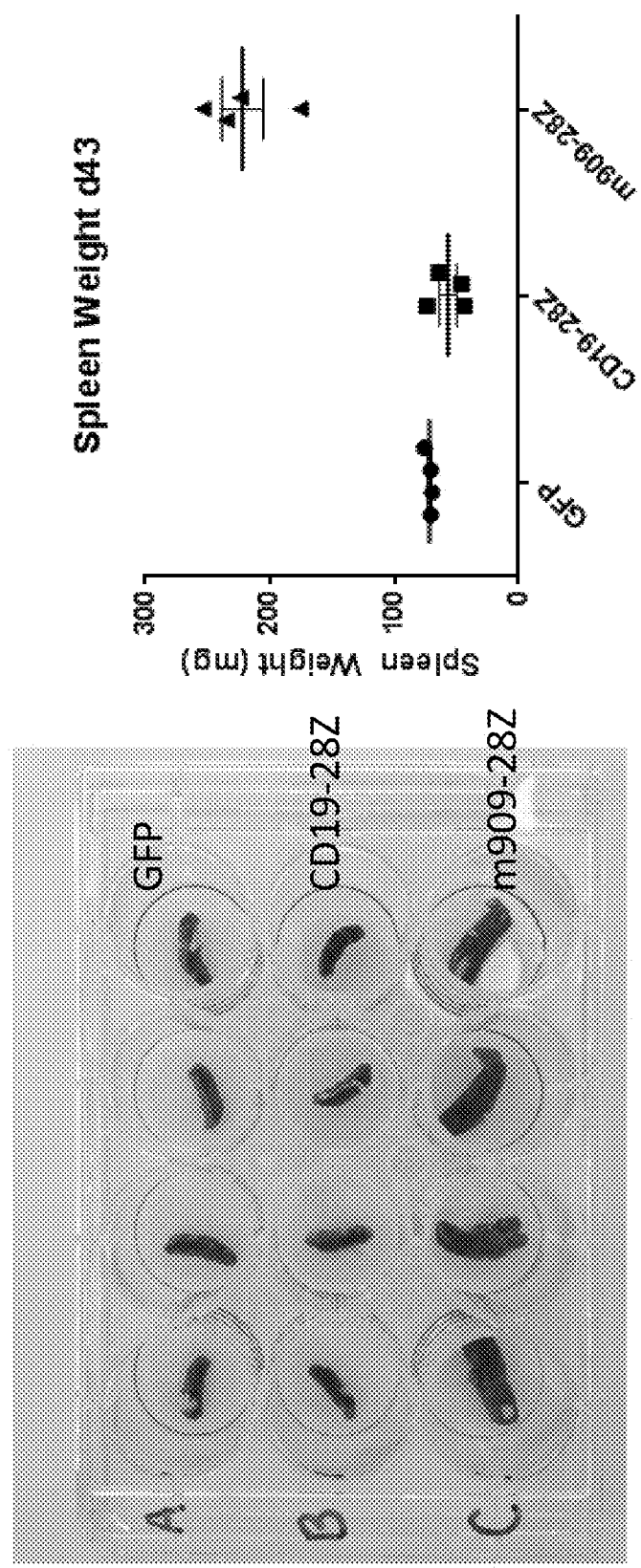
FIG. 41 is a panel of images showing increased size and weight of the spleens in m909 CAR T cell treated mice bearing THP1 tumor at day 43.
Figure 42:
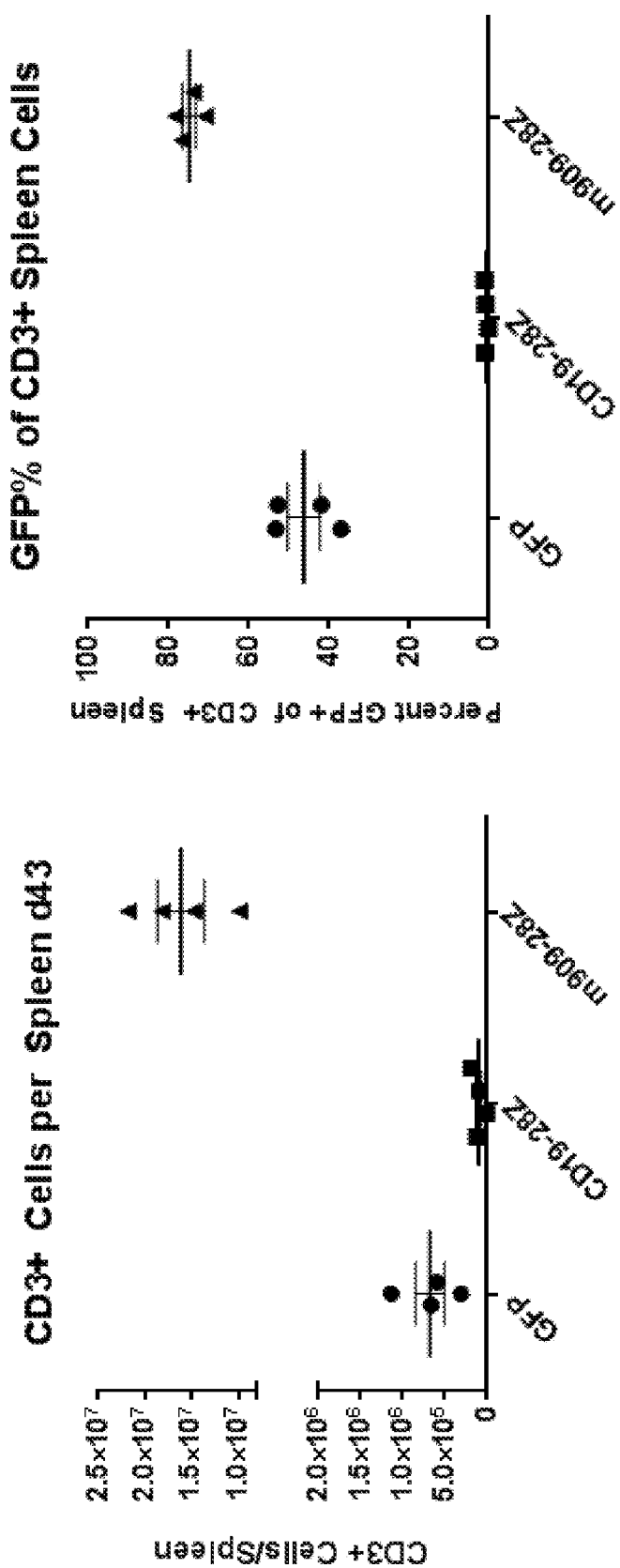
FIG. 42 is a panel of graphs showing increased CD3+ human cells and m909 CAR T cells in the spleens of THP1 tumor-bearing mice at day 43.
Figure 43:
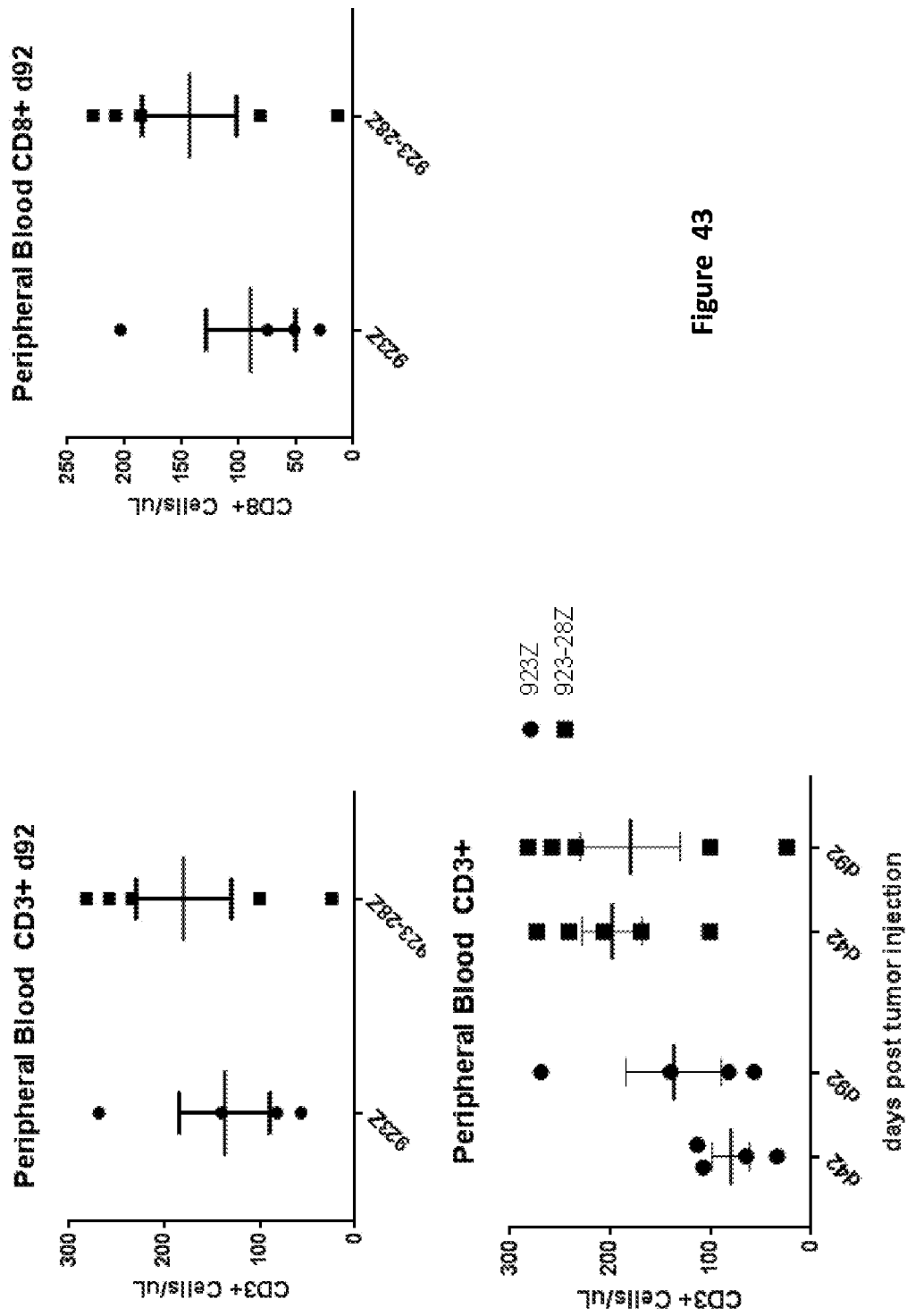
FIG. 43 is a panel of graphs showing m923 CAR T cell (CD3+ cells, left graphs, and CD8+ cells, right graph) persistent accumulation in the periphery of treated THP1-tumor bearing NOD/SCID mice at 92 days, and m923 CAR T cell (CD3+ cells) at 42 and 92 days.

When testing the relative efficacy of m909 and m923 CAR T cells in vivo using THP1 engrafted in NSG mice, both an early treatment (8-10 day engraftment, FIG. 25) and late treatment (3 weeks—palpable tumors, FIG. 26) model of CAR therapy was investigated. The m909 CAR T cells were found to control THP1 tumor growth when treated early (FIG. 26), but lacked efficacy in controlling large tumor outgrowth (FIG. 28). m923 CAR T cells, however, were able to completely eliminate the tumor in vivo in both early (FIG. 27) and late treatment models (FIG. 28). FIGS. 29 through 36 further illustrate m923 CAR therapy controlled tumor outgrowth more than m909 CAR therapy in the early and late treatment models. Tumor expansion was measured in tumors after overnight digestion with DNase/collagenase and single cell suspensions were stained with antibodies against CD3 (T cell) and CD33 (tumor cell) markers. FIGS. 37 through 40 show the overall expansion of T cells and selective expansion of m909 CAR T cells in THP1 tumors. FIGS. 41 and 42 show the increased m909 CAR T cells in the spleens and increased weight of the spleens in THP1 tumor mice at day 43. FIG. 43 shows the persistence of m923 CAR T cell (CD3+ cells, left graphs, and CD8+ cells, right graph) in the periphery of treated THP1-tumor bearing NOD/SCID mice at 42 and 92 days.

Figure 44:
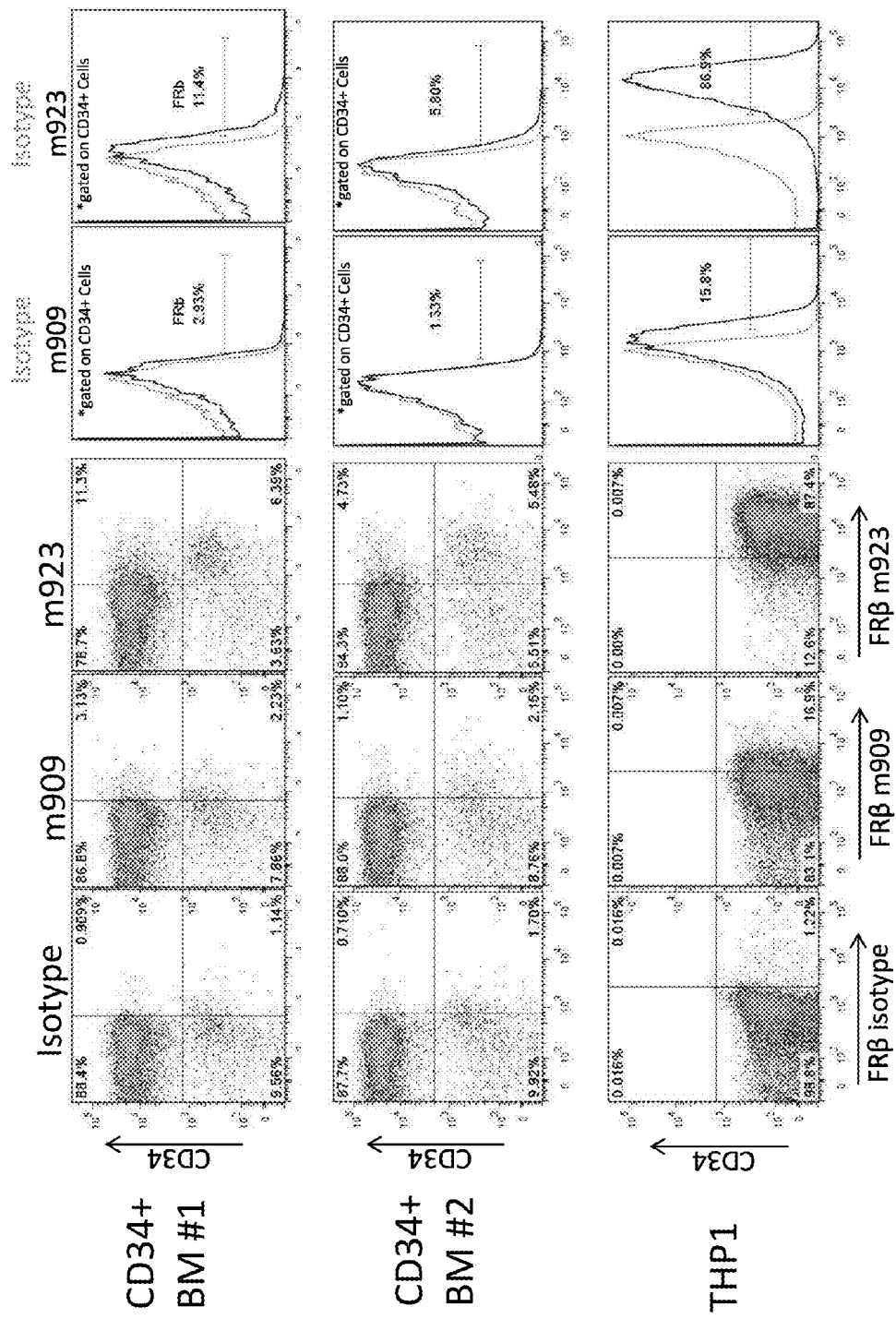
FIG. 44 is a panel of graphs showing m909 and m923 antibody binding of FRβ in CD34+ bone marrow hematopoetic stem cells.

Since FRβ is expressed in certain hematopoietic lineages, further studies carefully examining possible off-tumor effects of FRβ-CAR T cell therapy will be important. Since peripheral differentiated hematopoietic populations are derived from bone marrow (BM) CD34+ stem cells, it is of great importance that the FRβ-targeted CARs do not recognize this healthy progenitor population. FIG. 44 shows FRβ expression in human bone marrow CD34+ hematopoetic stem cells. Many of the other antigens overexpressed on AML that are being developed for CAR therapy are expressed at some level on CD34+ cells (ex: CD33, CD123, CD38) and show activity against these cells in vitro and in humanized mice. FRβ expression in BM CD34+ cells from 3 normal donors was investigated and verified that very low levels of detectable FRβ (<10%) were found.

Figure 45:
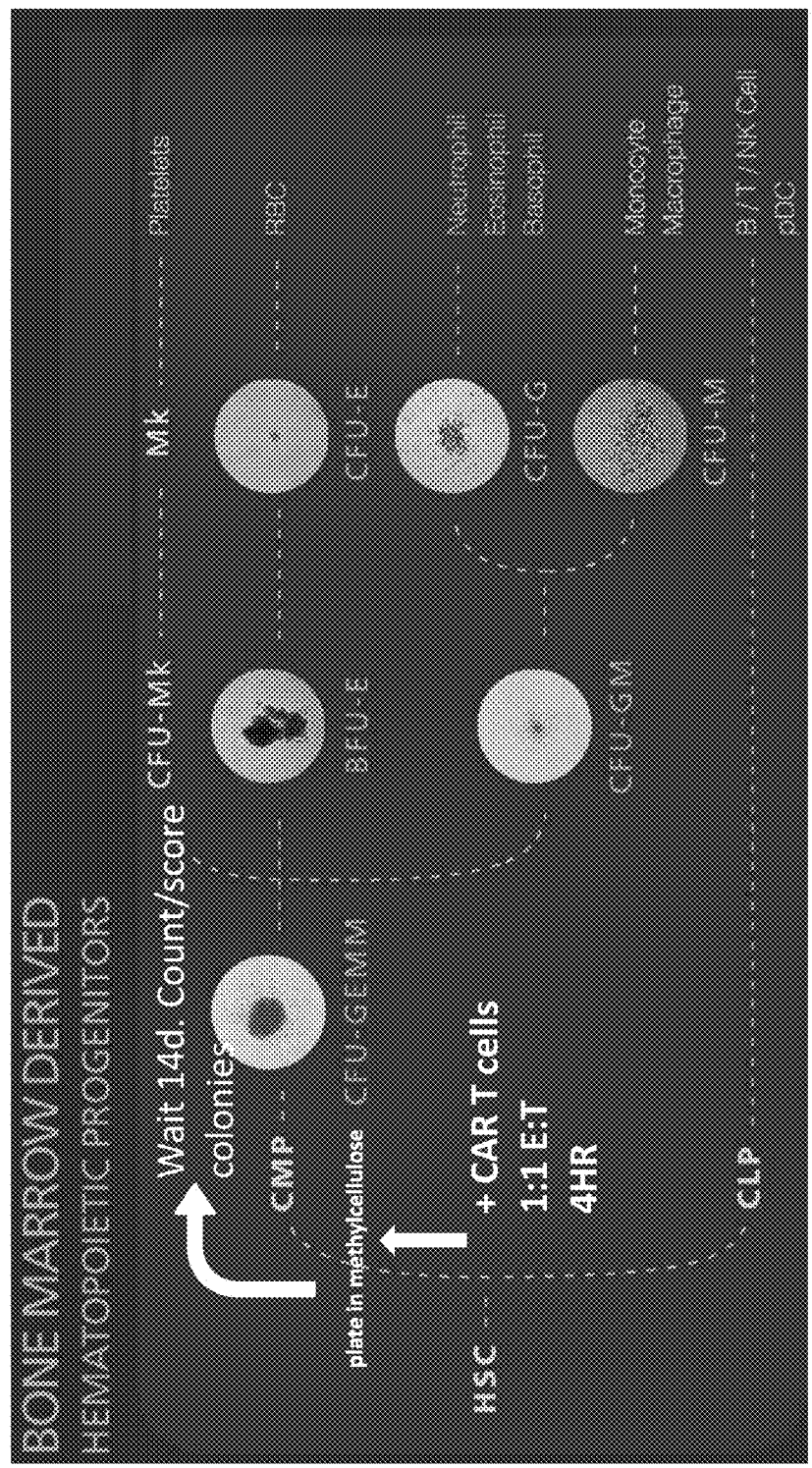
FIG. 45 is a diagram illustrating the colony forming assay.
Figure 46:
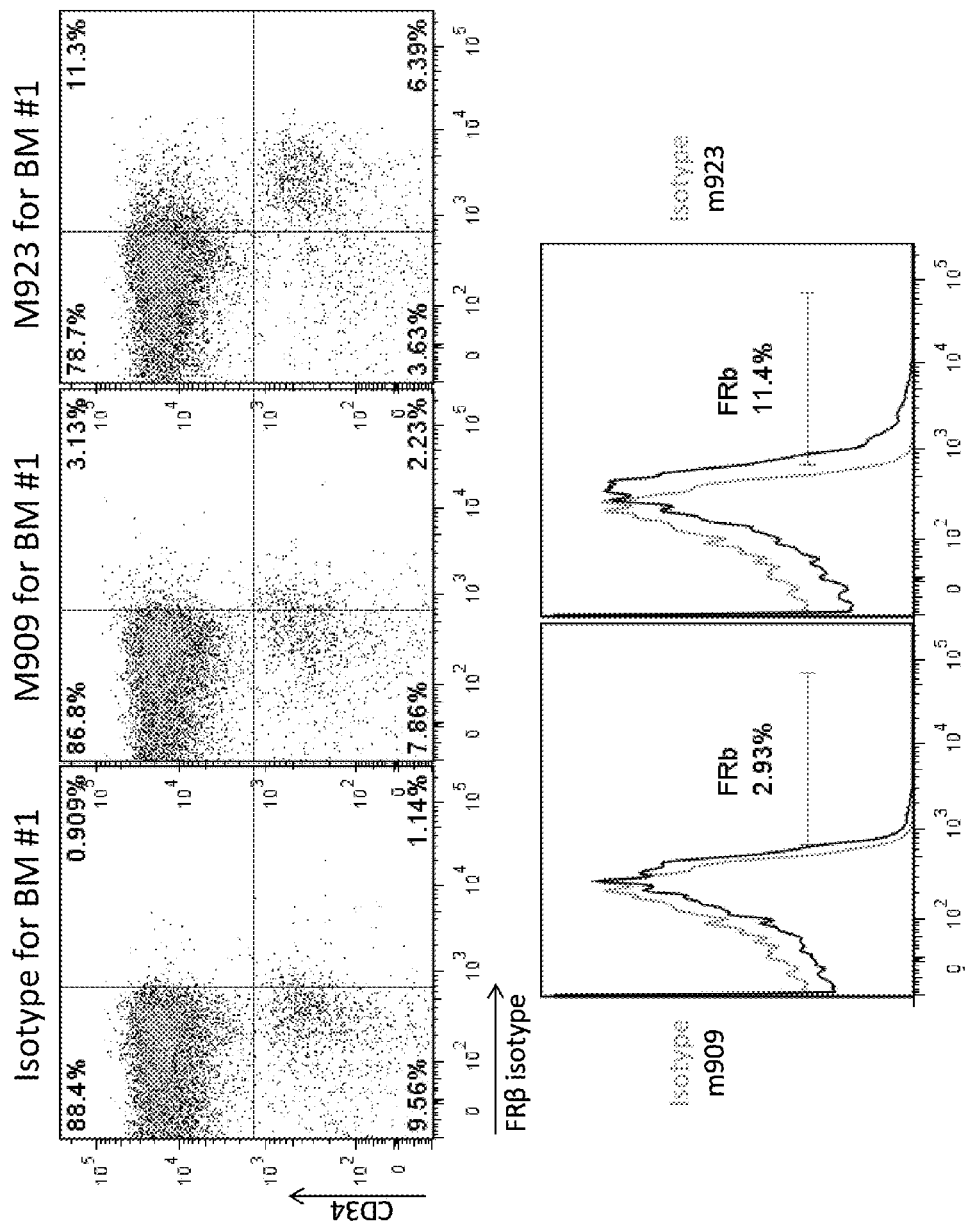
FIG. 46 is a panel of graphs showing CD34+ and FRβ expression in bone marrow cells harvested from donor BM #1 for use in colony forming assay.
Figure 47:
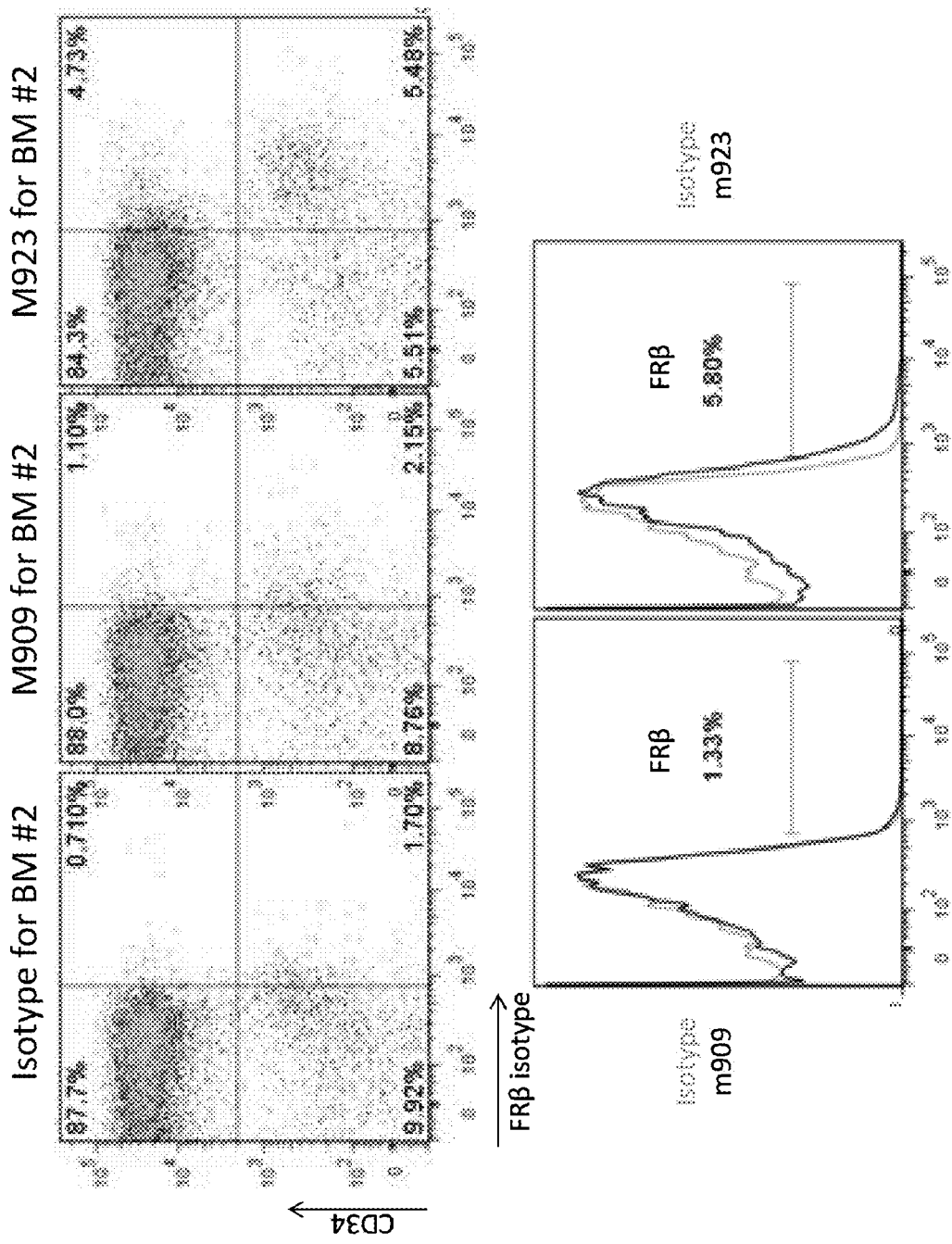
FIG. 47 is a panel of graphs showing CD34+ and FRβ expression in bone marrow cells harvested from donor BM #2 for use in colony forming assay.
Figure 48:
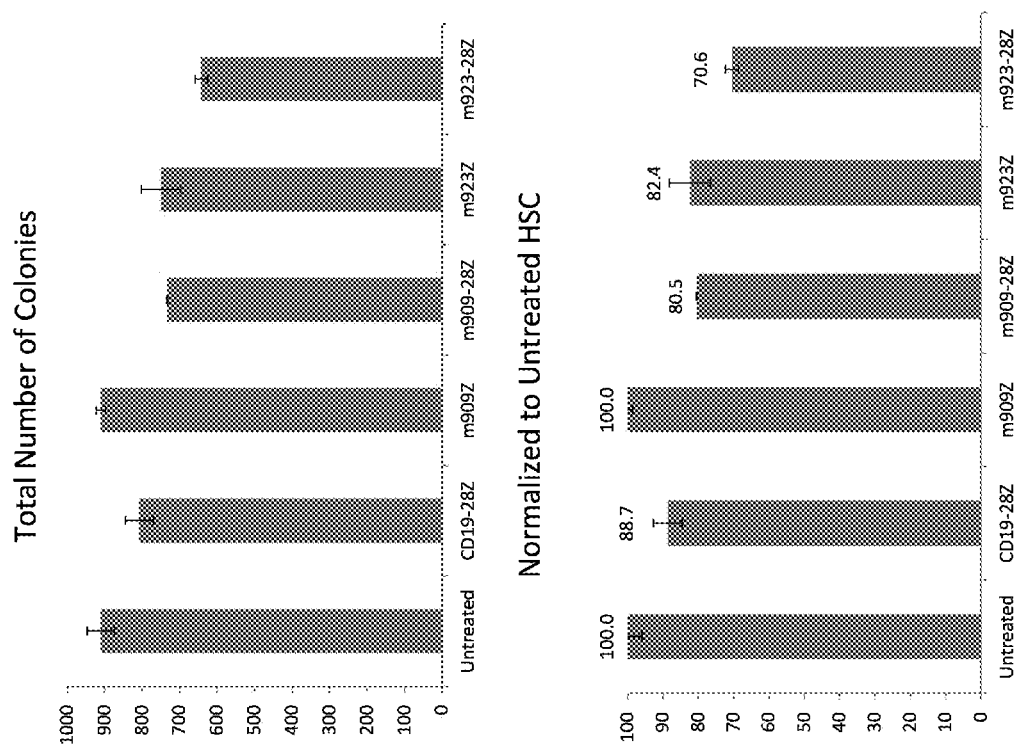
FIG. 48 is a panel of graphs showing the number of colonies formed from T cell-treated HSCs in the BM #1 colony forming assay after 14 days.
Figure 49:
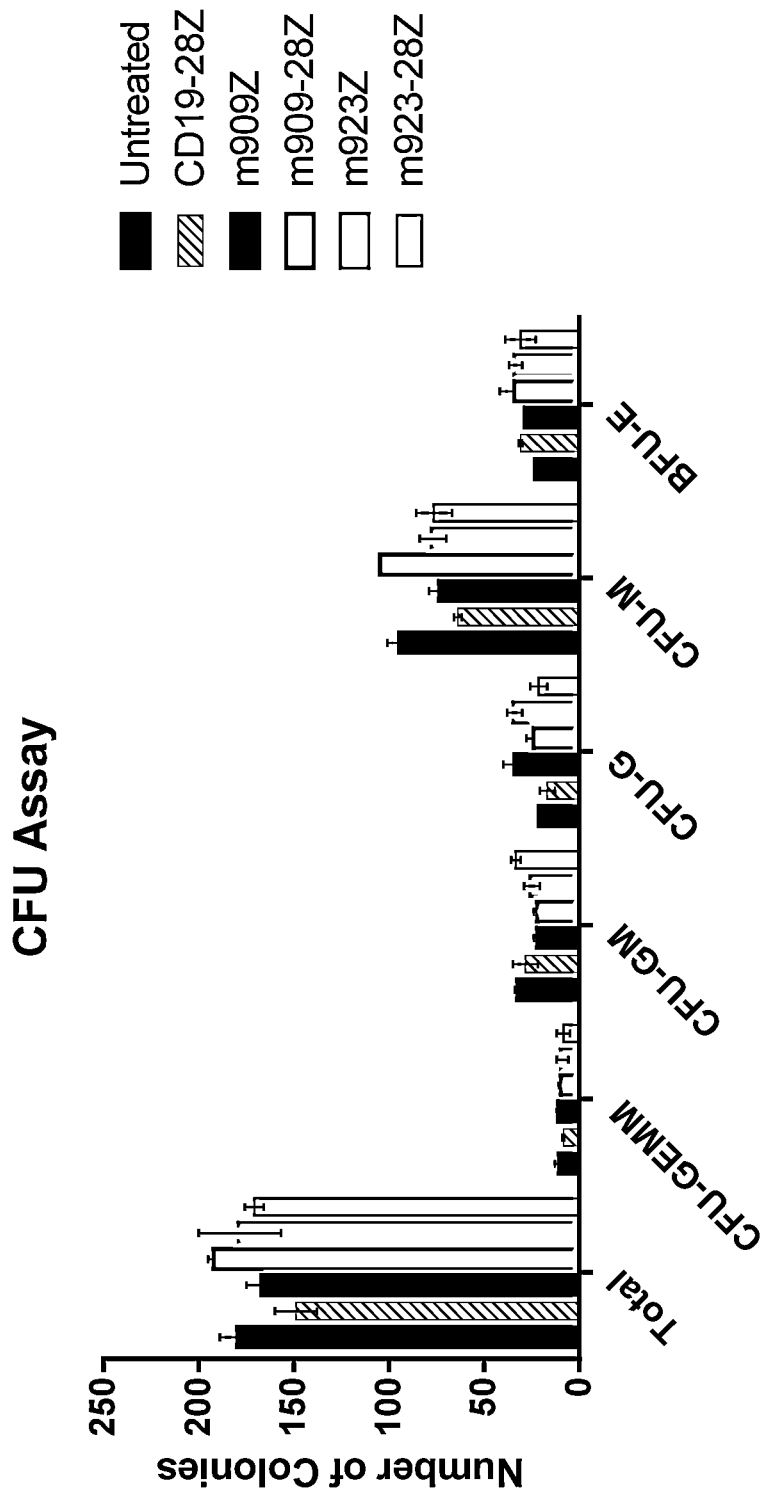
FIG. 49 is a panel of graphs showing the number of various colonies formed by T cell-treated HSCs in the BM #2 colony forming assay after 14 days.

To test toxicity against CD34+ HSCs, a 4 hr co-culture of CAR T cells with CD34+ BM cells was performed (FIG. 45), followed by a 14 day colony forming (CFU) assay in methylcellulose (FIGS. 46 and 47). No significant effects of m909 or m923 CAR T cells were found on colony formation (FIGS. 48 and 49).

Figure 51:
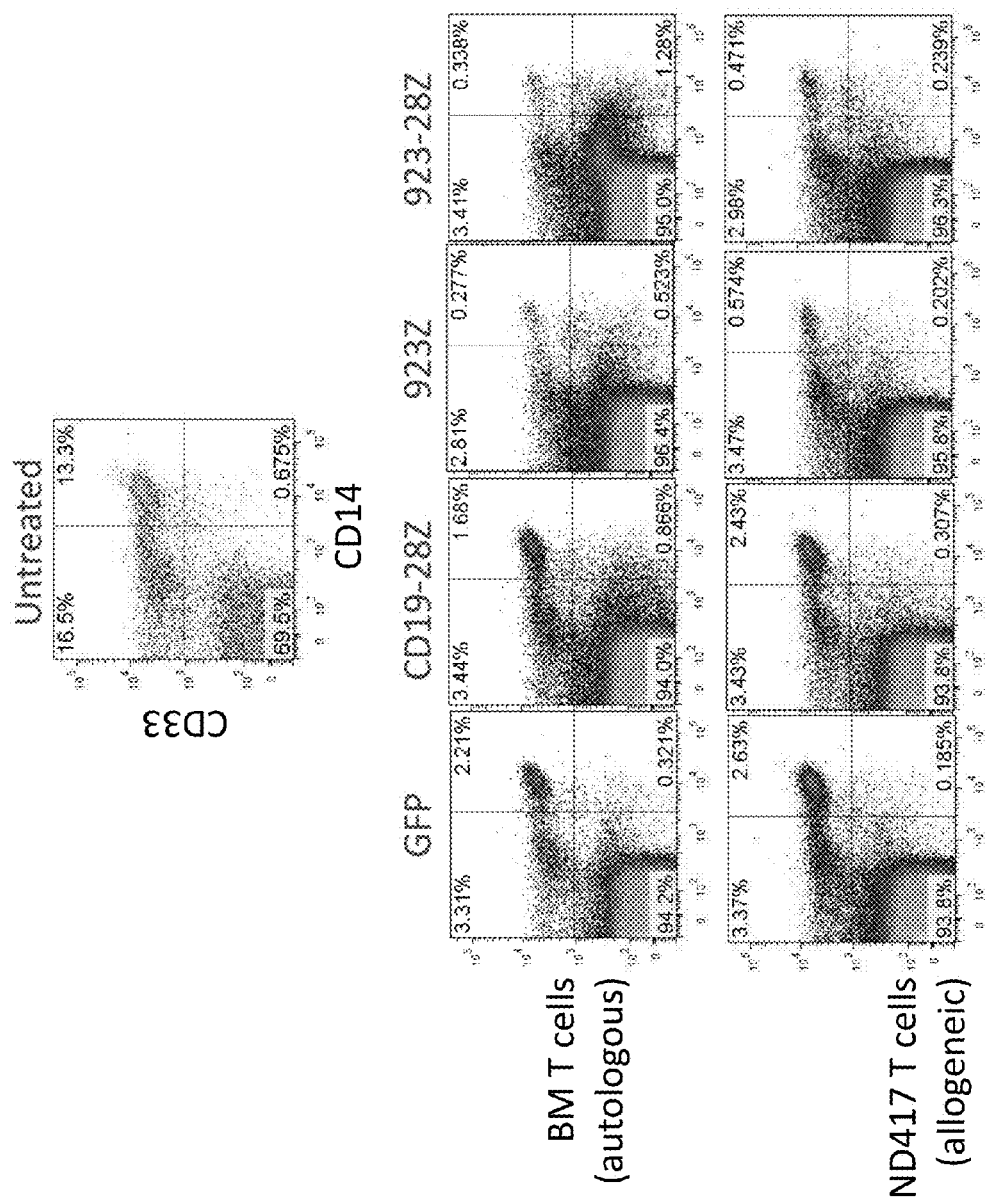
FIG. 51 is a panel of graphs showing m923 CAR T cells eliminated auotologous or allogeneic $CD14^{hi}$ CD33+ cells after 4 hours co-culture.
Figure 52:
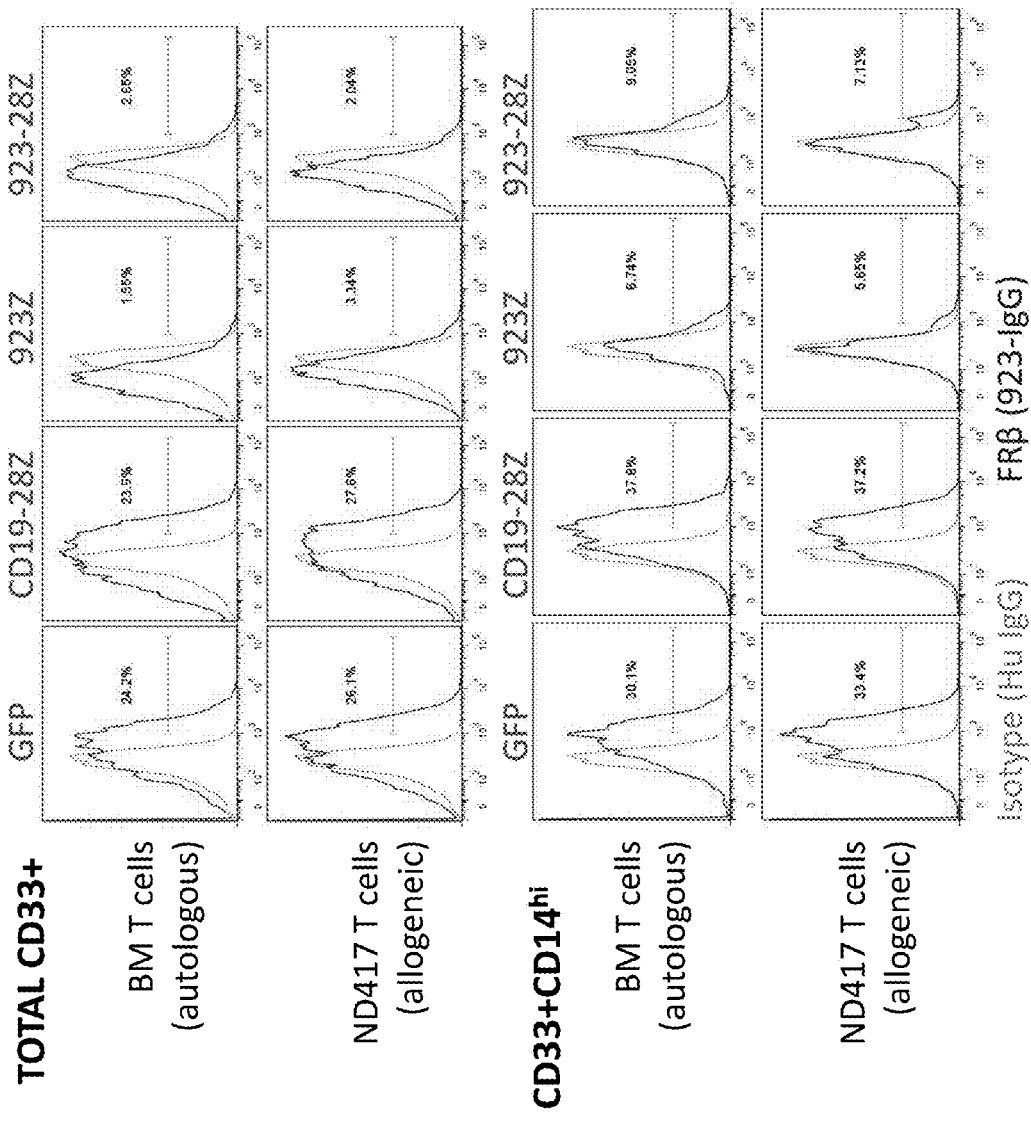
FIG. 52 is a panel of graphs showing m923 CAR T cells decreased bone marrow FRβ expression after 4 hours co-culture.
Figure 53:
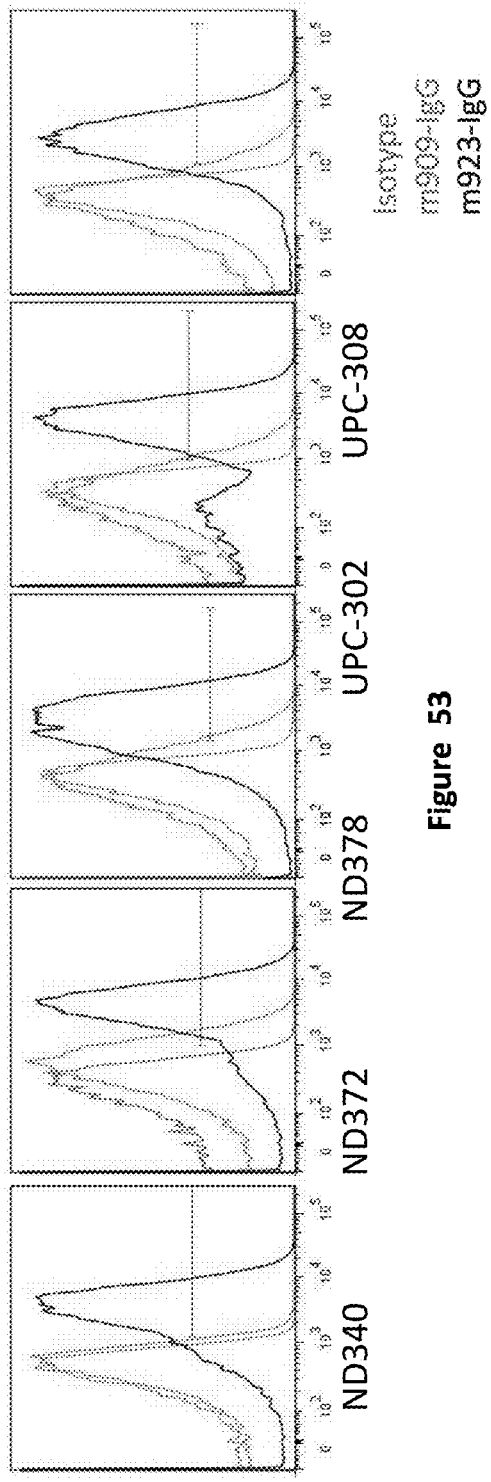
FIG. 53 is a panel of graphs showing FRβ expression on human peripheral blood monocytes.
Figure 54:
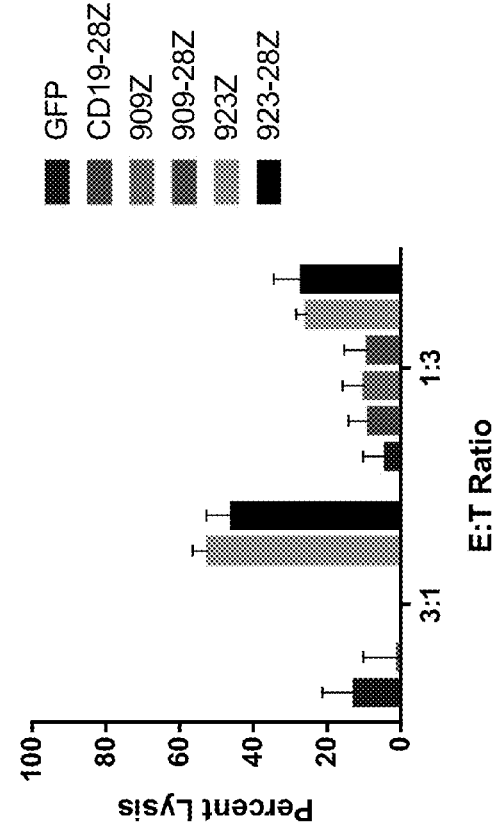
FIG. 54 is a panel of graphs showing m923 CAR T cells exhibited lytic activity against FRβ+ monocytes.

Next FRβ expression was examined in more differentiated (CD34(−)) bone marrow cells. Increasing FRβ expression was found along the myeloid differentiation axis with highest expression in $CD14^{hi}$ monocytes (FIGS. 50A-50E). Co-culture of m923 CAR T cells with whole CD34(−) BM resulted in elimination of the $CD14^{hi}$ monocyte population (FIG. 51), consistent with a loss of FRβ expression in surviving cells (FIG. 52). Also, FRβ expression was confirmed in human peripheral blood monocytes (FIG. 53). In a 4 hr flow-based lysis assay, m923 CARs displayed some lytic capability against monocytes, however, no significant effects were seen from m909 CARs (FIG. 54).

Tumor Associated Macrophages (TAMs)

Figure 55:
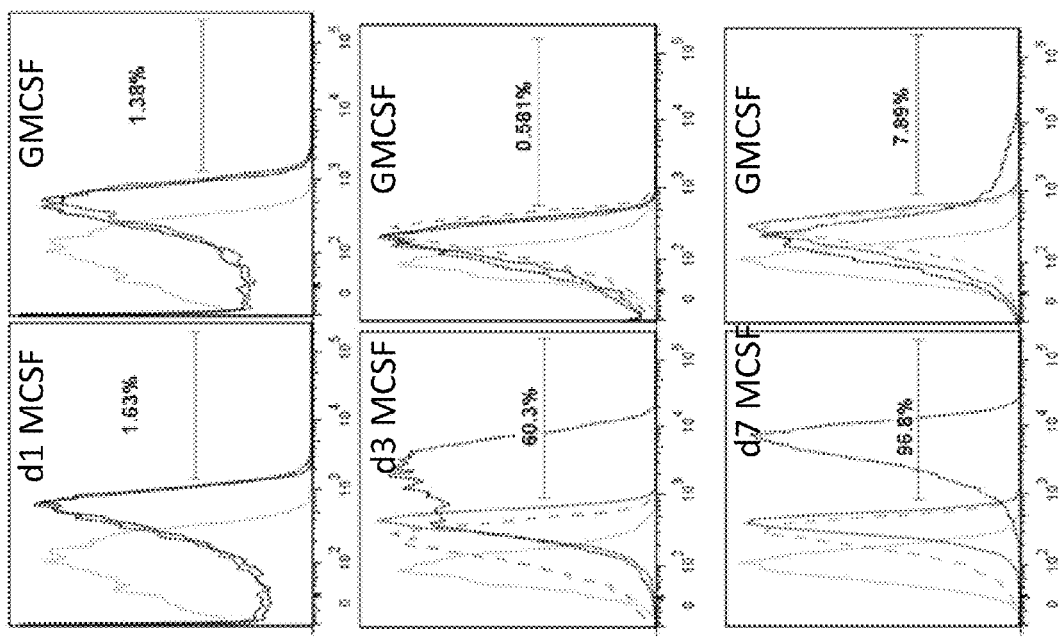
FIG. 55 is a panel of graphs showing FRβ expression on monocytes, induced by MCSF and inhibited by GM-CSF during in vitro differentiation.

In addition to AML, FRβ is also highly expressed on mature macrophages in the tumor microenvironment (TAMs), where they promote tumor growth, angiogenesis, and immune evasion. Other strategies for eliminating TAMs have proven effective against tumor growth; however, no one has successfully targeted TAMs with a CAR T cells. It is hypothesized that elimination of TAMs with CAR T cells could be a promising approach, either alone or in combination with traditional CARs targeting the tumor. FRβ expression was confirmed as induced on in vitro differentiated macrophages in the presence of MCSF (FIG. 55), a key cytokine promoting recruitment to the tumor microenvironment.

Figure 56A:
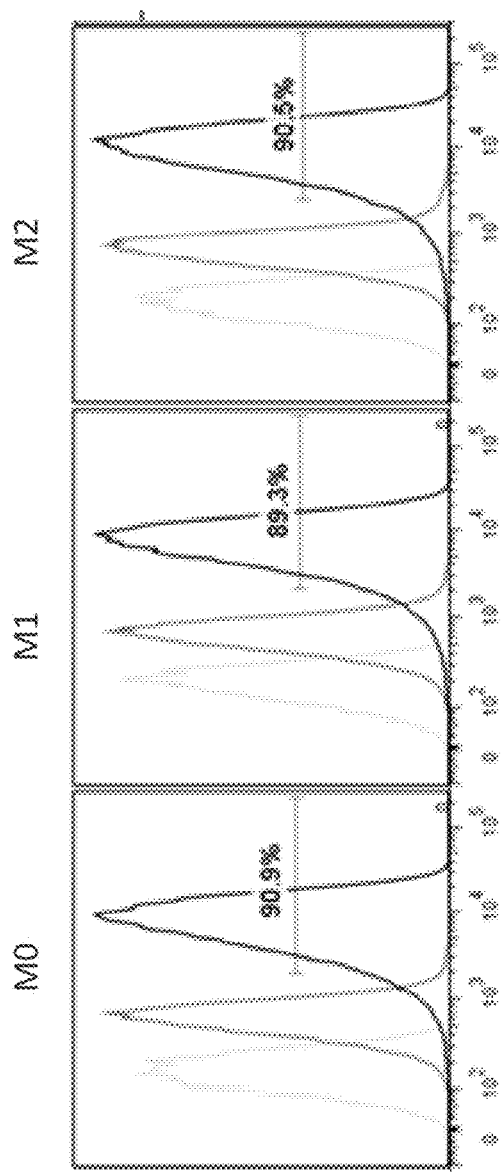
FIG. 56A is a panel of graphs showing FRβ expression on monocytes during cytokine induced polarization at day 1.
Figure 56B:
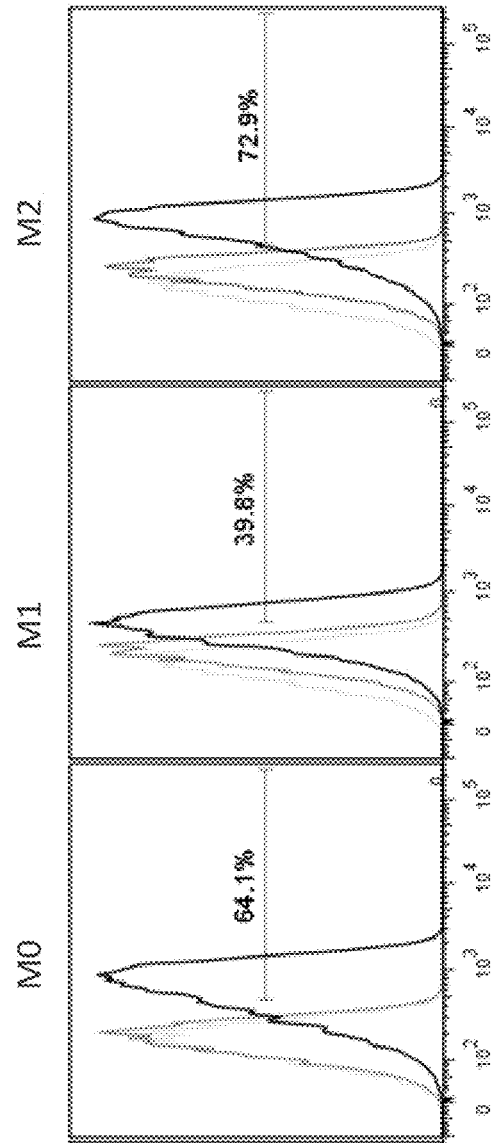
FIG. 56B is a panel of graphs showing FRβ expression on monocytes during cytokine induced polarization at day 3.
Figure 57:
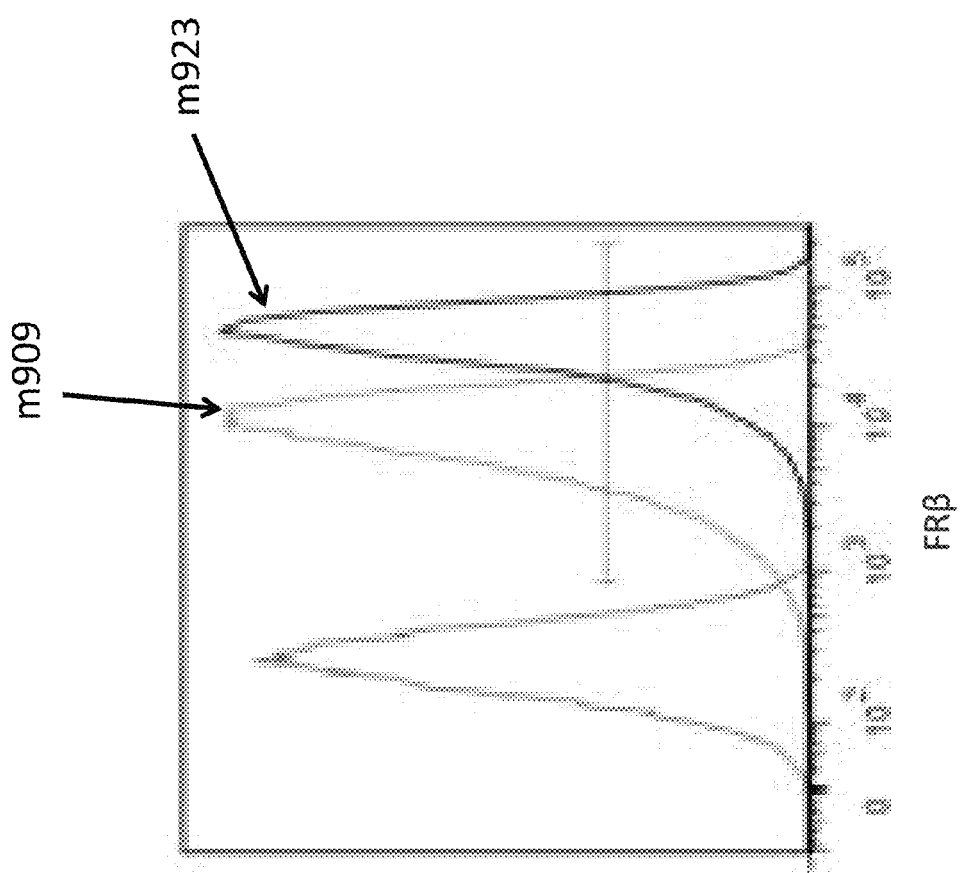
FIG. 57 is a graph showing FRβ expression on day 8 MCSF monocyte-derived macrophage.
Figure 58A:
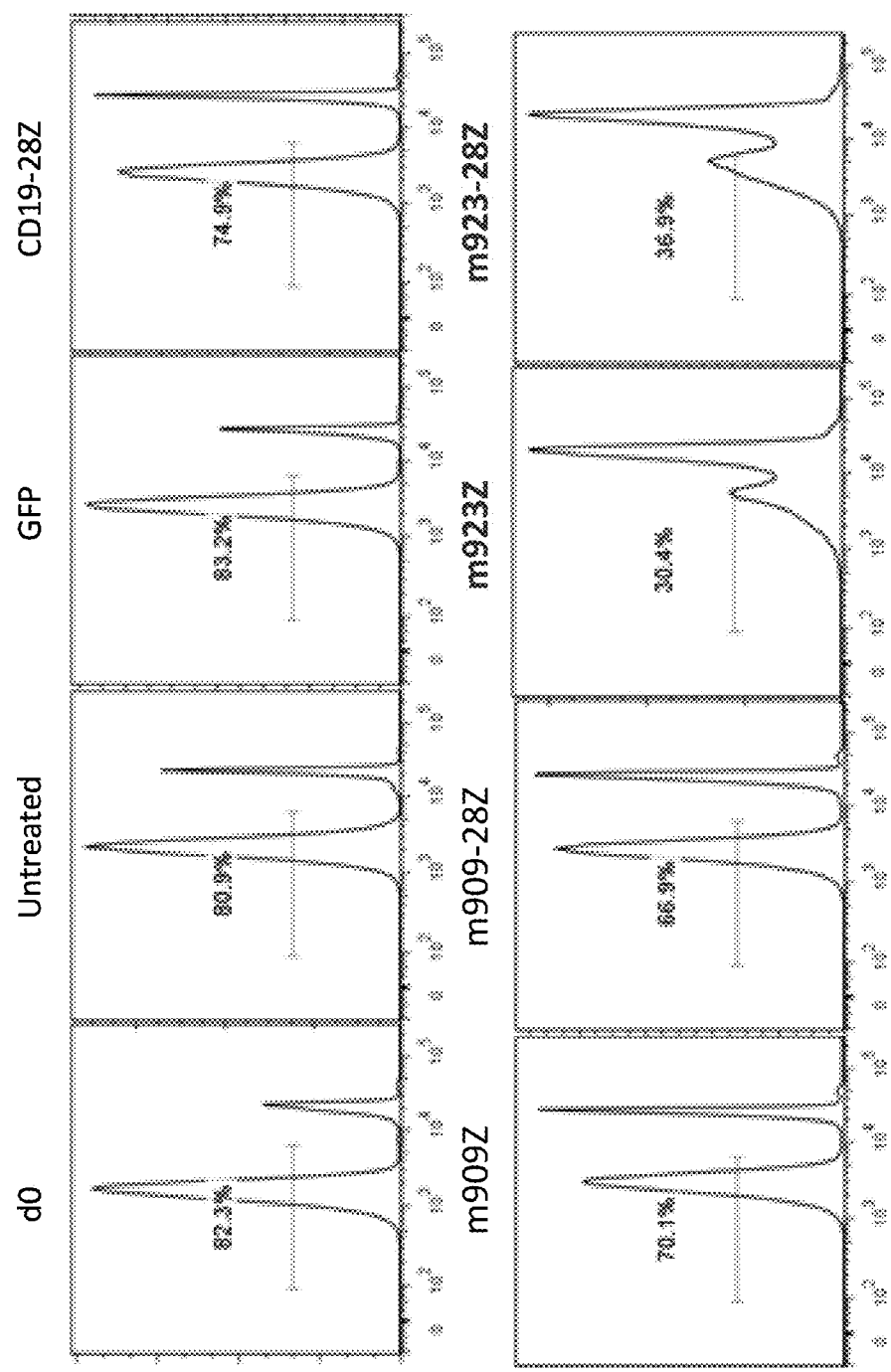
FIG. 58A is a panel of graphs showing macrophage viability after co-culture with CAR T cells.
Figure 58B:
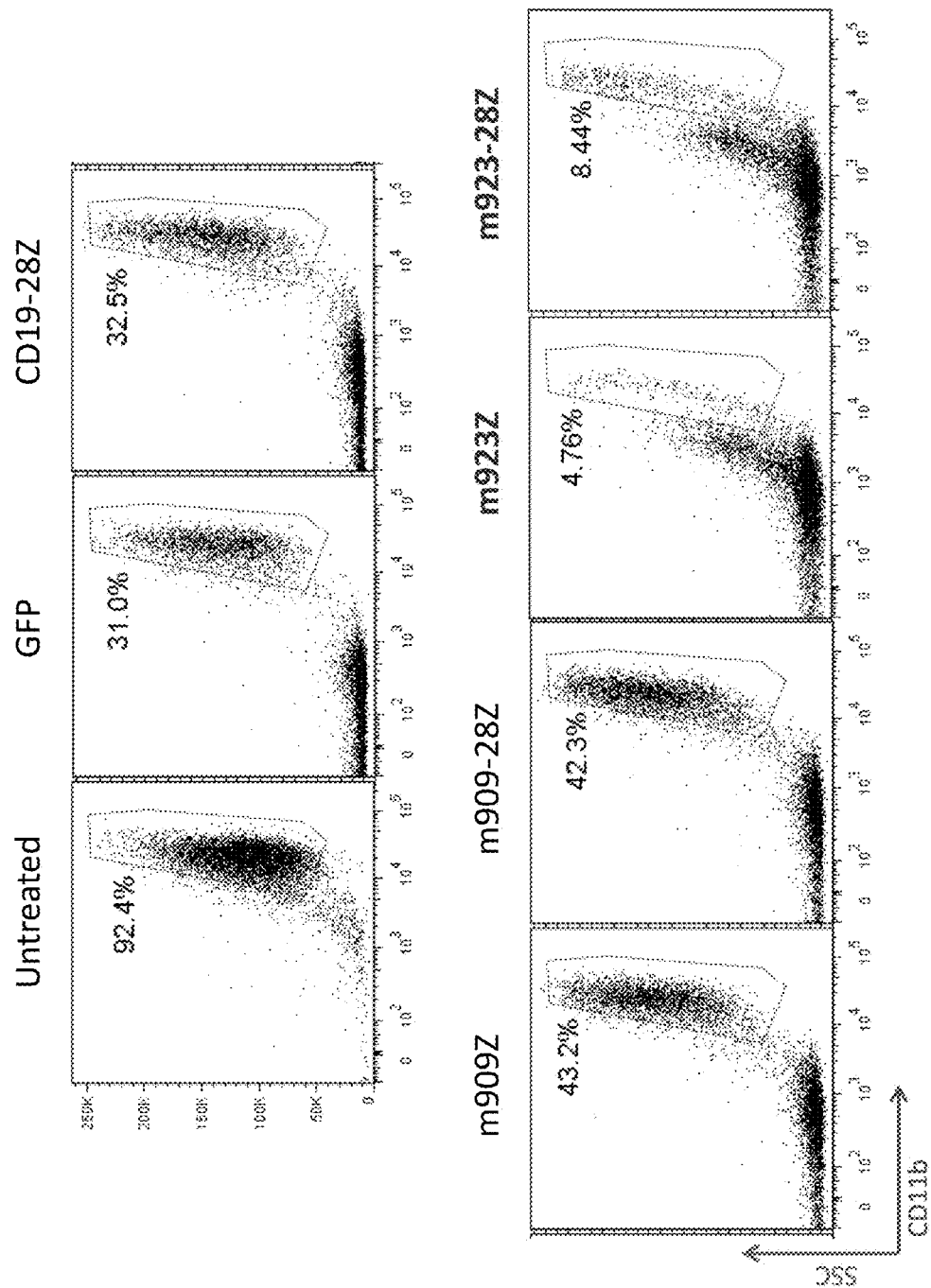
FIG. 58B is a panel of graphs showing CD11b expression after co-culture with CAR T cells.
Figure 59:
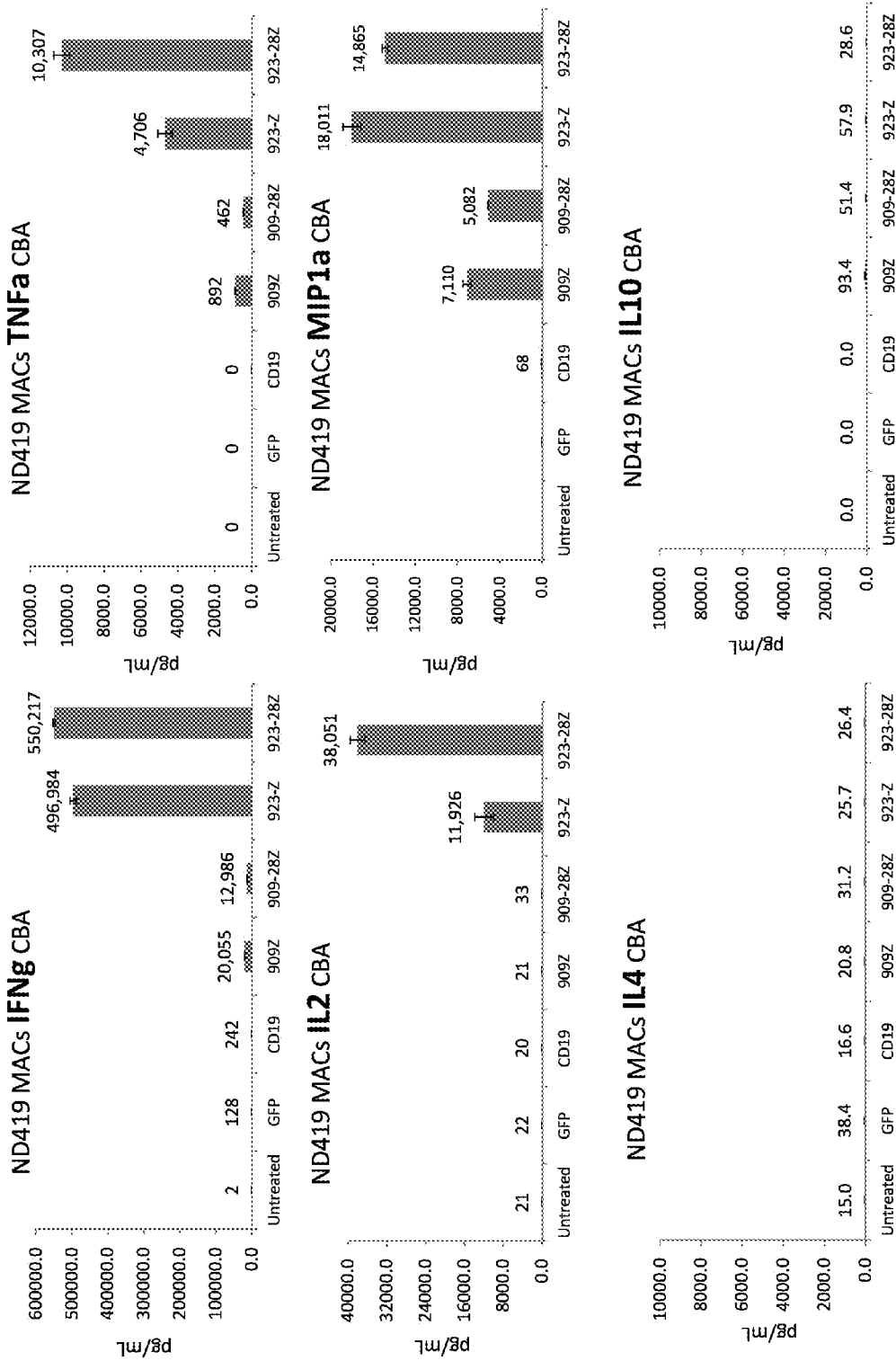
FIG. 59 is a panel of graphs showing cytokine secretion of m923 CAR T cells after co-culture with MCSF-polarized macrophages.

FRβ expression was detectable on M0, M1 and M2 monocytes during cytokine polarization at day 1 (FIG. 56A) and day 3 (FIG. 56B). FRβ expression was also detectable with m909 and m923 (FIG. 57). Upon co-culture with FRβ CAR T cells, macrophage viability decreased significantly (FIG. 58A), as well as the presence of CD11b+ cells (FIG. 58B). FRβ CAR T cells targeted the macrophages and secreted high levels of proinflammatory cytokines (FIG. 59).

Figures 60A, 60B:
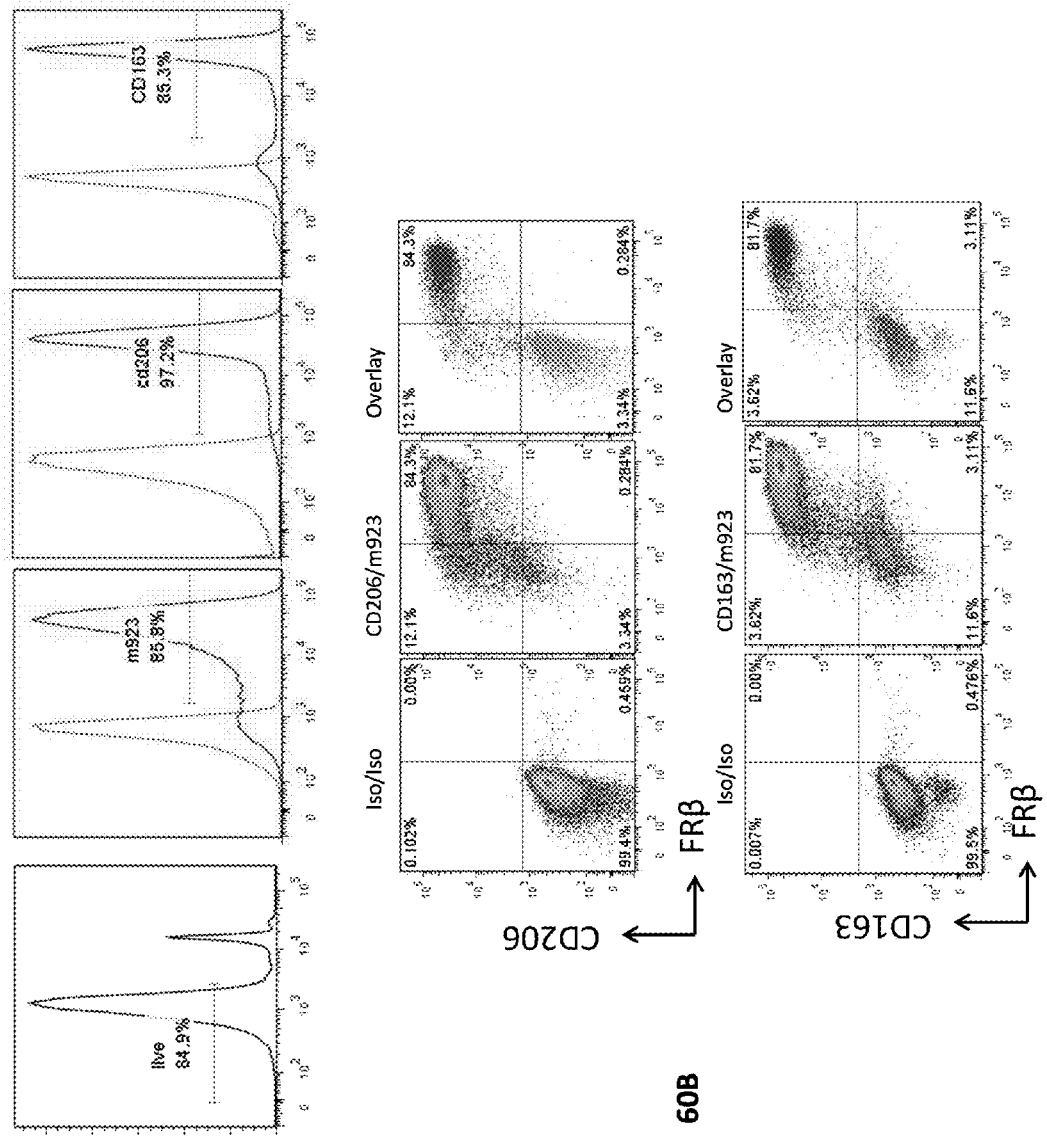
FIG. 60A is a panel of graphs showing FRβ expression on MCSF monocyte-derived macrophages M2 polarized with IL-10 and IL-4.
FIG. 60B is a panel of graphs showing FRβ expression on CD206+ and CD163+ M2 polarized macrophages.
Figure 61A:
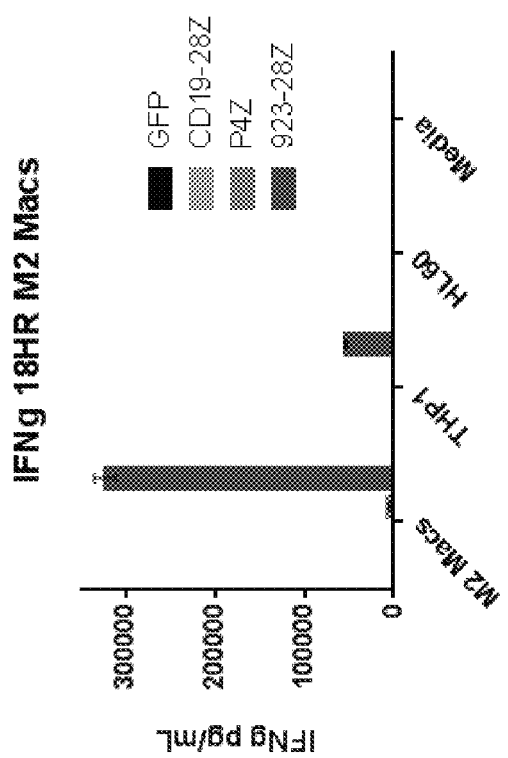
FIG. 61A is a graph showing m923 CAR T cells specifically recognized M2 polarized macrophages by secreting proinflammatory cytokine, IFNγ.
Figure 61B:
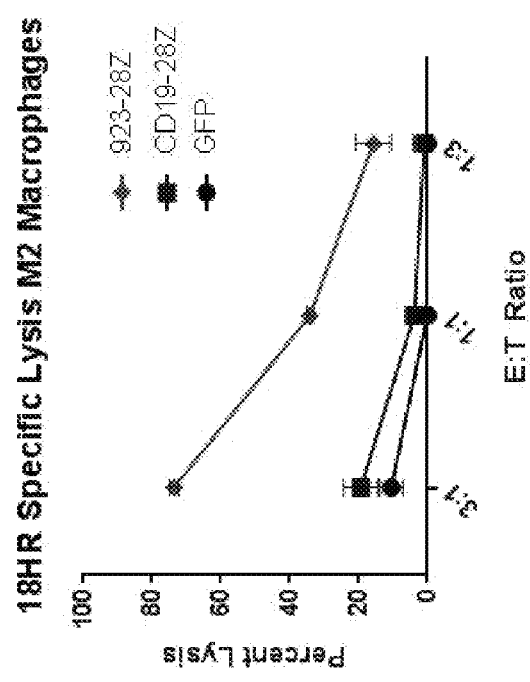
FIG. 61B is a graph showing m923 CAR T cells specifically lysed M2 polarized macrophages.
Figure 62:
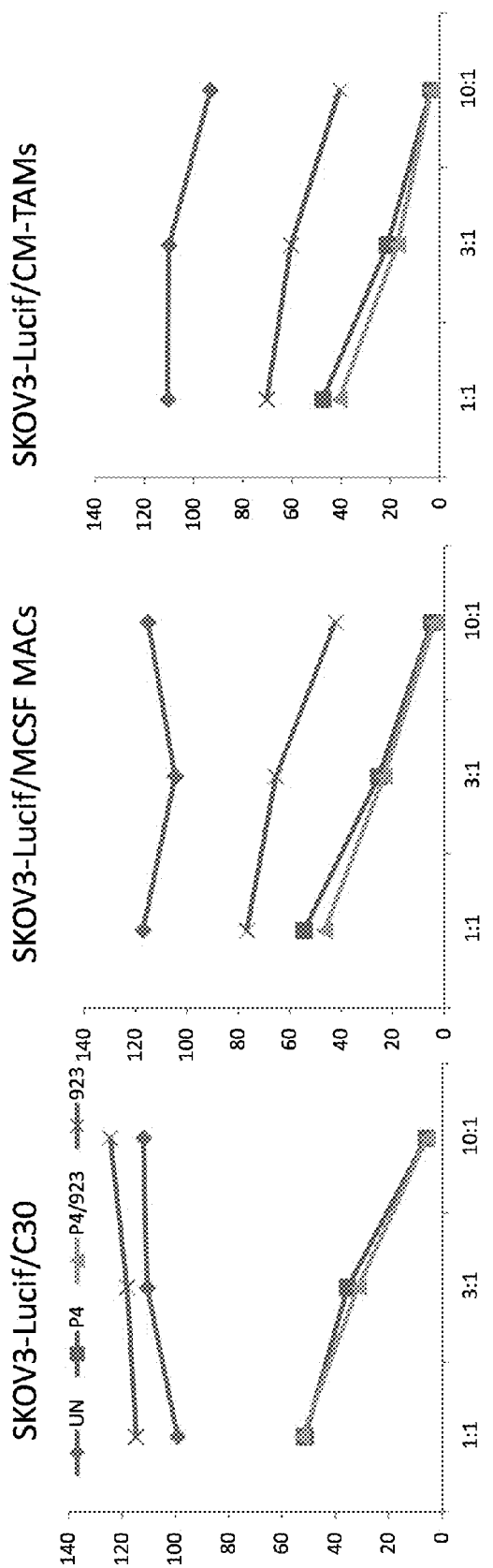
FIG. 62 is a panel of graphs showing m923 CAR T cells mediated bystander killing of skov3 ovarian cancer cells in the presence of FRβ+ macrophages.

In addition, macrophages further polarized to M2 phenotype by IL10 and IL4 maintained very high levels of FRβ (FIG. 60A). Upon co-culture, FRβ CAR T cells target MCSF-polarized macrophages (FIG. 60B), secreted high levels of proinflammatory cytokines (FIG. 61A) and mediated lysis of MCSF-differentiated or M2 polarized macrophages (FIG. 61B), suggesting these CAR T cells were quite effective in eliminating immunosuppressive myeloid cells in the tumor microenvironment.

m923 CAR are envisioned as useful for targeting TAMs and conventional tumor-targeted CARs simultaneously. An in vitro multi-party co-culture system was setup to test this idea. Bystander lysis of FRβ-negative skov3 ovarian cancer cells was observed when m923 CAR T cells were exposed to a mixed population of both TAMs (FRβ+ macrophages) and tumor cells (FIG. 62).

Figure 63A:
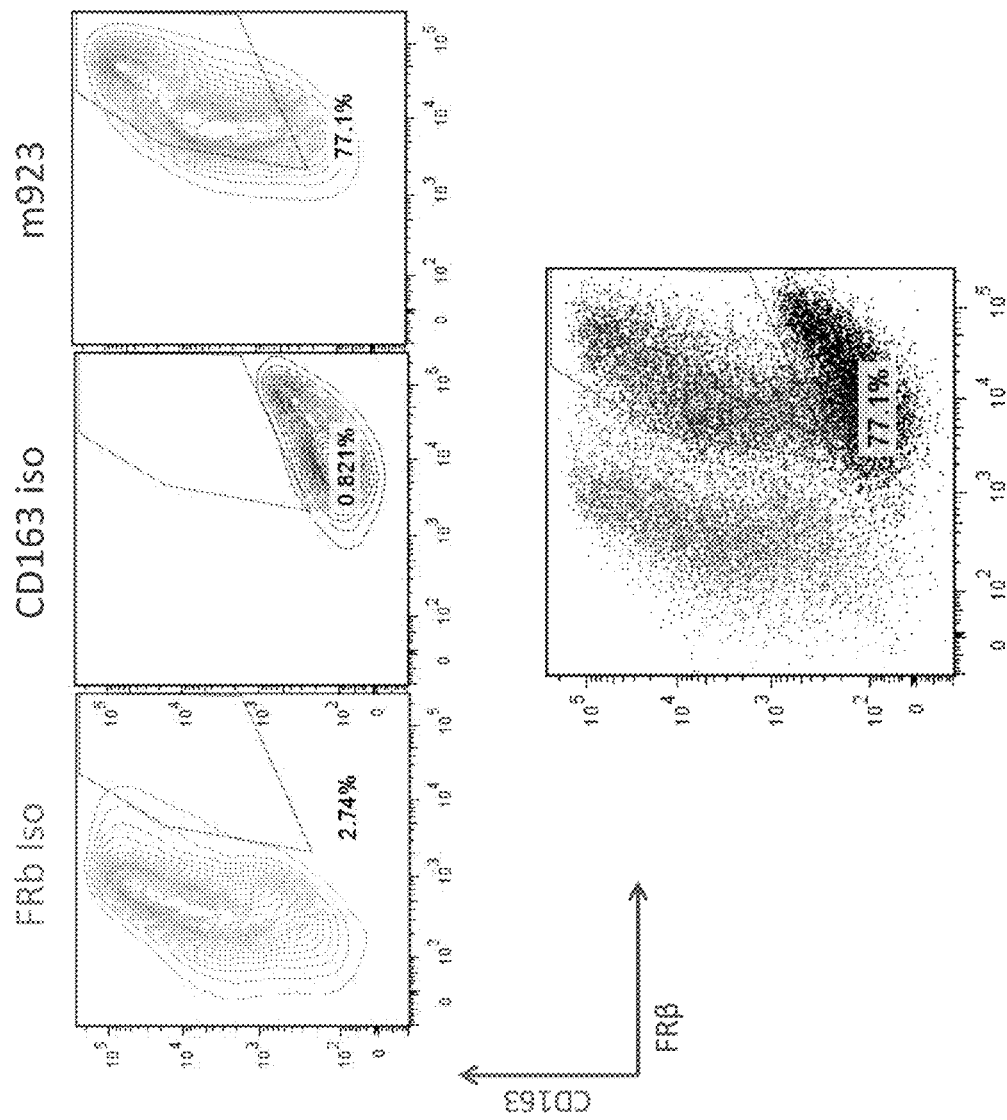
FIG. 63A is a panel of graphs showing FRβ expression on primary ovarian tumor associated macrophages from ascites from ovarian cancer patients.
Figure 63B:
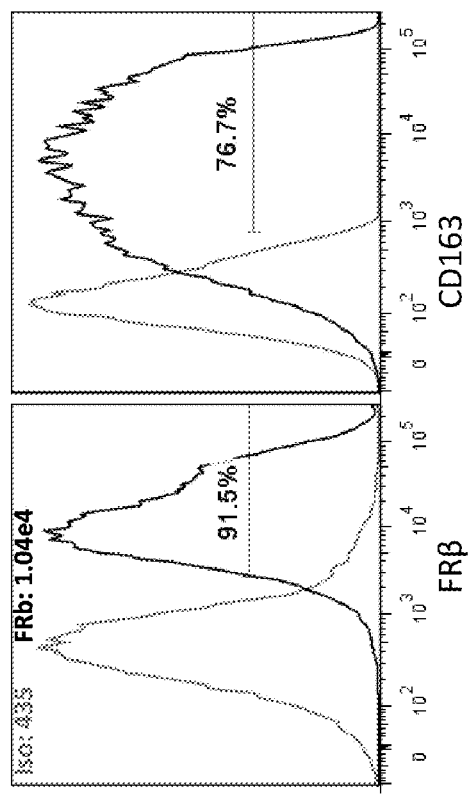
FIG. 63B is a panel of graphs showing FRβ (left graph) and CD163 (right graph) expression on primary CD14+ tumor associated macrophages from ascites of ovarian cancer patients.
Figure 63C:
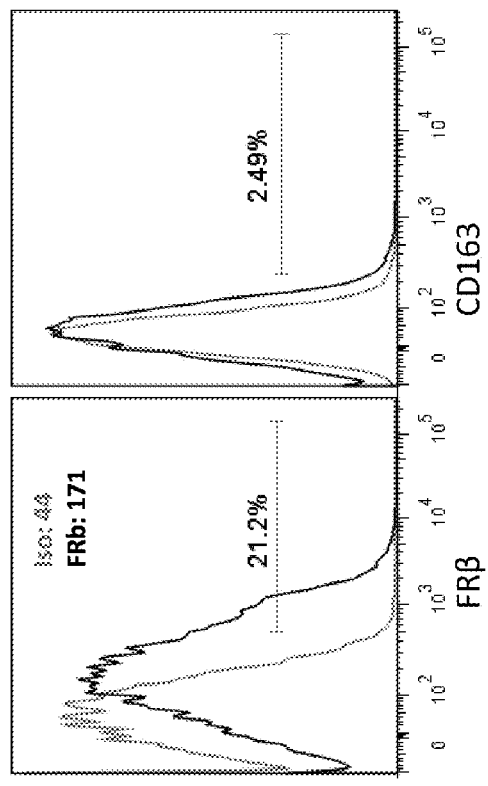
FIG. 63C is a panel of graphs showing FRβ (left graph) and CD163 (right graph) expression on CD14− primary ovarian cells from ovarian cancer patients.
Figure 64B:
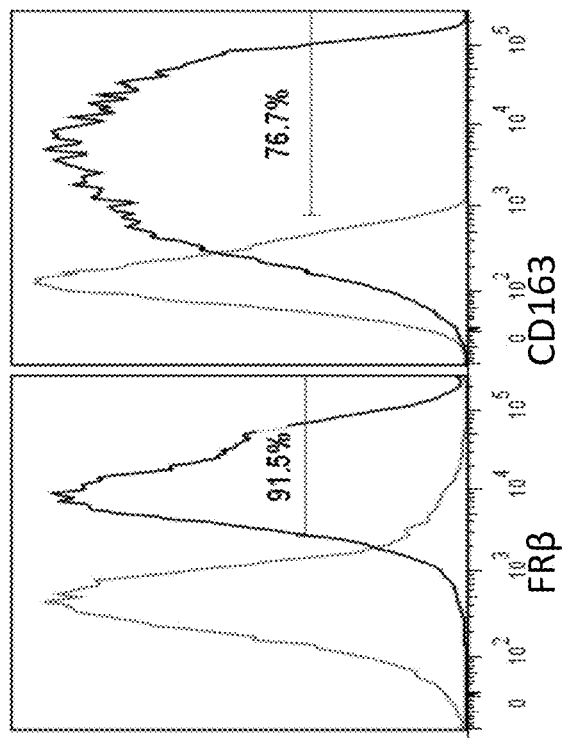
FIG. 64B is a graph showing FRβ expression on CD14+ primary ovarian ascites cells from ovarian cancer patients.
Figure 64A:
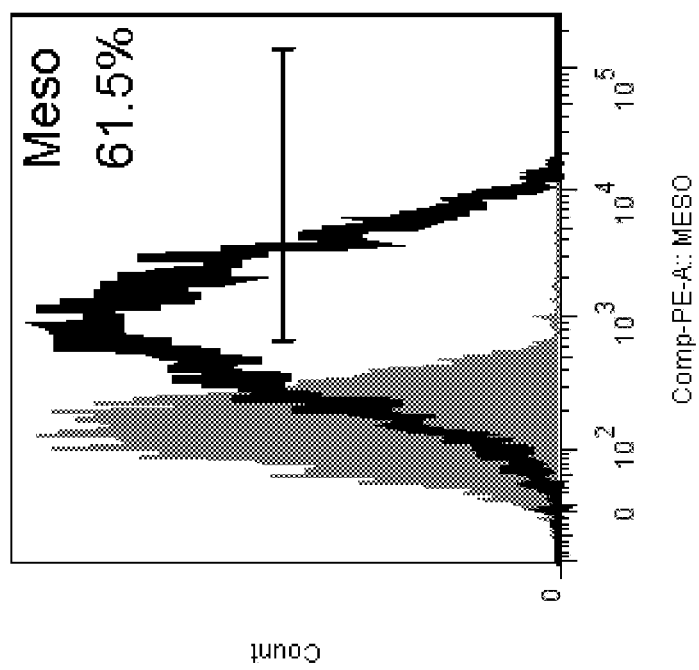
FIG. 64A is a graph showing tumor mesothelin expression on primary ovarian ascites cells from ovarian cancer patients.
Figure 65:
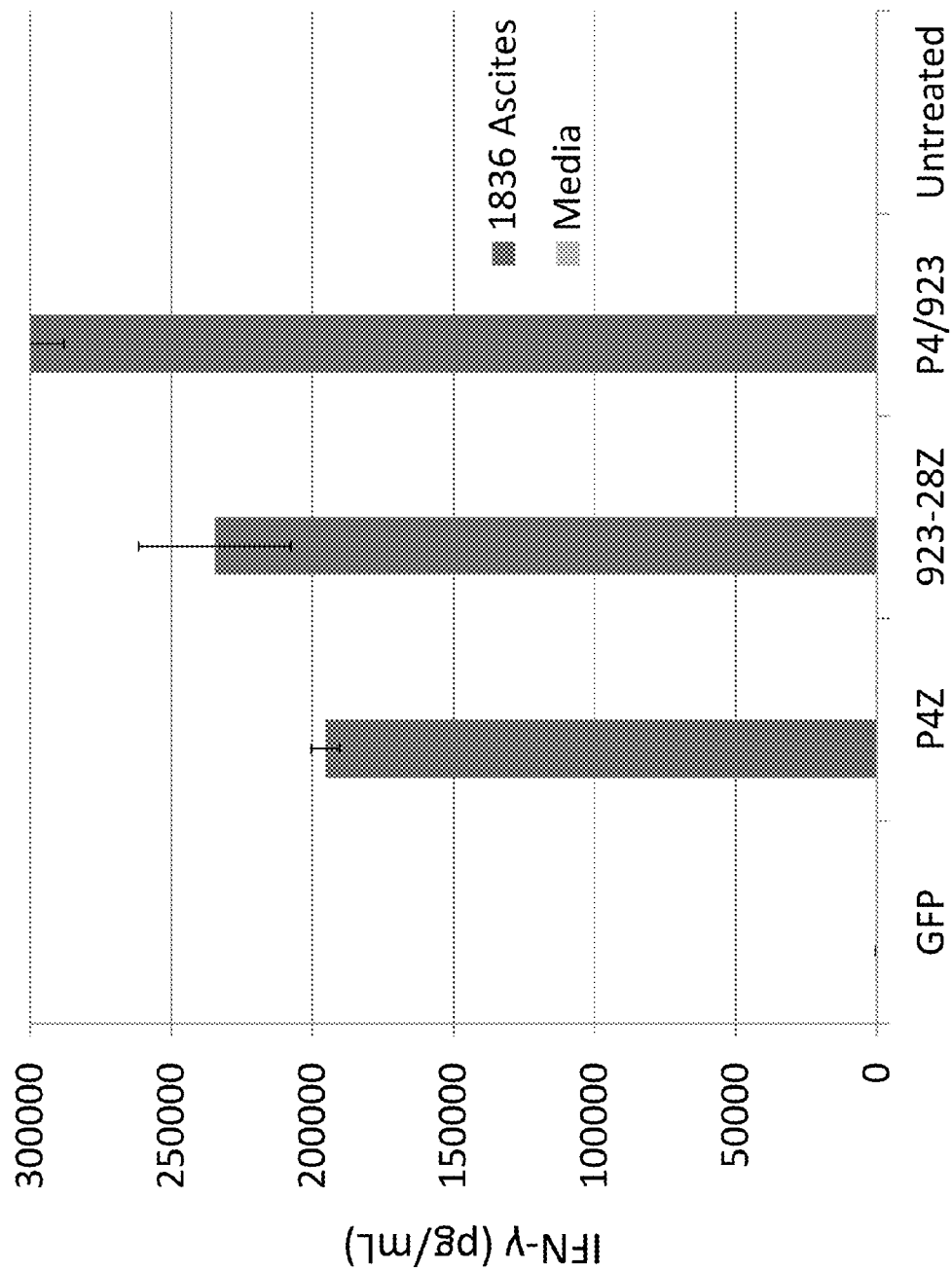
FIG. 65 is a graph showing m923 CAR T cells specifically recognized primary ovarian ascites cells by secreting proinflammatory cytokine, IFNγ. 1e5 live ascites cells/well were plated (~50% viability after thaw) (~70% in clumps of 5-15 cells) and ~1e5 CAR+ cells were added per well (~55% transduction efficiency).

Finally, primary TAMs from ovarian cancer patients were found to co-express high levels of FRβ (FIG. 63A) and CD163 (FIGS. 63B and 63C), a marker for M2 polarized macrophages. m923 CAR T cells were highly responsive when exposed to primary ovarian tumor ascites that expressed meothelin (FIG. 64A) and FRβ (FIG. 64B). Upon co-culture, FRβ CAR T cells secreted high levels of proinflammatory cytokines (FIG. 65).

Translating m923 to an RNA CAR Platform

Figure 66B:
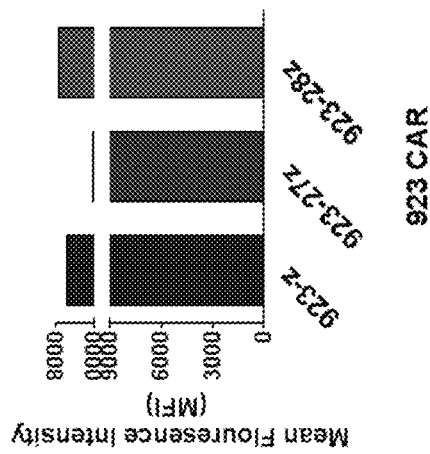
FIG. 66B is a graph showing CAR expression 12 hours after RNA electroporation to transiently express m923 CAR in T cells.
Figure 66A:
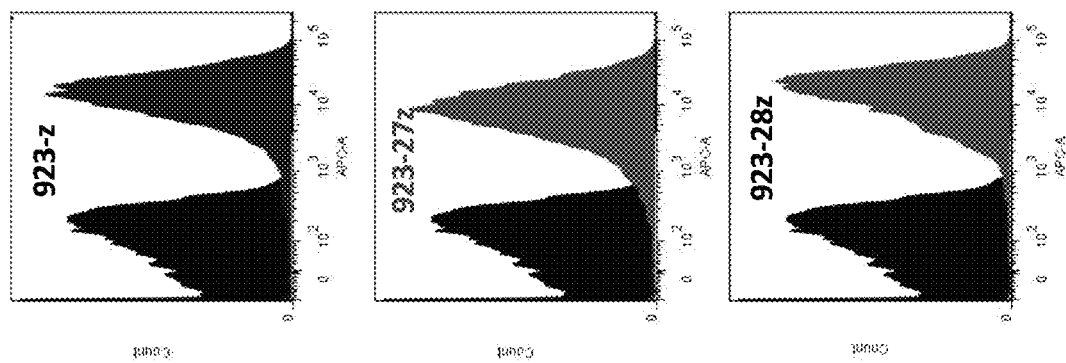
FIG. 66A is a panel of graphs showing CAR expression 12 hours after RNA electroporation to transiently express m923 CAR in T cells.
Figure 66B:
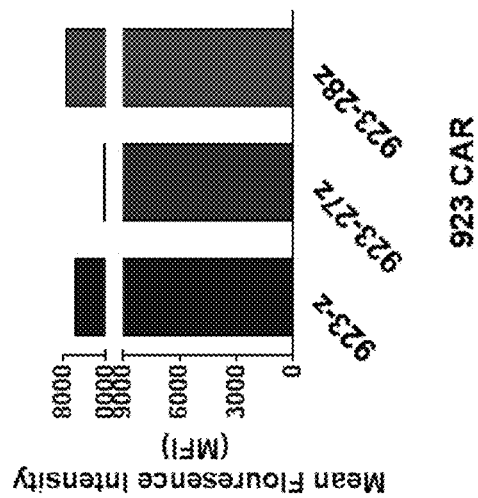
Figure 66A:
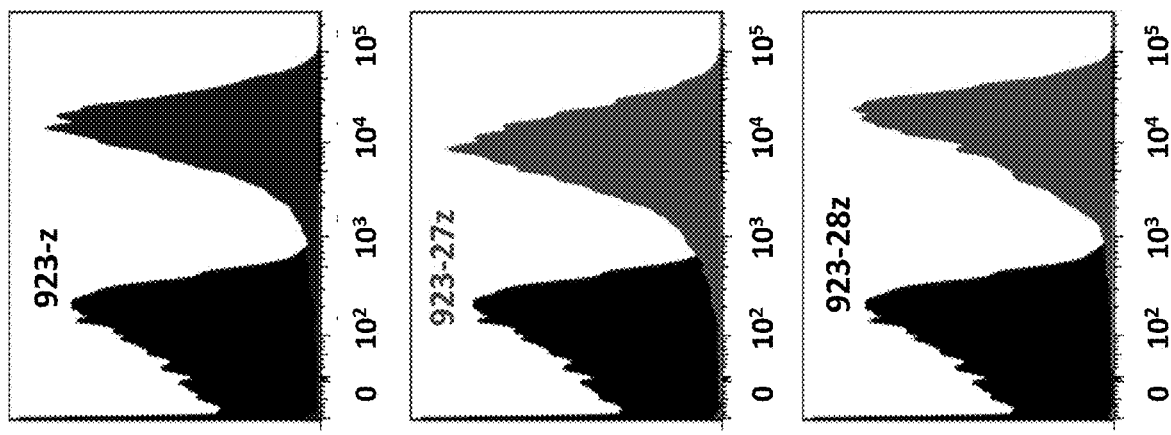
Figure 70:
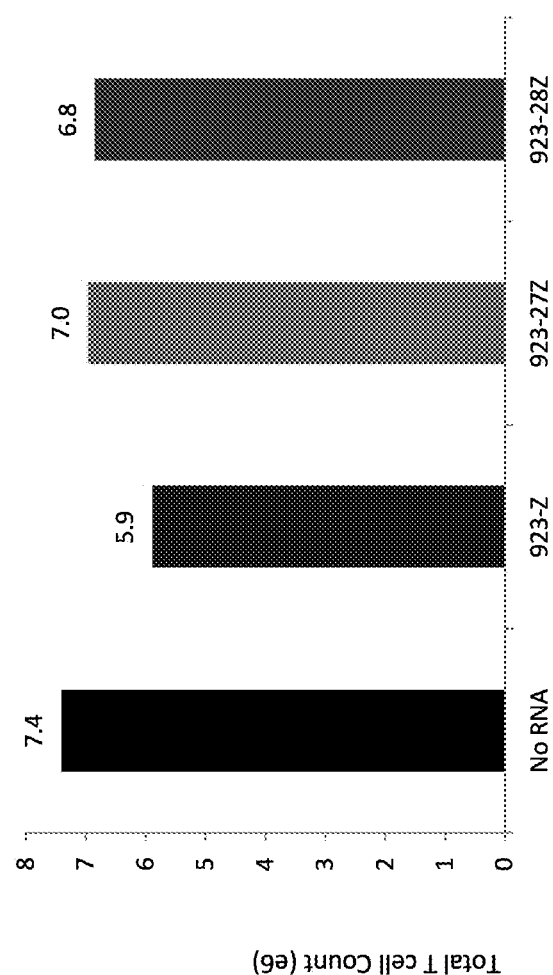
Figure 71B:
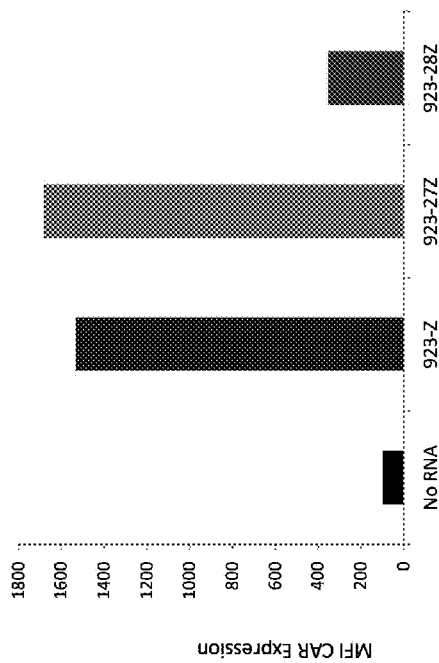
Figure 71A:
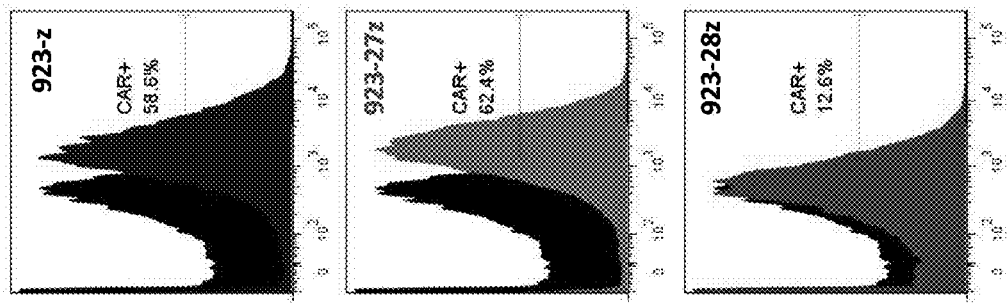
Figure 73:
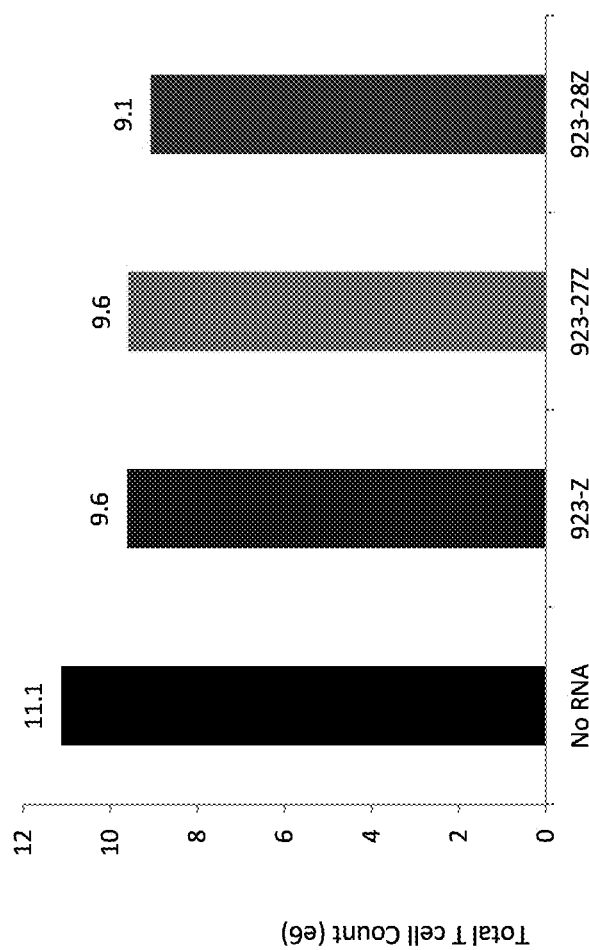

Because long-term persistence of lentivirally-transduced FRβ CAR T cells poses the potential for ongoing myeloid toxicity following tumor clearance, RNA electroporation has been utilized as a way to transiently express m923 CAR in T cells. RNA-based m923 CAR T cells will mediate potent anti-tumor effects in the short term, however, due to RNA dilution and degradation, may not be able to maintain long-lasting (and potentially toxic) effects. First and second generation RNA vectors were designed with m923-Z, CD28-Z, and CD27-Z. Very high CAR surface expression was observed within 12 hours of RNA electroporation (FIGS. 66A and 66B) as well as high cell viability (FIGS. 67A and 67B). In unstimulated cells, surface expression decreased gradually (FIGS. 68A and 68B at day 3, FIGS. 71A and 71B at day 5, FIGS. 74A and 74B at day 8) over a period of 7-10 days while maintaining high cell viability (FIGS. 69A and 69B at day 3, FIGS. 72A and 72B at day 5, FIGS. 75A and 75B at day 8) and overall T cell counts (FIG. 70 at day 3, FIG. 73 at day 5, FIG. 76 at day 8). RNA m923 CAR T cells exhibited robust activity against THP1 on day 1 following CAR electroporation (FIG. 78), with gradual decrease in activity over time, consistent with a loss of CAR surface expression.

When RNA CAR T cells were compared with lentiviral CAR T cells (FIGS. 79A and 79B), both mediated efficient lysis of THP1 (FIGS. 80A, 80B and 80C) and secreted high levels of IFNγ (FIGS. 80A-80C for overnight, FIGS. 81A-81 for 2 days and FIG. 81C for 3 and 5 days). Both m923 RNA and lenti CAR T cells expanded in the presence of THP1 target cells. Both m923 RNA and lenti CAR T cells significantly reduced the number of THP1 cells (FIG. 82 at 3 days and FIG. 84 at 5 days). Expansion of lenti CARs was superior to the RNA CAR T cells. Expansion of RNA CAR T cells was also accompanied by rapid loss of surface CAR expression (within 3 days, FIGS. 83A and 83B), while lenti CAR T cells maintained high surface expression even at 5 days (FIGS. 85A and 85B).

Example 6 m923-Z CAR Sequence (Nucleic Acid Sequence is SEQ ID NO: 5, Amino Acid Sequence SED ID NO: 6)

```
                                    M     A     L     P     V     T     A •
5501                                ATGGC CTTAC CAGTG ACCGC
                                    TACCG GAATG CTCAC TGCCG
                                                                              CD8a

• L     L     L     P     L     A     L     L     L     H     A     A     R     P     G     S     A •
5551  CTTGC TCCTG CCGCT GGCCT TGCTG CTCCA CGCCG CCAGG CCGGG ATCAG
      GAACG AGGAC GGCGA CCGGA ACGAC GAGGT GCGGC GGTCC GGCCC TAGTC

• E     V     Q     L     V     Q     S     G     A     E     V     K     K     P     G     A
5601  CCGAA GTGCA GCTGG TGCAG TCTGG GGCTG AGGTG AAGAA GCCTG GGGCC
      GGCTT CACGT CGACC ACGTC AGACC CCGAC TCCAC TTCTT CGGAC CCCGG

S     V     K     V     S     C     K     A     S     G     Y     T     F     T     S     Y     A •
5651  TCAGT GAAGG TTTCC TGCAA GGCTT CTGGA TACAC CTTCA CTAGC TATGC
      AGTCA CTTCC AAAGG ACGTT CCGAA GACCT ATGTG GAAGT GATCG ATACG

• M     H     W     V     R     Q     A     P     G     Q     R     L     E     W     M     G     W •
5701  TATGC ATTGG GTGCG CCAGG CCCCC GGACA AAGGC TTGAG TGGAT GGGAT
      ATACG TAACC CACGC GGTCC GGGGG CCTGT TTCCG AACTC ACCTA CCCTA

• I     N     A     G     N     G     N     T     K     Y     S     Q     K     F     Q     G
5751  GGATC AACGC TGGCA ATGGT AACAC AAAAT ATTCA CAGAA GTTCC AGGGC
      CCTAG TTGCG ACCGT TACCA TTGTG TTTTA TAAGT GTCTT CAAGG TCCCG

R     V     T     I     T     R     D     T     S     A     S     T     A     Y     M     E     L •
5801  AGAGT CACCA TTACC AGGGA CACAT CCGCG AGCAC AGCCT ACATG GAGCT
      TCTCA GTGGT AATGG TCCCT GTGTA GGCGC TCGTG TCGGA TGTAC CTCGA

• S     S     L     R     S     E     D     T     A     V     Y     Y     C     A     R     D     I •
5851  GAGCA GCCTG AGATC TGAAG ACACG GCTGT GTATT ACTGT GCGAG AGACA
      CTCGT CGGAC TCTAG ACTTC TGTGC CGACA CATAA TGACA CGCTC TCTGT

• S     Y     G     S     F     D     Y     W     G     Q     G     T     L     V     T     V
5901  TCAGC TATGG TTCGT TTGAC TACTG GGGCC AGGGA ACCCT GGTCA CCGTC
      AGTCG ATACC AAGCA AACTG ATGAC CCCGG TCCCT TGGGA CCAGT GGCAG

S     S     G     G     G     G     S     G     G     G     G     S     G     G     G     G     S •
5951  TCCTC AGGTG GAGGC GGTTC AGGCG GAGGT GGCTC TGGCG GTGGC GGATC
      AGGAG TCCAC CTCCG CCAAG TCCGC CTCCA CCGAG ACCGC CACCG CCTAG
                                                                              m923 scFv

• S     S     E     L     T     Q     D     P     A     V     S     V     A     L     G     Q     T •
6001  ATCTT CTGAG CTGAC TCAGG ACCCT GCTGT GTCTG TGGCC TTGGG ACAGA
      TAGAA GACTC GACTG AGTCC TGGGA CGACA CAGAC ACCGG AACCC TGTCT

• V     R     I     T     C     Q     G     D     S     L     R     S     N     Y     A     N
6051  CAGTC AGGAT CACCT GCCAA GGAGA CAGCC TCAGA AGCAA CTATG CAAAC
      GTCAG TCCTA GTGGA CGGTT CCTCT GTCGG AGTCT TCGTT GATAC GTTTG

W     Y     Q     Q     K     P     G     Q     A     P     V     L     V     I     Y     G     Q •
6101  TGGTA CCAGC AGAAG CCAGG ACAGG CCCCT GTACT TGTCA TCTAT GGTCA
      ACCAT GGTCG TCTTC GGTCC TGTCC GGGGA CATGA ACAGT AGATA CCAGT

• N     N     R     P     S     G     I     P     D     R     F     S     G     S     S     S     G •
6151  AAACA ACCGG CCCTC AGGGA TCCCA GACCG ATTCT CTGGC TCCAG CTCAG
      TTTGT TGGCC GGGAG TCCCT AGGGT CTGGC TAAGA GACCG AGGTC GAGTC

• N     T     A     S     L     T     I     T     G     A     Q     A     A     D     E     A
6201  GAAAC ACAGC TTCCT TGACC ATCAC TGGGG CTCAG GCGGC ACATG AGGCT
      CTTTG TGTCG AAGGA ACTGG TAGTG ACCCC GAGTC CGCCG TGTAC TCCGA

D     Y     Y     C     D     S     R     V     S     T     G     N     H     V     V     F     G •
6251  GACTA TTACT GTGAC TCCCG GGTCA GCACT GGTAA CCATG TGGTA TTCGG
      CTGAT AATGA CACTG AGGGC CCAGT CGTGA CCATT GGTAC ACCAT AAGCC
```

-continued

```
         • G   G   T   K   L   T   V   L   G   Q   A   S   T   T   T   P   A •
    6301 CGGAG GGACC AAGCT GACCG TCCTA GGCCA GGCTA GCACC ACGAC GCCAG
         GCCTC CCTGG TTCGA CTGGC AGGAT CCGGT CCGAT CGTGG TGCTG CGGTC

• P   R   P   P   T   P   A   P   T   I   A   S   Q   P   L   S
    6351 CGCCG CGACC ACCAA CACCG GCGCC CACCA TCGCG TCGCA GCCCC TGTCC
         GCGGC GCTGG TGGTT GTGGC CGCGG GTGGT AGCGC AGCGT CGGGG ACAGG

L   R   P   E   A   C   R   P   A   A   G   G   A   V   H   T   R •
    6401 CTGCG CCCAG AGGCG TGCCG GCCAG CGGCG GGGGG CGCAG TGCAC ACGAG
         GACGC GGGTC TCCGC ACGGC CGGTC GCCGC CCCCC GCGTC ACGTG TGCTC

• G   L   D   F   A   C   D   I   Y   I   W   P   L   A   G   T •
    6451 GGGGC TGGAC TTCGC CTGTG ATATC TACAT CTGGG CGCCC TTGGC CGGGA
         CCCCG ACCTG AAGCG GACAC TATAG ATGTA GACCC GCGGG AACCG GCCCT

• C   G   V   L   L   L   S   L   V   I   T   L   Y   C   R   V
    6501 CTTGT GGGGT CCTTC TCCTG TCACT GGTTA TCACC CTTTA CTGCA GAGTG        [CD8a tm]
         GAACA CCCCA GGAAG AGGAC AGTGA CCAAT AGTGG GAAAT GACGT CTCAC

K   F   S   R   S   A   D   A   P   A   Y   Q   Q   G   Q   N   Q •
    6551 AAGTT CAGCA GGAGC GCAGA CGCCC CCGCG TACCA GCAGG GCCAG AACCA
         TTCAA GTCGT CCTCG CGTCT GCGGG GGCGC ATGGT CGTCC CGGTC TTGGT

• L   Y   N   E   L   N   L   G   R   R   E   E   Y   D   V   L   D •
    6601 GCTCT ATAAC GAGCT CAATC TAGGA CCAAG ACACG ACTAC GATCT TTTCG
         CGAGA TATTG CTCGA GTTAG ATCCT GGTTC TGTGC TGATG CTAGA AAAGC

• K   R   R   G   R   D   P   E   M   G   G   K   P   R   R   K
    6651 ACAAG AGACG TGGCC GGGAC CCTGA GATGG GGGGA AAGCC GAGAA GGAAG
         TGTTG TCTGC ACCGG CCCTG GGACT CTACC CCCCT TTCGG GTCTT CCTTC

N   P   Q   E   G   L   Y   N   E   L   Q   K   D   K   M   A   E •
    6701 AACCC TCAGG AAGGC CTGTA CAATG AACTG CAGAA AGATA AGATG GCGGA        [CD3Z ICD]
         TTGGG AGTCC TTCCG GACAT GTTAC TTGAC GTCTT TCTAT TCTAC CCCCT

• A   Y   S   E   I   G   M   K   G   E   R   R   R   G   K   G   H •
    6751 GGCCT ACAGT GACAT TGGGA TGAAA GGCGA GCGCC GGAGG GGCAA GGGGC
         CCGGA TGTCA CTGTA ACCCT ACTTT CCGCT CGCGG CCTCC CCGTT CCCCG

• D   G   L   Y   Q   G   L   S   T   A   T   K   D   T   Y   D
    6801 ACGAT GGCCT TTACC AGGGT CTCAG TACAG CCACC AAGGA CACCT ACGAC
         TGCTA CCGGA AATGG TCCCA GAGTC ATGTC GGTGG TTCCT GTGGA TGCTG

A   L   H   M   Q   A   L   P   P   R   *
    6851 GCCCT TCACA TGCAG GCCCT GCCCC CTCGC TAA
         CGGGA AGTGT ACGTC CGGGA CGGGG GAGCG ATT
```

Example 7 m923-27Z CAR Sequence (Nucleic Acid Sequence is SEQ ID NO: 7, Amino Acid Sequence SED ID NO: 8)

```
              M     A     L     P     V     T     A •
5501                ATGGC CTTAC CAGTG ACCGC
                    TACCG GAATG CTCAC TGCCG

• L     L     L     P     L     A     L     L     H     A     A     R     P     G     S     A •        ┌───────┐
5551  CTTGC TCCTG CCGCT GGCCT TGCTG CTCCA CGCCG CCAGG CCGGG ATCAG                                            │ CD8a  │
      GAACG AGGAC GGCGA CCGGA ACGAC GAGGT GCGGC GGTCC GGCCC TAGTC                                            └───────┘

• E     V     Q     L     V     Q     S     G     A     E     V     K     K     P     G     A
5601  CCGAA GTGCA GCTGG TGCAG TCTGG GGCTG AGGTG AAGAA GCCTG GGGCC
      GGCTT CACGT CGACC ACGTC AGACC CCGAC TCCAC TTCTT CGGAC CCCGG

S     V     K     V     S     C     K     A     S     G     Y     T     F     T     S     Y     A •
5651  TCAGT GAAGG TTTCC TGCAA GGCTT CTGGA TACAC CTTCA CTAGC TATGC
      AGTCA CTTCC AAAGG ACGTT CCGAA GACCT ATGTG GAAGT GATCG ATACG

• M     H     W     V     R     Q     A     P     G     Q     R     L     E     W     M     G     W •
5701  TATGC ATTGG GTGCG CCAGG CCCCC GGACA AAGGC TTGAG TGGAT GGGAT
      ATACG TAACC CACGC GGTCC GGGGG CCTGT TTCCG AACTC ACCTA CCCTA

• I     N     A     G     N     G     N     T     K     Y     S     Q     K     F     Q     G
5751  GGATC AACGC TGGCA ATGGT AACAC AAAAT ATTCA CAGAA GTTCC AGGGC
      CCTAG TTGCG ACCGT TACCA TTGTG TTTTA TAAGT GTCTT CAAGG TCCCG

R     V     T     I     T     R     D     T     S     A     S     T     A     Y     M     E     L •
5801  AGAGT CACCA TTACC AGGGA CACAT CCGCG AGCAC AGCCT ACATG GAGCT
      TCTCA GTGGT AATGG TCCCT GTGTA GGCGC TCGTG TCGGA TGTAC CTCGA

• S     S     L     R     S     E     D     T     A     V     Y     Y     C     A     R     D     I •
5851  GAGCA GCCTG AGATC TGAAG ACACG GCTGT GTATT ACTGT GCGAG AGACA
      CTCGT CGGAC TCTAG ACTTC TGTGC CGACA CATAA TGACA CGCTC TCTGT

• S     Y     G     S     F     D     Y     W     G     Q     G     T     L     V     T     V
5901  TCAGC TATGG TTCGT TTGAC TACTG GGGCC AGGGA ACCCT GGTCA CCGTC
      AGTCG ATACC AAGCA AACTG ATGAC CCCGG TCCCT GGGAC CAGTG GCAG

S     S     G     G     G     G     S     G     G     G     G     S     G     G     G     G     S •    ┌──────────┐
5951  TCCTC AGGTG GAGGC CGTTC AGGCG GAGGT GGCTC TGGCG GTGGC GGATC                                              │ m923 scFv │
      AGGAG TCCAC CTCCG CCAAG TCCGC CTCCA CCGAG ACCGC CACCG CCTAG                                              └──────────┘

• S     S     E     L     T     Q     D     P     A     V     S     V     A     L     G     Q     T •
6001  ATCTT CTGAG CTGAC TCAGG ACCCT GCTGT GTCTG TGGCC TTGGG ACAGA
      TAGAA GACTC GACTG AGTCC TGGGA CGACA CAGAC ACCGG AACCC TGTCT

• V     R     I     T     C     Q     G     D     S     L     R     S     N     Y     A     N
6051  CAGTC AGGAT CACCT GCCAA GGAGA CAGCC TCAGA AGCAA CTATG CAAAC
      GTCAG TCCTA GTGGA CGGTT CCTCT GTCGG AGTCT TCGTT GATAC GTTTG

W     Y     Q     Q     K     P     G     Q     A     P     V     L     V     I     Y     G     Q •
6101  TGGTA CCAGC AGAAG CCAGG ACAGG CCCCT GTACT TGTCA TCTAT GGTCA
      ACCAT GGTCG TCTTC GGTCC TGTCC GGGGA CATGA ACAGT AGATA CCAGT

• N     N     R     P     S     G     I     P     D     R     F     S     G     S     S     S     G •
6151  AAACA ACCGG CCCTC AGGGA TCCCA GACCG ATTCT CTGGC TCCAG CTCAG
      TTTGT TGGCC GGGAG TCCCT AGGGT CTGGC TAAGA GACCG AGGTC GAGTC

• N     T     A     S     L     T     I     T     G     A     Q     A     A     D     E     A
6201  GAAAC ACAGC TTCCT TGACC ATCAC TGGGG CTCAG GCGGC ACATG AGGCT
      CTTTG TGTCG AAGGA ACTGG TAGTG ACCCC GAGTC CGCCG TGTAC TCCGA

D     Y     Y     C     D     S     R     V     S     T     G     N     H     V     V     F     G •
6251  GACTA TTACT GTGAC TCCCG GGTCA GCACT GGTAA CCATG TGGTA TTCGG
      CTGAT AATGA CACTG AGGGC CCAGT CGTGA CCATT GGTAC ACCAT AAGCC
```

```
            • G  G   T    K    L    T    V    L   G   Q    A    S    T    T    P    A •
       6301 CGGAG GGACC AAGCT GACCG TCCTA GGCCA GGCTA GCACC ACGAC GCCAG
            GCCTC CCTGG TTCGA CTGGC AGGAT CCGGT CCGAT CGTGG TGCTG CSGTC       [CD8a Hinge]

• S  S   E    L    T    Q    D    P    A   V    S    V    A    L    G    Q    T •
       6351 CGCCG CGACC ACCAA CACCG GCGCC CACCA TCGCG TCGCA GCCCC TGTCC
            GCGGC GCTGG TGGTT GTGGC CGCGG GTGGT AGCGC AGCGT CGGGG ACAGG

L   R   P    E    A    C    R    P    A   A    G    G    A    V    H    T    R •
       6401 CTGCG CCCAG AGGCG TGCCG GCCAG CGGCG GGGGG CGCAG TGCAC ACGAG
            GACGC GGGTC TCCGC ACGGC CGGTC GCCGC CCCCC GCGTC ACGTG TGCTC

W   Y   Q    Q    K    P    G    Q    A   P    V    L    V    I    Y    G    Q •
       6451 GGGGC TGGAC TTCGC CTGTG ATATC TACAT CTGGG CGCCC TTGGC CGGGA
            CCCCG ACCTG AAGCG GACAC TATAG ATGTA GACCC GCGGG AACCG GCCCT         [CD8a tm]

• C   G   V    L    L    L    S    L    V   I    T    L    Y    C    R    V
       6501 CTTST GGGGT CCTTC TCCTG TCACT GGTTA TCACC CTTTA CTGCC AACGA
            GAACA CCCCA GGAAG AGGAC AGTGA CCAAT AGTGG GAAAT GACGG TTGCT

R  K   Y    R    S    N    K    G    E   S    P    V    E    P    A    E    P •
       6551 AGGAA ATATA GATCA AACAA AGGAG AAAGT CCTGT GGAGC CTGCA GAGCC
            TCCTT TATAT CTAGT TTGTT TCCTC TTTCA GGACA CCTCG GACGT CTCGG         [CD27 ICD]

• C  R   Y    S    C    P    R    E    E   E    G    S    T    I    P    I    Q •
       6601 TTGTC GTTAC AGCTG CCCCA GGGAG GAGGA GGGCA GCACC ATCCC CATCC
            AACAG CAATG TCGAC GGGGT CCCTC CTCCT CCCGT CGTGG TAGGG GTAGG

• E   D   Y    R    K    P    E    P    A   C    S    P    R    V    K    F
       6651 AGGAG GATTA CCGAA AACCG GAGCC TGCCT GCTCC CCCAG AGTGA AGTTC
            TCCTC CTAAT GGCTT TTGGC CTCGG ACGGA CGAGG GGGTC TCACT TCAAG

S   R   S    A    D    A    P    A    Y   Q    Q    G    Q    N    Q    L    Y •
       6701 AGCAG GAGCG CAGAC GCCCC CGCGT ACCAG CAGCG CCAGA ACCAG CTCTA
            TCGTC CTCGC GTCTG CGGGG GCGCA TGGTC GTCCC GGTCT TGGTC GAGAT

• N  E   L    N    L    G    R    R    E   E   Y    D    V    L    D    K    R •
       6751 TAACG AGCTC AATCT AGGAC GAAGA GAGGA GTACG ATGTT TTGGA CAAGA
            ATTGC TCGAG TTAGA TCCTG CTTCT CTCCT CATGC TACAA AACCT GTTCT

• R   G   R    D    P    E    M    G    G   K    P    R    R    K    N    P
       6801 GACGT GGCCG GGACC CTGAG ATGGG GGGAA AGCCG AGAAG GAAGA ACCCT
            CTGCA CCGGC CCTGG GACTC TACCC CCCTT TCGGC TCTTC CTTCT TGGGA         [CD3Z ICD]

Q   E   G    L    Y    N    E    L    Q   K    D    K    M    A    E    A    Y •
       6851 CAGGA AGGCC TGTAC AATGA ACTGC AGAAA GATAA GATGG CGGAG GCCTA
            GTCCT TCCGG ACATG TTACT TGACG TCTTT CTATT CTACC GCCTC CGGAT

• S  E   I    G    M    K    G    E    R   R    R    G    K    G    H    D    G •
       6901 CAGTG AGATT GGGAT GAAAG GCGAG CGCCG GAGGG GCAAG GGGCA CGATG
            GTCAC TCTAA CCCTA CTTTC CGCTC GCGGC CTCCC CGTTC CCCGT GCTAC

• L   Y   Q    G    L    S    T    A    T   K    D    T    Y    D    A    L
       6951 GCCTT TACCA GGGTC TCAGT ACAGC CACCA AGGAC ACCTA CGACG CCCTT
            CGGAA ATGGT CCCAG AGTCA TGTCG GTGGT TCCTG TGGAT GCTGC GGGAA

H   M   Q    A    L    P    P    R    *
       7001 CACAT GCAGG CCCTG CCCCC TCGCT AA
            GTGTA CGTCC GGGAC GGGGG AGCGA TT
```

Example 8 m923-28Z CAR Sequence (Nucleic Acid Sequence is SEQ ID NO: 9, Amino Acid Sequence SED ID NO: 10)

```
                          M   A   L   P   V   T   A •
5501                     ATGGC CTTAC CAGTG ACCGC        [CD8a]
                         TACCG GAATG GTCAC TGGCG

• L   L   L   P   L   A   L   L   L   H   A   A   R   P   G   S   A •
5551  CTTGC TCCTG CCCCT CGCCT TGCTG CTCCA CGCCG CCAGG CCGGG ATCAG
      GAACG AGGAC GCGGA CGGGA AGGAC GAGGT CCGGC GGTCC GGCGC TAGTC

• E   V   Q   L   V   Q   S   G   A   E   V   K   K   P   G   A
5601      CCGAA GTGCA GCTGG TGCAG TCTGG GGCTG AGGTG AAGAA GCCTG GGGCC
          GGCTT CACGT CGACC ACGTC AGACC CCGAC TCCAC TTCTT CGGAC CCCGG

S   V   K   V   S   C   K   A   S   G   Y   T   F   T   S   Y   A •
5651      TCAGT GAAGG TTTCC TGCAA GGCTT CTGGA TACAC CTTCA CTAGC TATGC
          AGTCA CTTCC AAAGG ACGTT CCGAA GACCT ATGTG GAAGT GATCG ATACG

• M   H   W   V   R   Q   A   P   G   Q   R   L   E   W   M   G   W •
5701  TATGC ATTGG GTGCG CCAGG CCCCC GGACA AAGGC TTGAG TGGAT GGGAT
      ATACG TAACC CACGC GGTCC GGGGG CCTGT TTCCG AACTC ACCTA CCCTA

• I   N   A   G   N   G   N   T   K   Y   S   Q   K   F   Q   G
5751        GGATC AACGC TGGCA ATGGT AACAC AAAAT ATTCA CAGAA GTTCC AGGGC
            CCTAG TTGCG ACCGT TACCA TTGTG TTTTA TAAGT GTCTT CAAGG TCCCG

R   V   T   I   T   R   D   T   S   A   S   T   A   Y   M   E   L •
5801      AGAGT CACCA TTACC AGGGA CACAT CCGCG AGCAC AGCCT ACATG GAGCT
          TCTCA GTGGT AATGG TCCCT GTGTA GGCGC TCGTG TCGGA TGTAC CTCGA

• S   S   L   R   S   E   D   T   A   V   Y   Y   C   A   R   D   I •
5851  GAGCA GCCTG AGATC TGAAG ACACG GCTGT GTATT ACTGT GCGAG AGACA
      CTCGT CGGAC TCTAG ACTTC TGTGC CGACA CATAA TGACA CGCTC TCTGT

• S   Y   G   S   F   D   Y   W   G   Q   G   T   L   V   T   V            [m923 scFv]
5901  TCAGC TATGG TTCGT TTGAC TACTG GGGCC AGGGA ACCCT GGTCA CCGTC
      AGTCG ATACC AAGCA AACTG ATGAC CCCGG TCCCT TGGGA CCAGT GGCAG

S   S   G   G   G   G   S   G   G   G   G   S   G   G   G   G   S •
5951      TCCTC AGGTG GAGGC GGTTC AGGCG GAGGT GGCTC TGGCG GTGGC GGATC
          AGGAG TCCAC CTCCG CCAAG TCCGC CTCCA CCGAG ACCGC CACCG CCTAG

• S   Y   G   S   F   D   Y   W   G   Q   G   T   L   V   T   V
6001      ATCTT CTGAG CTGAC TCAGG ACCCT GCTGT GTCTG TGGCC TTGGG ACAGA
          TAGAA GACTC GACTG AGTCC TGGGA CGACA CAGAC ACCGG AACCC TGTCT

• V   R   I   T   C   Q   G   D   S   L   R   S   N   Y   A   N
6051      CAGTC AGGAT CACCT GCCAA GGAGA CAGCC TCAGA AGCAA CTATG CAAAC
          GTCAG TCCTA GTGGA CGGTT CCTCT GTCGG AGTCT TCGTT GATAC GTTTG

W   Y   Q   Q   K   P   G   Q   A   P   V   L   V   I   Y   G   Q •
6101      TGGTA CCAGC AGAAG CCAGG ACAGG CCCCT GTACT TGTCA TCTAT GGTCA
          ACCAT GGTCG TCTTC GGTCC TGTCC GGGGA CATGA ACAGT AGATA CCAGT

• N   N   T   P   S   G   I   P   D   R   F   S   G   S   S   S   G •
6151      AAACA ACCGG CCCTC AGGGA TCCCA GACCG ATTCT CTGGC TCCAG CTCAG
          TTTGT TGGCC GGGAG TCCCT AGGGT CTGGC TAAGA GACCG AGGTC GAGTC

• N   T   A   S   L   T   I   T   G   A   Q   A   A   D   E   A
6201      GAAAC ACAGC TTCCT TGACC ATCAC TGGGG CTCAG GCGGC AGATG AGGCT
          CTTTG TGTCG AAGGA ACTGG TAGTG ACCCC GAGTC CGCCG TCTAC TCCGA

D   Y   Y   C   D   S   R   V   S   T   G   N   H   V   V   F   G •
6251      GACTA TTACT GTGAC TCCCG GGTCA GCACT GGTAA CCATG TGGTA TTCGG
          CTGAT AATGA CACTG AGGGC CCAGT CGTGA CCATT GGTAC ACCAT AAGCC
```

```
      • G   G   T   K   L   T   V   L   G   Q   A   S   T   T   T   P   A •
6301  CGGAG GGACC AAGCT GACCG TCCTA GGCCA GGCTA GCACC ACGAC GCCAG          [CD8a Hinge]
      GCCTC CCTGG TTCGA CTGGC AGGAT CCGGT CCGAT CGTGG TGCTG CGGTC

•  P   R   P   P   T   P   A   P   T   I   A   S   Q   P   L   S
6351  CGCCG CGACC ACCAA CACCG GCGCC ACCA TCGCG TCGCA GCCCC TGTCC
      GCGGC GCTGG TGGTT GTGGC CGCGG GTGGT AGCGC AGCGT CGGGG ACAGG

L   R   P   E   A   C   R   P   A   A   G   G   A   V   H   T   R •
6401  CTGCG CCCAG AGGCG TGCCG GCCAG CGGCG GGGGG CGCAG TGCAC ACGAG
      GACGC GGGTC TCCGC ACGGC CGGTC GCCGC CCCCC GCGTC ACGTG TGCTC

• G   L   D   F   A   C   D   F   W   V   L   V   V   V   G   V •
6451  GGGGC TGGAC TTCGC CTGTG ATTTT GGGT GCTGG TGGTG GTTGG TGGAG
      CCCCG ACCTG AAGCG GACAC TAAAA CCCA CGACC ACCAC CAACC ACCTC         [CD28tm]

•  S   Y   G   S   F   D   Y   W   G   Q   G   T   L   V   T   V
6501  TCCTC CCTTG CTATA CCTTG CTAGT AACAG TGCCC TTTAT TATTT CTGG
      AGGAC CGAAC GATAT CGAAC GATCA TTGTC ACCGG AAATA ATAAA AGACC

V   R   S   K   R   S   R   L   L   H   S   D   Y   M   N   M   T •
6551  GTGAG GAGTA AGAGG AGCAG CTCC TGCAC AGTGA CTACA TGAAC ATGAC          [CD28 ICD]
      CACTC CTCAT TCTCC TCGTC CGAGG ACGTG TCACT GATGT ACTTG TACTG

•  P   R   R   P   G   P   T   R   K   H   Y   Q   P   Y   A   P   P •
6601  TCCCC GCCGC CCCGG GCCCA CCCGC AAGCA TTACC AGCCC TATGC CCCAC
      AGGGG CGGCG GGGCC CGGGT GGGCG TTCGT AATGG TCGGG ATACG GGGTG

•  R   D   F   A   A   Y   R   S   I   D   R   V   K   F   S   R
6651  CACGC GACTT CGCAG CCTAT CCCTC CATCG ATAGA GTGAA GTTCA GCAGG
      GTGCG CTGAA GCGTC GGATA GGGAG GTAGC TATCT CACTT CAAGT CGTCC

S   A   D   A   P   A   Y   Q   Q   G   Q   N   Q   L   Y   N   E •
6701  AGCGC AGACG CCCCC GCGTA CCAGC AGGGC CAGAA CCAGC TCTAT AACGA
      TCGCG TCTGC GGGGG CGCAT GGTCG TCCCG GTCTT GGTCG AGATA TTGCT

• L   N   L   G   R   R   E   E   Y   D   V   L   D   K   R   R   G •
6751  GCTCA ATCTA GGACG AAGAG AGGAG TACGA TGTTT TGGAC AAGAG ACGTG
      CGAGT TAGAT CCTGC TTCTC TCCTC ATGCT ACAAA ACCTG TTCTC TGCAC         [CD3Z ICD]

•  R   D   P   E   M   G   G   K   P   R   R   K   N   P   Q   E
6801  GCCGG GACCC TGAGA TGGGG GGAAA GCCGA GAAGG AAGAA CCCTC AGGAA
      CGGCC CTGGG ACTCT ACCCC CCTTT CGGCT CTTCC TTCTT GGGAG TCCTT

G   L   Y   N   E   L   Q   K   D   K   M   A   E   A   Y   S   E •
6851  GGCCT GTACA ATGAA CTGCA GAAAG ATAAG ATGGC GGAGG CCTAC AGTGA
      CCGGA CATGT TACTT GACGT CTTTC TATTC TACCG CCTCC GGATG TCACT

•  I   G   M   K   G   E   R   R   R   G   K   G   H   D   G   L   Y •
6901  GATTG GGATG AAAGG CGAGC GCCGG AGGGG CAAGG GGCAC GATGG CCTTT
      CTAAC CCTAC TTTCC GCTCG CGGCC TCCCC GTTCC CCGTG CTACC GSAAA

•  Q   G   L   S   T   A   T   K   D   T   Y   D   A   L   H   M
6951  ACCAG GGTCT CAGTA CAGCG ACGAA GGACA GCTAC GACGC CCTTC ACATG
      TGGTC CCAGA GTCAT GTCGG TGCTT CCTGT CGATG CTGCG GGAAG TGTAC

Q   A   L   P   P   R   *
7001  CAGGC CCTGC CCCCT CGCTA A
      GTCCG GGACG GGGGA GCGAT T
```

Example 9 m923-BBZ CAR Sequence (Nucleic Acid Sequence is SEQ ID NO: 11, Amino Acid Sequence SED ID NO: 12)

```
                    M    A    L    P    V    T    A  •
5501                ATGGC CTTAC CACTG ACCGC
                    TACCG GAATG GTCAC TGGCG              CD8a

• L    L    L    P    L    A    L    L    L    H    A    A    R    P    G    S    A •
5551    CTTGC CTCTG CCGCT GGCCT TGCTG CTCCA CGCCG CCAGG CCGGG ATCAG
        GAACG AGGAC GGCGA CCGGA ACGAC GAGGT GGGGC GGTCC GGCCC TAGTC

•  E    V    Q    L    V    Q    S    G    A    E    V    K    K    P    G    A
5601    CCGAA GTGCA GCTGG TGCAG TCTGG GGCTG AGGTG AAGAA GCCTG GGGCC
        GGCTT CACGT CGACC ACGTC AGACC CCGAC TCCAC TTCTT CGGAC CCCGG

S    V    K    V    S    C    K    A    S    G    Y    T    F    T    S    Y    A •
5651    TCAGT GAAGG TTTCC TGCAA GGCTT CTGGA TACAC CTTCA CTAGC TATGC
        AGTCA CTTCC AAAGG ACGTT CCGAA GACCT ATGTG GAAGT GATCG ATACG

• M    H    W    V    R    Q    A    P    G    Q    R    L    E    W    M    G    W •
5701    TATGC ATTGG GTGCG CCAGG CCCCC GGACA AAGGC TTGAG TGGAT GGGAT
        ATACG TAACC CACGC GGTCC GGGGG CCTGT TTCCG AACTC ACCTA CCCTA

•  I    N    A    G    N    G    N    T    K    Y    S    Q    K    F    Q    G
5751    GGATC AACGC TGGCA ATGGT AACAC AAAAT ATTCA CAGAA GTTCC AGGGC
        CCTAG TTGCG ACCGT TACCA TTGTG TTTTA TAAGT GTCTT CAAGG TCCCG

R    V    T    I    T    R    D    T    S    A    S    T    A    Y    M    E    L •
5801    AGAGT CACCA TTACC AGGGA CACAT CCGCG AGCAC AGCCT ACATG GAGCT
        TCTCA GTGGT AATGG TCCCT GTGTA GGCGC TCGTG TCGGA TGTAC CTCGA

• S    S    L    R    S    E    D    T    A    V    Y    Y    C    A    R    D    I •
5851    GAGCA GCCTG AGATC TGAAG ACACG GCTGT GTATT ACTGT GCGAG AGACA
        CTCGT CGGAC TCTAG ACTTC TGTGC CGACA CATAA TGACA CGCTC TCTGT

• S    Y    G    S    F    D    Y    W    G    Q    G    T    L    V    T    V
5901    TCAGC TATGG TTCGT TTGAC TACTG GGGCC AGGGA ACCCT GGTCA CCGTC
        AGTCG ATACC AAGCA AACTG ATGAC CCCGG TCCCT TGGGA CCAGT GGCAG

S    S    G    G    G    G    S    G    G    G    G    S    G    G    G    G    S •
5951    TCCTC AGGTG GAGGC GGTTC AGGCG GAGGT GGCTC TGGCG GTGGC GGATC           m923 scFv
        AGGAG TCCAC CTCCG CCAAG TCCGC CTCCA CCGAG ACCGC CACCG CCTAG

• S    S    E    L    T    Q    D    P    A    V    S    V    A    L    G    Q    T •
6001    ATCTT CTGAG CTGAC TCAGG ACCCT GCTGT GTCTG TGGCC TTGGG ACAGA
        TAGAA GACTC GACTG AGTCC TGGGA CGACA CAGAC ACCGG AACCC TGTCT
```

```
                •  V    R    I    T    C    Q    G    D    S    L    R    S    N    Y    A    N
          6051 CAGTC AGGAT CACCT GCCAA GGAGA CAGCC TCAGA AGCAA CTATG CAAAC
               GTCAG TCCTA GTGGA CGGTT CCTCT GTCGG AGTCT TCGTT GATAC GTTTG

W    Y    Q    Q    K    P    G    Q    A    P    V    L    V    I    Y    Q •
          6101 TGGTA CCAGC AGAAG CCAGG ACAGG CCCCT GTACT TGTCA TCTAT GGTCA
               ACCAT GGTCG TCTTC GGTCC TGTCC GGGGA CATGA ACAGT AGATA CCAGT

• N    N    R    P    S    G    I    P    D    R    F    S    G    S    S    S   G•
          6151 AAACA ACCGG CCCTC AGGGA TCCCA GACCG ATTCT CTGGC TCCAG CTCAG
               TTTGT TGGCC GGGAG TCCCT AGGGT CTGGC TAAGA CACCG AGGTC GAGTC

•  N   T    A    S    L    T    I    T    G    A    Q    A    A    D    E   A
          6201 GAAAC ACAGC TTCCT TGACC ATCAC TGGGG CTCAG GCGGC AGATG AGGCT
               CTTTG TGTCG AAGGA ACTGG TAGTG ACCCC GAGTC CGCCG TCTAC TCCGA

D    Y    Y    C    D    S    R    V    S    T    G    N    H    V    V    F   G •
          6251 GACTA TTACT GTGAC TCCCG GGTCA GCACT GGTAA CCATG TGGTA TTCGG
               CTGAT AATGA CACTG AGGGC CCAGT CGTGA CCATT GGTAC ACCAT AAGCC

• G    G    T    K    L    T    V    L    G    Q    A    S    T    T    T    P    A •
          6301 CGGAG GGACC AAGCT GACCG TCCTA CGCCA GGCTA GCACC ACGAC GCCAG
               GCCTC CCTGG TTCGA CTGGC AGGAT CCGGT CCGAT CGTGG TGCTG CGGTC

• P    R    P    P    T    P    A    P    T    I    A    S    Q    P    L    S                    ┌───────────┐
          6351 CGCCG CGACC ACCAA CACCG GCGCC CACCA TCGCG TCGCA GCCCC TGTCC                    │ CD8a Hinge│
               GCGGC GCTGG TGGTT GTGGC CGCGG GTGGT AGCGC AGCGT CGGGG ACAGG                    └───────────┘

L    R    P    E    A    C    R    P    A    A    G    G    A    V    H    T    R •
          6401 CTGCG CCCAG AGGGG TGCCG GCCAG CGGCG GGGGG CGCAG TGCAC ACGAG
               GACGC GGGTC TCCGC ACGGC CGGTC GCCGC CCCCC GCGTC ACGTG TGCTC

• G    L    D    F    A    C    D    I    Y    I    W    A    P    L    A    G   T •                    ┌───────────┐
          6451 GGGGC TGGAC TTCGC CTGTG ATATC TACAT CTGGG CGCCC TTGGC CGGGA                    │  CD8a tm │
               CCCCG ACCTG AAGCG GACAC TATAG ATGTA GACCC GCGGG AACCG GCCCT                    └───────────┘

•  C   G    V    L    L    L    S    L    V    I    T    L    Y    C    R    V
          6501 CTTGT GGGGT CCTTC TCCTG TCACT GGTTA TCACC CTTTA CTGCA ACGG
               GAACA CCCCA GGAAG AGGAC AGTGA CCAAT AGTGG GAAAT GACGT TGCC
```

```
       G  R  K  K     L  L  Y     I  F     K  Q     P     M     R     P  V •
6551 GGCAG AAAGA AACTC CTGTA TATAT TCAAA CAACC ATTTA TGAGA CCAGT
     TTCTT CCTCC TACAC TTGAC TCTCA CTTCA ACTCG TCCTC GCGTC TGCGG

• Q  T     T     Q  E     D     G     C     S     R  F     P  E     E  E •
6601 ACAAA CTACT CAAGA GGAAG ATGGC TGTAG CTGCC GATTT CCAGA AGAAG
     TGTTT GATGA GTTCT CCTTC TACCG ACATC GACGG CTAAA GGTCT TCTTC

• E     G  G     C  E  L     R  V     K  F     S     R  S     A  D     A
6651 AAGAA GGAGG ATGTG AACTG AGAGT GAAGT TCAGC AGGAG CGCAG ACGCC
     TTTGT TGGCC GGGAG TCCCT AGGGT CTGGC TAAGA CACCG AGGTC GAGTC

P  A     Y  Q     Q     G  Q     N  Q     L     Y  N     E  L     N     L  G •
6701 CCCGC GTACC AGCAG GGCCA GAACC AGCTC TATAA CGAGC TCAAT CTAGG
     GGGCG CATGG TCGTC CCGGT CTTGG TCGAG ATATT GCTCG AGTTA GATCC

• R  R     E     E  Y     D  V     L     D  K     R  R     G  R  D     P  E •
6751 ACGAA GAGAG GAGTA CGATG TTTTG GACAA GAGAC GTGGC CGGGA CCCTG
     TGCTT CTCTC CTCAT GCTAC AAAAC CTGTT CTCTG CACCG GCCCT GGGAC  [CD3Z ICD]

• M     G  G     K  P     R  R  K     N  P     Q     E  G     L  Y     N
6801 AGATG GGGGG AAAGC CGAGA AGGAA GAACC CTCAG GAAGG CCTGT ACAAT
     TCTAC CCCCC TTTCG GCTCT TCCTT CTTGG GAGTC CTTCC GGACA TGTTA

E  L     Q  K     D     K  M     A  E     A     Y  S     E  I     G  M  K •
6851 GAACT GCAGA AAGAT AAGAT GGCGG AGGCG TACAG TGAGA TTGGG ATGAA
     CTTGA CGTCT TTCTA TTCTA CCGCC TCCGG ATGTC ACTCT AACCC TACTT

• G  E     R  R     R  G  K     G     H  D     G  L     Y     Q  G     L  S •
6901 AGGCG ACCGC CGGAG GGGCA ACGCG CACCA TGGCC TTTAC CAGGG TCTCA
     TCCGC TCGCG GCCTC CCCGT TCCCC GTGCT ACCGG AAATG GTCCC AGAGT

• T     A  T     K  D     T     Y  D     A  L     H     M  Q     A  L     P
6951 GTACA GCCAC CAAGG ACACC TACGA CGCCC TTCAC ATGCA GGCCC TGCCC
     CATGT CGGTG GTTCC TGTGG ATGCT GCGGG AAGTG TACGT CCGGG ACGGG

P  R     *
7001 CCTCG CTAA
     GGAGC GATT
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An isolated nucleic acid sequence encoding a chimeric antigen receptor (CAR), wherein the CAR comprises an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

2. The isolated nucleic acid sequence of claim 1, comprising a nucleic acid sequence selected from the group consisting of SEQ ID NO: 1, SEQ ID NO: 3, SEQ ID NO: 5, SEQ ID NO: 7, SEQ ID NO: 9, and SEQ ID NO: 11.

3. An isolated chimeric antigen receptor (CAR) encoded by the isolated nucleic acid sequence of claim 1.

4. The isolated CAR of claim 3, wherein the CAR comprises an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

5. A genetically modified T cell comprising an isolated nucleic acid sequence encoding a chimeric antigen receptor (CAR), wherein the CAR comprises an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

6. The T cell of claim 5, wherein the isolated nucleic acid sequence comprises a nucleic acid sequence selected from the group consisting of SEQ ID NO: 1, SEQ ID NO: 3, SEQ ID NO: 5, SEQ ID NO: 7, SEQ ID NO: 9, and SEQ ID NO: 11.

7. A vector comprising an isolated nucleic acid sequence encoding a chimeric antigen receptor (CAR), wherein the CAR comprises an amino acid sequence selected from the group consisting of SEQ ID NO: 2, SEQ ID NO: 4, SEQ ID NO: 6, SEQ ID NO: 8, SEQ ID NO: 10, and SEQ ID NO: 12.

8. The vector of claim 7, wherein the vector is a lentiviral vector.

9. The vector of claim 7, wherein the vector is a RNA vector.

* * * * *

```
                          SEQUENCE LISTING

<160> NUMBER OF SEQ ID NOS: 12

<210> SEQ ID NO 1
<211> LENGTH: 1353
<212> TYPE: DNA
<213> ORGANISM: Artificial Sequence
<220> FEATURE:
<223> OTHER INFORMATION: Chimeric antigen receptor

<400> SEQUENCE: 1
atggccttac cagtgaccgc cttgctcctg ccgctggcct tgctgctcca cgccgccagg      60
ccgggatcag ccgaagtgca gctggtgcag tctggggctg aggtgaagaa gcctggggcc     120
tcagtgaagg tttcctgcaa ggcttctgga tacaccttca ctagctatgc tatgcattgg     180
gtgcgccagg cccccggaca aaggcttgag tggatgggat ggatcaacgc tggcaatggt     240
aacacaaaat attcacagaa gttccagggc agagtcacca ttaccaggga cacatccgcg     300
agcacagcct acatggagct gagcagcctg agatctgaag acacggctgt gtattactgt     360
```

```
gcgagagaca tcagctatgg ttcgtttgac tactggggcc agggaaccct ggtcaccgtc      420
tcctcaggtg gaggcggttc aggcggaggt ggctctggcg gtggcggatc atcttctgag      480
ctgactcagg accctgctgt gtctgtggcc ttgggacaga cagtcaggat cacatgccaa      540
ggagacaacc tcagaagcta ttatgcaagc tggtaccggc agaagtcagg acaggcccct      600
gtacttgtca tctatggtaa aaacaaccgg ccctcaggga tcccagaccg attctctggc      660
tccagctcag gaaacacagc ttccttgacc atcactgcgg ctcaggcgga agatgaggct      720
gactattact gtcactcccg gaaaagccgc ggtaaccatc tgctattcgg cggagggacc      780
aagctgaccg tcctaggcca ggctagcacc acgacgccag cgccgcgacc accaacaccg      840
gcgcccacca tcgcgtcgca gcccctgtcc ctgcgcccag aggcgtgccg gccagcggcg      900
gggggcgcag tgcacacgag ggggctggac ttcgcctgtg atatctacat ctgggcgccc      960
ttggccggga cttgtggggt ccttctcctg tcactggtta tcacccttta ctgcagagtg     1020
aagttcagca ggagcgcaga cgccccgcg taccagcagg gccagaacca gctctataac     1080
gagctcaatc taggacgaag agaggagtac gatgttttgg acaagagacg tggccgggac     1140
cctgagatgg ggggaaagcc gagaaggaag aaccctcagg aaggcctgta caatgaactg     1200
cagaaagata agatggcgga ggcctacagt gagattggga tgaaaggcga gcgccggagg     1260
ggcaaggggc acgatggcct ttaccagggt ctcagtacag ccaccaagga cacctacgac     1320
gcccttcaca tgcaggccct gccccctcgc taa                                  1353
```

```
<210> SEQ ID NO 2
<211> LENGTH: 450
<212> TYPE: PRT
<213> ORGANISM: Artificial Sequence
<220> FEATURE:
<223> OTHER INFORMATION: Chimeric antigen receptor

<400> SEQUENCE: 2

Met Ala Leu Pro Val Thr Ala Leu Leu Leu Pro Leu Ala Leu Leu Leu
1               5                   10                  15

His Ala Ala Arg Pro Gly Ser Ala Glu Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Ser Tyr Ala Met His Trp Val Arg Gln Ala
    50                  55                  60

Pro Gly Gln Arg Leu Glu Trp Met Gly Trp Ile Asn Ala Gly Asn Gly
65                  70                  75                  80

Asn Thr Lys Tyr Ser Gln Lys Phe Gln Gly Arg Val Thr Ile Thr Arg
                85                  90                  95

Asp Thr Ser Ala Ser Thr Ala Tyr Met Glu Leu Ser Ser Leu Arg Ser
            100                 105                 110

Glu Asp Thr Ala Val Tyr Tyr Cys Ala Arg Asp Ile Ser Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Asn Leu Arg Ser Tyr Tyr Ala Ser Trp Tyr
```

|              |     | 180 |     |     |     | 185 |     |     |     | 190 |     |     |
|---|---|---|---|---|---|---|---|---|---|---|---|---|

```
                        180                 185                 190
        Arg Gln Lys Ser Gly Gln Ala Pro Val Leu Val Ile Tyr Gly Lys Asn
                        195                 200                 205
        Asn Arg Pro Ser Gly Ile Pro Asp Arg Phe Ser Gly Ser Ser Ser Gly
                        210                 215                 220
        Asn Thr Ala Ser Leu Thr Ile Thr Ala Ala Gln Ala Glu Asp Glu Ala
        225                 230                 235                 240
        Asp Tyr Tyr Cys His Ser Arg Lys Ser Arg Gly Asn His Leu Leu Phe
                        245                 250                 255
        Gly Gly Gly Thr Lys Leu Thr Val Leu Gly Gln Ala Ser Thr Thr Thr
                        260                 265                 270
        Pro Ala Pro Arg Pro Pro Thr Pro Ala Pro Thr Ile Ala Ser Gln Pro
                        275                 280                 285
        Leu Ser Leu Arg Pro Glu Ala Cys Arg Pro Ala Ala Gly Gly Ala Val
                        290                 295                 300
        His Thr Arg Gly Leu Asp Phe Ala Cys Asp Ile Tyr Ile Trp Ala Pro
        305                 310                 315                 320
        Leu Ala Gly Thr Cys Gly Val Leu Leu Leu Ser Leu Val Ile Thr Leu
                        325                 330                 335
        Tyr Cys Arg Val Lys Phe Ser Arg Ser Ala Asp Ala Pro Ala Tyr Gln
                        340                 345                 350
        Gln Gly Gln Asn Gln Leu Tyr Asn Glu Leu Asn Leu Gly Arg Arg Glu
                        355                 360                 365
        Glu Tyr Asp Val Leu Asp Lys Arg Arg Gly Arg Asp Pro Glu Met Gly
                        370                 375                 380
        Gly Lys Pro Arg Arg Lys Asn Pro Gln Glu Gly Leu Tyr Asn Glu Leu
        385                 390                 395                 400
        Gln Lys Asp Lys Met Ala Glu Ala Tyr Ser Glu Ile Gly Met Lys Gly
                        405                 410                 415
        Glu Arg Arg Arg Gly Lys Gly His Asp Gly Leu Tyr Gln Gly Leu Ser
                        420                 425                 430
        Thr Ala Thr Lys Asp Thr Tyr Asp Ala Leu His Met Gln Ala Leu Pro
                        435                 440                 445
        Pro Arg
            450

<210> SEQ ID NO 3
<211> LENGTH: 1491
<212> TYPE: DNA
<213> ORGANISM: Artificial Sequence
<220> FEATURE:
<223> OTHER INFORMATION: Chimeric antigen receptor

<400> SEQUENCE: 3 atggcettac cagtgaccgc cttgctcctg ccgctggcct tgctgctcca cgccgccagg      60
ccgggatcag ccgaagtgca gctggtgcag tctggggctg aggtgaagaa gcctggggcc    120
tcagtgaagg tttcctgcaa ggcttctgga tacaccttca ctagctatgc tatgcattgg    180
gtgcgccagg cccccggaca aaggcttgag tggatgggat ggatcaacgc tggcaatggt    240
aacacaaaat attcacagaa gttccagggc agagtcacca ttaccaggga cacatccgcg    300
agcacagcct acatggagct gagcagcctg agatctgaag acacggctgt gtattactgt    360
gcgagagaca tcagctatgg ttcgtttgac tactggggcc agggaaccct ggtcaccgtc    420
tcctcaggtg aggcggttc aggcggaggt ggctctggcg gtggcggatc atcttctgag    480
```

```
ctgactcagg accctgctgt gtctgtggcc ttgggacaga cagtcaggat cacatgccaa    540
ggagacaacc tcagaagcta ttatgcaagc tggtaccggc agaagtcagg acaggcccct    600
gtacttgtca tctatggtaa aaacaaccgg ccctcaggga tcccagaccg attctctggc    660
tccagctcag gaaacacagc ttccttgacc atcactgcgg ctcaggcgga agatgaggct    720
gactattact gtcactcccg gaaaagccgc ggtaaccatc tgctattcgg cggagggacc    780
aagctgaccg tcctaggcca ggctagcacc acgacgccag cgccgcgacc accaacaccg    840
gcgcccacca tcgcgtcgca gccoctgtcc ctgcgcccag aggcgtgccg gccagcggcg    900
gggggcgcag tgcacacgag ggggctggac ttcgcctgtg attttggggt gctggtggtg    960
gttggtggag tcctggcttg ctatagcttg ctagtaacag tggcctttat tattttctgg   1020
gtgaggagta agaggagcag gctcctgcac agtgactaca tgaacatgac tccccgccgc   1080
cccgggccca cccgcaagca ttaccagccc tatgccccac cacgcgactt cgcagcctat   1140
cgctccatcg atagagtgaa gttcagcagg agcgcagacg cccccgcgta ccagcagggc   1200
cagaaccagc tctataacga gctcaatcta ggacgaagag aggagtacga tgttttggac   1260
aagagacgtg gccgggaccc tgagatgggg ggaaagccga aaggaagaa ccctcaggaa   1320
ggcctgtaca atgaactgca gaaagataag atggcggagg cctacagtga gattgggatg   1380
aaaggcgagc gccggagggg caaggggcac gatggccttt accagggtct cagtacagcc   1440
accaaggaca cctacgacgc ccttcacatg caggccctgc ccctcgcta a   1491
```

<210> SEQ ID NO 4
<211> LENGTH: 496
<212> TYPE: PRT
<213> ORGANISM: Artificial Sequence
<220> FEATURE:
<223> OTHER INFORMATION: Chimeric antigen receptor

<400> SEQUENCE: 4

```
Met Ala Leu Pro Val Thr Ala Leu Leu Leu Pro Leu Ala Leu Leu Leu
1               5                   10                  15

His Ala Ala Arg Pro Gly Ser Ala Glu Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Tyr Thr Phe Thr Ser Tyr Ala Met His Trp Val Arg Gln Ala
        50                  55                  60

Pro Gly Gln Arg Leu Glu Trp Met Gly Trp Ile Asn Ala Gly Asn Gly
65                  70                  75                  80

Asn Thr Lys Tyr Ser Gln Lys Phe Gln Gly Arg Val Thr Ile Thr Arg
                85                  90                  95

Asp Thr Ser Ala Ser Thr Ala Tyr Met Glu Leu Ser Ser Leu Arg Ser
            100                 105                 110

Glu Asp Thr Ala Val Tyr Tyr Cys Ala Arg Asp Ile Ser Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Asn Leu Arg Ser Tyr Tyr Ala Ser Trp Tyr
            180                 185                 190
```

```
Arg Gln Lys Ser Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Ala Ala Gln Ala Glu Asp Glu Ala
225                 230                 235                 240

Asp Tyr Tyr Cys His Ser Arg Lys Ser Arg Gly Asn His Leu Leu Phe
                245                 250                 255

Gly Gly Gly Thr Lys Leu Thr Val Leu Gly Gln Ala Ser Thr Thr Thr
                260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
                340                 345                 350

Tyr Met Asn Met Thr Pro Arg Arg Pro Gly Pro Thr Arg Lys His Tyr
            355                 360                 365

Gln Pro Tyr Ala Pro Pro Arg Asp Phe Ala Ala Tyr Arg Ser Ile Asp
        370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 5
<211> LENGTH: 1353
<212> TYPE: DNA
<213> ORGANISM: Artificial Sequence
<220> FEATURE:
<223> OTHER INFORMATION: Chimeric antigen receptor

<400> SEQUENCE: 5

```
atggccttac cagtgaccgc cttgctcctg ccgctggcct tgctgctcca cgccgccagg      60
ccgggatcag ccgaagtgca gctggtgcag tctggggctg aggtgaagaa gcctggggcc    120
tcagtgaagg tttcctgcaa ggcttctgga tacaccttca ctagctatgc tatgcattgg    180
gtgcgccagg cccccggaca aaggcttgag tggatgggat ggatcaacgc tggcaatggt    240
aacacaaaat attcacagaa gttccagggc agagtcacca ttaccaggga cacatccgcg    300
agcacagcct acatggagct gagcagcctg agatctgaag acacggctgt gtattactgt    360
```

```
gcgagagaca tcagctatgg ttcgtttgac tactggggcc agggaaccct ggtcaccgtc    420
tcctcaggtg gaggcggttc aggcggaggt ggctctggcg gtggcggatc atcttctgag    480
ctgactcagg accctgctgt gtctgtggcc ttgggacaga cagtcaggat cacctgccaa    540
ggagacagcc tcagaagcaa ctatgcaaac tggtaccagc agaagccagg acaggcccct    600
gtacttgtca tctatggtca aaacaaccgg ccctcaggga tcccagaccg attctctggc    660
tccagctcag gaaacacagc ttccttgacc atcactgggg ctcaggcggc agatgaggct    720
gactattact gtgactcccg ggtcagcact ggtaaccatg tggtattcgg cggagggacc    780
aagctgaccg tcctaggcca ggctagcacc acgacgccag cgccgcgacc accaacaccg    840
gcgcccacca tcgcgtcgca gcccctgtcc ctgcgcccag aggcgtgccg gccagcggcg    900
gggggcgcag tgcacacgag ggggctggac ttcgcctgtg atatctacat ctgggcgccc    960
ttggccggga cttgtggggt ccttctcctg tcactggtta tcaccctttta ctgcagagtg   1020 aagttcagca ggagcgcaga cgccccgcg taccagcagg gccagaacca gctctataac    1080
gagctcaatc taggacgaag agaggagtac gatgttttgg acaagagacg tggccgggac    1140
cctgagatgg ggggaaagcc gagaaggaag aaccctcagg aaggcctgta caatgaactg    1200
cagaaagata gatggcgga ggcctacagt gagattggga tgaaaggcga gcgccggagg    1260
ggcaaggggc acgatggcct ttaccagggt ctcagtacag ccaccaagga cacctacgac    1320
gcccttcaca tgcaggccct gccccctcgc taa                                 1353
```

<210> SEQ ID NO 6
<211> LENGTH: 450
<212> TYPE: PRT
<213> ORGANISM: Artificial Sequence
<220> FEATURE:
<223> OTHER INFORMATION: Chimeric antigen receptor

<400> SEQUENCE: 6

```
Met Ala Leu Pro Val Thr Ala Leu Leu Leu Pro Leu Ala Leu Leu Leu
1               5                   10                  15

His Ala Ala Arg Pro Gly Ser Ala Glu Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Ser Tyr Ala Met His Trp Val Arg Gln Ala
    50                  55                  60

Pro Gly Gln Arg Leu Glu Trp Met Gly Trp Ile Asn Ala Gly Asn Gly
65                  70                  75                  80

Asn Thr Lys Tyr Ser Gln Lys Phe Gln Gly Arg Val Thr Ile Thr Arg
                85                  90                  95

Asp Thr Ser Ala Ser Thr Ala Tyr Met Glu Leu Ser Ser Leu Arg Ser
            100                 105                 110

Glu Asp Thr Ala Val Tyr Tyr Cys Ala Arg Asp Ile Ser Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Asn Tyr Ala Asn Trp Tyr
```

```
                    180                 185                 190
Gln Gln Lys Pro Gly Gln Ala Pro Val Leu Val Ile Tyr Gly Gln Asn
            195                 200                 205
Asn Arg Pro Ser Gly Ile Pro Asp Arg Phe Ser Gly Ser Ser Ser Gly
        210                 215                 220
Asn Thr Ala Ser Leu Thr Ile Thr Gly Ala Gln Ala Ala Asp Glu Ala
225                 230                 235                 240
Asp Tyr Tyr Cys Asp Ser Arg Val Ser Thr Gly Asn His Val Val Phe
                245                 250                 255
Gly Gly Gly Thr Lys Leu Thr Val Leu Gly Gln Ala Ser Thr Thr Thr
            260                 265                 270
Pro Ala Pro Arg Pro Pro Thr Pro Ala Pro Thr Ile Ala Ser Gln Pro
        275                 280                 285
Leu Ser Leu Arg Pro Glu Ala Cys Arg Pro Ala Ala Gly Gly Ala Val
        290                 295                 300
His Thr Arg Gly Leu Asp Phe Ala Cys Asp Ile Tyr Ile Trp Ala Pro
305                 310                 315                 320
Leu Ala Gly Thr Cys Gly Val Leu Leu Leu Ser Leu Val Ile Thr Leu
                325                 330                 335
Tyr Cys Arg Val Lys Phe Ser Arg Ser Ala Asp Ala Pro Ala Tyr Gln
                340                 345                 350
Gln Gly Gln Asn Gln Leu Tyr Asn Glu Leu Asn Leu Gly Arg Arg Glu
            355                 360                 365
Glu Tyr Asp Val Leu Asp Lys Arg Arg Gly Arg Asp Pro Glu Met Gly
        370                 375                 380
Gly Lys Pro Arg Arg Lys Asn Pro Gln Glu Gly Leu Tyr Asn Glu Leu
385                 390                 395                 400
Gln Lys Asp Lys Met Ala Glu Ala Tyr Ser Glu Ile Gly Met Lys Gly
                405                 410                 415
Glu Arg Arg Arg Gly Lys Gly His Asp Gly Leu Tyr Gln Gly Leu Ser
            420                 425                 430
Thr Ala Thr Lys Asp Thr Tyr Asp Ala Leu His Met Gln Ala Leu Pro
        435                 440                 445
Pro Arg
    450

<210> SEQ ID NO 7
<211> LENGTH: 1497
<212> TYPE: DNA
<213> ORGANISM: Artificial Sequence
<220> FEATURE:
<223> OTHER INFORMATION: Chimeric antigen receptor

<400> SEQUENCE: 7
atggccttac cagtgaccgc cttgctcctg ccgctggcct tgctgctcca cgccgccagg      60
ccgggatcag ccgaagtgca gctggtgcag tctggggctg aggtgaagaa gcctggggcc     120
tcagtgaagg tttcctgcaa ggcttctgga tacaccttca ctagctatgc tatgcattgg     180
gtgcgccagg cccccggaca aaggcttgag tggatgggat ggatcaacgc tggcaatggt     240
aacacaaaat attcacagaa gttccagggc agagtcacca ttaccaggga cacatccgcg     300
agcacagcct acatggagct gagcagcctg agatctgaag acacggctgt gtattactgt     360
gcgagagaca tcagctatgg ttcgtttgac tactggggcc agggaaccct ggtcaccgtc     420
tcctcaggtg gaggcggttc aggcggaggt ggctctggcg gtggcggatc atcttctgag     480
```

-continued

```
ctgactcagg accctgctgt gtctgtggcc ttgggacaga cagtcaggat cacctgccaa    540
ggagacagcc tcagaagcaa ctatgcaaac tggtaccagc agaagccagg acaggccccct   600
gtacttgtca tctatggtca aaacaaccgg ccctcaggga tcccagaccg attctctggc    660
tccagctcag gaaacacagc ttccttgacc atcactgggg ctcaggcggc agatgaggct    720
gactattact gtgactcccg ggtcagcact ggtaaccatg tggtattcgg cggagggacc    780
aagctgaccg tcctaggcca ggctagcacc acgacgccag cgccgcgacc accaacaccg    840
gcgcccacca tcgcgtcgca gccccttgtcc ctgcgcccag aggcgtgccg gccagcggcg    900
gggggcgcag tgcacacgag ggggctggac ttcgcctgtg atatctacat ctgggcgccc    960
ttggccggga cttgtggggt ccttctcctg tcactggtta tcacccttta ctgccaacga   1020
aggaaatata gatcaaacaa aggagaaagt cctgtggagc ctgcagagcc ttgtcgttac   1080
agctgccccca gggaggagga gggcagcacc atccccatcc aggaggatta ccgaaaaccg   1140
gagcctgcct gctcccccag agtgaagttc agcaggagcg cagacgcccc cgcgtaccag   1200
cagggccaga accagctcta taacgagctc aatctaggac aagagagga gtacgatgtt    1260
ttggacaaga cgtggccg ggaccctgag atgggggaa agccgagaag gaagaaccct       1320
caggaaggcc tgtacaatga actgcagaaa gataagatgg cggaggccta cagtgagatt   1380
gggatgaaag gcgagcgccg gaggggcaag gggcacgatg ccttttacca gggtctcagt   1440
acagccacca aggacaccta cgacgccctt cacatgcagg ccctgccccc tcgctaa      1497
```

<210> SEQ ID NO 8
<211> LENGTH: 498
<212> TYPE: PRT
<213> ORGANISM: Artificial Sequence
<220> FEATURE:
<223> OTHER INFORMATION: Chimeric antigen receptor

<400> SEQUENCE: 8

```
Met Ala Leu Pro Val Thr Ala Leu Leu Leu Pro Leu Ala Leu Leu Leu
1               5                   10                  15

His Ala Ala Arg Pro Gly Ser Ala Glu Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Ser Tyr Ala Met His Trp Val Arg Gln Ala
    50                  55                  60

Pro Gly Gln Arg Leu Glu Trp Met Gly Trp Ile Asn Ala Gly Asn Gly
65                  70                  75                  80

Asn Thr Lys Tyr Ser Gln Lys Phe Gln Gly Arg Val Thr Ile Thr Arg
                85                  90                  95

Asp Thr Ser Ala Ser Thr Ala Tyr Met Glu Leu Ser Ser Leu Arg Ser
            100                 105                 110

Glu Asp Thr Ala Val Tyr Tyr Cys Ala Arg Asp Ile Ser Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Ser Gly Gly Gly Gly Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Asn Tyr Ala Asn Trp Tyr
            180                 185                 190
```

Gln Gln Lys Pro Gly Gln Ala Pro Val Leu Val Ile Tyr Gly Gln Asn
        195                 200                 205

Asn Arg Pro Ser Gly Ile Pro Asp Arg Phe Ser Gly Ser Ser Ser Gly
210                 215                 220

Asn Thr Ala Ser Leu Thr Ile Thr Gly Ala Gln Ala Ala Asp Glu Ala
225                 230                 235                 240

Asp Tyr Tyr Cys Asp Ser Arg Val Ser Thr Gly Asn His Val Val Phe
                245                 250                 255

Gly Gly Gly Thr Lys Leu Thr Val Leu Gly Gln Ala Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Arg Val Arg Lys Tyr Arg Ser Asn Lys Gly Glu Ser Pro Val
            340                 345                 350

Glu Pro Ala Glu Pro Cys Arg Tyr Ser Cys Pro Arg Glu Glu Glu Gly
        355                 360                 365

Ser Thr Ile Pro Ile Gln Glu Asp Tyr Arg Lys Pro Glu Pro Ala Cys
370                 375                 380

Ser Pro Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 9
<211> LENGTH: 1491
<212> TYPE: DNA
<213> ORGANISM: Artificial Sequence
<220> FEATURE:
<223> OTHER INFORMATION: Chimeric antigen receptor

<400> SEQUENCE: 9
atggccttac cagtgaccgc cttgctcctg ccgctggcct tgctgctcca cgccgccagg      60
ccgggatcag ccgaagtgca gctggtgcag tctggggctg aggtgaagaa gcctggggcc     120
tcagtgaagg tttcctgcaa ggcttctgga tacaccttca ctagctatgc tatgcattgg     180
gtgcgccagg cccccggaca aaggcttgag tggatgggat ggatcaacgc tggcaatggt     240
aacacaaaat attcacagaa gttccagggc agagtcacca ttaccaggga cacatccgcg     300

```
agcacagcct acatggagct gagcagcctg agatctgaag acacggctgt gtattactgt    360
gcgagagaca tcagctatgg ttcgtttgac tactggggcc agggaaccct ggtcaccgtc    420
tcctcaggtg gaggcggttc aggcggaggt ggctctggcg gtggcggatc atcttctgag    480
ctgactcagg accctgctgt gtctgtggcc ttgggacaga cagtcaggat cacctgccaa    540
ggagacagcc tcagaagcaa ctatgcaaac tggtaccagc agaagccagg acaggcccct    600
gtacttgtca tctatggtca aaacaaccgg ccctcaggga tcccagaccg attctctggc    660
tccagctcag gaaacacagc ttccttgacc atcactgggg ctcaggcggc agatgaggct    720
gactattact gtgactcccg ggtcagcact ggtaaccatg tggtattcgg cggagggacc    780
aagctgaccg tcctaggcca ggctagcacc acgacgccag cgccgcgacc accaacaccg    840
gcgcccacca tcgcgtcgca gcccctgtcc ctgcgcccag aggcgtgccg gccagcggcg    900
gggggcgcag tgcacacgag ggggctggac ttcgcctgtg attttgggt gctggtggtg     960
gttggtggag tcctggcttg ctatagcttg ctagtaacag tggcctttat tattttctgg   1020
gtgaggagta agaggagcag gctcctgcac agtgactaca tgaacatgac tccccgccgc   1080
cccgggccca cccgcaagca ttaccagccc tatgccccac cacgcgactt cgcagcctat   1140
cgctccatcg atagagtgaa gttcagcagg agcgcagacg ccccccgcgta ccagcagggc   1200
cagaaccagc tctataacga gctcaatcta ggacgaagag aggagtacga tgttttggac   1260
aagagacgtg gccgggaccc tgagatgggg ggaaagccga aaggaagaa ccctcaggaa    1320
ggcctgtaca atgaactgca gaaagataag atggcggagg cctacagtga gattgggatg   1380
aaaggcgagc gccggagggg caaggggcac gatggccttt accagggtct cagtacagcc   1440
accaaggaca cctacgacgc ccttcacatg caggccctgc cccctcgcta a             1491
```

<210> SEQ ID NO 10
<211> LENGTH: 496
<212> TYPE: PRT
<213> ORGANISM: Artificial Sequence
<220> FEATURE:
<223> OTHER INFORMATION: Chimeric antigen receptor

<400> SEQUENCE: 10

```
Met Ala Leu Pro Val Thr Ala Leu Leu Leu Pro Leu Ala Leu Leu Leu
1               5                   10                  15

His Ala Ala Arg Pro Gly Ser Ala Glu Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Ser Tyr Ala Met His Trp Val Arg Gln Ala
    50                  55                  60

Pro Gly Gln Arg Leu Glu Trp Met Gly Trp Ile Asn Ala Gly Asn Gly
65                  70                  75                  80

Asn Thr Lys Tyr Ser Gln Lys Phe Gln Gly Arg Val Thr Ile Thr Arg
                85                  90                  95

Asp Thr Ser Ala Ser Thr Ala Tyr Met Glu Leu Ser Ser Leu Arg Ser
            100                 105                 110

Glu Asp Thr Ala Val Tyr Tyr Cys Ala Arg Asp Ile Ser Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
```

```
                145                 150                 155                 160
Leu Thr Gln Asp Pro Ala Val Ser Val Ala Leu Gly Gln Thr Val Arg
                    165                 170                 175
Ile Thr Cys Gln Gly Asp Ser Leu Arg Ser Asn Tyr Ala Asn Trp Tyr
                    180                 185                 190
Gln Gln Lys Pro Gly Gln Ala Pro Val Leu Val Ile Tyr Gly Gln Asn
                    195                 200                 205
Asn Arg Pro Ser Gly Ile Pro Asp Arg Phe Ser Gly Ser Ser Ser Gly
                    210                 215                 220
Asn Thr Ala Ser Leu Thr Ile Thr Gly Ala Gln Ala Ala Asp Glu Ala
225                 230                 235                 240
Asp Tyr Tyr Cys Asp Ser Arg Val Ser Thr Gly Asn His Val Val Phe
                    245                 250                 255
Gly Gly Gly Thr Lys Leu Thr Val Leu Gly Gln Ala Ser Thr Thr Thr
                    260                 265                 270
Pro Ala Pro Arg Pro Pro Thr Pro Ala Pro Thr Ile Ala Ser Gln Pro
                    275                 280                 285
Leu Ser Leu Arg Pro Glu Ala Cys Arg Pro Ala Ala Gly Gly Ala Val
                    290                 295                 300
His Thr Arg Gly Leu Asp Phe Ala Cys Asp Phe Trp Val Leu Val Val
305                 310                 315                 320
Val Gly Gly Val Leu Ala Cys Tyr Ser Leu Leu Val Thr Val Ala Phe
                    325                 330                 335
Ile Ile Phe Trp Val Arg Ser Lys Arg Ser Arg Leu Leu His Ser Asp
                    340                 345                 350
Tyr Met Asn Met Thr Pro Arg Arg Pro Gly Pro Thr Arg Lys His Tyr
                    355                 360                 365
Gln Pro Tyr Ala Pro Pro Arg Asp Phe Ala Ala Tyr Arg Ser Ile Asp
                    370                 375                 380
Arg Val Lys Phe Ser Arg Ser Ala Asp Ala Pro Ala Tyr Gln Gln Gly
385                 390                 395                 400
Gln Asn Gln Leu Tyr Asn Glu Leu Asn Leu Gly Arg Arg Glu Glu Tyr
                    405                 410                 415
Asp Val Leu Asp Lys Arg Arg Gly Arg Asp Pro Glu Met Gly Gly Lys
                    420                 425                 430
Pro Arg Arg Lys Asn Pro Gln Glu Gly Leu Tyr Asn Glu Leu Gln Lys
                    435                 440                 445
Asp Lys Met Ala Glu Ala Tyr Ser Glu Ile Gly Met Lys Gly Glu Arg
                    450                 455                 460
Arg Arg Gly Lys Gly His Asp Gly Leu Tyr Gln Gly Leu Ser Thr Ala
465                 470                 475                 480
Thr Lys Asp Thr Tyr Asp Ala Leu His Met Gln Ala Leu Pro Pro Arg
                    485                 490                 495

<210> SEQ ID NO 11
<211> LENGTH: 1479
<212> TYPE: DNA
<213> ORGANISM: Artificial Sequence
<220> FEATURE:
<223> OTHER INFORMATION: Chimeric antigen receptor

<400> SEQUENCE: 11
atggccttac cagtgaccgc cttgctcctg ccgctggcct tgctgctcca cgccgccagg      60
ccgggatcag ccgaagtgca gctggtgcag tctggggctg aggtgaagaa gcctggggcc     120
```

```
tcagtgaagg tttcctgcaa ggcttctgga tacaccttca ctagctatgc tatgcattgg    180
gtgcgccagg cccccggaca aaggcttgag tggatgggat ggatcaacgc tggcaatggt    240
aacacaaaat attcacagaa gttccagggc agagtcacca ttaccaggga cacatccgcg    300
agcacagcct acatggagct gagcagcctg agatctgaag acacggctgt gtattactgt    360
gcgagagaca tcagctatgg ttcgtttgac tactggggcc agggaaccct ggtcaccgtc    420
tcctcaggtg gaggcggttc aggcggaggt ggctctggcg gtggcggatc atcttctgag    480
ctgactcagg accctgctgt gtctgtggcc ttgggacaga cagtcaggat cacctgccaa    540
ggagacagcc tcagaagcaa ctatgcaaac tggtaccagc agaagccagg acaggcccct    600
gtacttgtca tctatggtca aaacaaccgg ccctcaggga tcccagaccg attctctggc    660
tccagctcag gaaacacagc ttccttgacc atcactgggg ctcaggcggc agatgaggct    720
gactattact gtgactcccg ggtcagcact ggtaaccatg tggtattcgg cggagggacc    780
aagctgaccg tcctaggcca ggctagcacc acgacgccag cgccgcgacc accaacaccg    840
gcgcccacca tcgcgtcgca gcccctgtcc ctgcgcccag aggcgtgccg gccagcggcg    900
gggggcgcag tgcacacgag ggggctggac ttcgcctgtg atatctacat ctgggcgccc    960
ttggccggga cttgtggggt ccttctcctg tcactggtta tcacccttta ctgcaaacgg   1020
ggcagaaaga aactcctgta tatattcaaa caaccattta tgagaccagt acaaactact   1080
caagaggaag atggctgtag ctgccgattt ccagaagaag aagaaggagg atgtgaactg   1140
agagtgaagt tcagcaggag cgcagacgcc cccgcgtacc agcagggcca gaaccagctc   1200
tataacgagc tcaatctagg acgaagagag gagtacgatg ttttggacaa gagacgtggc   1260
cgggaccctg agatgggggg aaagccgaga aggaagaacc ctcaggaagg cctgtacaat   1320
gaactgcaga agataagat ggcggaggcc tacagtgaga ttgggatgaa aggcgagcgc   1380
cggaggggca aggggcacga tggcctttac cagggtctca gtacagccac caaggacacc   1440
tacgacgccc ttcacatgca ggccctgccc cctcgctaa                         1479
```

<210> SEQ ID NO 12
<211> LENGTH: 492
<212> TYPE: PRT
<213> ORGANISM: Artificial Sequence
<220> FEATURE:
<223> OTHER INFORMATION: Chimeric antigen receptor

<400> SEQUENCE: 12

Met Ala Leu Pro Val Thr Ala Leu Leu Leu Pro Leu Ala Leu Leu Leu
1               5                   10                  15

His Ala Ala Arg Pro Gly Ser Ala Glu Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Tyr Thr Phe Thr Ser Tyr Ala Met His Trp Val Arg Gln Ala
        50                  55                  60

Pro Gly Gln Arg Leu Glu Trp Met Gly Trp Ile Asn Ala Gly Asn Gly
65                  70                  75                  80

Asn Thr Lys Tyr Ser Gln Lys Phe Gln Gly Arg Val Thr Ile Thr Arg
                85                  90                  95

Asp Thr Ser Ala Ser Thr Ala Tyr Met Glu Leu Ser Ser Leu Arg Ser
            100                 105                 110

Glu Asp Thr Ala Val Tyr Tyr Cys Ala Arg Asp Ile Ser Tyr Gly Ser
        115                 120                 125

```
-continued

Phe Asp Tyr Trp Gly Gln Gly Thr Leu Val Thr Val Ser Ser Gly Gly
    130                 135                 140

Gly Gly Ser Gly Gly Gly Ser Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Asn Tyr Ala Asn Trp Tyr
            180                 185                 190

Gln Gln Lys Pro Gly Gln Ala Pro Val Leu Val Ile Tyr Gly Gln Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Ala Asp Glu Ala
225                 230                 235                 240

Asp Tyr Tyr Cys Asp Ser Arg Val Ser Thr Gly Asn His Val Val Phe
                245                 250                 255

Gly Gly Gly Thr Lys Leu Thr Val Leu Gly Gln Ala Ser Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Arg Val Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```